US010155816B2

(12) United States Patent
Parren et al.

(10) Patent No.: US 10,155,816 B2
(45) Date of Patent: *Dec. 18, 2018

(54) RECOMBINANT MONOVALENT ANTIBODIES AND METHODS FOR PRODUCTION THEREOF

(75) Inventors: Paul Parren, Utrecht (NL); Janine Schuurman, Utrecht (NL); Tom Vink, Alphen aan den Rijn (NL); Willem Karel Bleeker, Amsterdam (NL); Jan Van De Winkel, Zeist (NL); Patrick Van Berkel, Utrecht (NL); Frank Beurskens, Utrecht (NL)

(73) Assignee: GENMAB A/S, Copenhagen V (DK)

( * ) Notice: Subject to any disclaimer, the term of this patent is extended or adjusted under 35 U.S.C. 154(b) by 598 days.

This patent is subject to a terminal disclaimer.

(21) Appl. No.: 12/095,023

(22) PCT Filed: Nov. 28, 2006

(86) PCT No.: PCT/DK2006/000669
§ 371 (c)(1),
(2), (4) Date: Aug. 26, 2008

(87) PCT Pub. No.: WO2007/059782
PCT Pub. Date: May 31, 2007

(65) Prior Publication Data
US 2009/0226421 A1    Sep. 10, 2009

Related U.S. Application Data

(60) Provisional application No. 60/852,611, filed on Oct. 18, 2006, provisional application No. 60/852,479, filed on Oct. 17, 2006, provisional application No. 60/740,403, filed on Nov. 28, 2005.

(51) Int. Cl.
| C07K 16/18 | (2006.01) |
| C07K 19/00 | (2006.01) |
| C07K 16/28 | (2006.01) |

(52) U.S. Cl.
CPC ........ *C07K 16/2863* (2013.01); *C07K 16/283* (2013.01); *C07K 16/2812* (2013.01); *C07K 16/2887* (2013.01); *C07K 2317/21* (2013.01); *C07K 2317/53* (2013.01); *C07K 2317/54* (2013.01); *C07K 2317/55* (2013.01); *C07K 2317/56* (2013.01); *C07K 2317/732* (2013.01); *C07K 2317/734* (2013.01); *C07K 2317/76* (2013.01); *C07K 2317/77* (2013.01)

(58) Field of Classification Search
CPC ................................ A61K 39/00; C07K 16/00
USPC ............. 435/972, 326; 530/861, 866, 867; 424/130.1, 141.1, 177.1
See application file for complete search history.

(56) References Cited

U.S. PATENT DOCUMENTS

| 5,624,821 | A | 4/1997 | Winter et al. | |
| 5,939,598 | A | 8/1999 | Kucherlapati et al. | |
| 6,046,310 | A * | 4/2000 | Queen et al. | 530/391.7 |
| 7,083,784 | B2 | 8/2006 | Dall'Acqua et al. | |
| 7,300,916 | B2 | 11/2007 | Yasuda et al. | |
| 7,317,091 | B2 | 1/2008 | Lazar et al. | |
| 8,911,726 | B2 | 12/2014 | Takahashi et al. | |
| 2003/0118592 | A1 * | 6/2003 | Ledbetter et al. | 424/178.1 |
| 2004/0033561 | A1 * | 2/2004 | O'Keefe et al. | 435/69.1 |
| 2005/0048572 | A1 | 3/2005 | Reilly et al. | |
| 2005/0136049 | A1 * | 6/2005 | Ledbetter et al. | 424/132.1 |
| 2007/0105199 | A1 | 5/2007 | Yan et al. | |
| 2008/0181892 | A1 | 7/2008 | Ledbetter et al. | |
| 2009/0226421 | A1 | 9/2009 | Parren et al. | |
| 2010/0317834 | A1 * | 12/2010 | Lazar et al. | 530/387.1 |
| 2010/0325744 | A1 | 12/2010 | Schuurman et al. | |
| 2011/0045007 | A1 | 2/2011 | Schuurman et al. | |

FOREIGN PATENT DOCUMENTS

| EP | 953639 | * 11/1999 |
| JP | 2002-522076 | 7/2002 |
| JP | 2004-525620 | 8/2004 |
| WO | 03/000176 A2 | 1/2003 |
| WO | 04/026427 A2 | 4/2004 |
| WO | 04/045512 A2 | 6/2004 |
| WO | 04/056847 A2 | 7/2004 |
| WO | WO2004/085478 | * 10/2004 |
| WO | 05/014780 A2 | 2/2005 |
| WO | 05/021592 A2 | 3/2005 |
| WO | WO-05/023872 A1 | 3/2005 |
| WO | 05/047335 A1 | 5/2005 |
| WO | 05/063815 A2 | 7/2005 |
| WO | WO-05/063816 A2 | 7/2005 |
| WO | 05/100605 A1 | 10/2005 |

(Continued)

OTHER PUBLICATIONS

Tan, Shopes, Ol, and Morrison. Influence of the hinge region on complement activation, C1q binding, and segmental flexibility in chimeric human immunoglobulins. Proceedings of the National Academy of Sciences, 1990. vol. 87, pp. 162-166.*

(Continued)

*Primary Examiner* — Michael Allen
(74) *Attorney, Agent, or Firm* — Nelson Mullins Riley & Scarborough LLP; Jane E. Remillard, Esq.; Christopher L. Frank

(57) ABSTRACT

The present invention provides monovalent antibodies with a long half-life when administered in vivo, methods of making such monovalent antibodies, pharmaceutical compositions comprising such antibodies, and uses of the monovalent antibodies.

17 Claims, 29 Drawing Sheets
Specification includes a Sequence Listing.

(56) References Cited

FOREIGN PATENT DOCUMENTS

| WO | WO-06/031994 | 3/2006 |
|---|---|---|
| WO | 07/038658 A2 | 4/2007 |
| WO | 07/059782 A1 | 5/2007 |
| WO | 07/068255 A1 | 6/2007 |

OTHER PUBLICATIONS

Skolnick and Fetrow. From genes to protein structure and function: novel applications of computational approaches in the genomic era. Trends in Biotechnology, 2000. vol. 18, pp. 34-39.*
Burgess, Shaheen, Ravera, Jaye, Donohue, and Winkles. Possible dissociation of the heparin binding and mitogenic activities of heparin binding (acidic fibroblast) growth factor-1 from its receptor binding activities by site directed mutagenesis of a single lysine residue. Journal of Cell Biology, 1990. vol. 111, pp. 2129-2138.*
Lazar, Watanabe, Dalton, and Sporn. Transforming growth factor alpha: mutation of aspartic acid 47 and leucine 48 results in different biological activities. Molecular and Cellular Biology, 1988. vol. 8, pp. 1247-1252.*
Wu, Journal of Molecular Biology, vol. 294, p. 151-162, 1999.*
Huck, Immunogenetics, vol. 30, p. 250-257, 1989.*
Paul, Fundamental Immunology, 3rd Edition, 1993, pp. 292-295.*
Bendig, Methods: A Companion to Methods in Enzymology, vol. 8, p. 83-93, 1995.*
Portolano, Journal of Immunology, vol. 150, No. 3, p. 880-887, 1993.*
Goldsby, Immunology, Fifth Edition, 2003, p. 126.*
Aalberse, Rob C. et al., "IgG4 breaking the rules," *Immunology*, vol. 105:9-19 (2002).
Aalberse, Rob C. et al., "Serologic Aspects of IgG4 Antibodies I. Prolonged Immunization Results in an IgG4-Restricted Response," *The Journal of Immunology*, vol. 130(2):722-726 (1983).
Aalberse, Rob C. et al., "The Apparent Monovalency of Human IgG4 is Due to Bispecificity," *Int. Arch. Allergy Immunol.*, vol. 118:187-189 (1999).
Akkerdaas, J.H. et al., "Multiplicity of cross-reactive epitopes on Bet v I as detected with monoclonal antibodies and human IgE," *Allergy*, vol. 50:215-220 (1995).
Angel, S. et al., "A Single Amino Acid Substitution Abolishes the Heterogeneity of Chimeric Mouse/Human (IgG4) Antibody," *Molecular Immunology*, vol. 30(1):105-108 (1993).
Bannerji, Rajat et al., "Apoptotic-Regulatory and Complement-Protecting Protein Expression in Chronic Lymphocytic Leukemia: Relationship to In Vivo Rituximab Resistance," *Journal of Clinical Oncology*, vol. 21(8):1466-1471 (2003).
Bernier, George M. et al., "Structural and Biosynthetic Studies of a Human IgA Half Molecule," *The Journal of Immunology*, vol. 119(4):1260-1265 (1977).
Biewenga, Jeike et al., "IgA1 half molecules in human multiple myeloma and the in vitro production of similar fragments from intact IGA1 molecules," *Clin. Exp. Immunol.*, vol. 51:395-400 (1983).
Binz, H. Kaspar et al., "Engineering novel binding proteins from nonimmunoglobulin domains," *Nature Biotechnology*, vol. 23(10):1257-1268 (2005).
Bloom, James W. et al., "Intrachain disulfide bond in the core hinge region of human IgG4," Protein Science, vol. 6:407-415 (1997).
Brekke, Ole Henrik et al., "Activation of complement by an IgG molecule without a genetic hinge," Nature, vol. 363:628-630 (1993).
Brekke, Ole Henrik et al., "Activation of complement by an IgG molecule without a genetic hinge," correction, Nature, vol. 383:103 (1996).
Brüggemann, Marianne et al.; "Comparison of the Effector Functions of Human Immunoglobulins Using a Matched Set of Chimeric Antibodies," J. Exp. Med., vol. 166:1351-1361 (1987).
Colcher, David et al., "Characterization and Biodistribution of Recombinant and Recombinant/Chimeric Constructs of Monoclonal Antibody B72.3," Cancer Research, vol. 49:1738-1745 (1989).

Cragg, Mark S. et al., "Antibody specificity controls in vivo effector mechanisms of anti-CD20 reagents," Blood, vol. 103(7):2738-3743 (2004).
Cragg, Mark S. et al., "Complement-mediated lysis by anti-CD20 mAb correlates with segregation into lipid rafts," Blood, vol. 101(3):1045-1052 (2003).
Dall'Acqua, William et al., "A Mutational Analysis of Binding Interactions in an Antigen-Antibody Protein-Protein Complex," Biochemistry, vol. 37:7981-7991 (1998).
Dall'Acqua, William et al., "Contribution of Domain Interface Residues to the Stability of Antibody CH3 Domain Homodimers," Biochemistry, vol. 37:9266-9273 (1998).
Dall'Acqua, William F. et al., "Modulation of the Effector Functions of a Human IgG1 through Engineering of Its Hinge Region," The Journal of Immunology, vol. 177:1129-1138 (2006).
Dall'Acqua, William F. et al.; "Properties of Human IgG1s Engineered for Enhanced Binding to the Neonatal fc Receptor (FcRn)," The Journal of Biological Chemistry, vol. 281(33):23514-23524 (2006).
Deng, Liang et al., "Detection and qualification of the human IgG4 half-molecule, HL, from unpurified cell-culture supernatants," Biotechnol. Appl. Biochem., vol. 40:261-269 (2004).
Di Gaetano, Nicola et al., "Complement Activation Determines the Therapeutic Activity of Rituximab In Vivo," The Journal of Immunology, vol. 171:1581-1587 (2003).
Fahey, John L. et al., "Factors Controlling Serum □-Globulin Concentration," The Journal of Experimental Medicine, vol. 118:845-868 (1963).
Gallango, Maria L. et al., "An Unusual Case of Waldenström Macroglobulinemia with Half Molecules of IgG in Serum and Urine," Blut, vol. 48:91-97 (1983).
Genmab, "Genmab hosts Research, Development and Business Update, Building for a Commercial Future," Press Release (2006).
Genmab, "Genmab, Building for a Commercial Future, Research, Development and Business Update," PowerPoint Presentation (2006).
Gregory, L. et al., "The Solution Conformations of the Subclasses of Human IgG Deduced from Sedimentation and Small Angle X-Ray Scattering Studies," Molecular Immunology, vol. 24(8):821-829 (1987).
Guddat, Luke W. et al., "Three-dimensional structure of a human immunoglobulin with a hinge deletion," Proc. Natl. Acad. Sci. USA, vol. 90:4271-4275 (1993).
Hale, Geoffrey et al., "Therapeutic Potential of Rat Monoclonal Antibodies: Isotype Specificity of Antibody-Dependent Cell-Mediated Cytotoxicity with Human Lymphocytes," The Journal of Immunology, vol. 134(5):3056-3061 (1985).
Hinton, Paul R. et al., "Engineered Human IgG Antibodies with Longer Serum Half-lives in Primates," The Journal of Biological Chemistry, vol. 279(8):6213-6216 (2004).
Hobbs, J.R. et al., "A Half-Molecule GK Plasmacytoma," Clin. Exp. Immunol., vol. 5:199-207 (1969).
Hobbs, J.R., "Immunocytoma o' Mice an' Men," British Medical Journal, vol. 2:67-72 (1971).
Horgan, Carol et al., "Studies on Antigen Binding by Intact and Hinge-Deleted Chimeric Antibodies," The Journal of Immunology, vol. 150(12):5400-5407 (1993).
Humphrey, J.H. et al., "The Metabolism of Normal Plasma Proteins and Gamma-Myeloma Protein in Mice Bearing Plasma-Cell Tumors," J. Clin. Invest., vol. 40(9):1696-1705 (1961).
Igarashi, Takako et al., "Structure of a Mouse Immunoglobulin G That Lacks the Entire CH1 Domain: Protein Sequencing and Small-Angle X-ray Scattering Studies," Biochemistry, vol. 29:5727-5733 (1990).
Junghans, R.P. et al., "The protection receptor for IgG catabolism is the □2-microglobulin-containing neonatal intestinal transport receptor," Proc. Natl. Acad. Sci. USA, vol. 93:5512-5516 (1996).
Kawai, Tadashi et al., "Identification and Quantification of Half-Molecule Immunoglobulins," Annals Academy of Medicine, vol. 9(1):50-53(1980).
King, David J. et al., "Expression, purification and characterization of a mouse-human chimeric antibody and chimeric Fab' fragment," Biochem. J., vol. 281:317-323 (1992).

(56) References Cited

OTHER PUBLICATIONS

Klein, Michel et al., "Expression of biological effector functions by immunoglobulin G molecules lacking the hinge region," Proc: Natl. Acad. Sci. USA, vol. 78(10):524-528 (1981).
Kozak, Marilyn et al., "Initiation of translation in prokaryotes and eukaryotes," Gene, vol. 234:187-208 (1999).
Larson, Steven B. et al., "The Structure of an Antitumor CH2-domain-deleted Humanized Antibody," J. Mol. Biol., vol. 348:1177-1190 (2005).
Manches, Olivier, et al., "In vitro mechanisms of action of rituximab on primary non-Hodgkin lymphomas," Blood, vol. 101(3):949-954 (2003).
Martens, Tobias et al., "A Novel One-Armed Anti-c-Met Antibody Inhibits Glioblastoma Growth In Vivo," Clin. Cancer Res., vol. 12(20):6144-6152 (2006).
Michaelsen, Terje E. et al., "Antibody Dependent Cell-Mediated Cytotoxicity Induced by Chimeric Mouse-Human IgG Subclasses and IgG3 Antibodies with Altered Hinge Region," Molecular Immunology, vol. 29(3):319-326 (1992).
Murakami, Masato et al., "Signaling of vascular endothelial growth factor receptor-1 tyrosine kinase promotes rheumatoid arthritis through activation of monocytes/macrophages," Blood, vol. 108(6):1849-1856 (2006).
Mushinski, J. Frederic, "□A Half Molecules: Defective Heavy Chain Mutant in Mouse Myeloma Proteins," The Journal of Immunology, vol. 106(1):41-50 (1971).
Mushinski, J. Frederic et al., "IgA Half Molecules II. Genetic Variants of IgA Detected in Normal Mouse Intestinal Contents," The Journal of Immunology, vol. 117(5):1668-1675 (1976).
Ober, Raimund J. et al., "Visualizing the Site and Dynamics of IgG Salvage by the MHC Class I-Related Receptor, FcRn," The Journal of Immunology, vol. 172:2021-2029 (2004).
Parham, Peter, "On the Fragmentation of Monoclonal IgG1, IgG2a, and IgG2b From BALB/c Mice," The Journal of Immunology, vol. 131(6):2895-2902 (1983).
Petersen, Jens G. Litske et al., "An in Vitro System for Studying the Kinetics of Interchain Disulfide Bond Formation in Immunoglobulin G," The Journal of Biological Chemistry, vol. 249(17):5633-5641 (1974).
Petkova, Stefka B. et al., "Enhanced half-life of genetically engineered human IgG1 antibodies in a humanized FcRn mouse model: potential application in humorally mediated autoimmune disease," International Immunology, vol. 18(12):1759-1769 (2006).
Potter, M. et al., "Disorders in the Differentiation of Protein Secretion in Neoplastic Plasma Cells," J. Mol. Biol., vol. 9:537-544 (1964).
Rajan, S.S. et al., "Three-Dimensional Structure of the Mcg IgG1 Immunoglobulin," Molecular Immunology, vol. 20(7):787-799 (1983).
Robinson, Elizabeth A. et al., "Chemical Characterization of a Mouse Immunoglobulin a Heavy Chain with a 100-Residue Deletion," The Journal of Biological Chemistry, vol. 249(20):6605-6610 (1974).
Sakurabayashi, Ikunosuke et al., "Human IgA, Half-Molecules: Clinical and Immunologic Features in a Patient With Multiple Myeloma," Blood, vol. 53(2):269-278 (1979).
Saphire, Erica Ollmann et al., "Contrasting IgG Structures Reveal Extreme Asymmetry and Flexibility," J. Mol. Biol., vol. 319:9-18 (2002).
Sarma, R. et al., "The Three-Dimensional Structure of a Human-IgG1 Immunoglobulin at 4 Å Resolution: A Computer Fit of Various Structural Domains on the Electron Density Map," J. Appl. Cryst., vol. 15:476-481 (1982).
Schuurman, J. et al., "Normal human immunoglobulin G4 is bispecific: it has two different antigen-combining sites," Immunology, vol. 97:693-698 (1999).
Schuurman, Janine et al., "The inter-heavy chain disulfide bonds of IgG4 are in equilibrium with intra-chain disulfide bonds," Molecular Immunology, vol. 38:1-8 (2001).
Seligmann, M. et al., "Immunochemical Study of a Human Myeloma IgG1 Half Molecule," Ann. Immunol. (Inst. Pasteur), vol. 129(C):855-870 (1978).
Sell, Stewart et al., "Relationship Between □-Globulin Metabolism and Low Serum □-Globulin in Germfree Mice," The Journal of Immunology, vol. 93:81-87 (1964).
Silverton, E.W. et al., "Three-dimensional structure of an intact human immunoglobulin," Proc. Natl. Acad. Sci. USA, vol. 74(11):5140-5144 (1977).
Spiegelberg, Hans L. et al., "Human Myeloma IgA Half-Molecules," The Journal of Clinical Investigation, vol. 58:1259-1265. (1976).
Spiegelberg, Hans L., "Human Myeloma IgG Half-Molecules," The Journal of Clinical Investigation, vol. 56:588-594 (1975).
Spiegelberg, Hans L. et al., "Human Myeloma IgG Half-Molecules. Structural and Antigenic Analyses," Biochemistry, vol. 14(10):2157-2163 (1975).
Spiegelberg, Hans L. et al., "IgG Half-Molecules: Clinical and Immunologic Features in a Patient With Plasma Cell Leukemia," Blood, vol. 45(3):305-313 (1975).
Steiner, Lisa A. et al., "Amino Acid Sequence of the Heavy-Chain Variable Region of the Crystallizable Human Myeloma Protein Dob," Biochemistry, vol. 18(19):4068-4080 (1979).
Tan, Lee K. et al., "Influence of the hinge region on complement activation, C1q binding, and segmental flexibility in chimeric human immunoglobulins," Proc. Natl. Acad. Sci. USA, vol. 87:162-166 (1990).
Treon, Steven P. et al., "Tumor Cell Expression of CD59 is Associated With Resistance to CD20 Serotherapy in Patients With B-Cell Malignancies," Journal of Immunotherapy, vol. 24(3):263-271 (2001).
Van der Neut Kolfschoten, Marijn et al., "Anti-Inflammatory Activity of Human IgG4 Antibodies by Dynamic Fab Arm Exchange," Science, vol. 317:1554-1557 (2007).
Van der Zee, Jaring S. et al., "Serologic Aspects of IgG4 Antibodies II. IgG4 Antibodies Form Small, Nonprecipitating Immune Complexes Due to Functional Monovalency," The Journal of Immunology, vol. 137(11):3566-3571 (1986).
Waldmann, Thomas A. et al., "Metabolism of Immunoglobulins," Progr. Allergy, vol. 13:1-110 (1969).
Zack, Donald J. et al., "Somatically Generated Mouse Myeloma Variants Synthesizing IgA Half-Molecules," J. Exp. Med., vol. 154:1554-1569 (1981).
Zijlstra, Maarten et al., "Germ-like transmission of a disrupted β2-microglobulin gene produced by homologous recombination in embryonic stem cells," Nature, vol. 342:435-438 (1989).
International Search Report for Application No. PCT/DK2006/000668, dated Mar. 22, 2007.
International Search Report for Application No. PCT/DK2006/000669, dated Mar. 22, 2007.
Holliger, Philipp et al., "Engineered antibody fragments and the rise of single domains," Nature Biotechnology, vol. 23(9):1126-1136 (2005).
Jefferis, Roy et al., "IgG-Fc-mediated effector functions: molecular definition of interaction sites for effector ligands adn the role of glycosylation," Immunological Reviews, vol. 163:59-76 (1998).
Magnusson, Carl G.M. et al., "Human IgG is Substrate for the Thioredoxin System: Differential Cleavage Pattern of Interchain Disulfide Bridges in IgG Subclasses," Molecular Immunology, vol. 34(10):709-717 (1997).
Schuster, Manfred et al., "Improved Effector Functions of a Therapeutic Monoclonal Lewis Y-Specific Antibody by Glycoform Engineering," Cancer Res., vol. 65(17):7934-7941 (2005).
Stevenson, George T. et al., "Conjugation of Human Fcgamma in Closed-Hinge or Open-Hinge Configuration to Fab'gamma and Analogous Ligands," The Journal of Immunology, vol. 158:2242-2250 (1997).
Watts, H.F. et al., "Activation of Complement Pathways by Univalent Antibody Derivatives with Intact Fc Zones," Molecular Immunology, vol. 22(7):803-810 (1985).
Nielsen, Soren U. et al., "Human T cells resistant to complement lysis by bivalent antibody can be efficiently lysed by dimers of monovalent antibody," Blood, vol. 100:4067-4073 (2002).

(56) References Cited

OTHER PUBLICATIONS

U.S. Appl. No. 12/602,404, filed Jul. 15, 2010, Janine Schuurman.
U.S. Appl. No. 12/602,416, filed Jul. 6, 2010, Janine Schuurman.
U.S. Appl. No. 12/602,404, filed Apr. 18, 2013, Chun Wu Dahle.
U.S. Appl. No. 12/602,404, filed Sep. 13, 2012, Chun Wu Dahle.
U.S. Appl. No. 12/602,404, filed Apr. 25, 2012, Chun Wu Dahle.
U.S. Appl. No. 12/602,416, filed May 10, 2012, Anne Gussow.
Brummell, David A. et al., "Probing the Combining Site of an Anti-Carbohydrate Antibody by Saturation-Mutagenesis: Rolf of the Heavy-Chain CDR3 Residues," Biochemistry, vol. 32:1180-1187 (1993).
Dall'Acqua, William F. et al., "Increasing the Affinity of a Human IgG1 for the Neonatal Fc Receptor: Biological Consequences," The Journal of Immunology, vol. 169:5171-5180 (2002).
D'Andrea, Alan D. et al., "Anti-Erythropoietin Receptor (EPO-R) Monoclonal Antibodies Inhibit Erythropoietin Binding and Neutralize Bioactivity," Blood, vol. 82(1):46-52 (1993).
Finkelman, Fred D. et al., "Anti-Cytokine Antibodies as Carrier Proteins, Prolongation of in Vivo Effects of Exogenous Cytokines by Injection of Cytokine-Anti-Cytokine Antibody Complexes," The Journal of Immunology, vol. 151(3):1235-1244 (1993).
Goldenberg, David M. et al., "Cancer imaging and therapy with bispecific antibody pretargeting," Update on Cancer Therapeutics, vol. 2:19-31 (2007).
Hinton, Paul R. et al., "An Engineered Human IgG1 Antibody wtih Longer Serum Half-Life," The Journal of Immunology, vol. 176:346-356 (2006).
Kanamaru, Yutaka et al., "IgA Fc receptor I signals apoptosis through the FcRg ITAM and affects tumor growth," Blood, vol. 109(1):203-211 (2007).
Li, Yili et al., "Three-Dimensional Structures of the Free and Antigen-Bound Fab from Monoclonal Antilysozyme Antibody HyHEL-63," Biochemistry, vol. 39:6296-6309 (2000).
Lund, John et al., "Multiple Interactions of IgG with Its Core Oligosaccharide Can Modulate Recognition by Complement and Human Fcγ Receptor I and Influence the Synthesis of Its Oligosaccharide Chains," The Journal of Immunology, vol. 157:4963-4969 (1996).
Padlan, Eduardo A. et al., "Identification of specificity-determining residues in antibodies," FASEB J., vol. 9:133-139 (1995).
Satoh, Mitsuo et al., "Non-fucosylated therapeutic antibodies as next-generation therapeutic antibodies," Expert Opin. Biol. Ther., vol. 6(11):1161-1173 (2006).
Sheridan, Cormac, "Pharma consolidates its grip on post-antibody landscape," Nature Biotechnology, vol. 25(4):365-366 (2007.
Shields, Robert L. et al., "High Resolution Mapping of the Binding Site on Human IgG1 for FcgRI, FcgRII, FcgRIII, and FcRn and Design of IgG1 Variants with Improved Binding to the FcgR," The Journal of Biological Chemistry, vol. 276(9):6591-6604 (2001).
Van Walle, Ivo et al., "Immunogenicity screening in protein drug development," Expert Opin. Biol. Ther., vol. 7 (3):405-418 (2007).
Vitetta, Ellen S. et al., "Considering Therapeutic Antibodies," Science, vol. 313:308-309 (2006).
International Preliminary Report on Patentability for Application No. PCT/DK2008/050124, 7 pages, dated Dec. 1, 2009.
International Preliminary Report on Patentability for Application No. PCT/DK2008/050126, 6 pages, dated Dec. 1, 2009.
U.S. Appl. No. 12/602,404, Janine Schuurman, filed Jul. 15, 2010, Mar. 16, 2015.
U.S. Appl. No. 12/602,404, Janine Schuurman, filed Jul. 15, 2010, Jul. 15, 2014.
Bleeker, Wim K. et al., "Dual Mode of Action of a Human Anti-Epidermanl Growth Factor Receptor Monoclonal Antibody for Cancer Therapy," The Journal of Immunotherapy, vol. 173:4699-4707 (2004).
Office Action, U.S. Appl. No. 12/602,404, dated Aug. 25, 2016, 12 pages.
Office Action, U.S. Appl. No. 12/602,404, dated Feb. 27, 2017, 10 pages.

* cited by examiner

Figure 18

| Name | | Oligo Sequence |
|---|---|---|
| VLexbetv1rev | P1 | AGCCACCGTACGTTTGATTTCCAGCTTGGTGCCTCC |
| VLex betv1for | P2 | GATGCAAGCTTGCCGCCACCATGGAGTCACAGATTCAGGCATTT |
| VHexbetv1rev | P3 | CGATGGGCCCTTGGTGCTGGCTGAGGAGACGGTGACTGAGGT |
| VHexbetv1for | P4 | GATGCAAGCTTGCCGCCACCATGAAATGCAGCTGGGTTATCTTC |
| LCseq3 | P5 | TGTACTTTGGCCTCTCTGGGATA |
| 7D8VLexrev | P6 | CTGGAGATTAAACGTACGGTGGCTGCACC |
| 7D8VLexfor | P7 | GCGACTAAGCTTGCCGCCACCATGGAAGCCCCAGCTCAGCTTCTC |
| 7D8VHexfor | P8 | GCTGAAAGCTTGCCGCCACCATGGAGTTGGGACTGAGCTGGATT |
| pConKseq1 | P9 | GTAGTCTGAGCAGTACTCGTTGC |
| pConG1seq1 | P10 | GAAGACTTAAGGCAGCGGCAGAA |
| HCseq5 | P11 | GGTCAGGGCGCCTGAGTTCCACG |
| HCseq11 | P12 | ATGCAGGCTACTCTAGGGCACCT |
| 2f8HCexrev | P13 | GAAGACCGATGGGCCCTTGGTGCTAGCTGAGGAGAC |
| IGG4gene2r | P14 | TGAGAATTCGGTGGGTGCTTTATTTCCATGCT |
| IGG4gene2f | P15 | GTAGAAGCTTACCATCGCGGATAGACAAGAACC |
| IGG4S228Pf | P16 | GGTCCCCCATGCCCACCATGCCCGGGTAAGCCA |
| IGG4S228Pr | P17 | TGGCTTACCCGGGCATGGTGGGCATGGGGGACC |
| RACEKmm1 | P18 | TGTTAACTGCTCACTGGATGGTGGGA |
| RACEG1mm1 | P19 | TCCCTGGGCACAATTTTCTTGTCCACC |
| ShortUPMH3 | P20 | TGAAAGCTTCTAATACGACTCACTATAGGGC |
| LongUPMH3 | P21 | TGAAAGCTTCTAATACGACTCACTATAGGGCAAGCAGTGGTATCAACGCAGAGT |

FIGURE 19

| Name | Length | Oligo Sequence |
|---|---|---|
| A77VHfor1 | 62 | TCTTCTTCCTGATGGCAGTGGTTACAGGGGTCAATTCAGAGGTCCAGCTGCAGCAGACTGGA |
| A77VHfor2 | 61 | GATAAGCTTGCCGCCACCATGAAATGCAGCTGGGTTATCTTCTTCCTGATGGCAGTGGTTA |
| A77VHrev | 45 | GGATGGGCCCTTGGTGCTGGCCGCAGAGACAGTGACCAGAGTCCC |
| A77VLfor1 | 64 | CCTCATGTCCCTGCTGTTCTGGGTATCTGGTACCTGTGGGGACGTTGTGATGACCCAGACTCCA |
| A77VLfor2 | 62 | ACGAAGCTTGCCGCCACCATGGAATCACAGACTCAGGTCCTCATGTCCTGCTGTTCTGGGT |
| IgG4delfor | 44 | AACTCCCAATCTTCTCTCTGCAGCTCAAGGCGGGACAGGTGCCC |
| IgG4delrev | 44 | GGGCACCTGTCCCGCCTTGAGCTGCAGAGAGAAGATTGGGAGTT |
| RACEG1A1 | 22 | GGGAGTAGAGTCCTGAGGACTG |
| RACEKA1` | 22 | TATCCACCTTCCACTGTACTTT |
| 2f8HCexfor | 45 | CGATGGAAGCTTGCCGCCACCATGGAATTGGGGCTGAGCTGGGTT |
| 2f8HCexrev | 36 | GAAGACCGATGGGCCCTTGGTGCTAGCTGAGGAGAC |

| HIV-1 isolate | HuMax-CD4 starting conc (ug/ml) | Inhibition HuMax-CD4 IC50 (nM) | Fab fragments starting conc (ug/ml) | Inhibition Fab IC50 (nM) |
|---|---|---|---|---|
| YU2 | 10 | 9.9 | 30 | 119.9 |
| IIIB | 20 | 4.7 | 60 | 46.4 |
| ADA | 10 | 2.5 | 30 | 32.9 |
| 89.6 | 3 | 1.8 | 9 | 17.8 |
| US143 | 1 | 0.6 | 3 | 11.9 |
| JR-FL | 1 | 2.1 | 30 | 29.1 |
| JR-CSF | 1 | 0.3 | 30 | 9.5 |
| SF 162 | 1 | 0.6 | 30 | 6.3 |

Figure 26

| Date of reconsitution: 8/11/03 | | | Date of infection: 8/26/03 | | | Date of single injection: 9/08/03 | | | | | |
|---|---|---|---|---|---|---|---|---|---|---|---|
| Mouse number | Molecule i.p. | Genre | N. of cells (x106) | Vol. (ml) | % Hu cells | % Murine cells | % CD4 cells | % CD8 cells | CD4/CD8 | AVG | SD |
| 754 | 1mg Ig-CD4 | F | 1.5 | 7 | 0 | 5.61 | 0.03 | 0 | 0 | | |
| 757 | 1mg Ig-CD4 | F | 1 | 6 | 9.53 | 82.77 | 1.12 | 10.5 | 0.106 | | |
| 750 | 1mg Ig-CD4 | F | 2 | 7 | 22.25 | 69.45 | 1.82 | 20.8 | 0.08 | 0.1 | 0.01 |
| 759 | 1mg Ig-CD4 | M | 3 | 8 | 35.44 | 46.27 | 2.34 | 20.53 | 0.114 | | |
| 755 | 1mg Ig-cont | F | 2 | 6 | 86.29 | 10.03 | 2.46 | 84.87 | 0.028 | | |
| 746 | 1mg Ig-cont | F | 1 | 7 | 83.9 | 13.14 | 1.15 | 82.95 | 0.013 | 0.02 | 0.01 |
| 749 | 1mg Ig-cont | F | 3.2 | 8 | 86.48 | 10.76 | 1.69 | 86.08 | 0.019 | | |
| 756 | Non treated | F | 3 | 6 | 58.88 | 38.57 | 1.19 | 58.7 | 0.02 | | |
| 748 | Non treated | F | 4 | 7 | 95.52 | 2.44 | 0.82 | 96.3 | 0.008 | 0.04 | 0.04 |
| 758 | Non treated | M | 3 | 6 | 86.28 | 10.73 | 7.37 | 79.72 | 0.092 | | |
| 761 | Non infected | M | 4 | 8 | 80.85 | 17.39 | 22.94 | 53.77 | 0.426 | 0.48 | 0.06 |
| 762 | Non infected | M | 4 | 7 | 48.5 | 13.2 | 16.6 | 30.93 | 0.536 | | |

RECOMBINANT MONOVALENT ANTIBODIES AND METHODS FOR PRODUCTION THEREOF

FIELD OF INVENTION

The present invention relates to monovalent antibodies that may be used in therapeutic applications. The invention also relates to methods for producing the monovalent antibody, pharmaceutical compositions comprising such monovalent antibodies and use thereof for different therapeutic applications.

BACKGROUND OF THE INVENTION

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each light chain is comprised of a light chain variable region (abbreviated herein as $V_L$) and a light chain constant region (abbreviated herein as $C_L$). Each heavy chain is comprised of a heavy chain variable region ($V_H$) and a heavy chain constant region ($C_H$) consisting of three domain, $C_H1$, $C_H2$ and $C_H3$). $C_H1$ and $C_H2$ of the heavy chain are separated from each other by the socalled hinge region. The hinge region normally comprises one or more cysteine residues, which may form disulphide bridges with the cysteine residues of the hinge region of the other heavy chain in the antibody molecule.

Recently, antibodies have become a major focus area for therapeutic applications, and many antibody drug products have been approved or are in the process of being approved for use as therapeutic drugs. The desired characteristics of therapeutic antibodies may vary according to the specific condition which is to be treated. For some indications, only antigen binding is required, for instance where the therapeutic effect of the antibody is to block interaction between the antigen and one or more specific molecules otherwise capable of binding to the antigen. For such indications, the use of Fab fragments, the only function of which is to bind antigen, may be preferred. For other indications, further effects may also be required, such as for instance the ability to induce complement activation and/or the ability to for instance bind Fc receptors, protect from catabolism, recruit immune cells, etc. For such use, other parts of the antibody molecule, such as the Fc region, may be required. Some full-length antibodies may exhibit agonistic effects (which may be considered to be undesirable) upon binding to the target antigen, even though the antibody works as an antagonist when used as a Fab fragment. In some instances, this effect may be attributed to "cross-linking" of the bivalent antibodies, which in turn promotes target dimerization, which may lead to activation, especially when the target is a receptor. In the case of soluble antigens, dimerization may form undesirable immune complexes.

In some cases, monovalent binding to an antigen, such as in the case of FcαRI may induce apoptotic signals (Kanamura et al, Blood published on line Sep. 25, 2006))

For some indication, monovalent antibodies may thus be preferable. The presently available Fab fragments show inferior pharmacokinetics due to their small size resulting to filtration in the kidneys as well as their inability to interact with the Brambell receptor FcRn (Junghans R P et al., Proc Natl Acad Sci USA 93(11), 5512-6 (1996)), therefore being unstable in vivo and having very rapid clearance after administration.

Dimeric, monovalent antibodies (Fab/c), wherein the Fc region comprises two Fc polypeptides, have also been described (WO200563816 to Genentech and Parham P, J. Immunol. 131(6), 2895-902 (1983).

There is thus a need for stable monovalent antibodies for use as therapeutics.

Deletion of one or more of the domains of full-length antibodies, covering for instance regions comprising amino acid residues necessary for forming di-sulphide bridges or providing non-covalent inter-heavy chain contacts in the antibody may be a way of constructing monovalent antibodies.

Igarashi et al. (Igarashi, T M. et al., Biochemistry 29, 5727 (1990)) have described the structure of a mouse IgG2a molecule in which the entire $C_H1$ domain was deleted, but the hinge region was intact. The $C_H1$ deleted antibody is shown to exist as an elongated structure with a relatively small hinge angle. The molecule however retained the regular tetrameric configuration consisting of two light chains and two heavy chains expected for IgGs, and was thus still bivalent, and the $C_H1$ deletion did not affect the affinity of the mutated antibody.

Larson et al. (Larson, S B. et al., J Mol Biol 348, 1177 (2005)) have described the structure of a humanized IgG1 antibody in which the $C_H2$ domain has been deleted. Such antibody exists in two molecular forms, termed form A and form B. Form A contains two inter-chain disulphide bonds in the hinge, whereas form B does not contain inter-chain disulphide bonds. Form B exists as ~122 kDa molecule which seems to be held together by non-covalent interactions within the $C_H3$ domain. The antibody displays rapid serum clearance because of an inability to bind and recycle through FcRn receptors.

Ig half-molecules, which have a dimeric configuration consisting of only one light chain and only one heavy chain, have been described as the result of rare deletions in human and murine plasmacytomas. Several patients suffering from extramedullary soft-tissue plasmacytoma, Waldenström macroglobulinemia, plasma cell leukemia and multiple myeloma, excreted IgG half molecules into their urine. Half-molecules were also found to be present in their serum. Studies on the biochemical nature of these half-molecules showed that they consist of IgG1 molecules in which the heavy chain $C_H1$, hinge and $C_H2$ regions appeared normal, whereas deletions were found in the $C_H3$ region. The deletion on the $C_H3$ constant domain in the IgG1 half-molecule analyzed by Spiegelberg was shown to encompass 5,000-8,000 dalton and the hinge peptide sequence was identical to wild type IgG1. The mutations appeared to be located in $C_H3$ and the hinge peptide appeared normal (Hobbs, J R et al., Clin Exp Immunol 5, 199 (1969); Hobbs, J R, Br Med J 2, 67 (1971); Spiegelberg, H L et al., Blood 45, 305 (1975); Spiegelberg, H L et al., Biochemistry 14, 2157 (1975); Seligmann M E et al., Ann Immunol (Paris) 129C, 855-870 (1978); Gallango, M L et al., Blut 48, 91 (1983)). It was also showed that this human IgG1 half-molecule is rapidly catabolized (half-life in man was 4.3 days) and, in monomeric form, is unable to bind C1q or Fc receptors on human lymphocytes, monocytes or neutrophils (Spiegelberg, H L. J Clin Invest 56, 588 (1975)). It was concluded from these studies that the IgG1 half-molecule lacks non-covalent interactions characteristic for the Fc portion of the IgG heavy chain which destabilizes the molecule, and that the $C_H3$ domain may be particularly important in maintaining the interactions between IgG heavy chains.

Murine IgA half-molecules which were generated by somatic mutation have also been described (Mushinski, J F, J Immunol 106, 41 (1971); Mushinski, J F et al., J Immunol 117, 1668 (1976); Potter, M et al., J Mol Biol 93, 537 (1964); Robinson, E A et al., J Biol Chem 249, 6605 (1974); Zack, D J et al., J Exp Med 154, 1554 (1981)). These molecules were shown to all contain deletions of the $C_H3$ domain or mutations at the $C_H2$-$C_H3$ boundary. Human IgA half-molecules have also been detected in patients with multiple myeloma. These molecules were found to have deletions located to the $C_H3$ regions as well (Spiegelberg, H L et al., J Clin Invest 58, 1259 (1976); Kawai, T. et al., Ann Acad Med Singapore 9, 50 (1980); Sakurabayashi, I. et al., Blood 53, 269 (1979); Biewenga, J. et al., Clin Exp Immunol 51, 395 (1983)).

Human IgG1 mutants with hinge deletions have been described and crystallized (Saphire, E O. et al., J Mol Biol 319, 95 (2002)). Dob and Mcg are human myeloma proteins of the human IgG1 subclass which contain a deletion of the hinge region. These hinge deleted IgG1 molecules form stable Igs with a structure consisting of two heavy and two light chains, which is the typical heterotetrameric structure of antibodies, that however form inter-chain disulphide bonds between the light chains resulting in molecules that are strongly conformationally restricted and which display little to no effector function (Burton D R et al., J Mol Biol 319, 9 (2002); Steiner, A et al., Biochemistry 18, 4068 (1979); Silverton, E W et al., Proc Natl Acad Sci USA 74, 5140 (1977); Rajan, S S et al., Mol Immunol 20 787 (1983); Guddat, W et al. Proc Natl Acad Sci USA 90, 4271 (1993); Sarma, R. et al., J. Applied Cryst. 15, 476 (1982); Klein, M., et al., Proc Natl Acad Sci USA 78, 524 (1981)).

An IgG3 molecule in which the upper and middle hinge regions or the full hinge region was deleted, has been designed (Brekke, O H et al., Nature 363, 628 (1993); Brekke, O H et al., Nature 383, 103 (1996)). The molecule with the complete hinge deleted showed the presence of half-molecules upon analysis on non-reducing SDS-PAGE. A second hinge deleted molecule in which the complete upper and lower IgG3 hinge were replaced by a single cysteine and the lower IgG3 hinge contained a single Ala deletion, also contained half-molecules when analyzed on SDS-PAGE. However, the results show that under physiological conditions, the two heavy-light chain half-molecules are held together by non-covalent interactions between the IgG3 $C_H3$ domains; and intact IgG molecules were therefore formed.

A matched set of chimeric IgG1 and IgG4 antibodies has also been prepared (Horgan, C. et al. J Immunol 150, 5400 (1993)). To investigate the role of the IgG hinge region in antibody binding to antigen, mutants were prepared of both IgG1 and IgG4 which lacked the hinge region. The mutants were generated at the DNA level by deleting the hinge region exon from the IgG1 and IgG4 heavy chain genes. It was reported that both the IgG1 and IgG4 hinge-deleted molecules were bivalent, therefore having the typical heterotetrameric structure. In support of this, the functional affinity of the hinge-deleted IgG4 showed better binding to antigen than the wild-type IgG4, indicating that the avidity of the hinge-deleted molecule is not affected by the hinge deletion thus generated.

Human IgG4 molecules exist in various molecular forms which differ by the absence or presence of inter-heavy chain disulphide bonds located in the hinge region. Thus IgG4 molecules exist in which two, one or no inter-heavy chain disulphide bonds have been formed (Schuurman, J. et al., Mol Immunol 38, 1 (2001)). Under physiological conditions, these molecular forms of IgG4 may be in equilibrium with each other. Human IgG4s exist as tetramers in solution consisting of two Ig heavy and two light chains, as common for immunoglobulin G molecules, irrespective of the absence or presence of these interchain disulphide bonds (Schuurman 2001 supra; Gregory, L. et al. Mol Immunol 24, 821 (1987)). Only upon denaturation under non-reducing conditions, the two non-covalently associated half-molecules dissociate as demonstrated by size-determination analysis such as SDS-PAGE (Schuurman, J. et al. Mol Immunol 38, 1 (2001); Deng, L. et al. Biotechnol Appl Biochem 40, 261 (2004)). It has been shown that mutation of the residues of the hinge region which are involved in inter-chain disulphide bond formation or deletion of the hinge region lead to creation of a homogeneous pool of IgG4 molecules in solution, which pool consists of tetrameric molecules consisting of two light chains and two heavy chains (Schuurman, J. et al. Mol Immunol 38, 1 (2001); Horgan, C. et al. J Immunol 150, 5400 (1993)). The IgG4 hinge-deleted and mutated antibodies also demonstrated an improved capability of antigen crosslinking when compared to native $IgG_4$ molecules (Horgan, C. (1993) supra).

A number of studies have now shown that mutation or deletion of the IgG constant region domains $C_H1$ and $C_H2$ do not affect the assembly of IgG molecules into their natural two heavy and two light chain heterotetrameric configuration. Recombinant antibody molecules containing different deletions in their constant regions of the heavy chain have been shown to be affected in their effector function, e.g. they are not capable of complement activating, however, they remain their ability of antigen crosslinking. Further, it has been demonstrated that antibody half-molecules containing one heavy chain and one light chain are not stable in vivo and/or have a decreased half-life in vivo. Deletions in/of the $C_H3$ region provides half-molecules having a rapid metabolization making them unfit for most therapeutic purposes.

There is thus a need for a simple procedure for the production of a stable monovalent antibody, which would be suitable for therapeutic applications, wherein blocking of an antigen-mediated activity requires monovalent antibody binding (absence of cross-linking).

SUMMARY OF THE INVENTION

The present invention provides a method for producing a monovalent antibody, said method comprising A)
i) providing a nucleic acid construct encoding the light chain of said monovalent antibody, said construct comprising a nucleotide sequence encoding the $V_L$ region of a selected antigen specific antibody and a nucleotide sequence encoding the constant $C_L$ region of an Ig, wherein said nucleotide sequence encoding the $V_L$ region of a selected antigen specific antibody and said nucleotide sequence encoding the $C_L$ region of an Ig are operably linked together, and wherein, in case of an IgG1 subtype, the nucleotide sequence encoding the $C_L$ region has been modified such that the $C_L$ region does not contain any amino acids capable of forming disulfide bonds or covalent bonds with other peptides comprising an identical amino acid sequence of the $C_L$ region in the presence of polyclonal human IgG or when administered to an animal or human being;

ii) providing a nucleic acid construct encoding the heavy chain of said monovalent antibody, said construct comprising a nucleotide sequence encoding the $V_H$ region of a selected antigen specific antibody and a nucleotide sequence encoding a constant $C_H$ region of a human Ig, wherein the nucleotide sequence encoding the $C_H$ region has been modified such that the region corresponding to the hinge region and, as required by the Ig subtype, other regions of the $C_H$ region, such as the $C_H3$ region, does not comprise any amino acid residues which participate in the formation of disulphide bonds or covalent or stable non-covalent inter-heavy chain bonds with other peptides comprising an identical amino acid sequence of the $C_H$ region of the human Ig in the presence of polyclonal human IgG or when administered to an animal human being, wherein said nucleotide sequence encoding the $V_H$ region of a selected antigen specific antibody and said nucleotide sequence encoding the $C_H$ region of said Ig are operably linked together;

iii) providing a cell expression system for producing said monovalent antibody;

iv) producing said monovalent antibody by co-expressing the nucleic acid constructs of (i) and (ii) in cells of the cell expression system of (iii).

In one embodiment of the method, the human Ig is an IgG1, IgG2, IgG3, IgG4, IgA or IgD antibody, such as an IgG1, IgG2 or IgG4 antibody.

B) Further, method is provided, wherein the human Ig is an IgG1 having the amino acid $C_H$ region as set forth in SEQ ID NO: 19, wherein the $C_H3$ region has been modified so that one or more of the following amino acid substitutions have been made: Arg (R) in position 238 has been replaced by Gln (Q); Asp (D) in position 239 has been replaced by Glu (E); Lys (K) in position 292 has been replaced by Arg (R); Gln (Q) in position 302 has been replaced by Glu (E); and Pro (P) in position 328 has been replaced by Leu (L).

A method according to B), wherein Arg (R) in position 238 has been replaced by Gln (Q).

A method according to B), wherein Arg (R) in position 238 has been replaced by Gln (Q), and Pro (P) in position 328 has been replaced by Leu (L).

A method according to B), wherein all five substitutions have been made.

C) A method according to A) or B, wherein the human Ig is an IgG1, and the $C_L$ region is a kappa light chain $C_L$ having the amino acid sequence as set forth in SEQ ID NO: 18, wherein the $C_L$ region has been modified so that the terminal cysteine residue in position 106 has been replaced with another amino acid residue or has been deleted.

D) A method according to A) or B), wherein the human Ig is an IgG1, and the $C_L$ region is a lambda light chain $C_L$ having the amino acid sequence as set forth in SEQ ID NO: 17, wherein the $C_L$ region has been modified so that the cysteine residue in position 104 has been replaced with another amino acid residue or has been deleted.

F) A method according to A) or B), C) or D), wherein the human Ig is an IgG1 having the amino acid $C_H$ region as set forth in SEQ ID NO: 19, wherein the $C_H1$ region has been modified so that Ser (S) in position 14 has been replaced by a cysteine residue.

G) A method according to A), wherein the human Ig is an IgG2 having the amino acid $C_H$ region as set forth in SEQ ID NO: 20, wherein the $C_H3$ region has been modified so that one or more of the of the following amino acid substitutions have been made: Arg (R) in position 234 has been replaced by Gln (Q); Met (M) in position 276 has been replaced by Val (V); Lys (K) in position 288 has been replaced by Arg (R); Gln (Q) in position 298 has been replaced by Glu (E); and Pro (P) in position 324 has been replaced by Leu (L).

A method according to G), wherein Arg (R) in position 234 has been replaced by Gln (Q).

A method according to G), wherein Arg (R) in position 234 has been replaced by Gln (Q); and Pro (P) in position 324 has been replaced by Leu (L).

A method according to G), wherein all five substitutions have been made.

H) A method according to A), wherein the human Ig is an IgG3 having the amino acid $C_H$ region as set forth in SEQ ID NO: 21, wherein the $C_H3$ region has been modified so that one or more of the of the following amino acid substitutions have been made: Arg (R) in position 285 has been replaced by Gln (Q); Ser (S) in position 314 has been replaced by Asn (N); Asn (N) in position 322 has been replaced by Lys (K); Met (M) in position 327 has been replaced by Val (V); Lys (K) in position 339 has been replaced by Arg (R); Gln (Q) in position 349 has been replaced by Glu (E); Ile (I) in position 352 has been replaced by Val (V); Arg (R) in position 365 has been replaced by His (H); Phe (F) in position 366 has been replaced by Tyr (Y); and Pro (P) in position 375 has been replaced by Leu (L).

A method according to H), wherein Arg (R) in position 285 has been replaced by Gln (Q).

A method according to H), wherein Arg (R) in position 285 has been replaced by Gln (Q); and Pro (P) in position 375 has been replaced by Leu (L).

A method according to H), wherein all 10 substitutions have been made.

The present invention also provides a method for producing a monovalent antibody, said method comprising i) providing a nucleic acid construct encoding the light chain of said monovalent antibody, said construct comprising a nucleotide sequence encoding the $V_L$ region of a selected antigen specific antibody and nucleic sequence encoding the constant ($C_L$) region of an Ig, wherein said nucleotide sequence encoding the $V_L$ region of a selected antigen specific antibody and said nucleic sequence encoding the $C_L$ region of an Ig are operably linked together;

ii) providing a nucleic acid construct encoding the heavy chain of said monovalent antibody, said construct comprising a nucleotide sequence encoding the $V_H$ region of a selected antigen specific antibody and nucleic acid encoding a $C_H$ region of a human IgG4 wherein the nucleic acid sequence encoding the heavy chain has been modified such that the region corresponding to the hinge region of the heavy chain does not comprise any amino acid residues capable of participating in the formation of disulphide bonds with other peptides comprising an identical amino acid sequence of the constant ($C_H$) region of human IgG4, wherein said nucleic acid encoding the $V_H$ region of a selected antigen specific antibody and said nucleic acid encoding the $C_H$ region of IgG4 are operably linked together;

iii) providing a cell expression system for the producing said antibody;

iv) producing said monovalent antibody by co-expressing the nucleic acid constructs of (i) and (ii) in cells of the cell expression system of (iii).

The present invention also provides a monovalent antibody obtained by use of a method according to the invention.

The present invention also provides a monovalent antibody obtainable by use of a method according to the invention.

The present invention also provides a monovalent antibody comprising a light chain and a heavy chain, wherein
a) said light chain comprises the amino acid sequence of the variable ($V_L$) region of a selected antigen specific antibody and the amino acid sequence of the constant ($C_L$) region of an Ig, and
b) said heavy chain comprises the amino acid sequence of the variable ($V_H$) region of said selected antigen specific antibody and the amino acid sequence of the constant ($C_H$) region of human IgG4, wherein the amino acid sequence of the heavy chain has been modified such that none of any amino acid residues present in the region corresponding to the hinge region are capable of participating in the formation of disulphide bonds with other peptides comprising an identical amino acid sequence of the constant ($C_H$) region of human IgG4.

The present invention also provides a method of preparing a monovalent antibody according to the invention, the method comprising the steps of:
a) culturing a host cell comprising a nucleic acid encoding said monovalent antibody; and
b) recovering the monovalent antibody from the host cell culture.

The present invention also provides a nucleic acid construct comprising a nucleic acid sequence encoding the $C_H$ region of an IgG4, wherein the nucleic acid sequence encoding the $C_H$ region has been modified such that the region corresponding to the hinge region in said $C_H$ region does not comprise any amino acid residues capable of participating in the formation of disulphide bonds with peptides comprising an amino acid sequence identical to the amino acid sequence of said $C_H$ region, or a sequence complementary thereof.

The present invention also provides a method of preparing a monovalent antibody according to the invention comprising culturing a host cell comprising a nucleic acid construct according to the invention, and, if said nucleic acid construct does not encode the light chain of said antibody, also comprising a nucleic acid construct comprising a nucleic acid sequence encoding the light chain of said antibody, so that polypeptides are expressed, and recovering the monovalent antibody from the cell culture.

The present invention also provides the use of a nucleic acid construct according to the invention for the production of a monovalent antibody according to the invention.

The present invention also provides a host cell comprising a nucleic acid according to the invention.

The present invention also provides a method of preparing a monovalent antibody according to the invention comprising culturing a host cell according to the invention, which host cell comprises a nucleic acid sequence encoding the light chain of said antibody, so that polypeptides are expressed, and recovering the monovalent antibody from the cell culture.

The present invention also provides the use of a host cell according to the invention for the production of a monovalent antibody according to the invention.

The present invention also provides an immunoconjugate comprising a monovalent antibody according to the invention conjugated to a therapeutic moiety.

The present invention also provides a monovalent antibody according to the invention for use as a medicament.

The present invention also provides the use of a monovalent antibody according to the invention as a medicament.

The present invention also provides the use of an antibody according to the invention for the preparation of a pharmaceutical composition for the treatment of cancer, a cell proliferative disorder, an (auto)immune disorder, an inflammation disorder, an allergic disorder (asthma) and/or an angiogenesis disorder, wherein the antibody specifically binds a given target or target epitope, where the binding of an antibody to said target or target epitope is effective in treating said disease.

The present invention also provides the use of an antibody according to the invention for the preparation of a pharmaceutical composition for the treatment of a disease or disorder, which disease or disorder is treatable by administration of an antibody against a certain target, wherein the involvement of immune system-mediated activities is not necessary or is undesirable for achieving the effects of the administration of the antibody, and wherein said antibody specifically binds said antigen.

The present invention also provides the use of an antibody according to the invention for the preparation of a pharmaceutical composition for the treatment of a disease or disorder, which disease or disorder is treatable by blocking or inhibiting a soluble antigen, wherein multimerization of said antigen may form undesirable immune complexes, and wherein said antibody specifically binds said antigen.

The present invention also provides the use of an antibody according to the invention for the preparation of a pharmaceutical composition for the treatment of a disease or disorder, which disease or disorder is treatable by blocking or inhibiting a cell membrane bound receptor, wherein said receptor may be activated by dimerization of said receptor, and wherein said antibody specifically binds said receptor.

The present invention also provides a method for inhibiting an antigen in a subject suffering from a disease or disorder in which activity of the antigen is undesirable, comprising administering to a subject a monovalent antibody according to the invention, which antibody specifically binds said antigen, a pharmaceutical composition comprising said antibody, immunoconjugate comprising said antibody, or a nucleic acid construct according to the invention, such that the antigen activity in the subject is inhibited.

The present invention also provides a method of treating a disease or disorder, wherein said method comprises administering to a subject in need of treatment a therapeutically effective amount of a monovalent antibody according to the invention, a pharmaceutical composition comprising said antibody, immunoconjugate comprising said antibody, or a nucleic acid construct according to the invention, whereby the disease or disorder is treated.

The present invention also provides a pharmaceutical composition comprising a monovalent antibody according to the invention, together with one or more pharmaceutically acceptable excipients, diluents or carriers.

The present invention also provides a transgene animal comprising a nucleic acid construct according to the invention.

Lane 1: Marker SeuBlue plus2 prestained (Invitrogen BV, The Netherlands), Lane 2: internal control, Lane 3: 7D8-IgG1, Lane 4: 7D8-IgG4, and Lane 5: 7D8-HG.

Figure 2:
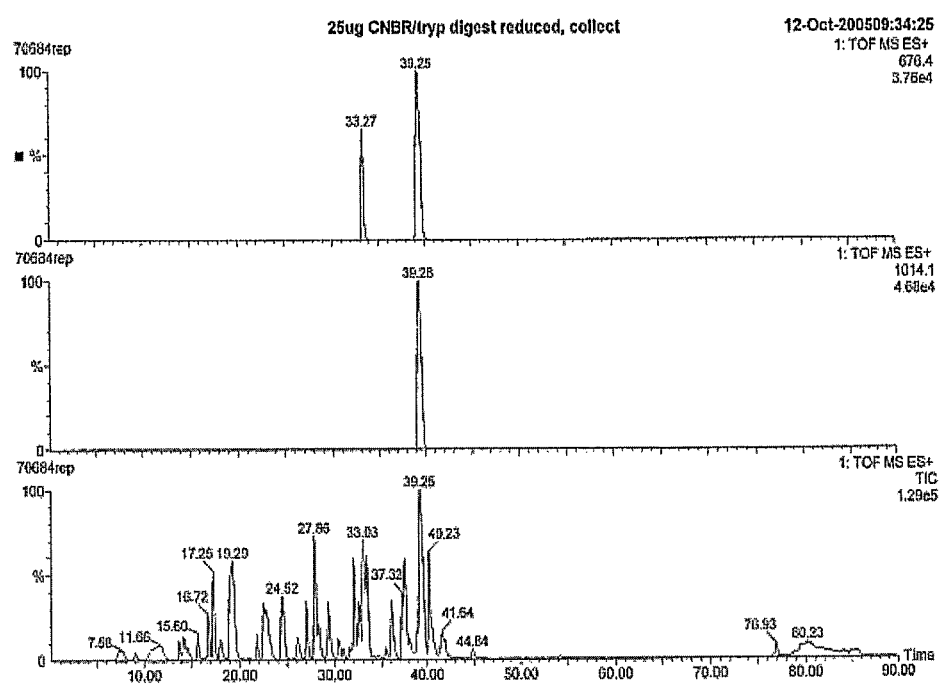

FIG. 2: Extracted ion chromatogram for [M+3H]3+ and [M+2H]2+ ions (m/z 676.4 and 1014.1 respectively) eluting at 39.3 mins TIC time in the reduced CNBr/tryptic digest of 7D8-HG.

Figure 3:
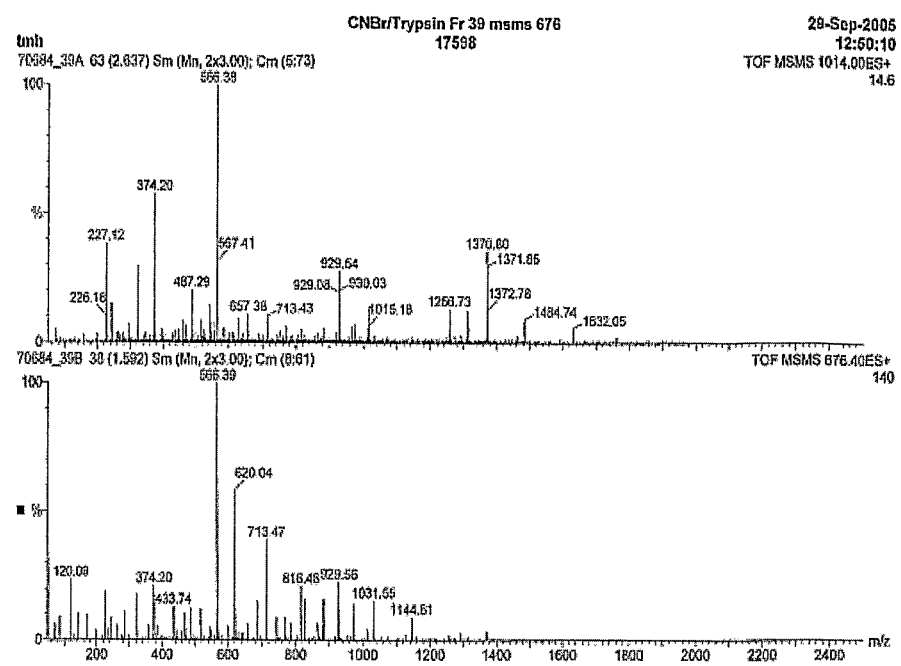

FIG. 3: The raw data obtained from nanospray-MS/MS analysis of the m/z signals consistent with a peptide covering amino acid residues 220 to 238 ($^{220}$VAPEFLGGPSV-FLFPPKPK$^{238}$) from a reduced CNBr/tryptic digest of 7D8-HG.

Figures 4A, 4B:
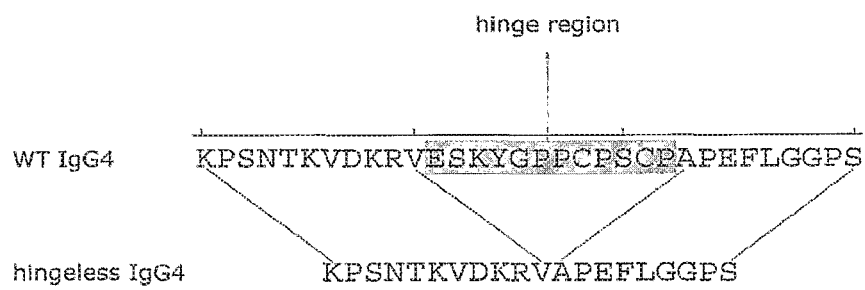

FIGS. 4A and 4B: Interpretation of the raw data obtained from nanospray-MS/MS analysis of the m/z signals consistent with a peptide covering amino acid residues 220 to 238 ($^{220}$VAPEFLGGPSVFLFPPKPK$^{238}$) from a reduced CNBr/tryptic digest of 7D8-HG.

Figure 5:
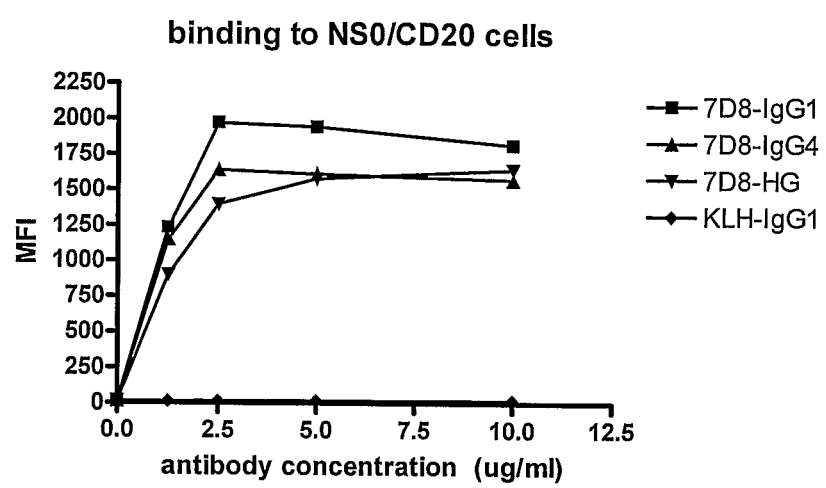

FIG. 5: The CD20-specific antibodies 7D8-IgG1, 7D8-IgG4 and 7D8-HG were evaluated on their binding to CD20 transfected cells.

Figure 6:
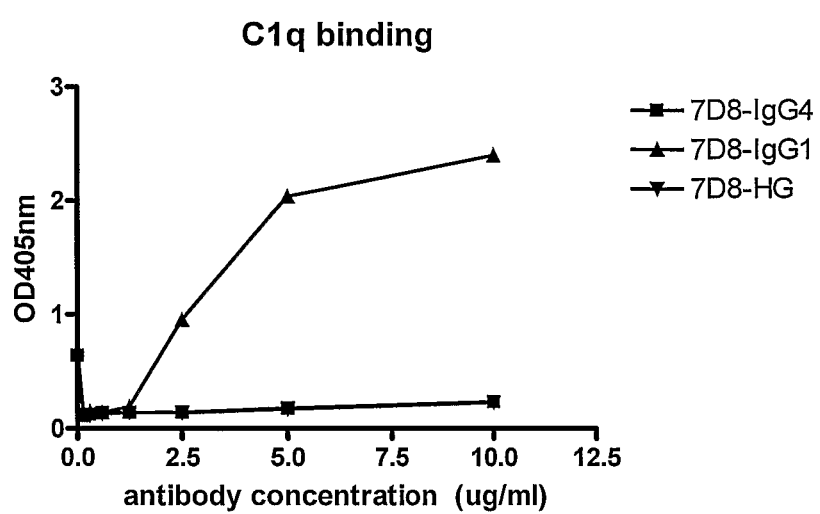

FIG. 6: The CD20-specific antibodies 7D8-IgG1, 7D8-IgG4 and 7D8-HG were coated on an ELISA plate (concentration range as indicated on x-axis). C1q binding (2 μg/ml) was evaluated.

Figure 7A:
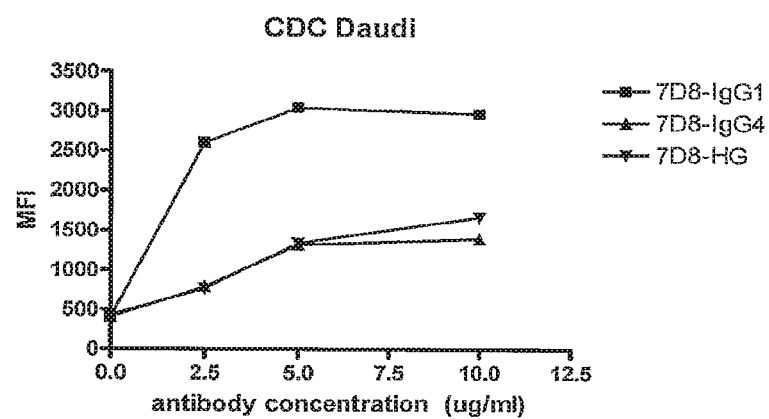

FIG. 7A: Daudi cells were pre-incubated with a concentration range of the CD20-specific antibodies for 10 minutes, before NHS was added. Forty-five minutes after induction of CDC, cells were resuspended in PI solution. Cell lysis (number of PI-positive cells) was measured by flow cytometry. Data show the Mean Fluorecence intensity of the PI-positive (dead) cells.

Figure 7B:
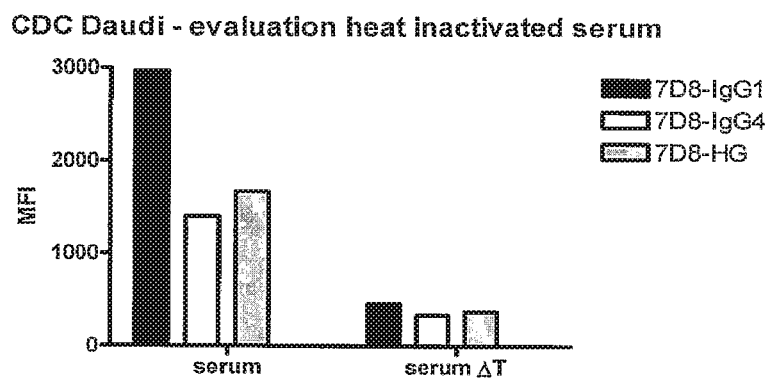

FIG. 7B: To evaluate the role of complement in the lysis measured, heat-inactivated serum (serum ΔT) was added to cells incubated with 10 μg antistof. Data show the mean fluorescence intensity of the PI-positive (dead) cells.

B) To evaluate the role of complement in the lysis measured, heat-inactivated serum (serum ΔT) was added to cells incubated with 10 μg antistof. Data show the mean fluorescence intensity of the PI-positive (dead) cells.

Figure 8:
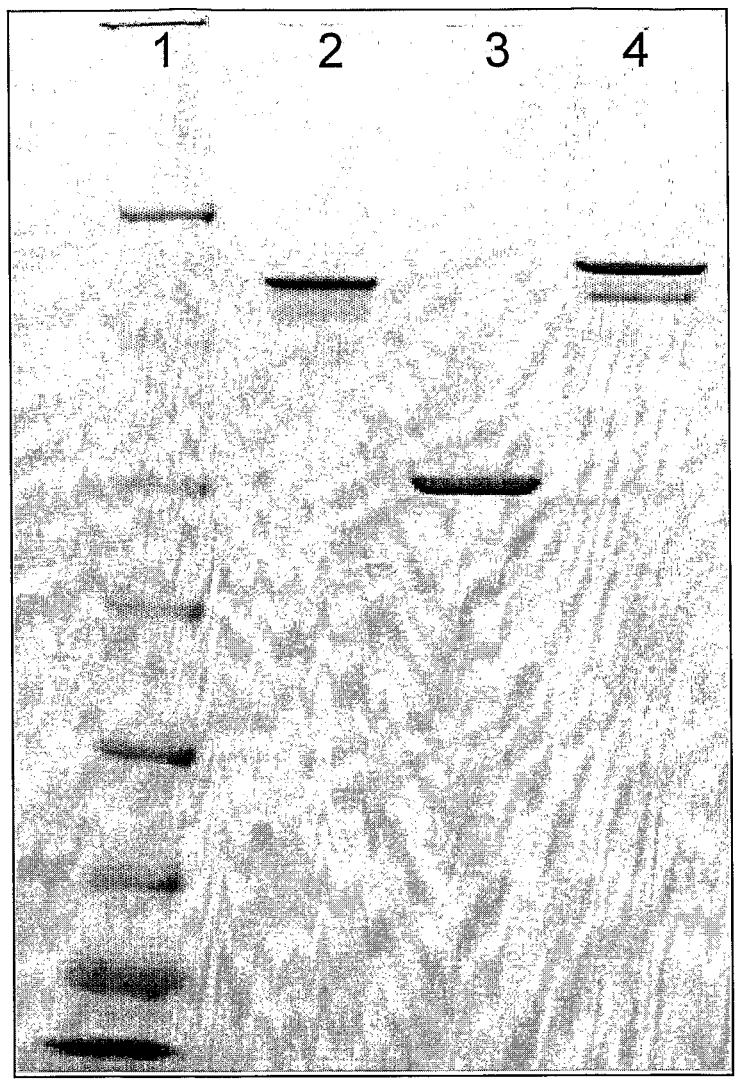

FIG. 8: The hingeless IgG4 antibody directed against Bet v 1 (Betv1-HG) was tested on non-reducing SDS-PAGE.

Lane 1: Marker SeaBlue plus2 prestained (Invitrogen BV, The Netherlands), lane 2: internal control, lane 3: BetV1-HG, lane 4: IgG1 control.

Figure 9:
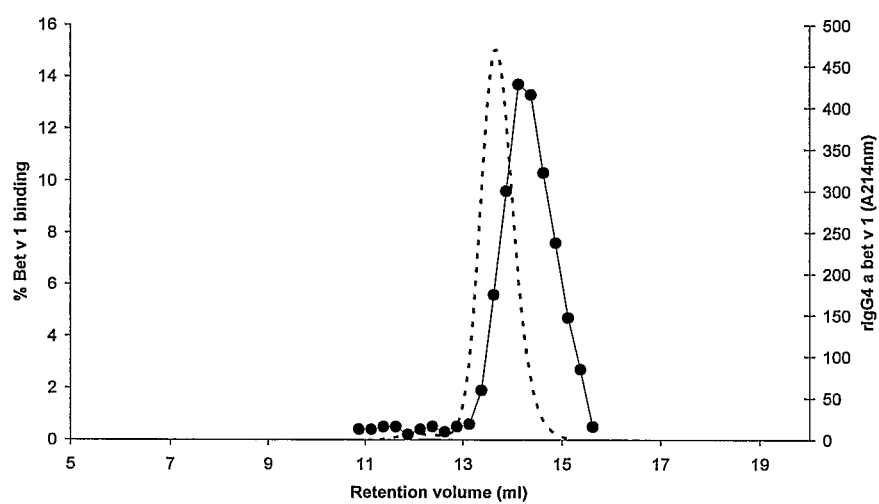

FIG. 9: Gelfiltration of Betv1-HG (hingeless IgG4 anti-Bet v 1). Conditioned medium from HEK cells containing hingeless rIgG4 Betv1-HG was fractionated on a Superdex200 column. A total 1 μg of Betv1-HG was applied to the column. In the fractions, Bet v 1 specific IgG (●) was measured by incubating 10 μl of each fraction in the Bet v 1 binding test. The results are expressed as percentage of radiolabeled Bet v 1 binding relative to the amount added. The dashed curve represents the elution of purified Betv1-IgG4 (10 μg), which was followed on the HPLC by measuring the absorption at 214 nm (A214 nm).

Figure 10:
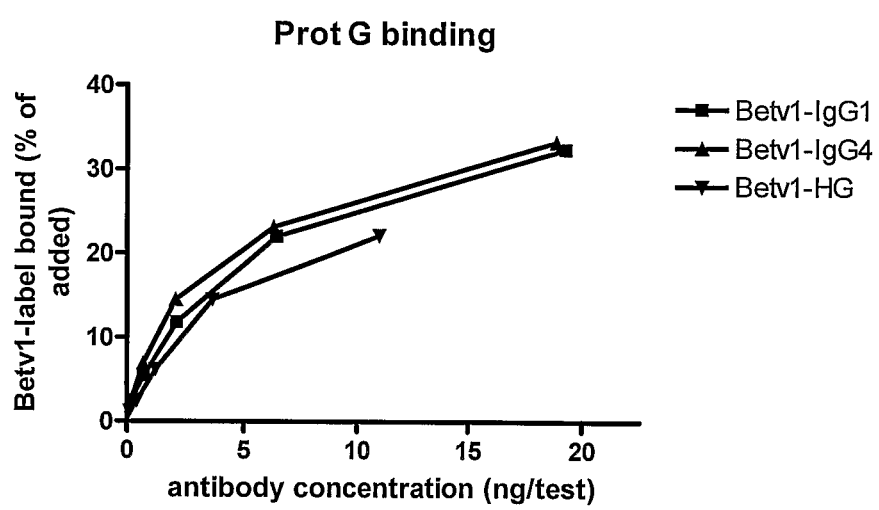

FIG. 10: The binding of Betv1-IgG1, Betv1-IgG4 and Betv1-HG was examined in an radio immuno assay. The binding of $^{125}$I-labelled Bet v1 to serial dilutions of the antibodies bound to Protein G Sepharose was examined.

Figure 11:
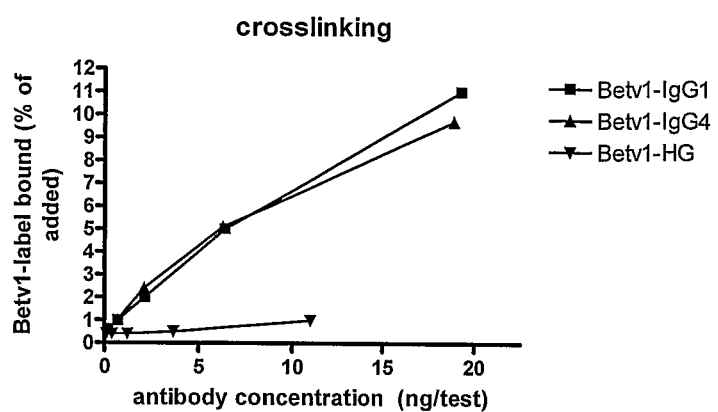

FIG. 11: The ability of Betv1-IgG1, Betv1-IgG4 and Betv1-HG to crosslink Sepharose bound Bet v 1 to radiolabelled Bet v 1 was examined in an radio immuno assay. The binding of $^{125}$I-labelled Bet v1 to serial dilutions of the antibodies bound to Bet v 1 Sepharose was examined.

Figure 12:
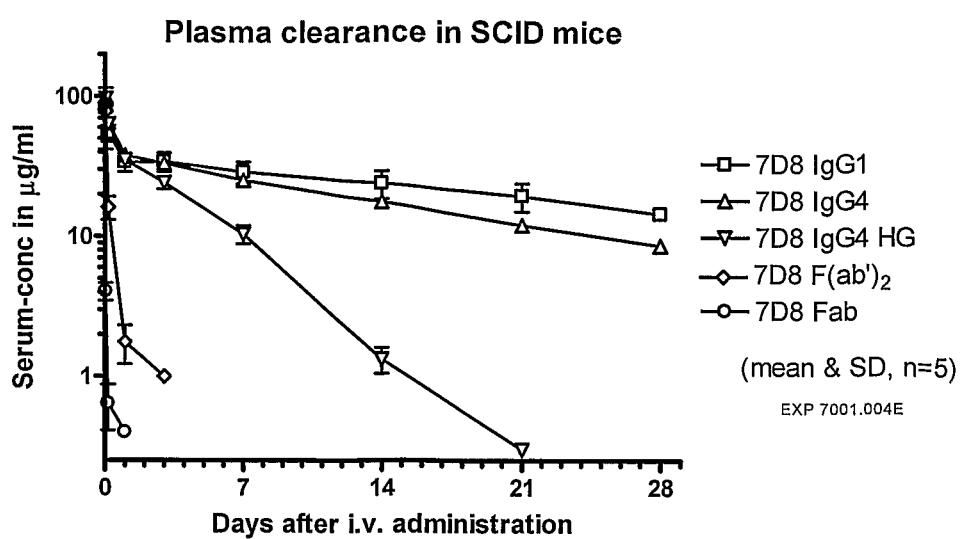

FIG. 12: Semilogarithmic plot of the mouse plasma concentrations of 7D8-HG in comparison with normal 7D8-IgG4, intact 7D8-IgG1, 7D8-IgG1, F(ab')2 and 7D8-IgG1 Fab fragments after intravenous administration of 100 μg per mouse.

Figure 13:
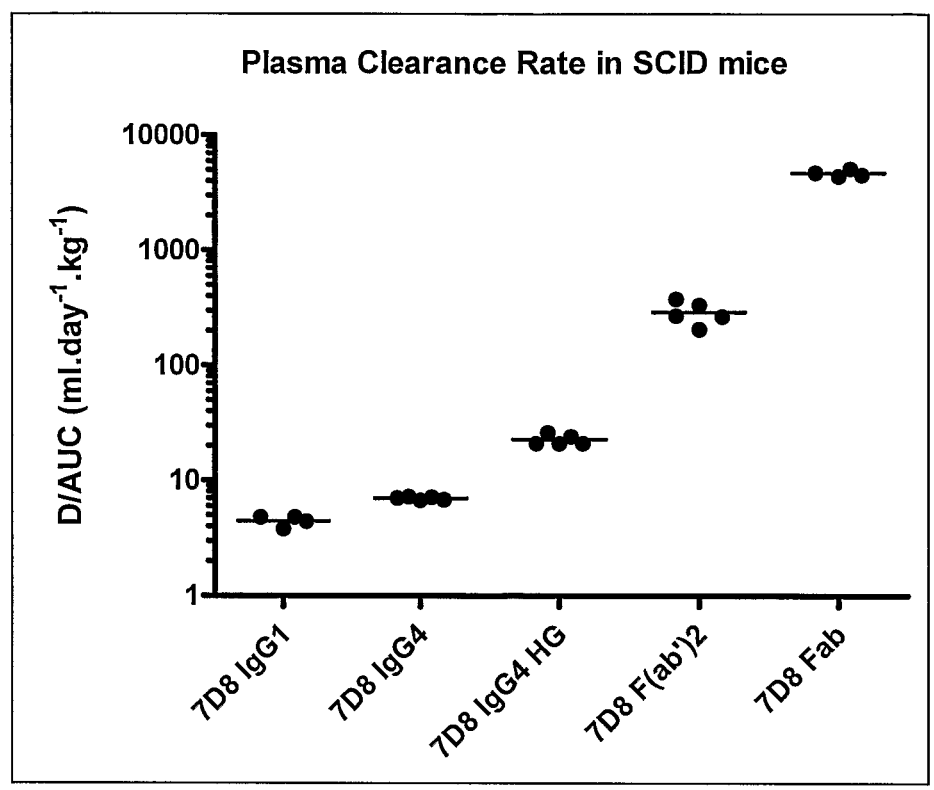

FIG. 13: Logarithmic plot of the plasma clearance rates as dose/area under the curve calculated from the concentration-time curves (D/AUC). The data represent individual mice and are expressed in ml·day$^{-1}$·kg$^{-1}$.

Figure 14:
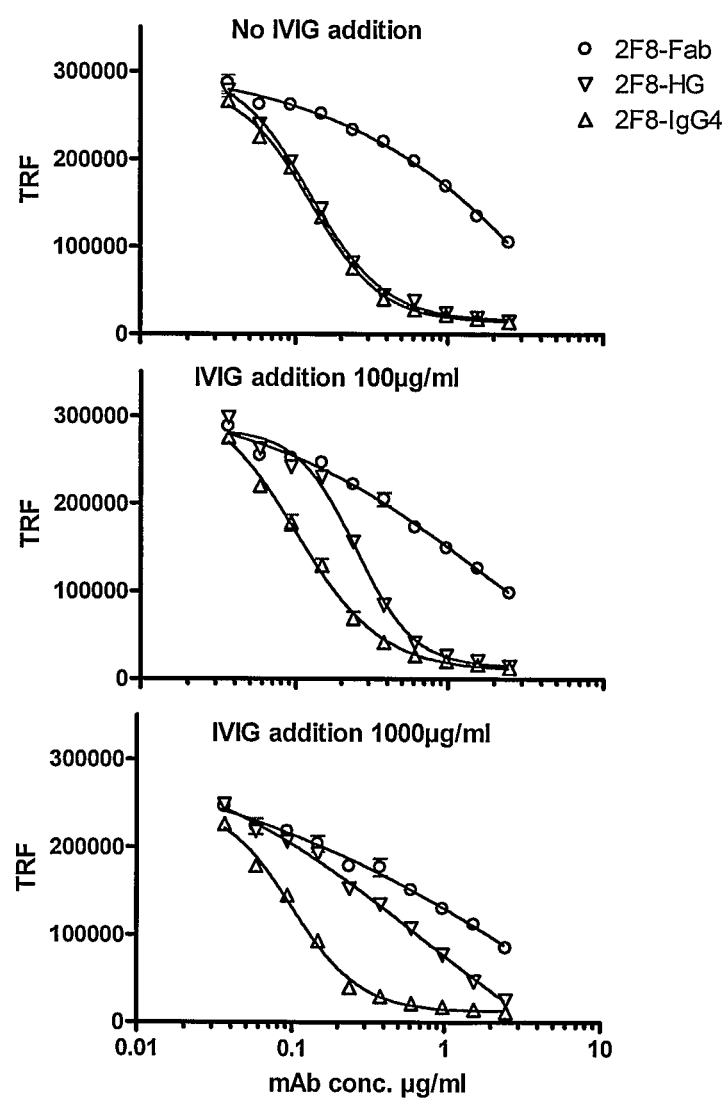

FIG. 14: Dose-response curves showing the inhibition of EGF-induced EGFr phosphorylation in A431 cells by anti-EGFr mAb 2F8-HG, compared with 2F8-IgG4 and 2F8-Fab fragments. The upper panel shows the inhibition curves in serum-deprived medium, the middle and lower panels the inhibition when IVIG was added to the medium at a concentration of 100 μg/ml and 1000 μg/ml, respectively. The y-axis represents Phosphorylated EGFr as detected with an anti-phosphotyrosine mAb and is expressed in time-resolved fluorescence units (TRF units). On the x-axis, the mAb concentration in μg/ml. Data points are mean and SEM of 4 replicates.

Figure 15:
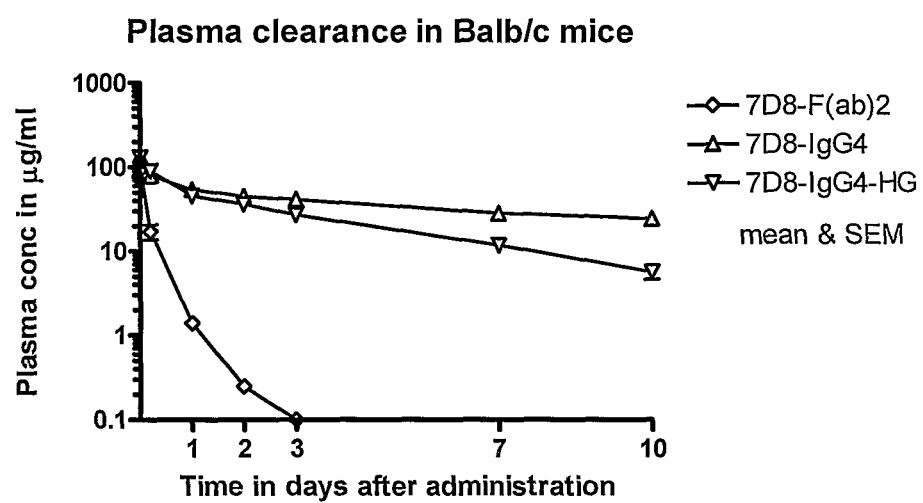

FIG. 15: A semilogarithmic plot of the concentrations in time. The initial plasma concentrations were all in the order of 100 μg/ml, which is consistent with an initial distribution into the plasma compartment of the mice. The clearance of the hingeless IgG4 variant was only slightly faster than that of normal IgG4. Importantly, the clearance of the hingeless variant was much slower than that of F(ab')$_2$ fragments, which have a comparable molecular size.

This experiment indicates that the Fc-part has a favorable effect on the plasma residence time in mice having a normal immune system and provides an indication of a functional interaction with the neonatal Fc receptor (FcRn) also in the presence of endogenous IgG.

Figure 16:
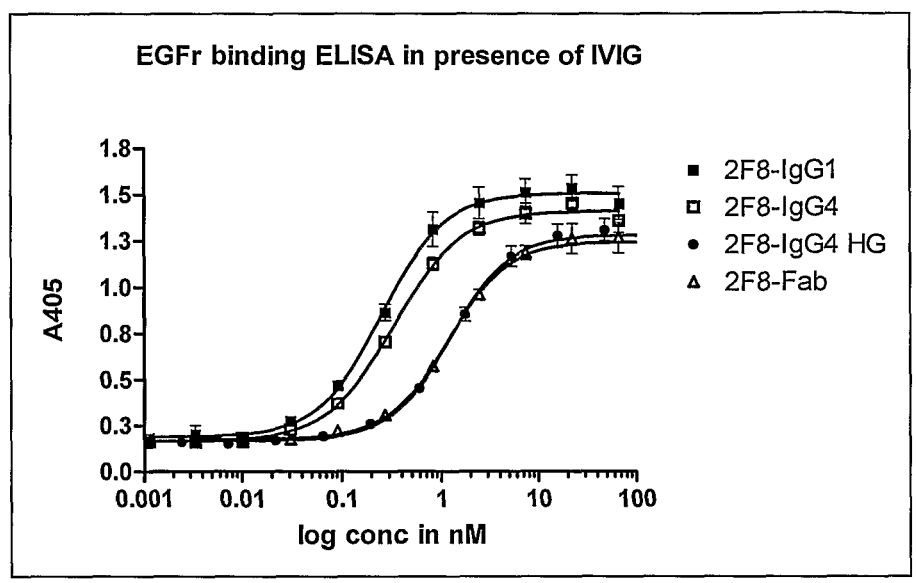

FIG. 16: The binding of 2F8-HG to a coat of EGFr protein was compared in an ELISA to that of 2F8-IgG4, 2F8-IgG1 and Fab fragments of 2F8-IgG1, in the presence of polyclonal human IgG (IVIG) at a concentration of 100 μg/ml.

Figure 17:
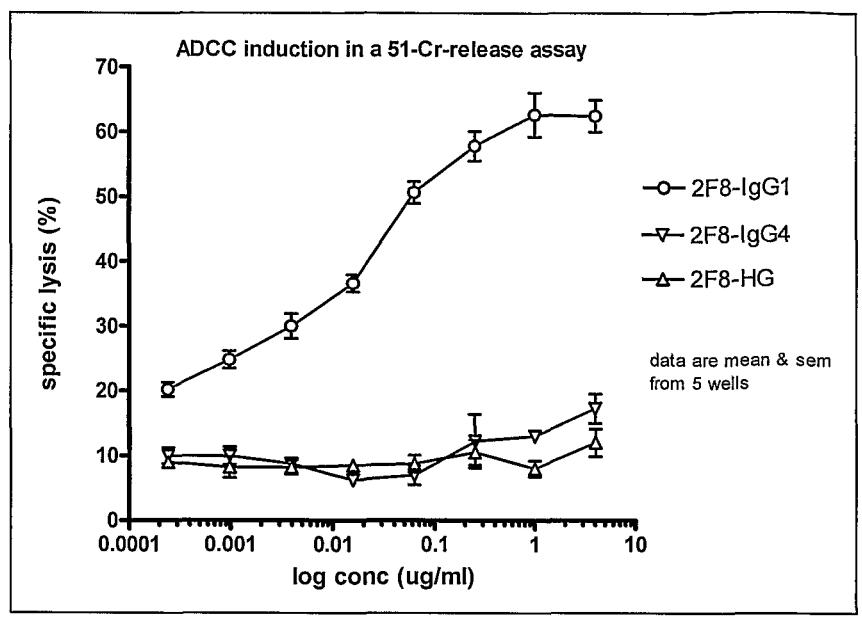

FIG. 17: The induction of ADCC by 2F8-HG was compared to that by 2F8-IgG1 and 2F8-IgG4. A431 cells were used as target cells and human peripheral blood mononuclear cells as effector cells FIG. 18: Sequence of primers used in the Examples.

FIG. 19: Sequences of primers used in the Examples.

Figure 20:
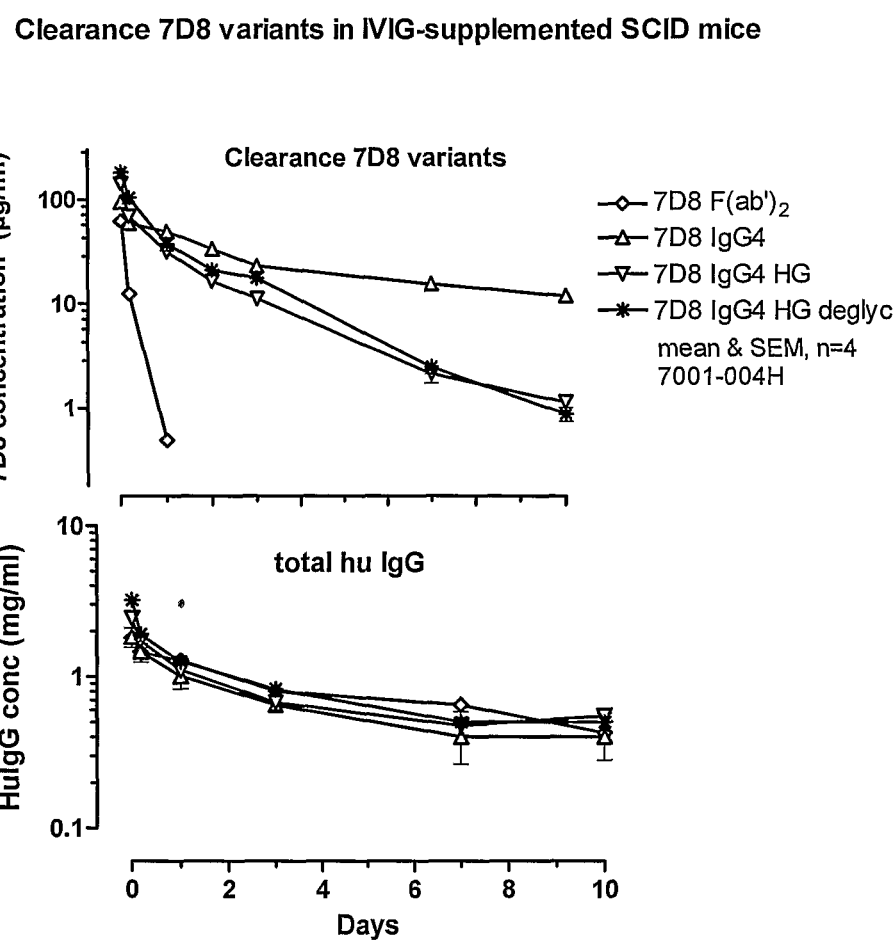

FIG. 20: Clearance of 7D8 variants in IVIG supplemented SCID mice. The figure shows in the upper panel semi-logarithmic plots of the concentrations of the mAb 7D8 variants in time and in the lower panel the total human IgG concentrations.

Figure 21:
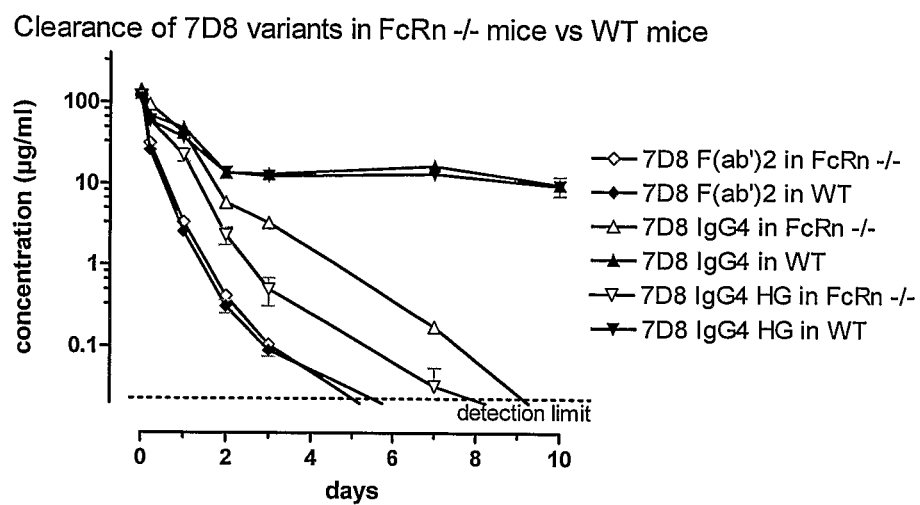

FIG. 21: Clearance with 7D8 variants in FcRn –/– mice vs wild type mice. The figure shows a semi-logarithmic plot of the concentrations in time. The initial plasma concentrations were all in the order of 100 μg/ml, which is consistent with an initial distribution in the plasma compartment of the mice. The hingeless IgG4 variant (7D8-HG), normal human IgG4 (7D8-IgG4) and F(ab')$_2$ fragments from 7D8 IgG1 (7D8-G1-F(ab')$_2$) were compared in the model.

Figure 22A:
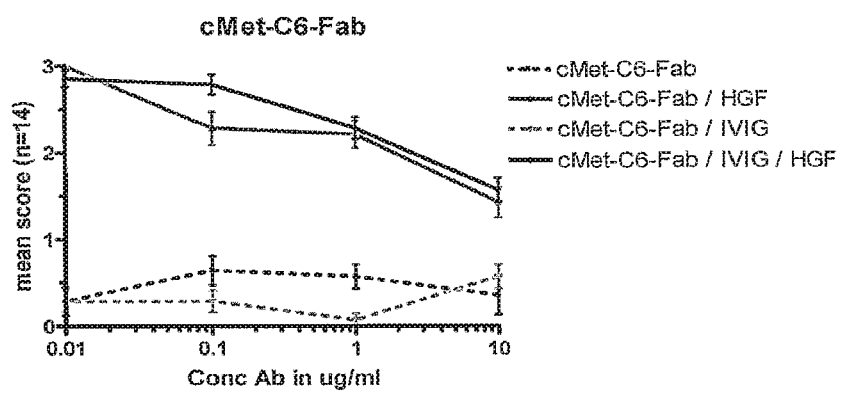
Figure 22B:
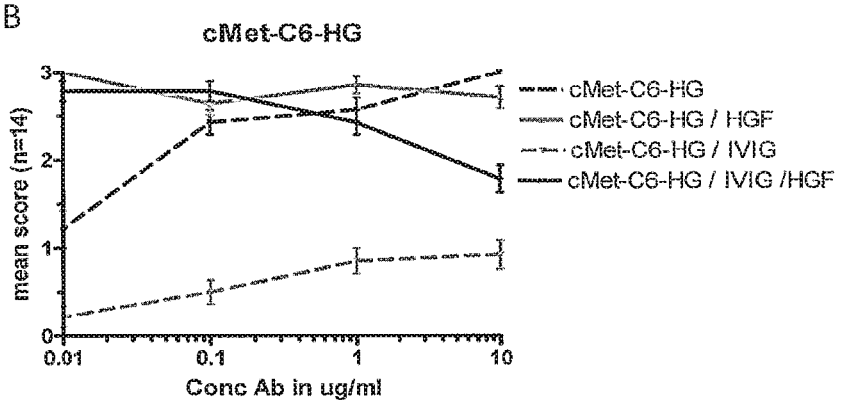

FIGS. 22A and 22B: DU-145 cells were cultured and incubated with a serial dilution of (FIG. 22A) cMet-Fab, cMet-Fab and IVIG, cMet-Fab and HGF, cMet-Fab and IVIG and HGF (FIG. 22B) cMet-HG, cMet-HG and IVIG, cMet-HG and HGF, cMet-HG and IVIG and HGF. Scattering was observed double-blinded (scored by 14 people) by microscope after 48 h and the averaged score±SEM is plotted.

Figure 23:
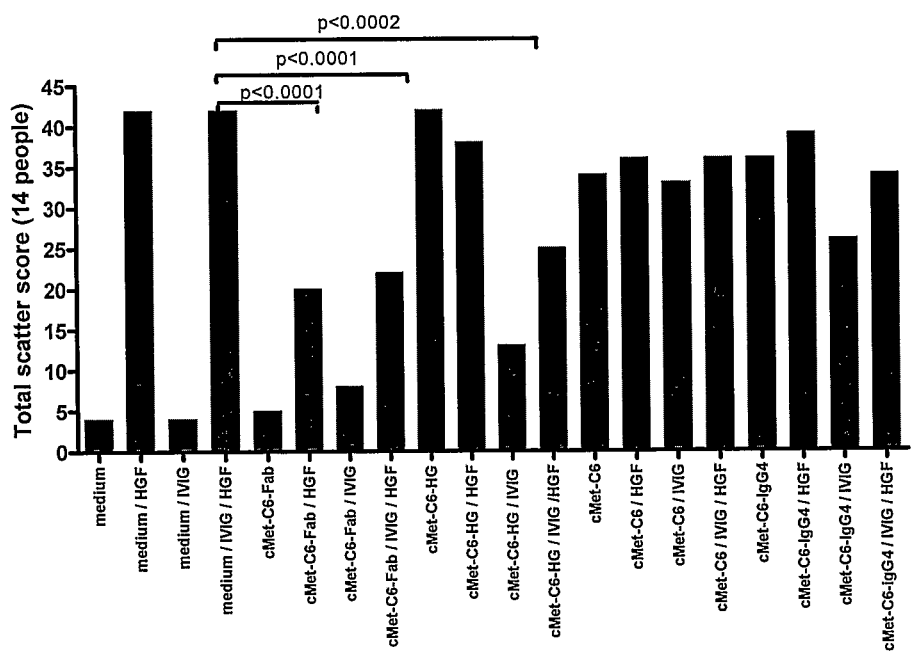

FIG. 23: DU-145 cells were cultured and incubated with 10 μg/ml of (A) cMet-Fab, cMet-Fab and IVIG, cMet-Fab and HGF, cMet-Fab and IVIG and HGF (B) cMet-HG, cMet-HG and IVIG, cMet-HG and HGF, cMet-HG and IVIG and HGF. Scattering was observed double-blinded (scored by 14 people) by microscope after 48 h.

cMet-Fab with or without IVIG and cMet-HG pre-incubated with IVIG significantly inhibited the HGF induced scattering. For statistical analysis a two-tailed Wilcoxon signed ranked test was done with a hypothetical median value of 3 (maximal scattering).

Figure 24:
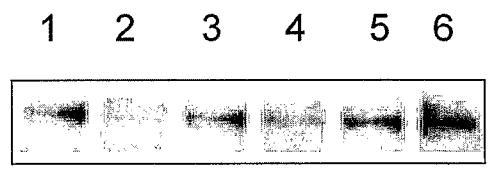

FIG. 24: Extracts prepared from A549 cells incubated with cMet-HG (lane 1), cMet-HG and IVIG (lane 2), cMet-HG and HGF (lane 3), cMet-HG, IVIG and HGF (lane 4), cMet-IgG1 (lane 5), cMet-IgG1 and IVIG (lane 6) were resolved by SDS-PAGE on a 4-20% Tris-HCl Criterion Precast gel and Western blotting on a nitrocellulose membrane. The membrane was incubated over night at 4° C. with anti-phospho-Met(pYpYpY 1230 1234 1235)-rabbit IgG, (Abcam, ab5662). After washing with TBST, the secondary antibodies, goat-anti-rabbit-HRP, Cell Signalling, 7074 in blocking reagent were incubated for 60 min. at room temperature on a roller bank. The membrane was washed 6 times with TBST. Finally the bands were developed with Luminol Echancer stop solution and analyzed on a Lumi-imager. The Western blot shows a 169 Kd band indicating phospho-Met(pYpYpY 1230 1234 1235).

FIG. 25: Starting concentration of addition of HuMax-CD4 or Fab fragments of HuMax-CD4 to the in vitro HIV-1 neutralization assay. The IC50 values of inhibition by HuMax-CD4 and Fab fragments of HuMax-CD4 are calculated by a 4 parameter logistic curve fit and indicated for each of the virus constructs.

FIG. 26: The % human T cells, % murine cells, and % CD4 and % CD8 cells, and the ratio CD4/CD8 of the individual PBMC reconstituted mice treated intraperitoneally with HuMax-CD4, IgG control or non treated, and infected with HIV-1.

Figure 27:
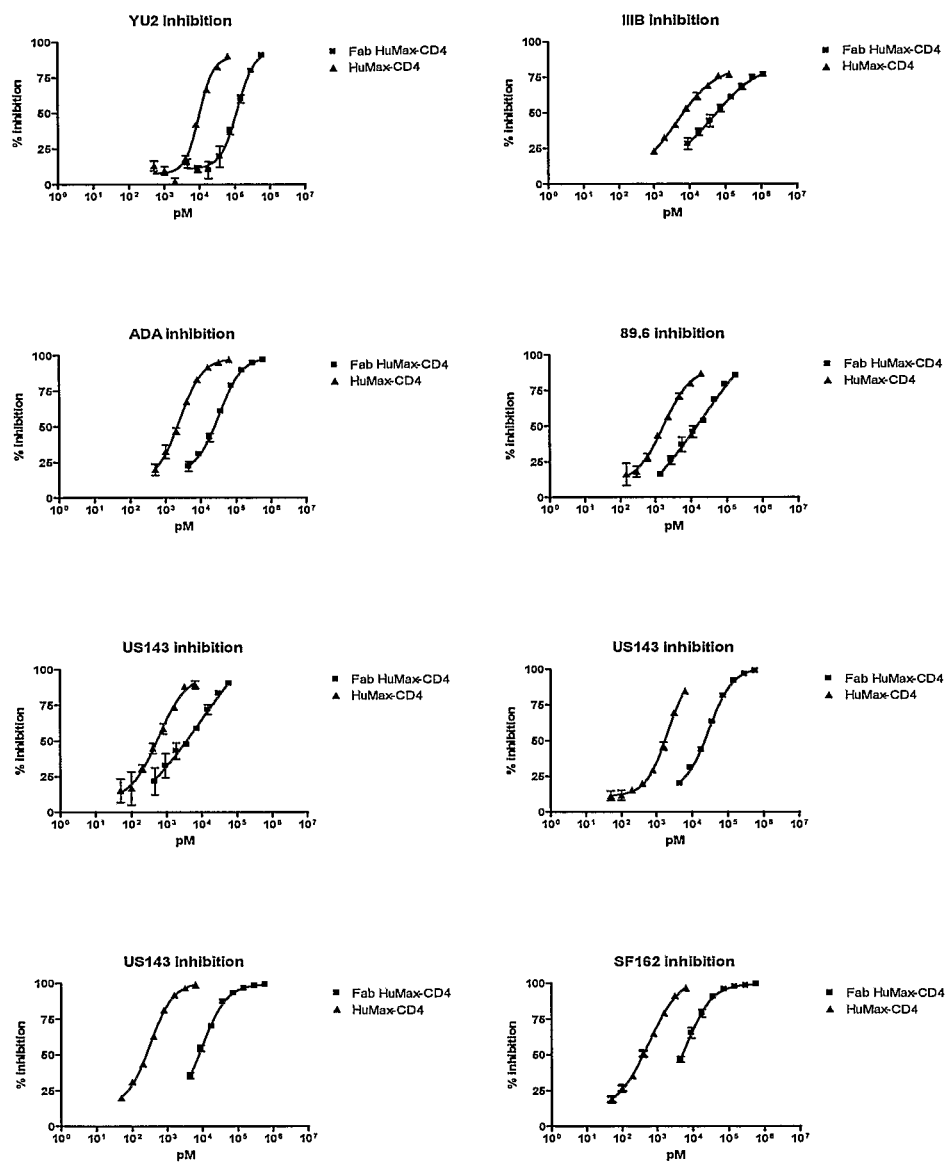

FIG. 27: The inhibition curves of HuMax-CD4 and the Fab fragments of HuMax-CD4 of the infection of several strains of HIV-1 of CD4-CCR5 or CD4-CXCR4 positive cells measured by luciferase activity (mean of triplicate measurements).

Figure 28:
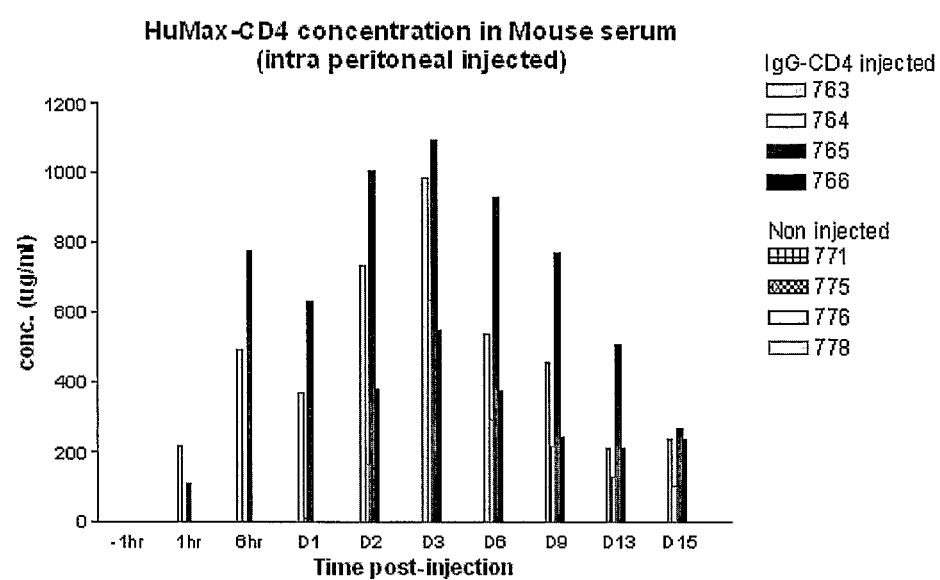

FIG. 28: The plasma HuMax-CD4 concentrations in time of the individual PBMC reconstituted mice treated intraperitoneally with HuMax-CD4, or non treated, and infected with HIV-1.

Figure 29:
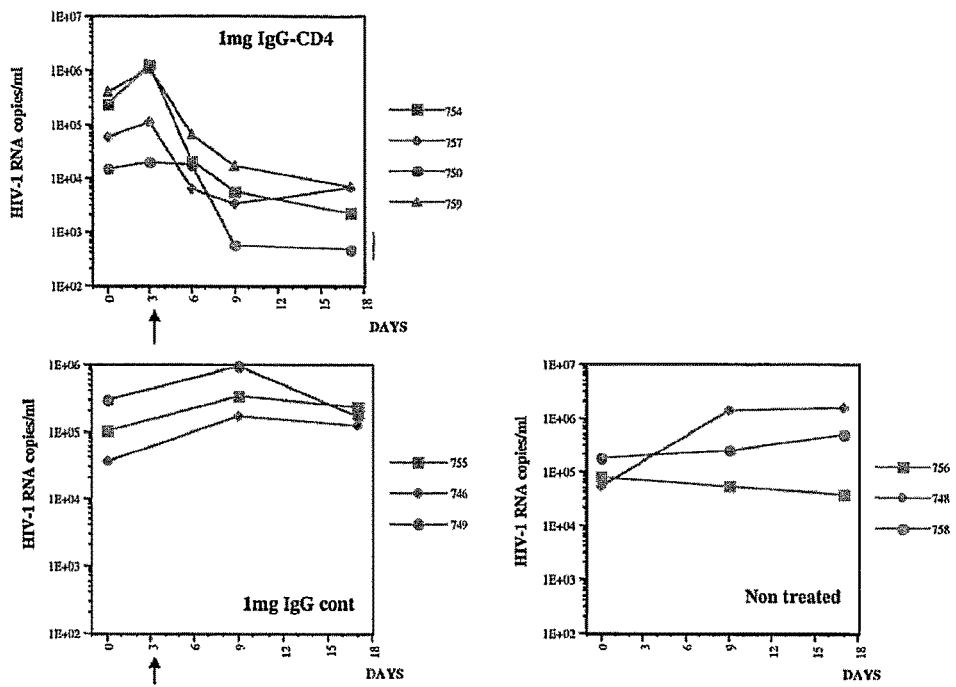

FIG. 29: The measured HIV-1 RNA copies in time of the individual PBMC reconstituted mice treated intraperitoneally with HuMax-CD4, of IgG control or non treated, and infected with HIV-1.

DETAILED DESCRIPTION OF THE SEQUENCE LISTINGS

SEQ ID No: 1: The nucleic acid sequence of $C_L$ kappa of human Ig
SEQ ID No: 2: The amino acid sequence of the kappa light chain of human Ig
SEQ ID No: 3: The nucleic acid sequence of $C_L$ lambda of human Ig
SEQ ID No: 4: The amino acid sequence of the lambda light chain of human Ig
SEQ ID No: 5: The nucleic acid sequence of the $V_H$ region of HuMab-7D8
SEQ ID No: 6: The amino acid sequence of the $V_H$ region of HuMab-7D8
SEQ ID No: 7: The nucleic acid sequence of the $V_H$ region of mouse anti-Betv-1
SEQ ID No: 8: The amino acid sequence for the $V_H$ region of mouse anti-Betv-1
SEQ ID No: 9: The nucleic acid sequence of the $V_L$ region of HuMab-7D8
SEQ ID No: 10: The amino acid sequence of the $V_L$ region of HuMab-7D8
SEQ ID No: 11: The nucleic acid sequence of the $V_L$ region of mouse anti-Betv1
SEQ ID No: 12: The amino acid sequence of the $V_L$ region of mouse anti-Betv1
SEQ ID No: 13: The nucleic acid sequence of the wildtype $C_H$ region of human IgG4
SEQ ID No: 14: The amino acid sequence of the wildtype $C_H$ region of human IgG4
SEQ ID No: 15: The nucleic acid sequence of the $C_H$ region of human IgG4 (SEQ ID No: 13) mutated in positions 714 and 722
SEQ ID No: 16: The amino acid sequence of the $C_H$ region of a human IgG4 generated by expression of the nucleic acid sequence of SEQ ID No: 15
SEQ ID NO: 17: The amino acid sequence of the lambda chain constant human (accession number S25751)
SEQ ID NO: 18: The amino acid sequence of the kappa chain constant human (accession number P01834)
SEQ ID NO: 19: The amino acid sequence of IgG1 constant region (accession number P01857)
SEQ ID NO: 20: The amino acid sequence of the IgG2 constant region (accession number P01859)
SEQ ID NO: 21: The amino acid sequence of the IgG3 constant region (accession number A23511)

DETAILED DESCRIPTION OF THE INVENTION

In order that the present invention may be more readily understood, certain terms are first defined. Additional definitions are set forth throughout the detailed description.

The term "antibody" as referred to herein includes whole antibody molecules, antigen binding fragments, monovalent antibodies, and single chains thereof. Antibody molecules belong to a family of plasma proteins called immunoglobulins, whose basic building block, the immunoglobulin fold or domain, is used in various forms in many molecules of the immune system and other biological recognition systems. Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain may also have regularly spaced intrachain disulfide bridges. Each light chain is comprised of a light chain variable region (abbreviated herein as $V_L$) and a light chain constant region (abbreviated herein as $C_L$). Each heavy chain is comprised of a heavy chain variable region ($V_H$) and a heavy chain constant region ($C_H$) consisting of three domaina, $C_H1$, $C_H2$ and $C_H3$, and the hinge region). The constant domain of the light chain is aligned with the first constant domain ($C_H1$) of the heavy chain, and the light chain variable domain is aligned with the variable domain of the heavy chain forming what is known as the "Fab fragment". $C_H1$ and $C_H2$ of the heavy chain are separated form each other by the socalled hinge region, which allows the Fab "arms" of the antibody molecule to swing to some degree. The hinge region normally comprises one or more cysteine residues, which are capable of forming disulphide bridges with the cysteine residues of the hinge region of the other heavy chain in the antibody molecule.

The variable regions of the heavy and light chains contain a binding domain that interacts with an antigen. The constant regions of the antibodies may mediate the binding of the immunoglobulin to host tissues or factors, including various cells of the immune system (for instance effector cells) and the first component (C1q) of the classical complement system Depending on the amino acid sequences of the constant domain of their heavy chains, immunoglobulins can be assigned to different classes. There are at least five (5) major classes of immunoglobulins: IgA, IgD, IgE, IgG and IgM, and several of these may be further divided into subclasses (isotypes), for instance IgG1, IgG2, IgG3 and IgG4; IgA1 and IgA2. The genes for the heavy chains constant domains that correspond to the different classes of immunoglobulins are called alpha (α), delta (δ), epsilon (ε), gamma (γ) and mu (μ), respectively. Immunoglobulin subclasses are encoded by different genes such as γ1, γ2, γ3 and γ4. The genes for the light chains of antibodies are assigned to one of two clearly distinct types, called kappa (κ) and lambda (λ), based on the amino sequences of their constant domain. The subunit structures and three-dimensional configurations of different classes of immunoglobulins are well known. Distinct allotypes of immunoglobulins exist within the human population such as G1m(a), G1m(x), G1m(f) and G1m(z) for IgG1 heavy chain and Km1, Km1,2 and Km3 for the kappa light chain. These allotypes differ at distinct amino acids in their region encoding the contant regions.

The term antibody also encompasses "derivatives" of antibodies, wherein one or more of the amino acid residues have been derivatised, for instance by acylation or glycosylation, without significantly affecting or altering the binding characteristics of the antibody containing the amino acid sequences.

In the context of the present invention, a derivative of a monovalent antibody may for instance be a monovalent antibody, in which one or more of the amino acid residues of the monovalent antibody have been chemically modified (for instance by alkylation, acylation, ester formation, or amide formation) or associated with one or more non-amino acid organic and/or inorganic atomic or molecular substituents (for instance a polyethylene glycol (PEG) group, a lipophilic substituent (which optionally may be linked to the amino acid sequence of the peptide by a spacer residue or group such as β-alanine, γ-aminobutyric acid (GABA), L/D-glutamic acid, succinic acid, and the like), a fluorophore, biotin, a radionuclide, etc.) and may also or alternatively comprise non-essential, non-naturally occurring, and/or non-L amino acid residues, unless otherwise stated or contradicted by context (however, it should again be recognized that such derivatives may, in and of themselves, be considered independent features of the present invention and inclusion of such molecules within the meaning of peptide is done for the sake of convenience in describing the present invention rather than to imply any sort of equivalence between naked peptides and such derivatives). Non-limiting examples of such amino acid residues include for instance 2-aminoadipic acid, 3-aminoadipic acid, β-alanine, β-aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2'-diaminopimelic acid, 2,3-diaminopropionic acid, N-ethylglycine, N-ethylasparagine, hydroxylysine, allohydroxylysine, 3-hydroxyproline, 4-hydroxyproline, isodesmosine, alloisoleucine, N-methylglycine, N-methylisoleucine, 6-N-methyllysine, N-methylvaline, norvaline, norleucine, ornithine, and statine halogenated amino acids.

The in vivo half-life of the antibodies may for instance be improved by modifying the salvage receptor epitope of the Ig constant domain or an Ig-like constant domain such that the molecule does not comprise an intact $C_H2$ domain or an intact Ig Fc region, cf. U.S. Pat. No. 6,121,022 and U.S. Pat. No. 6,194,551. The in vivo half-life may be furthermore increased by making mutations in the Fc region, for instance by substituting threonine for leucine at the position corresponding to position 252 of an intact antibody molecule, threonine for serine at the position corresponding to position 254 of an intact antibody molecule, or threonine for phenylalanine at the position corresponding to position 256 of an intact antibody molecule, cf. U.S. Pat. No. 6,277,375.

Furthermore, antibodies, and particularly Fab or other fragments, may be pegylated to increase the half-life. This can be carried out by pegylation reactions known in the art, as described, for example, in Focus on Growth Factors 3, 4-10 (1992), EP 154 316 and EP 401 384.

Mutations may also be introduced randomly along all or part of an antibody coding sequence, such as by saturation mutagenesis, and the resulting modified antibodies can be screened for binding activity and/or other characteristics.

The term "antibody derivatives" refers to any modified form of the antibody, for instance a conjugate of the antibody and another agent or antibody.

The term "antigen-binding portion" or "antigen-binding domain" of an antibody, such as a monovalent antibody, as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include
  (i) a Fab or Fab' fragment, a monovalent fragment consisting of the $V_L$, $V_H$, $C_L$ and $C_H$ domains;
  (ii) F(ab')$_2$ fragment, a bivalent fragment comprising two Fab' fragments linked by a disulfide bridge at the hinge region;
  (iii) a Fd fragment consisting essentially of the $V_H$ and $C_H$ domains;
  (iv) a Fv fragment consisting essentially of the $V_L$ and $V_H$ domains of a single arm of an antibody,
  (v) a dAb fragment (Ward et al., Nature 341, 544-546 (1989)), which consists essentially of a $V_H$ domain;
  (vi) an isolated complementarity determining region (CDR), and
  (vii) a combination of two or more isolated CDRs which may optionally be joined by a synthetic linker.

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain antibodies or single chain Fv (scFv), see for instance Bird et al., Science 242, 423-426 (1988) and Huston et al., PNAS USA 85, 5879-5883 (1988)). Such single chain antibodies are encompassed within the term antibody unless otherwise noted or clearly indicated by context.

A further example is antigen-binding-domain immunoglobulin fusion proteins comprising an antigen-binding domain polypeptide that is fused to
  (i) an immunoglobulin hinge region polypeptide,
  (ii) an immunoglobulin heavy chain $C_H2$ constant region fused to the hinge region, and
  (iii) an immunoglobulin heavy chain $C_H3$ constant region fused to the $C_H2$ constant region.

The antigen-binding domain polypeptide may be a heavy chain variable region or a light chain variable region, a scFv or any other polypeptide capable of binding specifically to the antigen. Such binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

The term "antibody half-molecule" is used herein to mean an antibody molecule as described above, but comprising no more than one light chain and no more than one heavy chain, and which exists in water solutions as a heterodimer of said single light and single heavy chain. Such antibody is by nature monovalent as only one antigen-binding portion is present.

The term "conservative sequence modification." in the context of nucleotide or amino acid sequences are modifications of nucleotide(s) and amino acid(s), respectively), which do not significantly affect or alter the binding characteristics of the antibody encoded by the nucleotide sequence or containing the amino acid sequence. Such conservative sequence modifications include nucleotide and amino acid substitutions, additions and deletions. Modifications may be introduced into the sequences by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (for instance lysine, arginine, histidine), acidic side chains (for instance aspartic acid, glutamic acid), uncharged polar side chains (for instance glycine, asparagine, glutamine, serine, threonine, tyrosine, cysteine, tryptophan), nonpolar side chains (for instance alanine, valine, leucine, isoleucine, proline, phenylalanine, methionine), beta-branched side chains (for instance threonine, valine, isoleucine) and aromatic side chains (for instance tyrosine, phenylalanine, tryptophan, histidine). Thus, a predicted nonessential amino acid residue in a human antibody specific for a certain antigen may be replaced with another amino acid residue from the same side chain family.

As used herein, a human antibody is "derived from" a particular germine sequence if the antibody is obtained from a system using human immunoglobulin sequences, for instance by immunizing a transgenic mouse carrying human immunoglobulin genes or by screening a human immunoglobulin gene library, and wherein the variable gene encoded region (not including the heavy or light chain CDR3) of the selected human antibody is at least 90%, more preferably at least 95%, even more preferably at least 96%, 97%, 98%, or 99% identical in nucleic acid sequence to the germline immunoglobulin gene. Typically, a human antibody derived from a particular human germline sequence will display no more than 10 amino acid differences, more preferably, no more than 5, or even more preferably, no more than 4, 3, 2, or 1 amino acid difference from the amino acid sequence encoded by the germline immunoglobulin gene.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "discontinuous epitope", as used herein, means a conformational epitope on a protein antigen which is formed from at least two separate regions in the primary sequence of the protein.

For nucleotide and amino acid sequences, the term "homology" indicates the degree of identity between two nucleic acid or amino acid sequences when optimally aligned and compared with appropriate insertions or deletions. Alternatively, substantial homology exists when the DNA segments will hybridize under selective hybridization conditions, to the complement of the strand.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, for instance as described in the following.

The percent identity between two nucleotide sequences may be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (Comput. Appl. Biosci., 4, 11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48, 444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The term "host cell" (or "recombinant host cell"), as used herein, is intended to refer to a cell into which a recombinant expression vector has been introduced. It should be understood that such terms are intended to refer not only to the particular subject cell but also to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as transfected CHO cells, NS/0 cells, and lymphocytic cells. The term "host cell" in singular form may also denote a culture of a specific kind of host cell.

The term "human antibody", as used herein, is intended to include antibodies having variable and constant regions derived from human germline immunoglobulin sequences. The human antibodies of the invention may include amino acid residues not encoded by human germline immunoglobulin sequences (for instance mutations introduced by random or site-specific mutagenesis in vitro or by somatic mutation in vivo). However, the term "human antibody", as used herein, is not intended to include antibodies in which CDR1 or CDR2 sequences derived from the germline of another mammalian species, such as a mouse, or the CDR3 region derived from an antibody from another species, such as mouse, have been grafted onto human framework sequences.

The term "$K_D$" (M), as used herein, refers to the dissociation equilibrium constant of a particular antibody-antigen interaction.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences.

The term "monovalent antibody" means in the present context that an antibody molecule is capable of binding a single molecule of the antigen, and thus is not able of antigen crosslinking.

The term "nucleic acid", nucleic acid construct" or "nucleic acid molecule", as used herein, is intended to include DNA molecules and RNA molecules. A nucleic acid molecule may be single-stranded or double-stranded.

The term "isolated nucleic acid", "isolated nucleic acid construct" or "isolated nucleic acid molecule", as used herein in reference to nucleic acids encoding antibodies, or fragments thereof is intended to refer to a nucleic acid molecule in which the nucleotide sequences encoding the intact antibody, or fragment thereof, are free of other nucleotide sequences. A nucleic acid may be isolated or rendered substantially pure, when purified away from other cellular components or other contaminants, for instance other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

A nucleic acid is "operably linked" when it is placed into a functional relationship with another nucleic acid sequence. For instance, a promoter or enhancer is operably linked to a coding sequence if it affects the transcription of the sequence. For switch sequences, operably linked indicates that the sequences are capable of effecting switch recombination.

When reference is made to "physiological condition" it is meant a condition that exists in vivo, within the organism, or an in vivo condition which is recreated by fully or partially mimicking said in vivo condition, for example a water solution with an equivalent osmotic value as the blood.

The term "recombinant human antibody", as used herein, includes all human antibodies that are prepared, expressed, created or isolated by recombinant means, such as for instance (a) antibodies isolated from an animal (for instance a mouse) that is transgenic or transchromosomal for human immunoglobulin genes or a hybridoma prepared therefrom, (b) antibodies isolated from a host cell transformed to express the antibody, for instance from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline immunoglobulin sequences. Such recombinant human antibodies may be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "specific binding" refers to the binding of an antibody, or antigen-binding fragment thereof, to a predetermined antigen. Typically, the antibody binds with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less, when measured for instance using sulfon plasmon resonance on BIAcore or as apparent affinities based on $IC_{50}$ values in FACS or ELISA, and binds to the predetermined antigen with an affinity corresponding to a $K_D$ that is at least ten-fold lower, such as at least 100 fold lower, for instance at least 1000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the antigen binding peptide, so that when the $K_D$ of the antigen binding peptide is very low (that is, the antigen binding peptide is highly specific), then the amount with which the affinity for the antigen is lower than the affinity for a non-specific antigen may be at least 10,000 fold.

As used herein, the term "subject" includes any human or non-human animal. The term "non-human animal" includes all vertebrates, for instance mammals and non-mammals, such as non-human primates, sheep, goat, dog, cow, mouse, rat, rabbit, chickens, amphibians, reptiles, etc.

When reference is made to a "therapeutically" effective dosage or a "therapeutically effective amount", it should be taken to mean a dosage or amount effective to achieve a desired therapeutic result over a certain period of time. A therapeutically effective dosage of a monovalent antibody of the invention will of course vary with the target of the antibody and may also vary according to factors such as the disease state, age, sex, and weight of the individual, and the ability of the monovalent antibody to elicit a desired response in the individual. A therapeutically effective dosage or amount may also be one in which any toxic or detrimental effects of the monovalent antibody are outweighed by the therapeutically beneficial effects.

The terms "transgenic, non-human animal" refers to a non-human animal having a genome comprising one or more human heavy and/or light chain transgenes or transchromosomes (either integrated or non-integrated into the animal's natural genomic DNA) and which is capable of expressing human antibodies. For example, a transgenic mouse can have a human light chain transgene and either a human heavy chain transgene or human heavy chain transchromosome, such that the mouse produces human antibodies when immunized with an antigen and/or cells expressing an antigen. The human heavy chain transgene can be integrated into the chromosomal DNA of the mouse, as is the case for transgenic, for instance HuMAb mice, such as HCo7 or HCo12 mice, or the human heavy chain transgene can be maintained extrachromosomally, as is the case for transchromosomal KM mice as described in WO 02/43478. Such transgenic and transchromosomal mice are capable of producing multiple classes and isotypes of monovalent antibodies to a given antigen (for instance IgM, IgG, IgA and/or IgE) by undergoing V-D-J recombination and isotype switching.

The term "transfectoma", as used herein, includes recombinant eukaryotic host cells expressing the antibody, such Chinese hamster ovary (CHO) cells, NS/0 cells, HEK293 cells, plant cells, or fungi, including yeast cells.

The term "treatment" or "treating" or "treat" means easing, ameliorating, or eradicating (curing) symptoms or disease states.

The term "valence of an antibody" means the maximum number of antigenic determinates with which the antibody can react. For example IgG antibodies contain two Fab regions and can bind two molecules of antigen or two identical sites on the same particle, and thus have a valence of two.

The term "vector", as used herein, is intended to refer to a nucleic acid molecule capable of transporting and inducing replication of another nucleic acid to which it has been linked. One type of vector is a "plasmid", which refers to a circular double stranded DNA loop into which additional DNA segments may be ligated. Another type of vector is a viral vector, wherein additional DNA or RNA segments may be ligated into the viral genome. Certain vectors are capable of autonomous replication in a host cell into which they are introduced (for instance bacterial vectors having a bacterial origin of replication and episomal mammalian vectors). Other vectors (for instance non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (for instance replication defective retroviruses, adenoviruses and adeno-associated viruses), which serve equivalent functions.

A number of references are made herein to a water solution or physiological conditions. When reference is made to "water solution" it is meant solution of any chemical matter in water, for example a salt solution, such as phosphate buffered saline (PBS). A water solution may be designed for the purpose and contain a number of different chemical matters, or it may be a natural body fluid, for example the blood.

Five different classes of immunoglobulins exist, i.e. IgM, IgD, IgG, IgA and IgE, and these classes can be distinguished by their C regions.

Within the IgG class of antibodies several subclasses exist, i.e. in human IgG1, IgG2, IgG3, and IgG4 (Jefferis, R. 1990. Molecular structure of human IgG subclasses. In The human IgG subclasses. F. Shakib, ed. Pergamon Press, Oxford, p. 15). Each IgG heavy chain is composed of structurally related peptide sequences (i.e. variable and constant region domains) that are encoded by distinct gene segments or exons. The hinge region linking the CH1 and CH2 domain is encoded by a separate exon. Each of the four IgG subclass heavy chains may be expressed in combination with either kappa or lambda light chains to give an essentially symmetrical molecule composed of two identical heavy chains and two identical kappa or lambda light chains. Comparison within the heavy chain defines the CH1, CH2 and CH3 homology regions. Comparisons between like homology regions of each of the four subclasses reveals >95% sequence identity (Jefferis, R. 1990. F. Shakib, ed. Pergamon Press, Oxford, p. 15). The sequence between the CH1 and CH2 domains is referred to as the hinge region because it allows molecular flexibility. The CH3 domains are paired and the non-covalent interactions are sufficient for the IgG molecule to maintain its structural integrity following reduction of the inter-heavy chain disulphide bridges under mild conditions. CH3 domain pairing is compact and similar to pairing in the Fab, with a nearly exact dyad between the two domains (Saphire, et al., 2002. *J Mol Biol* 319:9). This is in contrast to the CH2 domains, which do not associate closely and their contact is primarily mediated by the two carbohydrate chains attached to the Asn297 residues (Saphire, et al., 2002. *J Mol Biol* 319:9).

The characteristic IgG structure in which two heavy-light chain heterodimers are linked is thus maintained by the inter-heavy chain disulphide bridges of the hinge region and the non-covalent interactions of the CH3 domains.

The interaction in the CH3 region has shown to be important in IgG1. Ig half-molecules, which have a dimeric configuration consisting of only one light chain and only one heavy chain, have been described as the result of rare deletions in human and murine plasmacytomas. Several patients suffering from extramedullary soft-tissue plasmacytoma, Waldenström macroglobulinemia, plasma cell leukemia and multiple myeloma, excreted IgG half molecules into their urine. Half-molecules were also found to be present in their serum. Studies on the biochemical nature of these half-molecules showed that they consist of IgG1 molecules in which the heavy chain $C_H1$, hinge and $C_H2$ regions appeared normal, whereas deletions were found in the $C_H3$ region (already in patent application; page 3).

We show in this application that removal of the hinge region in IgG4 results in the formation of monovalent antibodies in which the linkage between the two heavy-light chain heterodimers is lost or diminished. Consequently, changes in hinge region disulphide bridges of other IgG subclasses alone or in combination with mutations in the CH3 domain interactions may result in the formation of monovalent antibodies for these other subclasses as well. It is well within the capability of the skilled artisan to use the intimate knowledge of structure of Ig subclasses, and the knowledge provided in the present invention, to select and to modify selected amino acids to prevent light chain interactions.

Accordingly, in one embodiment, the present invention relates to a monovalent antibody comprising a light chain and a heavy chain, wherein
  a) said light chain comprises the amino acid sequence of the variable ($V_L$) region of a selected antigen specific antibody and the amino acid sequence of the constant ($C_L$) region of an Ig, and
  b) said heavy chain comprises the amino acid sequence of the variable ($V_H$) region of said selected antigen specific antibody and the amino acid sequence of the constant ($C_H$) region of human Ig, wherein the amino acid sequence of the heavy chain has been modified such that none of any amino acid residues present in the region corresponding to the hinge region are capable of participating in the formation of disulphide bonds with other peptides comprising an identical amino acid sequence of the constant ($C_H$) region of human Ig
  c) said heavy or light chain, depending on Ig isotype is modified by point mutation or deletion in order to remove or change any amino acids i.e. cysteines, capable of causing the linking of the antibody, or modification in form of point mutation or deletion in order to make the heavy chain constant region similar to that of IgG4 with respect to ability to form disulfide bonds or covalently link the molecule with its counterpart forming a dimer.

The amino acid sequence of the light chain of a monovalent antibody of the invention comprises the variable ($V_L$) region of a selected antigen specific antibody and the amino acid sequence of the constant region ($C_L$) of an immunoglobulin.

According to the invention, the amino acid sequence of the $V_L$ region of the monovalent antibody does not contribute to the molecular properties of said antibody molecule which are of interest of the invention, in particular the inability of the monovalent antibody to form heterotetramers ("normal" antibodies), and therefore the invention is not limited to any particular amino acid sequences of the $V_L$ region. The amino acid sequence of the $V_L$ region may be derived from the amino acid sequence of any antigen specific antibody generated in any of the many ways known to a person skilled in the art.

According to the invention, the amino acid sequence of the $V_H$ region of the monovalent antibody does not contribute to the molecular properties of said antibody molecule which are of interest of the invention, in particular the inability of the monovalent antibody to form heterotetramers ("normal" antibodies), and therefore the invention is not limited to any particular amino acid sequences of the $V_H$ region. The amino acid sequence of the $V_H$ region may be derived from the amino acid sequence of any antigen specific antibody generated in any of the many ways known to a person skilled in the art.

In one embodiment, the monovalent antibody of the invention does not bind to the synthetic antigen (Tyr, Glu), Ala, Lys (Pincus et al. 1985, Molecular Immunolog, vol 22, 4; pp. 455-461)

In another embodiment, the antibody of the invention is a human antibody.

In another embodiment, the antibody of the invention is based on a human antibody.

In one embodiment, the present invention relates to a monovalent antibody comprising a light chain and a heavy chain, wherein
 a) said light chain comprises the amino acid sequence of the variable ($V_L$) region of a selected antigen specific antibody and the amino acid sequence of the constant ($C_L$) region of an Ig, and
 b) said heavy chain comprises the amino acid sequence of the variable ($V_H$) region of said selected antigen specific antibody and the amino acid sequence of the constant ($C_H$) region of human IgG4, wherein the amino acid sequence of the heavy chain has been modified such that none of any amino acid residues present in the region corresponding to the hinge region are capable of participating in the formation of disulphide bonds with other peptides comprising an identical amino acid sequence of the constant ($C_H$) region of human IgG4.

The amino acid sequence of the light chain of a monovalent antibody of the invention comprises the variable ($V_L$) region of a selected antigen specific antibody and the amino acid sequence of the constant region ($C_L$) of an immunoglobulin.

According to the invention, the amino acid sequence of the $V_L$ region of the monovalent antibody does not contribute to the molecular properties of said antibody molecule which are of interest of the invention, in particular the inability of the monovalent antibody to form heterotetramers ("normal" antibodies), and therefore the invention is not limited to any particular amino acid sequences of the $V_L$ region. The amino acid sequence of the $V_L$ region may be derived from the amino acid sequence of any antigen specific antibody generated in any of the many ways known to a person skilled in the art.

According to the invention, the amino acid sequence of the $V_H$ region of the monovalent antibody does not contribute to the molecular properties of said antibody molecule which are of interest of the invention, in particular the inability of the monovalent antibody to form heterotetramers ("normal" antibodies), and therefore the invention is not limited to any particular amino acid sequences of the $V_H$ region. The amino acid sequence of the $V_H$ region may be derived from the amino acid sequence of any antigen specific antibody generated in any of the many ways known to a person skilled in the art.

The invention provides an example of 1) a monovalent antibody comprising a $V_H$ region comprising the amino acid sequence of the $V_H$ region of HuMab-7D8 identified as SEQ ID No: 6 and the amino acid sequence encoding the hingeless $C_H$ of IgG4 identified as SEQ ID No: 16, wherein said sequences are operably linked together, and 2) a monovalent antibody comprising a $V_H$ region comprising the amino acid sequence of the $V_H$ region of mouse anti-Betv-1 identified as SEQ ID No: 8 and the amino acid sequence encoding the hingeless $C_H$ of IgG4 identified as SEQ ID No: 16, wherein said sequences are operably linked together.

In one embodiment, the $V_H$ and $V_L$ region of an antibody molecule of the invention are derived from the same antigen specific antibody.

According to the invention, the sequence of the $C_L$ region of the light chain of the antibody molecule may be derived from the sequence of $C_L$ region of an immunoglobulin. In one embodiment, the $C_L$ region is the constant region of the kappa light chain of human IgG. In one embodiment, the $C_L$ region comprises the amino acid sequence of SEQ ID No: 2. In one embodiment, the $C_L$ region is the constant region of the lambda light chain of human IgG. In one embodiment, the $C_L$ region comprises the amino acid sequence of SEQ ID No: 4.

In one embodiment, the light chain and the heavy chain of the monovalent antibody of the invention are connected to each other via one or more disulphide bond. It is evident that for such disulphide bonds, neither of the binding partners in the disulphide bond is present in the region corresponding to the hinge region.

In one embodiment, the light chain and the heavy chain are connected to each other via an amide bond, for instance as it is seen for single chain Fv's.

The hinge region is a region of an antibody situated between the $C_H1$ and $C_H2$ regions of the constant domain of the heavy chain. The extent of the hinge region is determined by the separate exon, which encodes the hinge region. The hinge region is normally involved in participating in ensuring the correct assembly of the four peptide chains of an antibody into the traditional tetrameric form via the formation of disulphide bonds, or bridges, between one or more cysteine residues in the hinge region of one of the heavy chains and one or more cysteine residues in the hinge region of the other heavy chain. A modification of the hinge region so that none of the amino acid residues in the hinge region are capable of participating in the formation of disulphide bonds may thus for instance comprise the deletion and/or substitution of the cysteine residues present in the unmodified hinge region. A region corresponding to the hinge region should for the purpose of this specification be construed to mean the region between region $C_H1$ and $C_H2$ of a heavy chain of an antibody. In the context of the present invention, such a region may also comprise no amino acid residues at all, corresponding to a deletion of the hinge region, resulting in the $C_H1$ and $C_H2$ regions being connected to each other without any intervening amino acid residues. Such a region may also comprise only one or a few amino acid residues, which residues need not be the amino acid residues present in the N- or C-terminal of the original hinge region.

Disulphide bonds is a well-known feature of certain proteins, for instance antibodies, where one cysteine residue form a disulphide bond with another cysteine residue on the same chain (intra-chain disulphide bonds) or other chains (inter-chain disulphide bonds) of the protein. There may be several such disulphide bonds within a given protein. For antibodies, the formation of disulphide bonds, both intra-chain and inter-chain, is an integral part of the correct assembly of the fully matured wildtype antibody, and the disulphide-bonds are normally at least partly responsible for the highly ordered and regular appearance of antibodies as well as for the stability of the antibody. In the monovalent antibodies of the invention, none of the amino acids of the hinge region are capable of participating in the formation of such disulphide bonds.

The modification of the amino acid sequence of the hinge region may be performed on DNA level by use of recombinant techniques enabling the deletion and/or substitution of amino acids in the expressed protein by the deletion and/or substitution of nucleic acids as it is well known in the art and as it is described elsewhere herein and exemplified in the Examples.

The modification may also be performed on an antibody expressed from a non-modified nucleic acid by for instance derivatizing the amino acid residues in the hinge region, which amino acid residues are capable of forming disulphide bonds. Such derivatization of the cysteine residues blocking them from forming disulphide bonds with other cysteine residues may be performed as it is known in the art.

The modification may also be performed by prepared the chains of the antibodies synthetically by using amino acid residues other than cysteine, for instance naturally occurring amino acids or non-naturally occurring amino acids, such as for instance derivatized cysteines, instead of the cysteine residues.

An IgG4 monovalent antibody of the present invention may also be an IgG4 variant. Such a variant antibody is an antibody that differs from a IgG4 antibody by one or more suitable amino acid residue alterations, that is substitutions, deletions, insertions, or terminal sequence additions, for instance in the constant domain, and/or the variable regions (or any one or more CDRs thereof) in a single variant antibody. Typically, amino acid sequence alterations, such as conservative substitution variations, desirably do not substantially change the structural characteristics of the parent sequence (e.g., a replacement amino acid should not tend to disrupt secondary structure that characterizes the function of the parent sequence), but which may be associated with advantageous properties, such as changing the functional or pharmacokinetic properties of the antibodies, for example increasing the half-life, altering the immunogenicity, providing a site for covalent or non-covalent binding to another molecule, reducing susceptibility to proteolysis, reducing susceptibility to oxidation, or altering the glycosylation pattern. Such amino acid sequence variants of an antibody may be obtained as described above for the modifications in the region corresponding to the hinge region.

In one embodiment, the amino acid sequence of the heavy chain has been modified such that the region corresponding to the hinge region does not comprise any cysteine residues.

In one embodiment, the amino acid sequence of the heavy chain has been modified such that at least one of the amino acid residues of the region corresponding to the hinge region, including any cysteine residues, have been deleted and/or substituted with other amino acid residues. The hinge region of antibodies of the invention may thus be modified in other positions than the positions, in which any cysteine residues are normally present, as also described above for variant IgG4 antibodies of the invention. Such modifications may be performed as described above or by any other means known in the art.

In the context of the present invention, the cysteine residues of the region corresponding to the hinge region may be substituted by any naturally occurring or non-naturally occurring, and/or non-L amino acid residues other than cysteine or with derivatives of such amino acid residues including derivatives of cysteine residues, which derivatized cysteine residues are incapable of participating in the formation of disulphide bonds.

In one embodiment, the amino acid sequence of the heavy chain has been modified such that the heavy chain comprises a CH region, wherein the amino acids corresponding to amino acids 106 and 109 of the sequence of SEQ ID No: 14 has been deleted (SEQ ID No: 22). SEQ ID No: 14 shows an amino acid sequence of a wildtype CH region of human IgG4 and positions 106 and 109 are the positions of the two cysteine residues.

In one embodiment, the amino acid sequence of the heavy chain has been modified such that the heavy chain comprises a $C_H$ region, wherein at least the amino acid residues corresponding to amino acid residues 106 to 109 of the sequence of SEQ ID No: 14 has been deleted (SEQ ID No: 22 corresponds to SEQ ID No: 14 with a deletion of amino acids 106 to 109).

In one embodiment, the amino acid sequence of the heavy chain has been modified such that the heavy chain comprises a $C_H$ region, wherein at least the amino acid residues corresponding to amino acid residues 99 to 110 of the sequence of SEQ ID No: 14 has been deleted (SEQ ID No: 23 corresponds to SEQ ID NO: 14 with a deletion of amino acids 99 to 110).

In one embodiment, the heavy chain comprises the amino acid sequence of SEQ ID No: 16. SEQ ID No: 16 is the amino acid sequence of the $C_H$ region of a human IgG4 generated by expression of the nucleic acid comprising the sequence of SEQ ID No: 15, which is a nucleic acid sequence encoding the $C_H$ region of human IgG4 (SEQ ID No: 13) carrying substitution mutations in positions 714 and 722. These substitutions in the splice donor site of the nucleic acid sequence has the effect that the splicing involving the exon encoding the hinge region will not be performed correctly resulting in a heavy chain without the amino acids residues encoded by the exon.

In one embodiment, the entire hinge region of the $C_H$ region has been deleted. This is the case where no amino acids encoded by the exon encoding the hinge region of the $C_H$ region is present in the heavy chain. For the IgG4 shown in SEQ ID No: 14, this will correspond to a $C_H$ region having the amino acid sequence of SEQ ID No: 16.

In one embodiment, the amino acid sequence of the heavy chain has been modified such that the heavy chain comprises a $C_H$ region, wherein the amino acid residues corresponding to amino acid residues 106 and 109 of the sequence of SEQ ID No: 14 has been substituted with amino acid residues different from cysteine.

In one embodiment, the amino acid sequence of the heavy chain has been modified such that the heavy chain comprises a $C_H$ region, wherein one of the amino acid residues corresponding to amino acid residues 106 and 109 of the sequence of SEQ ID No: 14 has been substituted with an amino acid residue different from cysteine and the other of the amino acid residues corresponding to amino acid residues 106 and 109 of the sequence of SEQ ID No: 14 has been deleted. In a further embodiment, it is the amino acid residue corresponding to amino acid residues 106, which has been substituted with an amino acid residue different from cysteine, and the amino acid residue corresponding to amino acid residues 109, which has been deleted. In another further embodiment, it is the amino acid residue corresponding to amino acid residues 106, which has been deleted, and the amino acid residue corresponding to amino acid residues 109, which has been substituted with an amino acid residue different from cysteine.

In one embodiment, a monovalent antibody of the invention is obtainable by a method comprising recombinant expression of the antibody in a cell expression system in vitro as described elsewhere herein.

In one embodiment, such method comprises
i) providing a nucleic acid construct encoding the light chain of said antibody, said construct comprising a nucleotide sequence encoding the $V_L$ region of a selected antigen specific antibody and a nucleotide sequence encoding the $C_L$ region of IgG;
ii) providing a nucleic acid construct encoding the heavy chain of said antibody, said construct comprising a nucleotide sequence encoding the $V_H$ region of a selected antigen specific antibody and a nucleotide sequence encoding the $C_H$ region of human IgG4, wherein the nucleic acid sequence encoding the $C_H$ region has been modified such that the region corresponding to the hinge region does not comprise any amino acid residues capable of participating in the formation of disulphide bonds;
iii) providing a cell expression system for the producing said monovalent antibody;
iv) producing said monovalent antibody comprising a light chain encoded by the nucleic acid construct of (i) and a heavy chain encoded by the nucleic acid construct of (ii) by co-expressing said nucleic acid constructs in cells of the cell expression system of (iii).

In one embodiment, the monovalent antibody of the invention has a plasma concentration above 10 µg/ml for more than 7 days when administered in vivo at a dose of 4 mg per kg, as measured in an pharmacokinetic study in SCID mice (for instance as shown in example 32). The clearance rate of a monovalent antibody of the invention may be measured by use of pharmacokinetic methods as it is known in the art. the antibody may for instance be injected intravenously (other routes such as i.p. or i.m. may also be used) in a human or animal after which blood samples are drawn by venipuncture at several time points, for instance 1 hour, 4 hours, 24 hours, 3 days, 7 days, 14 days, 21 days and 28 days after initial injection). The concentration of antibody in the serum is determined by an appropriate assay such as ELISA. Pharmacokinetic analysis is performed as known in the art and described in example 32. Monovalent antibodies of the invention may have a plasma residence time, which is as much as 100 times longer than the plasma residence time of for instance Fab fragments which are frequently used as monovalent antibodies.

In one embodiment, a monovalent antibody of the invention has a plasma clearance, which is more than 10 times slower than the plasma clearance of a $F(ab')_2$ fragment, which has a comparable molecular size. This may be an indication of the capability of the antibodies of the invention to bind to FcRn. FcRn is a major histocompatibility complex class I-related receptor and plays a role in the passive delivery of immunoglobulin (Ig)Gs from mother to young and in the regulation of serum IgG levels by protecting IgG from intracellular degradation (Ghetie V et al., Annu Rev Immunol. 18, 739-66 (2000)). In one embodiment, the $F(ab')_2$ fragment is directed at the same antigen as the monovalent antibody of the invention. In one embodiment, the $F(ab')_2$ fragment is directed at the same epitope as the monovalent antibody of the invention. In one embodiment, the $V_H$ region and the $V_L$ region of the $F(ab')_2$ fragment are identical to the $V_H$ region and the $V_L$ region of the monovalent antibody of the invention.

In one embodiment, a monovalent antibody of the invention has a half-life of at least 5 days when administered in vivo. The half-life of a monovalent antibody of the invention may be measured by any method known in the art, for instance as described above.

In one embodiment, a monovalent antibody of the invention has a half-life of at least 5 days and up to 14 days, when administered in vivo.

In one embodiment, a monovalent antibody of the invention has a half-life of at least 5 days and up to 21 days, when administered in vivo.

In one embodiment, a monovalent antibody of the invention is capable of binding to FcRn. Such binding may be determined by use of methods for determining binding as it is known in the art, for instance by use of ELISA assays. The binding of a monovalent antibody of the invention to FcRn may for instance be compared to the binding of a $F(ab')_2$ fragment, which $F(ab')_2$ fragment has a $V_H$ region and a $V_L$ region, which are identical to the $V_H$ region and the $V_L$ region of the monovalent antibody of the invention, to FcRn in the same assay. In one embodiment, the binding of an a monovalent antibody of the invention to FcRn is more than 10 times stronger than the binding of the $F(ab')_2$ fragment to FcRn.

In one embodiment, a monovalent antibody of the invention specifically binds a tumor antigen. Without being limited to specific tumor antigens, examples of such tumor antigens could be cMet and VEGF-R.

In one embodiment, a monovalent antibody of the invention specifically binds a cell surface receptor that is activated upon receptor dimerization. Monovalent antibodies, such as the monovalent antibodies of the invention, may often be useful in the treatment of diseases or disorders, where receptor activation is undesirable, since the antibody molecules of the inventions due to their monovalent nature are unable to induce such dimerization and thereby such activation. Without being limited to specific receptors, examples of such receptors could be erb-B1, erb-B2, erb-B3, erb-B4 and members of the ephrins and ephrin receptors such as ephrin-A1 through A6, ephA1 through A8, ephrin B1 through B3 and eph-B1 through eph-B6.

In one embodiment, a monovalent antibody of the invention, when bound to a target molecule, inhibits target molecule multimerization (such as dimerization). Again, monovalent antibodies, such as the monovalent antibodies of the invention, may often be useful in the treatment of diseases or disorders, where multimerization of the target antigen is undesirable, since the antibody molecules of the inventions due to their monovalent nature are unable to induce such multimerization. In the case of soluble antigens, multimerization may form undesirable immune complexes. Without being limited to specific targets, examples of such targets could be Toll-like receptors such as TLR-3 and TLR-9, or angiopoietin-1, or angiopoietin-2, or TNF receptor family members such as CD30, CD40 and CD95.

In one embodiment, a monovalent antibody of the invention is an inhibitor of TNF-alpha. In one embodiment of the invention, the monovalent antibody of the invention is a monovalent form of adalimumab, etanercept, or infliximab.

In one embodiment, a monovalent antibody of the invention is incapable of effector binding. The expression "incapable of effector binding" or "inability of effector binding" in the present context means that an IgG4 monovalent antibody of the invention is incapable of binding to the C1q component of the first component of complement (C1) and therefore is unable of activating the classical pathway of complement mediated cytotoxicity. In addition, the monovalent antibodies of the invention are unable to interact with Fc receptors and may therefore be unable to trigger Fc receptor-mediated effector functions such as phagocytosis, cell activation, induction of cytokine release In one embodiment, a monovalent antibody of the invention is produced by use of recombinant DNA technologies. Antibodies may be produced using recombinant eukaryotic host cells, such as chinese hamster ovary (CHO) cells, NS/0 cells, HEK293 cells, insect cells, plant cells, or fungi, including yeast cells. Both stable as well as transient systems may be used for this purpose. Transfection may be done using plasmid expression vectors by a number of established methods, such as electroporation, lipofection or nucleofection. Alternatively, infection may be used to express proteins encoded by recombinant viruses such as adeno, vaccinia or baculoviruses. Another method may be to use transgenic animals for production of antibodies.

A DNA sequence encoding the antibody may be prepared synthetically by established standard methods, for instance the phosphoamidine method described by Beaucage et al., Tetrahedron Lett. 22, 1859-1869 (1981), or the method described by Matthes et al., EMBO J. 3, 801-805 (1984). According to the phosphoamidine method, oligonucleotides are synthesised, for instance in an automatic DNA synthesiser, purified, annealed, ligated and cloned in suitable vectors.

A DNA sequence encoding the may also be of genomic or cDNA origin, for instance obtained by preparing a genomic or cDNA library and screening for DNA sequences coding for all or part of the antibody by hybridisation using synthetic oligonucleotide probes in accordance with standard techniques (cf. Sambrook et al., Molecular Cloning: A Laboratory Manual, 2nd Ed., Cold Spring Harbor, 1989). The DNA sequence may also be prepared by polymerase chain reaction using specific primers, for instance as described in U.S. Pat. No. 4,683,202 or Saiki et al. Science 239, 487-491 (1988).

The DNA sequence may then be inserted into a recombinant expression vector, which may be any vector, which may conveniently be subjected to recombinant DNA procedures. The choice of vector will often depend on the host cell into which it is to be introduced. Thus, the vector may be an autonomously replicating vector, i.e. a vector that exists as an extrachromosomal entity, the replication of which is independent of chromosomal replication, for instance a plasmid. Alternatively, the vector may be one which, when introduced into a host cell, is integrated into the host cell genome and replicated together with the chromosome(s) into which it has been integrated.

In the vector, a DNA sequence encoding the antibody should be operably connected to a suitable promoter sequence. The promoter may be any DNA sequence, which shows transcriptional activity in the host cell of choice and may be derived from genes encoding proteins either homologous or heterologous to the host cell. Examples of suitable promoters for directing the transcription of the coding DNA sequence in mammalian cells are the CMV promoter, the SV40 promoter, the MT-1 (metallothionein gene) promoter or the adenovirus 2 major late promoter. Other suitable promoters are known in the art. A suitable promoter for use in insect cells is for instance the polyhedrin promoter. Suitable promoters for use in yeast host cells include promoters from yeast glycolytic genes or alcohol dehydrogenase genes, or the TPI1 or ADH2-4-c promoters. Suitable promoters for use in filamentous fungus host cells are, for instance, the ADH3 promoter or the tpiA promoter.

The coding DNA sequence may also be operably connected to a suitable terminator, such as the human growth hormone terminator or (for fungal hosts) the TPI1 or ADH3 terminators. Other suitable terminators are known in the art. The vector may further comprise elements such as polyadenylation signals (for instance from SV40 or the adenovirus 5 Elb region), transcriptional enhancer sequences (for instance the SV40 enhancer) and translational enhancer sequences (for instance the ones encoding adenovirus VA RNAS). Other such signals and enhancers are known in the art.

The recombinant expression vector may further comprise a DNA sequence enabling the vector to replicate in the host cell in question. An example of such a sequence (when the host cell is a mammalian cell) is the SV40 origin of replication. Other origins of replications are known in the art. The vector may also comprise a selectable marker, for instance a gene the product of which complements a defect in the host cell, such as the gene coding for dihydrofolate reductase (DHFR), glutamine synthetase (GS) or one which confers resistance to a drug, for instance neomycin, hydromycin or methotrexate. Other selectable markers are known in the art.

The procedures used to ligate the DNA sequences coding the peptides or full-length proteins, the promoter and the terminator, respectively, and to insert them into suitable vectors containing the information necessary for replication, are well known to persons skilled in the art (cf., for instance, Sambrook et al., op.cit.).

To obtain recombinant monovalent antibodies of the invention, the DNA sequences encoding different parts of the polypeptide chain(s) of the antibody may be individually expressed in a host cell, or may be fused, giving a DNA construct encoding the fusion polypeptide, such as a polypeptide comprising both light and heavy chains, inserted into a recombinant expression vector, and expressed in host cells.

The host cell into which the expression vector may be introduced, may be any cell which is capable of expression of full-length proteins, and may for instance be a eukaryotic cell, such as invertebrate (insect) cells or vertebrate cells, for instance *Xenopus laevis* oocytes or mammalian cells, such as insect and mammalian cells. Examples of suitable mammalian cell lines are the HEK293 (ATCC CRL-1573), COS (ATCC CRL-1650), BHK (ATCC CRL-1632, ATCC CCL-10), NS/0 (ECACC 85110503) or CHO (ATCC CCL-61) cell lines. Other suitable cell lines are known in the art. In one embodiment, the expression system is a mammalian expression system, such as a mammalian cell expression system comprising various clonal variations of HEK293 cells.

Methods of transfecting mammalian cells and expressing DNA sequences introduced in the cells are described in for instance Kaufman et al., J. Mol. Biol. 159, 601-621 (1982); Southern et al., J. Mol. Appl. Genet. 1, 327-341 (1982); Loyter et al., Proc. Natl. Acad. Sci. USA 79, 422-426 (1982); Wigler et al., Cell 14, 725 (1978); Corsaro et al., Somatic Cell Genetics 7, 603 (1981); Graham et al., Virol. 52, 456 (1973); and Neumann et al., EMBO J. 1, 841-845 (1982). To obtain a monovalent antibody of the invention, host cells of the expression system may in one embodiment to be cotransfected with two expression vectors simultaneously, wherein first of said two expression vectors comprises a DNA sequence encoding the heavy chain of the antibody, and second of said two expression vectors comprises a DNA sequence encoding the light chain of the antibody. The two sequences may also be present on the same expression vector, or they may be fused giving a DNA construct encoding the fusion polypeptide, such as a polypeptide comprising both light and heavy chains.

In one embodiment, fungal cells (including yeast cells) may be used as host cells. Examples of suitable yeast cells include cells of *Saccharomyces* spp. or *Schizosaccharomyces* spp., in particular strains of *Saccharomyces cerevisiae*. Examples of other fungal cells are cells of filamentous fungi, for instance *Aspergillus* spp. or *Neurospora* spp., in particular strains of *Aspergillus oryzae* or *Aspergillus niger*. The use of *Aspergillus* spp. for the expression of proteins is described in, for instance EP 238 023.

The medium used to culture the cells may be any conventional medium suitable for growing mammalian cells, such as a serum-containing or serum-free medium containing appropriate supplements, or a suitable medium for growing insect, yeast or fungal cells. Suitable media are available from commercial suppliers or may be prepared according to published recipes (for instance in catalogues of the American Type Culture Collection).

The recombinantly produced monovalent antibody may then be recovered from the culture medium by conventional procedures including separating the host cells from the medium by centrifugation or filtration, precipitating the proteinaceous components of the supernatant or filtrate by means of a salt, for instance ammonium sulphate, purification by a variety of chromatographic procedures, for instance HPLC, ion exchange chromatography, affinity chromatography, Protein A chromatography, Protein G chromatography, or the like.

The present invention also relates to a method of preparing a monovalent antibody of the invention, wherein said method comprises the steps of:
(a) culturing a host cell comprising a nucleic acid encoding said monovalent antibody; and
(b) recovering the monovalent antibody from the host cell culture.

In one embodiment, said host cell is a prokaryotic host cell. In one embodiment, the host cell is an *E. coli* cell. In one embodiment, the *E. coli* cells are of a strain deficient in endogenous protease activities.

In one embodiment, said host cell is a eukaryotic cell. In one embodiment, the host cell is a HEK-293F cell. In another embodiment, the host cell is a CHO cell.

In one embodiment, the monovalent antibody is recovered from culture medium. In another embodiment, the monovalent antibody is recovered from cell lysate.

The antibodies of the present invention has the advantage of having a long halflive in vivo, leading to a longer therapeutic window, as compared to e.g. a FAB fragment of the same antibody which has a considerably shorter halflife in vivo.

Further, due to the long halflife and small size, the monovalent antibodies of the invention will have a potential having a better distribution in vivo, in example by being able to penetrate solid tumors. This leads to a great use potential of the monovalent antibodies of the invention, e.g. for treatment of cancer, since the antibodies of the invention could be used either to inhibit a target molecule, or as a target specific delivery mechanism for other drugs that would treat the disease.

Due to the absence of activation of the immune system by the monovalent antibodies of the invention, the antibodies of the invention are target cell inhibitory but not target cell killing. This may be an advantage when contemplating the treatment of a variety of diseases where inhibition of a mechanism is wanted without a desire for the cell to be killed.

In one embodiment, an anti-VEGF monovalent antibody is used for treatment of AMD (acute macular degeneration), and other diseases.

In one embodiment, the anti-VEGF monovalent antibody used is a monovalent form of Bevacizumab (Avastin).

Antibodies of the present invention are monovalent, are stable under physiological conditions, are unable to activate complement, and are thus suitable for use in treating disorders and diseases, in which the use of polyvalent antibodies, such as divalent antibodies, are unnecessary or disadvantageous, or wherein the activation of complement is unnecessary or disadvantageous. A monovalent antibody of the invention may be represented in water solutions by a heterodimer consisting of one light chain and one heavy chain.

The expression "stable under physiological conditions" or "stability under physiological conditions" in the present context means that the monovalent antibody retains its major structural and functional characteristics unchanged and is present in a therapeutically significant concentration for more than one week after said molecule is administered to a subject in vivo at a dose of 1 to 10 mg per kg. A plasma concentration of 5 µg/ml is considered to be significant for most therapeutic antibodies, because the antibodies may show saturation of target binding at this level. A time interval of 7 days is considered in this context to be relatively long.

Both in immune-deficient and in immune-competent mice, the clearance of the hingeless variant is much slower than that of F(ab')$_2$ fragments, which have a comparable molecular size. This indicates that the Fc-part has a favorable effect on the plasma residence time in and provides indication of a functional interaction with the neonatal Fc receptor (FcRn) which protects endocytosed IgG from intracellular degradation. The clearance rate of the hingeless variant was about 300 times lower than that of Fab fragments, indicating that it may be given at a 300 times lower dosing for obtaining equivalent sustained plasma concentrations.

The invention also relates to an immunoconjugate of the monovalent antibody of the invention. The present invention features in particular a monovalent antibody of the invention conjugated to a therapeutic moiety, such as a cytotoxin, a chemotherapeutic drug, an immunosuppressant or a radio-isotope. Such conjugates are referred to herein as "immunoconjugates". A cytotoxin or cytotoxic agent includes any agent that is detrimental to (for instance kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Suitable chemotherapeutic agents for forming immunoconjugates of the invention include, but are not limited to, antimetabolites (for instance methotrexate, 6-mercaptopurine, 6-thioguanine, cytarabine, fludarabin; 5-fluorouracil, decarbazine, hydroxyurea, azathiprin, gemcitabin and cladribin), alkylating agents (for instance mechlorethamine, thioepa, chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (for instance daunorubicin (formerly daunomycin) and doxorubicin), antibiotics (for instance dactinomycin (formerly actinomycin), bleomycin, mithramycin, and anthramycin (AMC)), and anti-mitotic agents (for instance vincristine, vinblastine, docetaxel, paclitaxel and vinorelbin).

Suitable radioisotopes are for instance iodine-131, yttrium-90 or indium-111.

Further examples of therapeutic moieties may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or biological response modifiers such as, for example, lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), or other growth factors.

In one embodiment, the therapeutic moiety is doxorubicin, cisplatin, bleomycin, carmustine, chlorambucil, cyclophosphamide or ricin A.

Techniques for conjugating such therapeutic moiety to antibodies are well known, see, for instance Arnon et al., "Monoclonal Antibodies For Immunotargeting Of Drugs In Cancer Therapy", Monoclonal Antibodies And Cancer Therapy, Reisfeld et al. (eds.), pp. 243-56 (Alan R. Liss, Inc. 1985); Hellstrom et al., "Antibodies For Drug Delivery", Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", Monoclonal Antibodies 1984: Biological And Clinical Applications, Pinchera et al. (eds.), pp. 475-506 (1985); "Analysis, Results, And Future Prospective Of The Therapeutic Use Of Radiolabeled Antibody In Cancer Therapy", Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

In one embodiment, the monovalent antibodies of the invention are attached to a linker-chelator, for instance tiuxetan, which allows for the antibody to be conjugated to a radioisotope.

In one embodiment, the present invention provides a pharmaceutical composition comprising a monovalent antibody of the present invention. The pharmaceutical compositions may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical composition may be administered by any suitable route and mode. As will be appreciated by the skilled artisan, the route and/or mode of administration will vary depending upon the desired results.

The pharmaceutical compositions of the present invention include those suitable for oral, nasal, topical (including buccal and sublingual), rectal, vaginal and/or parenteral administration.

Formulations of the present invention which are suitable for vaginal administration include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants.

In one embodiment, the pharmaceutical composition is suitable for parenteral administration.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

In one embodiment the pharmaceutical composition is administered by intravenous or subcutaneous injection or infusion.

In one embodiment, the monovalent antibodies of the invention are administered in crystalline form by subcutaneous injection, cf. Yang et al. PNAS, 100(12), 6934-6939 (2003).

Regardless of the route of administration selected, the monovalent antibodies of the present invention, which may be used in the form of a pharmaceutically acceptable salt or in a suitable hydrated form, and/or the pharmaceutical compositions of the present invention, are formulated into pharmaceutically acceptable dosage forms by conventional methods known to those of skill in the art.

As used herein, "pharmaceutically acceptable carrier" includes any and all solvents, dispersion media, coatings, antibacterial and antifungal agents, isotonicity agents, antioxidants and absorption delaying agents, and the like that are physiologically compatible.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the monovalent antibody, use thereof in the pharmaceutical compositions of the invention is contemplated.

In one embodiment, the carrier is suitable for parenteral administration, for instance intravenous or subcutaneous injection or infusion.

Pharmaceutical compositions typically must be sterile and stable under the conditions of manufacture and storage. The composition may be formulated as a solution, microemulsion, liposome, or other ordered structure suitable to high drug concentration. Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

The pharmaceutical compositions may also contain adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol, sorbic acid, and the like. It may also be desirable to include isotonicity agents, such as sugars, polyalcohols such as mannitol, sorbitol, glycerol or sodium chloride in the compositions. Pharmaceutically-acceptable antioxidants may also be included, for example (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Prolonged absorption of the injectable compositions may be brought about by including agents that delays absorption, for example, monostearate salts and gelatin.

Sterile injectable solutions may be prepared by incorporating the monovalent antibody in the required amount in an appropriate solvent with one or a combination of ingredients for instance as enumerated above, as required, followed by sterilization microfiltration. Generally, dispersions are prepared by incorporating the monovalent antibody into a sterile vehicle that contains a basic dispersion medium and the required other ingredients for instance from those enumerated above. In the case of sterile powders for the preparation of sterile injectable solutions, examples of methods for preparation are vacuum drying and freeze-drying (lyophilization) that yield a powder of the active ingredient plus any additional desired ingredient from a previously sterile-filtered solution thereof.

If appropriate, the monovalent antibody may be used in a suitable hydrated form or in the form of a pharmaceutically acceptable salt. A "pharmaceutically acceptable salt" refers to a salt that retains the desired biological activity of the parent compound and does not impart any undesired toxicological effects (see for instance Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methyl-glucamine, chloroprocaine, choline, diethanolamine, ethylenediamine, procaine and the like.

Depending on the route of administration, the monovalent antibody may be coated in a material to protect the compound from the action of acids and other natural conditions that may inactivate the compound. For example, the compound may be administered to a subject in an appropriate carrier, for example, liposomes. Liposomes include water-in-oil-in-water CGF emulsions as well as conventional liposomes (Strejan et al., J. Neuroimmunol. 7, 27 (1984)).

The monovalent antibody may be prepared with carriers that will protect the monovalent antibody against rapid release, such as a controlled release formulation, including implants, transdermal patches, and microencapsulated delivery systems. Biodegradable, biocompatible polymers may be used, such as ethylene vinyl acetate, polyanhydrides, polyglycolic acid, collagen, polyorthoesters, and polylactic acid. Methods for the preparation of such formulations are generally known to those skilled in the art, see for instance Sustained and Controlled Release Drug Delivery Systems, J. R. Robinson, ed., Marcel Dekker, Inc., New York, 1978.

The pharmaceutical compositions may be administered with medical devices known in the art. In one embodiment, a therapeutic composition of the invention may be administered with a needleless hypodermic injection device, such as the devices disclosed in U.S. Pat. No. 5,399,163; U.S. Pat. No. 5,383,851; U.S. Pat. No. 5,312,335; U.S. Pat. No. 5,064,413; U.S. Pat. No. 4,941,880; U.S. Pat. No. 4,790,824; or U.S. Pat. No. 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In one embodiment, the monovalent antibodies of the invention may be formulated to ensure proper distribution in vivo for instance by use of liposomes. For methods of manufacturing liposomes, see for instance U.S. Pat. No. 4,522,811; U.S. Pat. No. 5,374,548; and U.S. Pat. No. 5,399,331. The liposomes may comprise one or more moieties which are selectively transported into specific cells or organs, thus enhance targeted drug delivery (see, for instance V. V. Ranade, J. Clin. Pharmacol. 29, 685 (1989)). Exemplary targeting moieties include folate or biotin (see, for instance U.S. Pat. No. 5,416,016); mannosides (Umezawa et al., Biochem. Biophys. Res. Commun. 153, 1038 (1988)); other antibodies (Bloeman et al., FEBS Lett. 357, 140 (1995); Owais et al., Antimicrob. Agents Chemother. 39, 180 (1995)); surfactant protein A receptor (Briscoe et al., Am. J. Physiol. 1233, 134 (1995)), different species of which may comprise the formulations of the inventions, as well as components of the invented molecules; p120 (Schreier et al., J. Biol. Chem. 269, 9090 (1994)); see also Keinanen et al., FEBS Lett. 346, 123 (1994); Killion et al., Immunomethods 4, 273 (1994). The composition must be fluid to the extent that easy syringability exists. It must be stable under the conditions of manufacture and storage and must be preserved against the contaminating action of microorganisms such as bacteria and fungi.

In one embodiment, the monovalent antibodies of the invention may be formulated to prevent or reduce their transport across the placenta. This may be done by methods known in the art, for instance by PEGylation of the monovalent antibodies. Further references may be made to Cunningham-Rundles et al., J Immunol Methods. 152, 177-190 (1992); and to Landor et al., Ann. Allergy Asthma Immunol. 74, 279-283 (1995).

Dosage regimens are adjusted to provide the optimum desired response (for instance a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of monovalent antibody calculated to produce the desired therapeutic effect in association with the required pharmaceutical carrier. The specification for the dosage unit forms of the invention are dictated by and directly dependent on (a) the unique characteristics of the monovalent antibody and the particular therapeutic effect to be achieved, and (b) the limitations inherent in the art of compounding such a monovalent antibody for the treatment of sensitivity in individuals.

Actual dosage levels of the monovalent antibodies in the pharmaceutical compositions of the present invention may be varied so as to obtain an amount of the active ingredient which is effective to achieve the desired therapeutic response for a particular patient, composition, and mode of administration. The selected dosage level will depend upon a variety of pharmacokinetic factors including the activity of the particular monovalent antibodies of the present invention employed, the route of administration, the time of administration, the rate of excretion of the particular monovalent antibody being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable dose of a pharmaceutical composition of the invention will be that amount of the monovalent antibody which is the lowest dose effective to produce a therapeutic effect. Such an effective dose will generally depend upon the factors described above. As another example, the physician or veterinarian may start with a high loading dose followed by repeated administration of lower doses to rapidly build up a therapeutically effective dose and maintain it over longer periods of time.

A pharmaceutical composition of the invention may contain one or a combination of different monovalent antibodies of the invention. Thus, in a further embodiment, the pharmaceutical compositions include a combination of multiple (for instance two or more) monovalent antibodies of the invention which act by different mechanisms. The monovalent antibodies may also be thus combined with divalent antibodies.

The present invention also relates to a nucleic acid construct encoding the amino acid sequence of the $C_H$ region of the heavy chain of a monovalent antibody of the invention.

In one embodiment, the invention provides a nucleic acid construct comprising a nucleic acid sequence encoding the $C_H$ region of an IgG4, wherein the nucleic acid sequence encoding the $C_H$ region has been modified such that the region corresponding to the hinge region in said $C_H$ region does not comprise any amino acid residues capable of participating in the formation of disulphide bonds with peptides comprising an amino acid sequence identical to the amino acid sequence of said $C_H$ region, or a sequence complementary thereof.

A nucleic acid construct encoding the $C_H$ region of a monovalent antibody of the invention may be derived from nucleic acids encoding the $C_H$ region of IgG4. The nucleic acid construct encoding the full-length amino acid sequence of the $C_H$ region of IgG4 may be prepared by any of the methods discussed herein, for instance in the Examples, or in other ways known in the art. The methods of manipulation with recombinant DNA sequences are well known in the art, and may for instance be done by using site-directed mutagenises, such as described in the present specification. However, site-directed mutagenesis is just one of non-limited examples of the technologies that may be applied.

The modification of the nucleic acid sequence encoding the $C_H$ region may be performed as described above for the construction of the monovalent antibodies of the invention.

In one embodiment, the nucleic acid sequence encoding the $C_H$ region has been modified such that the region corresponding to the hinge region does not comprise any cysteine residues.

In one embodiment, the nucleic acid sequence encoding the $C_H$ region has been modified such that at least one of the amino acid residues of the region corresponding to the hinge region, including any cysteine residues, have been deleted and/or substituted with other amino acid residues.

In one embodiment, the nucleic acid sequence encoding the $C_H$ region has been modified such that the amino acids corresponding to amino acids 106 and 109 of the sequence of SEQ ID No: 14 have been deleted.

In one embodiment, the nucleic acid sequence encoding the $C_H$ region has been modified such that at least the amino acid residues corresponding to amino acid residues 106 to 109 of the sequence of SEQ ID No: 14 has been deleted.

In one embodiment, the nucleic acid sequence encoding the $C_H$ region has been modified such that at least the amino acid residues corresponding to amino acid residues 99 to 110 of the sequence of SEQ ID No: 14 has been deleted.

In one embodiment, the nucleic acid sequence encoding the $C_H$ region has been modified such that the entire hinge region has been deleted.

In one embodiment, mutation (substitution) of nucleotides corresponding to the splice donor site of the hinge region in the sequence encoding the $C_H$ region of IgG4, identified herein as SEQ ID No: 13, leads to expression of a polypeptide comprising a hingeless $C_H$ region of IgG4.

Accordingly, in one embodiment, the nucleic acid construct of the invention has been modified such that at least one nucleotide of the splice donor site of the nucleic acid sequence encoding the hinge region has been substituted with a nucleotide different than the nucleotide originally present in that position.

In one embodiment, the nucleotides corresponding to the nucleotides in position 714 and 722 of the sequence of SEQ ID No: 13 has been substituted with a nucleotide different than the nucleotide present at that position in SEQ ID No: 13.

In one embodiment, the nucleic acid sequence encoding the $C_H$ region of a nucleic acid construct of the invention comprises a sequence of SEQ ID No: 13, wherein nucleotides 714 and 722 of the sequence of SEQ ID No: 13 has been substituted with a nucleotide different than the nucleotide present at that position in SEQ ID No: 13.

In one embodiment, the nucleic acid sequence encoding the $C_H$ region of a nucleic acid construct of the invention comprises the nucleotide sequence of SEQ ID No: 15.

In one embodiment, the nucleic acid sequence encoding the $C_H$ region of a nucleic acid construct of the invention has been modified such that the amino acid residues corresponding to amino acid residues 106 and 109 of the sequence of SEQ ID No: 14 has been substituted with amino acid residues different from cysteine.

In one embodiment, the substituted nucleotides of the nucleic acid sequence encoding the $C_H$ region of a nucleic acid construct of the invention are substituted by using site-directed mutagenesis.

In one embodiment, a nucleic acid construct comprising a nucleic acid sequence encoding the $C_H$ region of an IgG4, wherein the nucleic acid sequence encoding the $C_H$ region has been modified such that the region corresponding to the hinge region does not comprise any amino acid residues capable of participating in the formation of disulphide bonds, is fused with a nucleic acid comprising a nucleic acid sequence encoding the $V_H$ region of the monovalent antibody of the invention.

Thus, in one embodiment, the nucleic acid construct comprises a nucleic acid sequence encoding the $V_H$ region of an antigen specific antibody, or a sequence complementary thereof.

In one embodiment, the nucleic acid sequence encoding the $V_H$ region of the nucleic acid construct is operably linked to the nucleic acid sequence encoding the $C_H$ region, or a sequence complementary thereof.

In one embodiment, the nucleic acid construct comprises a nucleotide sequence encoding the heavy chain of a monovalent antibody of the invention.

This may be achieved by using well-known technologies to obtain a nucleic acid construct wherein two different coding sequences are operably linked together. The nucleic acid sequence encoding the $V_H$ region of a monovalent antibody of the invention may be derived from nucleic acids encoding the $V_H$ region of any antigen specific antibody. In one embodiment, the $V_H$ region is derived from the same antibody from which the $V_L$ region of the monovalent antibody is derived from. The invention provides examples of how to make nucleic acid constructs comprising 1) the nucleic acid sequence encoding the $V_H$ of HuMab-7D8 identified as SEQ ID No: 5 and the nucleic acid sequence encoding the hingeless $C_H$ of IgG4 identified as SEQ ID No: 15, wherein said sequences are operably linked together, and 2) the nucleic acid sequence encoding the $V_H$ of mouse anti-Betv-1 identified as SEQ ID No: 7 and the nucleic acid sequence encoding the hingeless $C_H$ of IgG4 identified as SEQ ID No: 15, wherein said sequences are operably linked together.

A number of different nucleic acid constructs encoding monovalent antibodies capable of binding different specific antigens may be generated by using the method of the invention described above and therefore examples of specific monovalent antibodies are not limited to the examples of antibodies described herein.

In one embodiment, the nucleic acid construct of the invention also comprises a nucleic acid sequence encoding the light chain of a monovalent antibody of the invention.

In one embodiment, a nucleic acid construct of the invention comprises a nucleic acid sequence encoding the $V_L$ region of a monovalent antibody of the invention.

In one embodiment, a nucleic acid construct of the invention comprises a nucleic acid sequence encoding the $C_L$ region of a monovalent antibody of the invention. In one embodiment, the $C_L$ region is the $C_L$ region of Ig light chain kappa. In one embodiment, the $C_L$ region has the sequence of SEQ ID No: 1. In another embodiment, the $C_L$ region is the $C_L$ region of Ig light chain kappa. In one embodiment, the $C_L$ region has the sequence of SEQ ID No: 3.

Such nucleic acid construct may be prepared by any known recombinant technology discussed herein, or prepared according to the procedures described in the present application in provided examples.

The nucleic acid sequence encoding the $V_L$ region of the monovalent antibody of the invention may be derived from nucleic acids encoding the $V_H$ region of any antigen specific antibody. In one embodiment, the $V_L$ region is derived from the same antibody from which the $V_H$ region of the monovalent antibody is derived from. The invention provides examples of how to make 1) a nucleic acid construct comprising the nucleic acid sequence encoding the $V_L$ of HuMab-7D8 identified as SEQ ID No: 9 and the nucleic acid sequence encoding a $C_L$ kappa of an Ig identified as SEQ ID No: 1, wherein said sequences are operably linked together, and 2) a nucleic acid construct comprising the nucleic acid sequence encoding the $V_L$ of mouse anti-Betv-1 identified as SEQ ID No: 11 and the nucleic acid sequence encoding a $C_L$ kappa of an Ig identified as SEQ ID No: 1, wherein said sequences are operably linked together.

The nucleic acids may be present in whole cells, in a cell lysate, or in a partially purified or substantially pure form.

The nucleic acid constructs of the present invention, while often in a native sequence (except for modified restriction sites and the like), from either cDNA, genomic or mixtures thereof, may be mutated in accordance with standard techniques to provide gene sequences. For coding sequences, these mutations, may affect amino acid sequence as desired. In particular, DNA sequences substantially homologous to or derived from native V, D, J, constant, switch variants and other such sequences described herein are contemplated (where "derived" indicates that a sequence is identical or modified from another sequence).

In one embodiment, the nucleic acid construct is a DNA construct. In one embodiment, the nucleic acid construct is a double-stranded DNA construct.

In one embodiment, the nucleic acid construct is a RNA construct.

In one embodiment, the monovalent antibodies of the invention are prepared by allowing a nucleic acid construct as described above to be expressed in a cell.

Thus, the invention relates to a nucleic acid construct as described above, which is an expression vector. In one embodiment, the expression vector is a prokaryotic expression vector. In one embodiment, the expression vector is a eukaryotic expression vector. In one embodiment, the expression vector is a mammalian expression vector. Examples of different expression vectors, which may be used for the purpose of the invention, are discussed elsewhere herein and particular examples are described in the Example section.

The invention provides a method of preparing a monovalent antibody of the invention comprising culturing a host cell comprising a nucleic acid construct of the invention, and, if said nucleic acid construct does not encode the light chain of said antibody, also comprising a nucleic acid construct comprising a nucleic acid sequence encoding the light chain of said antibody, so that polypeptides are expressed, and recovering the monovalent antibody from the cell culture. In one embodiment, the monovalent antibody is recovered from the cell lysate. In another embodiment, the monovalent antibody is recovered from the cell culture medium.

The invention also provides the use of a nucleic acid construct of the invention for the production of a monovalent antibody of the invention. In one embodiment, said production includes the use of a method as described in further detail below.

A monovalent antibody of the invention may thus for instance be prepared by expressing an expression vector comprising a nucleic acid sequence encoding the light chain of the antibody of the invention and an expression vector comprising a nucleic sequence encoding the heavy chain of the antibody of the invention, or an expression vector comprising both, in host cells. The host cells may be selected from any cells suitable for expression of foreign proteins, for example mammalian cells, as described elsewhere herein. The invention relates to both in vivo and in vitro expression.

For transient in vitro expression mammalian HEK293 cells may be used. In this case cells in culture are to be transfected with the expressions vectors of above by any suitable methods for cell transfection which are well-known in the art, for example a suitable cell transfection kit may be purchased from a commercial manufacturer, for example Stratagene or Invitrogene. For in vivo expression the expression vector is administered in vivo by any suitable way of administration developed for this purpose. The methods for administration of the expression vectors in vivo are also well known in the art.

Accordingly, the invention provides a host cell comprising a nucleic acid construct as described above. In one embodiment, the host cell is a prokaryotic cell. In one embodiment, the host cell is an *E. coli* cell. In another embodiment, the host cell is a eukaryotic cell. In one embodiment, the host cell is a mammalian cell. In one embodiment, the host cell is a CHO cell. In another embodiment, the host cell is a HEK-293F cell.

The invention provides a method of preparing a monovalent antibody of the invention comprising culturing a host cell of the invention, which host cell comprises a nucleic acid sequence encoding the heavy chain of said antibody and a nucleic acid sequence encoding the light chain of said antibody, so that polypeptides are expressed, and recovering the monovalent antibody from the cell culture. The invention also provides the use of a host cell of the invention for the production of a monovalent antibody of the invention. In one embodiment, said production includes the use of a method as described in further detail below. The nucleic acid sequence may be present in the same nucleic acid construct as the nucleic acid sequence encoding the heavy chain or present in a separate nucleic acid construct. In one embodiment, the monovalent antibody is recovered from the cell lysate. In another embodiment, the monovalent antibody is recovered from the cell culture medium.

The invention also provides a transgene animal comprising a nucleic acid construct as described above.

The invention provides a method for recombinant production of a monovalent antibody, said method comprising
i) providing a nucleic acid construct encoding the light chain of said monovalent antibody, said construct comprising a nucleotide sequence encoding the $V_L$ region of a selected antigen specific antibody and nucleic sequence encoding the constant ($C_L$) region of an Ig, wherein said nucleotide sequence encoding the $V_L$ region of a selected antigen specific antibody and said nucleic sequence encoding the $C_L$ region of an Ig are operably linked together;
ii) providing a nucleic acid construct encoding the heavy chain of said monovalent antibody, said construct comprising a nucleotide sequence encoding the $V_H$ region of a selected antigen specific antibody and nucleic acid encoding a $C_H$ region of a human IgG4 wherein the nucleic acid sequence encoding the heavy chain has been modified such that the region corresponding to the hinge region of the heavy chain does not comprise any amino acid residues capable of participating in the formation of disulphide bonds with other peptides comprising an identical amino acid sequence of the constant ($C_H$) region of human IgG4, wherein said nucleic acid encoding the $V_H$ region of a selected antigen specific antibody and said nucleic acid encoding the $C_H$ region of IgG4 are operably linked together;
iii) providing a cell expression system for the production of said antibody;
iv) producing said monovalent antibody by co-expressing the nucleic acid constructs of (i) and (ii) in cells of the cell expression system of (iii).

After step (iv) the monovalent antibody may be purified and formulated as desired.

In one embodiment, the nucleic acid sequence encoding the heavy chain has been modified such that the region corresponding to the hinge region of the heavy chain does not comprise any cysteine residues as described above.

In one embodiment, the nucleic acid sequence encoding the heavy chain has been modified such that at least one of the amino acid residues of the region corresponding to the hinge region, including any cysteine residues, have been deleted and/or substituted with other amino acid residues as described above.

In one embodiment, the nucleic acid sequence encoding the heavy chain has been modified such that the heavy chain comprises a $C_H$ region, wherein the amino acids corresponding to amino acids 106 and 109 of the sequence of SEQ ID No: 14 have been deleted as described above.

In one embodiment, the nucleic acid sequence encoding the heavy chain has been modified such that the heavy chain comprises a $C_H$ region, wherein at least the amino acid residues corresponding to amino acid residues 106 to 109 of the sequence of SEQ ID No: 14 has been deleted as described above.

In one embodiment, the nucleic acid sequence encoding the heavy chain has been modified such that the heavy chain comprises a $C_H$ region, wherein at least the amino acid residues corresponding to amino acid residues 99 to 110 of the sequence of SEQ ID No: 14 has been deleted as described above.

In one embodiment, the nucleic acid sequence encoding the heavy chain has been modified such that the entire hinge region has been deleted as described above.

In one embodiment, the nucleic acid construct encoding the heavy chain of said monovalent antibody comprises a nucleotide sequence encoding a $C_H$ region of a human IgG4, wherein at least one nucleotide of the splice donor site of the nucleic acid sequence encoding the hinge region has been substituted with another nucleotide as described above.

In one embodiment, the nucleic acid construct encoding the heavy chain of said monovalent antibody comprises a nucleotide sequence encoding a $C_H$ region of a human IgG4, wherein the nucleotides corresponding to the nucleotides in position 714 and 722 of the sequence of SEQ ID No: 13 has been substituted with a nucleotide different than the nucleotide present at that position in SEQ ID No: 13 as described above.

In one embodiment, the nucleic acid construct encoding the heavy chain of said monovalent antibody comprises a nucleotide sequence encoding a $C_H$ region of a human IgG4 comprising a sequence of SEQ ID No: 13, wherein nucleotides 714 and 722 of the sequence of SEQ ID No: 13 has been substituted with a nucleotide different than the nucleotide present at that position in SEQ ID No: 13 as described above.

In one embodiment, the nucleic acid construct encoding the heavy chain of said monovalent antibody comprises the nucleotide sequence of SEQ ID No: 15 as described above.

In one embodiment, the nucleic acid sequence encoding the heavy chain has been modified such that the heavy chain comprises a $C_H$ region, wherein the amino acid residues corresponding to amino acid residues 106 and 109 of the sequence of SEQ ID No: 14 has been substituted with amino acid residues different from cysteine as described above.

In one embodiment, the substituted nucleotides of the nucleic acid sequence encoding the hinge region of the $C_H$ region are substituted by using site-directed mutagenesis as described above.

In one embodiment, the nucleic acid construct encoding the light chain of said monovalent antibody comprises a sequence encoding the $C_L$ region of the kappa chain of human IgG as described above.

In one embodiment, the nucleic acid construct comprises the nucleotide sequence of SEQ ID No: 1 as described above.

In one embodiment, the nucleic acid construct encoding the light chain of said monovalent antibody comprises a sequence encoding the $C_L$ region of the lambda chain of human IgG as described above.

In one embodiment, the nucleic acid construct comprises the nucleotide sequence of SEQ ID No: 3 as described above.

In one embodiment, the nucleic acid constructs are DNA constructs as described above.

In one embodiment, the nucleic acid construct of (i), (ii), (iii) and/or (iv) is a prokaryotic expression vector as described above. In a further embodiment, the cell expression system is a prokaryotic cell expression system as described above. In a further embodiment, the prokaryotic cell expression system comprises E. coli cells as described above. In a further embodiment, the E. coli cells are of a strain deficient in endogenous protease activities as described above.

In one embodiment, the nucleic acid construct of (i), (ii), (iii) and/or (iv) is a eukaryotic expression vector as described above. In a further embodiment, the cell expression system is a eukaryotic cell expression system as described above. In a further embodiment, the cell expression system is a mammalian cell expression system as described above. In a further embodiment, the mammalian cell expression system comprises CHO cells as described above. In another further embodiment, the mammalian cell expression system comprises HEK-293F cells as described above.

The present invention also provides a monovalent antibody obtainable by use of a method of the invention.

The present invention also provides a monovalent antibody obtained by use of a method of the invention.

According to the invention, any antigen specific monovalent antibody of the invention may be made by using a method as described above.

The monovalent antibody of the present invention have numerous in vitro and in vivo diagnostic and therapeutic utilities involving the diagnosis and treatment of disorders involving cells expressing the antigen which the antibody can recognize and bind to. The invention does not relate to monovalent antibodies directed at any specific antigen, as according to the invention the monovalent antibody described in the present specification may be made against any specific antigen. The invention discloses two different monovalent antibodies, 7D8-HG (HuMab 7D8, or simply 7D8, is an anti-CD20 antibody described in WO04/035607, and HuMab 7D8-HG, or simply 7D8-HG, is the same antibody having an IgG4 heavy chain comprising a $C_H$ region consisting of an amino acid sequence with SEQ ID No: 16) and anti-Betv1-HG (anti-Betv1 is a mouse antibody expressed by clone 2H8 from reference (Akkerdaas J H et al., Allergy 50(3), 215-20 (1995)) and anti-Betv1-HG is the same antibody having an IgG4 heavy chain comprising a $C_H$ region consisting of an amino acid sequence with SEQ ID No: 16), prepared by the method described in the present application, however the invention is not restricted to these two monovalent antibodies. In one embodiment, the CD20 monovalent antibodies according to the invention are monovalent antibodies of the antibodies disclosed in WO2005/103081.

In certain pathological conditions, it is necessary and/or desirable to utilize monovalent antibodies. Also, in some instances, it is preferred that a therapeutic antibody effects its therapeutic action without involving immune system-mediated activities, such as the effector functions, ADCC, phagocytosis and CDC. In such situations, it is desirable to generate forms of antibodies in which such activities are substantially reduced or eliminated. It is also advantageous if the antibody is of a form that can be made efficiently and with high yield. The present invention provides such antibodies, which may be used for a variety of purposes, for example as therapeutics, prophylactics and diagnostics.

The specific utility of a monovalent antibody of the invention is naturally dependent on the specific target of the antibody. The selection of targets for which a monovalent antibody of the invention is a useful antibody for therapeutics, prophylactics and diagnostics may be based on the therapeutic value of administering an antibody specific for the target, or specific for a given epitope on the target (such information is abundant in the art regarding a host of different targets) and the advantages of using a stable monovalent antibody for the specific target. Such considerations are within the skills of the person skilled in the art.

A monovalent antibody of the invention may be used as an antagonist to partially or fully block the specific antigen activity in vitro, ex vivo and/or in vivo. Moreover, a monovalent antibody of the invention may neutralize antigen activity from other species due to cross-binding caused by the different antigen sharing the same epitopes. Accordingly, the monovalent antibodies of the invention may be used to inhibit a specific antigen activity, for instance in a cell culture containing the antigen, in human subjects or in other mammalian subjects having the antigen with which an antibody of the invention cross-reacts (for instance chimpanzee, baboon, marmoset, cynomolgus and rhesus, pig or mouse). In one embodiment, a monovalent antibody of the invention may be used for inhibiting antigen activities by contacting the antibody with the antigen such that antigen activity is inhibited. In one embodiment, the antigen is a human protein molecule.

In one embodiment, a monovalent antibody of the invention is specific to a ligand antigen, and inhibits the antigen activity by blocking or interfering with the ligand-receptor interaction involving the ligand antigen, thereby inhibiting the corresponding signal pathway and other molecular or cellular events.

In one embodiment, a monovalent antibody of the invention is specific to a receptor antigen, which may be activated by contact with a ligand, and inhibits the antigen activity by blocking or interfering with the ligand-receptor interaction, thereby inhibiting the corresponding signal pathway and other molecular or cellular events.

In one embodiment, a monovalent antibody of the invention is directed to CD74 and inhibits MIF-induced signaling, but lacks Fc-mediated effector functions.

The invention also features receptor-specific monovalent antibodies which do not necessarily prevent ligand binding but interfere with receptor activation, thereby inhibiting any responses that would normally be initiated by the ligand binding. The invention also encompasses monovalent antibodies that either preferably or exclusively bind to ligand-receptor complexes.

In one embodiment, a monovalent antibody of the invention may act as an agonist of a particular antigen receptor, thereby potentiating, enhancing or activating either all or partial activities of the ligand-mediated receptor activation.

In one embodiment, a monovalent antibody of the invention may prevent binding of a virus or other pathogen to its receptor, such as inhibition of HIV binding to CD4 or coreceptor such as CCR5 or CXCR4.

In one embodiment, a monovalent antibody of the invention may be used to treat, inhibit, delay progression of, prevent/delay recurrence of, ameliorate, or prevent diseases, disorders or conditions associated with abnormal expression and/or activity of one or more antigen molecules, such as including but not limited to malignant and benign tumors; non-leukemias and lymphoid malignancies; neuronal, glial, astrocytal, hypothalamic and other glandular, macrophagal, epithelial, stromal and blastocoelic disorders; and inflammatory, angiogenic and immunologic disorders.

In one embodiment, a monovalent antibody of the invention may be used to treat, such as inhibit, delay progression of, prevent/delay recurrence of, or ameliorate, or to prevent diseases, disorders or conditions such as a cancer, a cell proliferative disorder, an (auto-) immune disorder, an inflammation disorder and/or an angiogenesis disorder. This will depend on the monovalent antibody being able to, through its antigen specificity, to interfer with cell proliferation, cell growth, cell viability, apoptosis, necrosis, cell-cell interaction, cell-matrix interaction, cell signaling, cell-surface molecule expression, cell-surface molecule interactions, ligand-receptor interactions.

The present invention provides a monovalent antibody of the invention for use as a medicament.

The present invention provides a monovalent antibody of the invention for use as a medicament for treating cancer, a cell proliferative disorder, an (auto-) immune disorder, an inflammation disorder and/or an angiogenesis disorder, wherein the antibody specifically binds a given target or target epitope, where the binding of an antibody to said target or target epitope is effective in treating said disease.

The present invention provides a monovalent antibody of the invention for use as a medicament for treating a disease or disorder, which disease or disorder is treatable by blocking or inhibiting a soluble antigen, wherein multimerization (such as dimerization) of said antigen may form undesirable immune complexes, and wherein said antibody specifically binds said antigen.

The present invention provides a monovalent antibody of the invention for use as a medicament for treating a disease or disorder, which disease or disorder is treatable by administration of an antibody against a certain target, wherein the involvement of immune system-mediated activities is not necessary or is undesirable for achieving the effects of the administration of the antibody, and wherein said antibody specifically binds said antigen.

The present invention provides a monovalent antibody of the invention for use as a medicament for treating a disease or disorder, which disease or disorder is treatable by blocking or inhibiting a cell membrane bound receptor, wherein said receptor may be activated by dimerization of said receptor, and wherein said antibody specifically binds said receptor.

The present invention provides the use of a monovalent antibody of the invention as a medicament.

The present invention provides the use of a monovalent antibody of the invention as a medicament for treating cancer, a cell proliferative disorder, an (auto-) immune disorder, an inflammation disorder and/or an angiogenesis disorder, wherein the antibody specifically binds a given target or target epitope, where the binding of an antibody to said target or target epitope is effective in treating said disease.

The present invention provides the use of a monovalent antibody of the invention as a medicament for treating a disease or disorder, which disease or disorder is treatable by blocking or inhibiting a soluble antigen, wherein multimerization (such as dimerization) of said antigen may form undesirable immune complexes.

The present invention provides the use of a monovalent antibody of the invention as a medicament for treating a disease or disorder, which disease or disorder is treatable by administration of an antibody against a certain target, wherein the involvement of immune system-mediated activities is not necessary or is undesirable for achieving the effects of the administration of the antibody, and wherein said antibody specifically binds said antigen.

The present invention provides the use of a monovalent antibody of the invention as a medicament for treating a disease or disorder, which disease or disorder is treatable by blocking or inhibiting a cell membrane bound receptor, wherein said receptor may be activated by dimerization of said receptor, and wherein said antibody specifically binds said receptor.

The present invention provides the use of a monovalent antibody of the invention for the preparation of a pharmaceutical composition for treating cancer, a cell proliferative disorder, an (auto-) immune disorder, an inflammation disorder and/or an angiogenesis disorder, wherein the antibody specifically binds a given target or target epitope, where the binding of an antibody to said target or target epitope is effective in treating said disease.

The present invention provides the use of a monovalent antibody of the invention for the preparation of a pharmaceutical composition for treating a disease or disorder, which disease or disorder is treatable by blocking or inhibiting a soluble antigen, wherein multimerization (such as dimerization) of said antigen may form undesirable immune complexes.

The present invention provides the use of a monovalent antibody of the invention for the preparation of a pharmaceutical composition for treating a disease or disorder, which disease or disorder is treatable by administration of an antibody against a certain target, wherein the involvement of immune system-mediated activities is not necessary or is undesirable for achieving the effects of the administration of the antibody, and wherein said antibody specifically binds said antigen.

The present invention provides the use of a monovalent antibody of the invention for the preparation of a pharmaceutical composition for treating a disease or disorder, which disease or disorder is treatable by blocking or inhibiting a cell membrane bound receptor, wherein said receptor may be activated by dimerization of said receptor, and wherein said antibody specifically binds said receptor.

The invention provides a method of treating a disease or disorder, wherein said method comprises administering to a subject in need of treatment a monovalent antibody of the invention, a pharmaceutical composition comprising said antibody, immunoconjugate comprising said antibody, or a nucleic acid construct of the invention, whereby the disease or disorder is treated.

The invention provides a method for inhibiting an antigen in a subject suffering from a disease or disorder in which activity of the antigen is undesirable, comprising administering to a subject in need of treatment a therapeutically effective amount of a monovalent antibody of the invention, which antibody specifically binds said antigen, a pharmaceutical composition comprising said antibody, immunoconjugate comprising said antibody, or a nucleic acid construct of the invention, such that the antigen activity in the subject is inhibited.

The present invention provides a method of treating cancer, a cell proliferative disorder, an (auto)immune disorder, an inflammation disorder and/or an angiogenesis disorder, wherein said method comprises administering to a subject in need of treatment a therapeutically effective amount of a monovalent antibody of the invention, a pharmaceutical composition comprising said antibody, immunoconjugate comprising said antibody, or a nucleic acid construct of the invention, and wherein the antibody specifically binds a given target or target epitope, where the binding of an antibody to said target or target epitope is effective in treating said disease.

In one embodiment, such disease or disorder is a disease or disorder treatable by blocking or inhibiting a soluble antigen, wherein multimerization (such as dimerization) of said antigen may form undesirable immune complexes, comprising administering to a subject in need of treatment a therapeutically effective amount of a monovalent antibody of the invention directed at said antigen, a pharmaceutical composition comprising said antibody, immunoconjugate comprising said antibody, or a nucleic acid construct of the invention.

In one embodiment, such disease or disorder is a disease or disorder treatable by administration of an antibody against a certain target, wherein the involvement of immune system-mediated activities is not necessary or is undesirable for achieving the effects of the administration of the antibody, comprising administering to a subject in need of treatment a therapeutically effective amount of a monovalent antibody of the invention, which antibody specifically binds said antigen, a pharmaceutical composition comprising said antibody, immuno-conjugate comprising said antibody, or a nucleic acid construct of the invention.

In one embodiment, such disease or disorder is a disease or disorder treatable by blocking or inhibiting a cell membrane bound receptor, wherein said receptor may be activated by dimerization of said receptor, comprising administering to a subject in need of treatment a therapeutically effective amount of a monovalent antibody of the invention, which antibody specifically binds said receptor, a pharmaceutical composition comprising said antibody, immunoconjugate comprising said antibody, or a nucleic acid construct of the invention.

The scientific literature is abundant with examples of targets, where the binding of antibodies against said target, or specific epitopes of said target, is shown to have, or is expected to have, a therapeutic effect. Given the teaching of this specification and as described elsewhere herein, it is within the skill of a person skilled in the art to determine, whether the use of a monovalent antibody, such as a monovalent antibody of the present invention, against such targets would be expected to produce the therapeutic effect. In the following, several examples of such targets are given; however, these examples are not meant to be construed as limiting for the scope of the invention.

A monovalent antibody of the invention, which antibody specifically binds a soluble antigen, wherein multimerization (such as dimerization) of said antigen may form undesirable immune complexes for instance resulting in aggregation, for instance where soluble antigens consists of multiple identical subunits.

A monovalent antibody of the invention, which antibody specifically binds a receptor, which may be activated by dimerization of said receptor, may for instance be directed at cmet, FcεRI, acetyl choline receptor, fas or fasL, TRAIL, or the VEGF receptor.

In one embodiment of the invention, the disease or disorder to be treated is treatable by interference with cell activation through FcαRI, by interference with FcαRI function, by inhibition of subsequent FcαRI activated IgE mediated responses, or by binding of soluble FcαRI. In one embodiment of the invention, the monovalent antibody is directed against FcαRI and induces apoptosis of FcαRI expressing cells. In one embodiment, such disease or disorder may for instance be allergic asthma or other allergic diseases such as allergic rhinitis, seasonal/perennial allergies, hay fever, nasal allergies, atopic dermatitis, eczema, hives, urticaria, contact allergies, allergic conjunctivitis, ocular allergies, food and drug allergies, latex allergies, or insect allergies, or IgA nephropathy, such as IgA pemphigus. In one such embodiment, the monovalent antibody of the invention is directed at FcαRI. Such monovalent antibodies may also be used for in vitro or in vivo screening for FcαRI in sample or patient or in an immunotoxin or radiolabel approach to treating these diseases and disorders.

In one embodiment of the invention, the disease or disorder to be treated is treatable by downregulating Fc receptor γ-chain mediated signaling through FcεR1 or Fcγ receptors. Monomeric binding of antibody to FcαRI is known to effect such inhibition. Monovalent antibodies may thus be used to inhibit immune activation through a range of Fc receptors including Fcγ, Fcα and Fcε receptors.

In one embodiment of the invention, the disease or disorder to be treated is treatable by inhibiting, killing and/or modulating activity and/or growth (for instance proliferation) of cells expressing CD25, though direct or indirect blocking of activated T cells or cells expressing CD25. In one embodiment, such disease or disorder may for instance be

- transplant rejection, including allograft and xenograft rejection, in patients undergoing or who have undergone organ or tissue transplantation, such as heart, lung, combined heart-lung, trachea, kidney, liver, pancreas, oesophagus, bowel, skin, limb, umbilical cord, stem cell, islet cell transplantation, etc, wherein a monovalent antibody of the invention may be used as prophylactics in allograft and xenograft rejection, or be used to reverse, treat, or otherwise ameliorate acute allograft or xenograft rejection episodes,
- graft-versus-host disease, for instance blood transfusion graft-versus-host disease and bone marrow graft-versus-host disease,
- inflammatory immune or autoimmune diseases, such as rheumatoid arthritis, ankylosing spondylitis, psoriatic arthritis, type 1 diabetes, insulin-requiring type 2 diabetes, multiple sclerosis, systemic lupus erythematosus, myasthenia gravis, inflammatory bowel disease, Crohn's disease, ulcerative colitis, dermato-polymyositis, Sjögren's syndrome, arteritides, including giant cell arteritis, aplastic anemia, asthma, scleroderma, and uveitis,
- inflammatory or hyperproliferative skin disorders, for instance psoriasis, including plaque psoriasis, pustulosis palmoplantaris (PPP), erosive lichen planus, pemphigus bullosa, epidermolysis bullosa, contact dermatitis and atopic dermatitis,
- lymphoid neoplasms, for instance T cell leukemia, Hodgkin's disease, hairy cell leukemia, or cutaneous T cell lymphoma, including mycosis fungoides, and Sezary's syndrome,
- malignancies, for instance gastric cancer, esophageal cancers, malignant melanoma, colorectal cancer, pancreas cancer, breast cancer, small cell lung cancer, non-small cell lung cancer, cervical cancer, ovarian cancer, and renal cell carcinoma,
- hematological disorders, such as adult T cell leukemia/lymphoma, anaplastic large cell lymphoma, chronic lymphocytic leukemia (CLL)/small lymphocytic lymphoma (SLL), peripheral T cell lymphoma, and secondary amyloidosis,
- skin disorders, such as pyoderma gangraenosum, granuloma annulare, allergic contact dermatitis, cicatricial pemphigoid, and herpes gestationis,
- hepato-gastrointestinal disorders, such as collagen colitis, sclerosing cholangitis, chronic active hepatitis, lupoid hepatitis, autoimmune hepatitis, alcoholic hepatitis, chronic pancreatis, and acute pancreatitis,
- cardiac disorders, such as myocarditis and pericarditis,
- vascular disorders, such as arteriosclerosis, giant cell arteritis/polymyalgia rheumatica, Takayasu arteritis, polyarteritis nodosa, Kawasaki syndrome, Wegener's granulomatosis, microscopic polyangiitis, Churg-Strauss syndrome, leukocytoclastic angiitis, and secondary leukocytoclastic vasculitis,
- renal disorders, such as acute glomerulonphritis, chronic glomerulonephritis, minimal change nephritis, and Goodpasture's syndrome,
- pulmonary disorders, such as alveolitis, bronchiolitis obliterans, silicosis, and berylliosis,
- neurological disorders, such as multiple sclerosis, Alzheimer's disease, myasthenia gravis, chronic demyelinating polyneuropathy, and polyradiculitis including Guillain-Barré syndrome, I
- connective tissue disorders, such as relapsing polychondritis, sarcoidosis, systemic lupus erythematosus, CNS lupus, discoid lupus, lupus nephritis, chronic fatigue syndrome, and fibromyalgia,
- endocrinological disorders, such as Graves' disease, Hashimoto's thyroiditis, and subacute thyroiditis, or
- viral infections, such as HIV-1/AIDS and tropical spastic paraparesis.

In one such embodiment, the monovalent antibody of the invention is directed at CD25. Such monovalent antibodies may also be used for in vitro or in vivo screening for CD25 in sample or patient or in an immunotoxin or radiolabel approach to treating these diseases and disorders.

In one embodiment of the invention, the disease or disorder to be treated is treatable by antagonizing and/or inhibiting IL-15 or IL5 receptor functions. In one embodiment, such disease or disorder may for instance be arthritides, gout, connective, neurological, gastrointestinal, hepatic, allergic, hematologic, skin, pulmonary, malignant, endocrinological, vascular, infectious, kidney, cardiac, circulatory, metabolic, bone, and muscle disorders. In one such embodiment, the monovalent antibody of the invention is directed at IL-15. Such monovalent antibodies may also be used for in vitro or in vivo screening for IL-15 in a sample or patient or in an immunotoxin or radiolabel approach to treating these diseases and disorders.

In one embodiment of the invention, the disease or disorder to be treated is treatable by preventing IL-8 binding to its receptor, or by blocking IL-8 function. In one embodiment, such disease or disorder may for instance be

- palmoplantar pustulosis (PPP), psoriasis, or other skin diseases,
- inflammatory, autoimmune and immune disorders, such as psoriatic arthritis, systemic scleroderma and sclerosis, inflammatory bowel disease (IBD), Crohn's disease, ulcerative colitis, acute lung injury, such as acute respiratory distress syndrome or adult respiratory distress syndrome, meningitis, encephalitis, uveitis, multiple myeloma, glomerulonephritis, nephritis, asthma, atherosclerosis, leukocyte adhesion deficiency, multiple sclerosis, Raynaud's syndrome, Sjögren's syndrome, juvenile onset diabetes, Reiter's disease, Behcet's disease, immune complex nephritis, IgA nephropathy, IgM polyneuropathies, immune-mediated thrombocytopenias, such as acute idiopathic thrombocytopenic purpura and chronic idiopathic thrombocytopenic purpura, hemolytic anemia, myasthenia gravis, lupus nephritis, lupus erythematosus, rheumatoid arthritis (RA), ankylosing spondylitis, pemphigus, Graves' disease, Hashimoto's thyroiditis, small vessel vasculitides, such as Wegener's granulomatosis, Omen's syndrome, chronic renal failure, autoimmune thyroid disease, acute infectious mononucleosis, HIV, herpes virus associated diseases, human virus infections, such as common cold as caused by human rhinovirus, coronavirus, other enterovirus, herpes virus, influenza virus, parainfluenza virus, respiratory syncytial virus or adenovirus infection, bacteria pneumonia, wounds, sepsis, cerebral stroke/cerebral edema, ischaemia-reperfusion injury and hepatitis C,
- alcoholic hepatitis and acute pancreatitis,
- diseases involving IL-8 mediated angiogenesis, such as tumors and cancers, for instance melanoma, thyroid carcinoma, transitional cell carcinoma, trichilemmona, squamous cell carcinoma and breast cancer.

In one such embodiment, the monovalent antibody of the invention is directed at IL-8. Such monovalent antibodies may also be used for in vitro or in vivo screening for IL-8 in a sample or patient or in an immunotoxin or radiolabel approach to treating these diseases and disorders.

In one embodiment of the invention, the disease or disorder to be treated is treatable by interfering with CD20 activity, by depleting B cells, interfering with B cell growth and/or proliferation through for instance an immunotoxin or radiolabel approach. In one embodiment, such disease or disorder may for instance be rheumatoid arthritis, (auto) immune and inflammatory disorders (as described above for IL-8 related diseases and disorders), non-Hodgkin's lymphoma, B-CLL, lymphoid neoplasms, malignancies and hematological disorders, infectious diseases and connective, neurological, gastrointestinal, hepatic, allergic, hematologic, skin, pulmonary, malignant, endocrinological, vascular, infectious, kidney, cardiac, circulatory, metabolic, bone and muscle disorders, and immune mediated cytopenia.

In one such embodiment, the monovalent antibody of the invention is directed at CD20. Such monovalent antibodies may also be used for in vitro or in vivo screening for CD20 in a sample or patient.

In one embodiment of the invention, the disease or disorder to be treated is treatable by interfering with CD38 activity, by depleting CD38 expressing cells, interfering with $CD38^+$ cell growth and/or proliferation through for instance an immunotoxin or radiolabel approach. In one embodiment, such disease or disorder may for instance be tumorigenic disorders, such as B cell lymphoma, plasma cell malignancies, T/NK cell lymphoma and myeloid malignancies, immune disorders in which CD38 expressing B cells, plasma cells, monocytes and T cells are involved, such as autoimmune disorders, such as psoriasis, psoriatic arthritis, dermatitis, systemic scleroderma and sclerosis, inflammatory bowel disease (IBD), Crohn's disease, ulcerative colitis, respiratory distress syndrome, meningitis, encephalitis, uveitis, glomerulonephritis, eczema, asthma, atherosclerosis, leukocyte adhesion deficiency, multiple sclerosis, Raynaud's syndrome, Sjögren's syndrome, juvenile onset diabetes, Reiter's disease, Behçet's disease, immune complex nephritis, IgA nephropathy, IgM polyneuropathies, immune-mediated thrombocytopenias, such as acute idiopathic thrombocytopenic purpura and chronic idiopathic thrombocytopenic purpura, hemolytic anemia, myasthenia gravis, lupus nephritis, systemic lupus erythematosus, rheumatoid arthritis (RA), atopic dermatitis, pemphigus, Graves' disease, Hashimoto's thyroiditis, Wegener's granulomatosis, Omenn's syndrome, chronic renal failure, acute infectious mononucleosis, HIV, and herpes virus associated diseases, acute respiratory distress syndrome and choreoretinitis, diseases and disorders such as those caused by or mediated by infection of B-cells with virus, such as Epstein-Barr virus (EBV), rheumatoid arthritis, inflammatory, immune and/or autoimmune disorders in which autoantibodies and/or excessive B and T lymphocyte activity are prominent, such as vasculitides and other vessel disorders, such as microscopic polyangiitis, Churg-Strauss syndrome, and other ANCA-associated vasculitides, polyarteritis nodosa, essential cryoglobulinaemic vasculitis, cutaneous leukocytoclastic angiitis, Kawasaki disease, Takayasu arteritis, giant cell arthritis, Henoch-Schönlein purpura, primary or isolated cerebral angiitis, erythema nodosum, thrombangiitis obliterans, thrombotic thrombocytopenic purpura (including hemolytic uremic syndrome), and secondary vasculitides, including cutaneous leukocytoclastic vasculitis (e.g., secondary to hepatitis B, hepatitis C, Waldenström's macroglobulinemia, B-cell neoplasias, rheumatoid arthritis, Sjögren's syndrome, or systemic lupus erythematosus); further examples are erythema nodosum, allergic vasculitis, panniculitis, Weber-Christian disease, purpura hyperglobulinaemica, and Buerger's disease, skin disorders, such as contact dermatitis, linear IgA dermatosis, vitiligo, pyoderma gangrenosum, epidermolysis bullosa acquisita, pemphigus vulgaris (including cicatricial pemphigoid and bullous pemphigoid), alopecia areata (including alopecia universalis and alopecia totalis), dermatitis herpetiformis, erythema multiforme, and chronic autoimmune urticaria (including angioneurotic edema and urticarial vasculitis), immune-mediated cytopenias, such as autoimmune neutropenia, and pure red cell aplasia, connective tissue disorders, such as CNS lupus, discoid lupus erythematosus, CREST syndrome, mixed connective tissue disease, polymyositis/dermatomyositis, inclusion body myositis, secondary amyloidosis, cryoglobulinemia type I and type II, fibromyalgia, phospholipid antibody syndrome, secondary hemophilia, relapsing polychondritis, sarcoidosis, stiff man syndrome, and rheumatic fever; a further example is eosinophil fasciitis, arthritides, such as ankylosing spondylitis, juvenile chronic arthritis, adult Still's disease, and SAPHO syndrome; further examples are sacroileitis, reactive arthritis, Still's disease, and gout, hematologic disorders, such as aplastic anemia, primary hemolytic anemia (including cold agglutinin syndrome), hemolytic anemia secondary to CLL or systemic lupus erythematosus; POEMS syndrome, pernicious anemia, and Waldemström's purpura hyperglobulinaemica; further examples are agranulocytosis, autoimmune neutropenia, Franklin's disease, Seligmann's disease, -chain disease, paraneoplastic syndrome secondary to thymoma and lymphomas, and factor VIII inhibitor formation, endocrinopathies, such as polyendocrinopathy, and Addison's disease; further examples are autoimmune hypoglycemia, autoimmune hypothyroidism, autoimmune insulin syndrome, de Quervain's thyroiditis, and insulin receptor antibody-mediated insulin resistance;

hepato-gastrointestinal disorders, such as celiac disease, Whipple's disease, primary biliary cirrhosis, chronic active hepatitis, and primary sclerosing cholangiitis; a further example is autoimmune gastritis, nephropathies, such as rapid progressive glomerulonephritis, post-streptococcal nephritis, Goodpasture's syndrome, membranous glomerulonephritis, and cryoglobulinemic nephritis; a further example is minimal change disease, neurological disorders, such as autoimmune neuropathies, mononeuritis multiplex, Lambert-Eaton's myasthenic syndrome, Sydenham's chorea, tabes dorsalis, and Guillain-Barré's syndrome; further examples are myelopathy/tropical spastic paraparesis, myasthenia gravis, acute inflammatory demyelinating polyneuropathy, and chronic inflammatory demyelinating polyneuropathy; multiple sclerosis, HIV-induced dementia.

cardiac and pulmonary disorders, such as COPD, fibrosing alveolitis, bronchiolitis obliterans, allergic aspergillosis, cystic fibrosis, Löffler's syndrome, myocarditis, and pericarditis; further examples are hypersensitivity pneumonitis, and paraneoplastic syndrome secondary to lung cancer, allergic disorders, such as bronchial asthma and hyper-IgE syndrome; a further example is amaurosis fugax, ophthalmologic disorders, such as idiopathic chorioretinitis, infectious diseases, such as parvovirus B infection (including hands-and-socks syndrome), gynecological-obstretical disorders, such as recurrent abortion, recurrent fetal loss, and intrauterine growth retardation; a further example is paraneoplastic syndrome secondary to gynecological neoplasms, male reproductive disorders, such as paraneoplastic syndrome secondary to testicular neoplasms; and transplantation-derived disorders, such as allograft and xenograft rejection, and graft-versus-host disease.

In one such embodiment, the monovalent antibody of the invention is directed at CD38. Such monovalent antibodies may also be used for in vitro or in vivo screening for CD38 in a sample or patient.

In one embodiment of the invention, the disease or disorder to be treated is treatable by blocking ligand-EGFr interaction, blocking EGFr function, depletion of EGFr expressing cells/interference with EGFr+ cell growth and/or proliferation through for instance an immunotoxin or radiolabel approach. In one embodiment, such disease or disorder may for instance be cancers (over)expressing EGFr, such as bladder, breast, colon, kidney, ovarian, prostate, renal cell, squamous cell, lung (non-small cell), and head and neck cancer, and glioma, other EGFr related diseases, such as autoimmune diseases, psoriasis, inflammatory arthritis.

In one such embodiment, the monovalent antibody of the invention is directed at EGFr. Such monovalent antibodies may also be used for in vitro or in vivo screening for EGFr in a sample or patient.

In one embodiment of the invention, the disease or disorder to be treated is treatable by interfering with CD4 function, depletion of CD4 expressing cells/interference with CD4+ cell growth and/or proliferation through for instance an immunotoxin or radiolabel approach. In one embodiment, such disease or disorder may for instance be rheumatoid arthritis, (auto)immune and inflammatory disorders (as described above for IL-8 related diseases and disorders), cutaneous T cell lymphomas, non-cutaneous T cell lymphomas, lymphoid neoplasms, malignancies and hematological disorders, infectious diseases, and connective, neurological, gastrointestinal, hepatic, allergic, hematologic, skin, pulmonary, malignant, endocrinological, vascular, infectious, kidney, cardiac, circulatory, metabolic, bone, and muscle disorders, and immune mediated cytopenia.

In one such embodiment, the monovalent antibody of the invention is directed at CD4. Such monovalent antibodies may also be used for in vitro or in vivo screening for CD4 in a sample or patient.

In one embodiment of the invention, a monovalent antibody directed at CD4 is used for treatment of HIV infection, or for the treatment of AIDS.

In one embodiment of the invention, the monovalent antibodies of the invention are monovalent antibodies of the CD4 antibodies disclosed in WO97/13852.

In one embodiment of the invention, the disease or disorder to be treated is treatable by antagonizing and/or inhibiting CD28 functions, such as preventing of co-stimulatory signals needed in T cell activation. In one embodiment, such disease or disorder may for instance be an inflammatory, autoimmune and immune disorder as indicated above. In one such embodiment, the monovalent antibody of the invention is directed at CD28.

In one embodiment of the invention, the disease or disorder to be treated is treatable by altering Tissue Factor functions, such as altering coagulation or inhibition of tissue factor signalling. In one embodiment, such disease or disorder may for instance be vascular diseases, such as myocardial vascular disease, cerebral vascular disease, retinopathia and macular degeneration, and inflammatory disorders as indicated above.

In one embodiment of the invention, the monovalent antibodies are directed at Tissue factor, or at a complex of Factor VII and Tissue Factor.

In one embodiment of the invention, the disease or disorder to be treated is treatable by interfering with Hepatitis C Virus (HCV) infection. In one such embodiment, the monovalent antibody of the invention is directed at HCV or an HCV receptor such as CD81.

In one embodiment of the invention, the monovalent antibody is a monovalent antibody according to the invention of an antibody as disclosed in WO2000/05266.

In one embodiment of the invention, the disease or disorder to be treated is treatable by prevention of binding of allergen to IgE-sensitized on mast cell. In one embodiment, such disease or disorder may for instance be allergen-immunotherapy of allergic diseases such as asthma, allergic rhinitis, seasonal/perennial allergies, hay fever, nasal allergies, atopic dermatitis, eczema, hives, urticaria, contact allergies, allergic conjunctivitis, ocular allergies, food and drug allergies, latex allergies, and insect allergies.

In one such embodiment, the monovalent antibody(s) of the invention are IgG4 hingeless antibodies directed towards allergen(s).

In certain embodiments, an immunoconjugate comprising a monovalent antibody conjugated with a cytotoxic agent is administered to the patient. In some embodiments, the immunoconjugate and/or antigen to which it is bound is/are internalized by the cell, resulting in increased therapeutic efficacy of the immunoconjugate in killing the target cell to which it binds. In one embodiment, the cytotoxic agent targets or interferes with nucleic acid in the target cell.

Examples of such cytotoxic agents include any of the chemotherapeutic agents noted herein (such as a maytansinoid or a calicheamicin), a radioactive isotope, or a ribonuclease or a DNA endonuclease.

In one embodiment, the antigen is a human protein molecule and the subject is a human subject. In one embodiment, the subject may be a non-human mammal expressing the antigen with which an antibody of the invention binds. In one embodiment, the subject may be a mammal into which the antigen has been introduced (for instance by administration of the antigen or by expression of an, antigen transgene). Moreover, a monovalent antibody of the invention may be administered to a non-human mammal expressing an antigen with which the immunoglobulin cross-reacts (for instance a primate, pig or mouse) for veterinary purposes or as an animal model of human disease. Regarding the latter, such animal models may be useful for evaluating the therapeutic efficacy of antibodies of the invention (for instance testing of dosages and time courses of administration).

Monovalent antibodies of the invention may be used either alone or in combination with other compositions in a therapy. For instance, a monovalent antibody of the invention may be co-administered with one or more other antibodies, such as monovalent antibodies of the present invention, one or more chemotherapeutic agent(s) (including cocktails of chemotherapeutic agents), one or more other cytotoxic agent(s), one or more anti-angiogenic agent(s), one or more cytokines, one or more growth inhibitory agent(s), one or more anti-inflammatory agent(s), one or more disease modifying antirheumatic drug(s) (DMARD), or one or more immunosuppressive agent(s), depending on the disease or condition to be treated. Where a monovalent antibody of the invention inhibits tumor growth, it may be particularly desirable to combine it with one or more other therapeutic agent(s) which also inhibits tumor growth. For instance, anti-VEGF antibodies blocking VEGF activities may be combined with anti-ErbB antibodies (for instance Trastuzumab (Herceptin), an anti-HER2 antibody) in a treatment of metastatic breast cancer. Alternatively, or additionally, the patient may receive combined radiation therapy (for instance external beam irradiation or therapy with a radioactive labeled agent, such as an antibody). Such combined therapies noted above include combined administration (where the two or more agents are included in the same or separate formulations), and separate administration, in which case, administration of the antibody of the invention may occur prior to, and/or following, administration of the adjunct therapy or therapies.

In one embodiment, the monovalent antibody of the invention is a monovalent form of Trastuzumab, for treatment of Her2 positive cancer.

A monovalent antibody composition of the invention may be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. In one embodiment, the monovalent antibody may be formulated with one or more agents currently used to prevent or treat the disorder in question. The effective amount of such other agents depends on the amount of monovalent antibodies of the invention present in the formulation, the type of disorder or treatment, and other factors discussed above.

The monovalent antibody of the invention (and adjunct therapeutic agent) may be administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the monovalent antibody may be suitably administered by pulse infusion, particularly with declining doses of the monovalent antibody. Dosing may be by any suitable route, for instance by injections, such as intravenous or subcutaneous injections, depending in part on whether the administration is brief or chronic.

For the prevention or treatment of disease, the appropriate dosage of a monovalent antibody of the invention (when used alone or in combination with other agents such as chemotherapeutic agents) will depend on the type of disease to be treated, the type of antibody, the severity and course of the disease, whether the monovalent antibody is administered for preventive, therapeutic or diagnostic purposes, previous therapy, the patient's clinical history and response to the antibody, and the discretion of the attending physician.

The monovalent antibody may be suitably administered to the patient at one time or over a series of treatments.

Such dosages may be administered intermittently, for instance every week or every three weeks (for instance such that the patient receives from about two to about twenty, for instance about six doses of the monovalent antibody). An initial higher loading dose, followed by one or more lower doses may be administered. An exemplary dosing regimen comprises administering an initial loading dose of about 4 mg/kg, followed by a weekly maintenance dose of about 2 mg/kg of the monovalent antibody. However, other dosage regimens may be useful. In one embodiment, the monovalent antibodies of the invention are administered in a weekly dosage of from 50 mg to 4000 mg, for instance of from 250 mg to 2000 mg, such as for example 300 mg, 500 mg, 700 mg, 1000 mg, 1500 mg or 2000 mg, for up to 8 times, such as from 4 to 6 times. The weekly dosage may be divided into two or three subdosages and administered over more than one day. For example, a dosage of 300 mg may be administered over 2 days with 100 mg on day one (1), and 200 mg on day two (2). A dosage of 500 mg may be administered over 3 days with 100 mg on day one (1), 200 mg on day two (2), and 200 mg on day three (3), and a dosage of 700 mg may be administered over 3 days with 100 mg on day 1 (one), 300 mg on day 2 (two), and 300 mg on day 3 (three). The regimen may be repeated one or more times as necessary, for example, after 6 months or 12 months.

The dosage may be determined or adjusted by measuring the amount of circulating monovalent antibodies of the invention upon administration in a biological sample for instance by using anti-idiotypic antibodies which target said monovalent antibodies.

In one embodiment, the monovalent antibodies of the invention may be administered by maintenance therapy, such as, for instance once a week for a period of 6 months or more.

In one embodiment, the monovalent antibodies of the invention may be administered by a regimen including one infusion of a monovalent antibody of the invention followed by an infusion of same monovalent antibody conjugated to a radioisotope. The regimen may be repeated, for instance 7 to 9 days later.

The progress of this therapy may be monitored by conventional techniques and assays.

The invention provides an article of manufacture containing materials useful for the treatment, prevention and/or diagnosis of the disorders described above. An article of manufacture of the present invention comprises a container and a label or package insert on or associated with the container. Suitable containers include, for example, bottles, vials, syringes, etc. The containers may be formed from a variety of materials such as glass or plastic. The container holds a composition which is by itself or when combined with other compositions effective for treating, preventing and/or diagnosing the condition and may have a sterile access port (for example the container may be an intravenous solution bag or a vial having a stopper pierceable by a hypodermic injection needle). At least one active agent in the composition is a monovalent antibody of the invention. The label or package insert indicates that the composition is used for treating the condition of choice, for instance cancer. Moreover, the article of manufacture may comprise (a) a first container with a composition contained therein, wherein the composition comprises a monovalent antibody of the invention; and (b) a second container with a composition contained therein, wherein the composition comprises a further cytotoxic agent. The article of manufacture in this embodiment of the invention may further comprise a package insert indicating that the first and second composition may be used to treat a particular condition, for instance cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Also within the scope of the present invention are kits comprising pharmaceutical compositions of the invention comprising one or more monovalent antibodies of the invention and instructions for use. The kit may further comprise one or more additional agents, such as an immunosuppressive reagent, a cytotoxic agent or a radiotoxic agent, depending on the disease or disorder to be treated, or one or more additional monovalent antibodies of the invention (for instance a monovalent antibody having a complementary activity).

In one embodiment, the invention provides methods for detecting the presence of the specific antigen to which the monovalent antibody binds, in a sample, or measuring the amount of said specific antigen, comprising contacting the sample, and a control sample, with a monovalent antibody, which specifically binds to said antigen, under conditions that allow for formation of a complex between the antibody or portion thereof and said antigen. The formation of a complex is then detected, wherein a difference complex formation between the sample compared to the control sample is indicative the presence of said antigen in the sample.

In one embodiment, monovalent antibodies of the invention may be used to detect levels of circulating specific antigen to which the monovalent antibody binds, or levels of cells which contain said specific antigen, on their membrane surface, which levels may then be linked to certain disease symptoms. Alternatively, the antibodies may be used to deplete or interact with the function of cells expressing said antigen, thereby implicating these cells as important mediators of the disease. This may be achieved by contacting a sample and a control sample with the monovalent antibody under conditions that allow for the formation of a complex between the antibody and said specific antigen. Any complexes formed between the antibody and said antigen are detected and compared in the sample and the control.

In one embodiment, the invention provides a method for detecting the presence or quantifying, in vivo or in vitro, the amount of cells expressing the specific antigen to which the monovalent antibody binds. The method comprises (i) administering to a subject a monovalent antibody of the invention conjugated to a detectable marker; (ii) exposing the subject to a means for detecting said detectable marker to identify areas containing cells expressing said antigen.

In one embodiment, monovalent antibodies of the invention may be used to target compounds (for instance therapeutic agents, labels, cytotoxins, radiotoxins immunosuppressants, etc.) to cells which have the specific antigen to which the monovalent antibody binds, expressed on their surface by linking such compounds to the monovalent antibody. Thus, the invention also provides methods for localizing ex vivo or in vitro cells expressing said antigen, such as Reed-Sternberg cells (for instance with a detectable label, such as a radioisotope, a fluorescent compound, an enzyme, or an enzyme co-factor).

The following is a list of selected embodiments of the present invention.

Embodiment 1

A method for producing a monovalent antibody, said method comprising
i) providing a nucleic acid construct encoding the light chain of said monovalent antibody, said construct comprising a nucleotide sequence encoding the $V_L$ region of a selected antigen specific antibody and nucleotide sequence encoding the constant $C_L$ region of an Ig, wherein said nucleotide sequence encoding the $V_L$ region of a selected antigen specific antibody and said nucleotide sequence encoding the $C_L$ region of an Ig are operably linked together, and wherein, in case of an IgG1 subtype, the nucleotide sequence encoding the $C_L$ region has been modified such that the $C_L$ region does not contain any amino acids capable of forming disulfide bonds or covalently bind with other peptides comprising an identical amino acid sequence of the $C_L$ region;
ii) providing a nucleic acid construct encoding the heavy chain of said monovalent antibody, said construct comprising a nucleotide sequence encoding the $V_H$ region of a selected antigen specific antibody and a nucleotide sequence encoding a constant $C_H$ region of a human Ig wherein the nucleotide sequence encoding the $C_H$ region has been modified such that the region corresponding to the hinge region and, as required by the Ig subtype, other regions of the $C_H$ region, such as the $C_H3$ region, does not comprise any amino acid residues which participate in the formation of disulphide bonds or covalent or non-covalent inter-heavy chain bonds with other peptides comprising an identical amino acid sequence of the $C_H$ region of the human Ig, wherein said nucleotide sequence encoding the $V_H$ region of a selected antigen specific antibody and said nucleotide sequence encoding the $C_H$ region of said Ig are operably linked together;
iii) providing a cell expression system for the producing said antibody;
iv) producing said monovalent antibody by co-expressing the nucleic acid constructs of (i) and (ii) in cells of the cell expression system of (iii).

Embodiment 2

A method according to embodiment 1, wherein the human Ig is an IgG1, IgG2, IgG3, IgG4 or IgA or IgD antibody, such as an IgG1, IgG2 or IgG4 antibody.

Embodiment 3

A method according to embodiment 1, wherein the human Ig is an IgG1 having the amino acid $C_H$ region as set forth in SEQ ID NO: 19, wherein the $C_H3$ region has been modified so that one or more of the following amino acid substitutions have been made: Arg (R) in position 238 has been replaced by Gln (Q); Asp (D) in position 239 has been replaced by Glu (E); Lys (K) in position 292 has been replaced by Arg (R); Gln (Q) in position 302 has been replaced by Glu (E); and Pro (P) in position 328 has been replaced by Leu (L).

Embodiment 4

A method according to embodiment 3, wherein Arg (R) in position 238 has been replaced by Gln (Q).

Embodiment 5

A method according to embodiment 3, wherein Arg (R) in position 238 has been replaced by Gln (Q), and Pro (P) in position 328 has been replaced by Leu (L).

Embodiment 6

A method according to embodiment 3, wherein all five substitutions have been made.

Embodiment 7

A method according to embodiment 1 or 3, wherein the human Ig is an IgG1, and the $C_L$ region is a kappa light chain $C_L$ having the amino acid sequence as set forth in SEQ ID NO: 18, wherein the $C_L$ region has been modified so that the terminal cysteine residue in position 106 has been replaced with another amino acid residue or deleted. In one embodiment it has been deleted.

Embodiment 8

A method according to embodiment 1 or 3, wherein the human Ig is an IgG1, and the $C_L$ region is a lambda light chain $C_L$ having the amino acid sequence as set forth in SEQ ID NO: 17, wherein the $C_L$ region has been modified so that the cysteine residue in position 104 has been replaced with another amino acid residue or deleted. In one embodiment it has been deleted.

Embodiment 9

A method according to embodiment 1, 3, 7 or 8, wherein the human Ig is an IgG1 having the amino acid $C_H$ region as set forth in SEQ ID NO: 19, wherein the $C_H1$ region has been modified so that Ser (S) in position 14 has been replaced by a cysteine residue.

Embodiment 10

A method according to embodiment 1, wherein the human Ig is an IgG2 having the amino acid $C_H$ region as set forth in SEQ ID NO: 20, wherein the $C_H3$ region has been modified so that one or more of the of the following amino acid substitutions have been made: Arg (R) in position 234 has been replaced by Gln (Q); Met (M) in position 276 has been replaced by Val (V); Lys (K) in position 288 has been replaced by Arg (R); Gln (Q) in position 298 has been replaced by Glu (E); and Pro (P) in position 324 has been replaced by Leu (L).

Embodiment 11

A method according to embodiment 10, wherein Arg (R) in position 234 has been replaced by Gln (Q).

Embodiment 12

A method according to embodiment 10, wherein Arg (R) in position 234 has been replaced by Gln (Q); and Pro (P) in position 324 has been replaced by Leu (L).

Embodiment 13

A method according to embodiment 10, wherein all five substitutions have been made.

Embodiment 14

A method according to embodiment 1, wherein the human Ig is an IgG3 having the amino acid $C_H$ region as set forth in SEQ ID NO: 21, wherein the $C_H3$ region has been modified so that one or more of the of the following amino acid substitutions have been made: Arg (R) in position 285 has been replaced by Gln (Q); Ser (S) in position 314 has been replaced by Asn (N); Asn (N) in position 322 has been replaced by Lys (K); Met (M) in position 327 has been replaced by Val (V); Lys (K) in position 339 has been replaced by Arg (R); Gln (Q) in position 349 has been replaced by Glu (E); Ile (I) in position 352 has been replaced by Val (V); Arg (R) in position 365 has been replaced by His (H); Phe (F) in position 366 has been replaced by Tyr (Y); and Pro (P) in position 375 has been replaced by Leu (L).

Embodiment 15

A method according to embodiment 14, wherein Arg (R) in position 285 has been replaced by Gln (Q).

Embodiment 16

A method according to embodiment 14, wherein Arg (R) in position 285 has been replaced by Gln (Q); and Pro (P) in position 375 has been replaced by Leu (L).

Embodiment 17

A method according to embodiment 14, wherein all 10 substitutions have been made.

Embodiment 18

A method for producing a monovalent antibody, said method comprising
i) providing a nucleic acid construct encoding the light chain of said monovalent antibody, said construct comprising a nucleotide sequence encoding the $V_L$ region of a selected antigen specific antibody and nucleic sequence encoding the constant ($C_L$) region of an Ig, wherein said nucleotide sequence encoding the $V_L$ region of a selected antigen specific antibody and said nucleic sequence encoding the $C_L$ region of an Ig are operably linked together;
ii) providing a nucleic acid construct encoding the heavy chain of said monovalent antibody, said construct comprising a nucleotide sequence encoding the $V_H$ region of a selected antigen specific antibody and nucleic acid encoding a $C_H$ region of a human IgG4 wherein the nucleic acid sequence encoding the heavy chain has been modified such that the region corresponding to the hinge region of the heavy chain does not comprise any amino acid residues capable of participating in the formation of disulphide bonds with other peptides comprising an identical amino acid sequence of the constant ($C_H$) region of human IgG4, wherein said nucleic acid encoding the $V_H$ region of a selected antigen specific antibody and said nucleic acid encoding the $C_H$ region of IgG4 are operably linked together;

iii) providing a cell expression system for the producing said antibody;
iv) producing said monovalent antibody by co-expressing the nucleic acid constructs of (i) and (ii) in cells of the cell expression system of (iii).

Embodiment 19

A method according to any one of embodiments 1 to 18, wherein the nucleic acid sequence encoding the heavy chain has been modified such that the region corresponding to the hinge region of the heavy chain does not comprise any cysteine residues.

Embodiment 20

A method according to any one of embodiments 1 to 19, wherein the monovalent antibody produced is a human antibody.

Embodiment 21

A method according to any one of embodiments 1 to 20, wherein the monovalent antibody produced does not bind to the synthetic antigen (Tyr, Glu)-Ala-Lys.

Embodiment 22

A method according to any one of embodiments 1 to 21, wherein the nucleic acid sequence encoding the heavy chain has been modified such that at least one of the amino acid residues of the region corresponding to the hinge region, including any cysteine residues, have been deleted and/or substituted with other amino acid residues.

Embodiment 23

A method according to embodiment 22, wherein the nucleic acid sequence encoding the heavy chain has been modified such that the cysteine residues of the hinge region have been substituted with amino acid residues that have an uncharged polar side chain, or a non polar side chain.

Embodiment 24

A method according to embodiment 22 or 23, wherein the amino acids with uncharged polar side chains are independently selected from glycine, asparagine, glutamine, serine, threonine, tyrosine, tryptophan, and the amino acid with the nonpolar side chain are independently selected from alanine, valine, leucine, isoleucine, proline, phenylalanine, methionine.

Embodiment 25

A method according to embodiment 22, wherein the nucleic acid sequence encoding the heavy chain has been modified such that the heavy chain comprises a IgG4 $C_H$ region, wherein the amino acids corresponding to amino acids 106 and 109 of the sequence of SEQ ID No: 14 have been deleted.

Embodiment 26

A method according to embodiment 22 or embodiment 25, wherein the nucleic acid sequence encoding the heavy chain has been modified such that the heavy chain comprises a IgG4 $C_H$ region, wherein at least the amino acid residues corresponding to amino acid residues 106 to 109 of the sequence of SEQ ID No: 14 has been deleted.

Embodiment 27

A method according to any of embodiments 22 to 26, wherein the nucleic acid sequence encoding the heavy chain has been modified such that the heavy chain comprises a $C_H$ region, wherein at least the amino acid residues corresponding to amino acid residues 99 to 110 of the sequence of SEQ ID No: 14 has been deleted.

Embodiment 28

A method according to any of embodiments 22 to 27, wherein the nucleic acid sequence encoding the heavy chain has been modified such that the entire hinge region has been deleted.

Embodiment 29

A method according to any of embodiments 1 to 28, wherein the nucleic acid construct encoding the heavy chain of said monovalent antibody comprises a nucleotide sequence encoding a $C_H$ region of a human IgG4, wherein at least one nucleotide of the splice donor site of the nucleic acid sequence encoding the hinge region has been substituted with another nucleotide.

Embodiment 30

A method according to embodiment 29, wherein the nucleic acid construct encoding the heavy chain of said monovalent antibody comprises a nucleotide sequence encoding a $C_H$ region of a human IgG4, wherein the nucleotides corresponding to the nucleotides in position 714 and 722 of the sequence of SEQ ID No: 13 has been substituted with a nucleotide different than the nucleotide present at that position in SEQ ID No: 13.

Embodiment 31

A method according to embodiment 30, wherein the nucleic acid construct encoding the heavy chain of said monovalent antibody comprises a nucleotide sequence encoding a $C_H$ region of a human IgG4 comprising a sequence of SEQ ID No: 13, wherein nucleotides 714 and 722 of the sequence of SEQ ID No: 13 has been substituted with a nucleotide different than the nucleotide present at that position in SEQ ID No: 13.

Embodiment 32

A method according to embodiment 31, wherein the nucleic acid construct encoding the heavy chain of said monovalent antibody comprises the nucleotide sequence of SEQ ID No: 15.

Embodiment 33

A method according to embodiment 22, wherein the nucleic acid sequence encoding the heavy chain has been modified such that the heavy chain comprises a $C_H$ region, wherein the amino acid residues corresponding to amino acid residues 106 and 109 of the sequence of SEQ ID No: 14 has been substituted with amino acid residues different from cysteine.

Embodiment 34

A method according to any of embodiments 29 to 33, wherein the substituted nucleotides of the nucleic acid sequence encoding the hinge region of the $C_H$ region are substituted by using site-directed mutagenesis.

Embodiment 35

A method according to any of embodiments 1 to 34, wherein the nucleic acid construct encoding the light chain of said monovalent antibody comprises a sequence encoding the $C_L$ region of the kappa chain of human IgG.

Embodiment 36

A method according to embodiment 35, wherein the nucleic acid construct comprises the nucleotide sequence of SEQ ID No: 1.

Embodiment 37

A method according to any of embodiments 1 to 34, wherein the nucleic acid construct encoding the light chain of said monovalent antibody comprises a sequence encoding the $C_L$ region of the lambda chain of human IgG.

Embodiment 38

A method according to embodiment 37, wherein the nucleic acid construct comprises the nucleotide sequence of SEQ ID No: 3.

Embodiment 39

A method according to any of embodiments 1 to 38, wherein the nucleic acid constructs are DNA constructs.

Embodiment 40

A method according to any of embodiments 1 to 39, wherein the nucleic acid construct of (i), (ii), (iii) and/or (iv) is a prokaryotic expression vector.

Embodiment 41

A method according to any of embodiments 1 to 40, wherein the cell expression system is a prokaryotic cell expression system.

Embodiment 42

A method according to embodiment 41, wherein the prokaryotic cell expression system comprises *E. coli* cells.

Embodiment 43

A method according to embodiment 42, wherein the *E. coli* cells are of a strain deficient in endogenous protease activities.

Embodiment 44

A method according to any of embodiments 1 to 39, wherein the nucleic acid construct of (i), (ii), (iii) and/or (iv) is a eukaryotic expression vector.

Embodiment 45

A method according to embodiment 44, wherein the cell expression system is a eukaryotic cell expression system.

Embodiment 46

A method according to embodiment 45, wherein the cell expression system is a mammalian cell expression system.

Embodiment 47

A method according to embodiment 46, wherein the mammalian cell expression system comprises CHO cells.

Embodiment 48

A method according to embodiment 46, wherein the mammalian cell expression system comprises HEK-293F cells.

Embodiment 49

A method according to any one of embodiments 1 to 39, wherein I and II of the expression system comprises DNA constructs suitable for gene therapy.

Embodiment 50

A method according to any one of embodiments 1-39, wherein I and II of the expression system are viral constructs suitable for gene therapy.

Embodiment 51

A method according to any one of embodiments 1-39, wherein III of the mammalian cell expression system are human cells comprising I and II, and which are suitable for implantation into a patient in need of therapy with the monovalent antibody produced.

Embodiment 52

A method according to any one of embodiment 51, wherein the human cells are derived from the patient.

Embodiment 53

A method according to any one of embodiments 1 to 51, wherein the monovalent antibody produced is for pharmaceutical use.

Embodiment 53a

A method according to any one of embodiments 1-53, wherein the nucleic acid constructs of i) and ii) are in the same plasmid.

Embodiment 53b

A method according to any one of embodiments 1-53, wherein the antibody is produced in two different cell lines, and the antibody is assembled after expression in vitro

Embodiment 54

A monovalent antibody obtained by use of a method according to any of embodiments 1 to 50 and 53.

Embodiment 55

A monovalent antibody obtainable by use of a method according to any of embodiments 1 to 50 and 53.

Embodiment 56

A monovalent antibody comprising a light chain and a heavy chain, wherein
  a) said light chain comprises the amino acid sequence of the variable ($V_L$) region of a selected antigen specific antibody and the amino acid sequence of the constant ($C_L$) region of an Ig, and wherein, in case of an IgG1 subtype, the amino sequence of the constant ($C_L$) region has been modified so that it does not contain any amino acids capable of participating in the formation of disulfide bonds or covalent bonds with other peptides comprising an identical amino acid sequence of the constant ($C_L$) region of the Ig, and
  b) said heavy chain comprises the amino acid sequence of the variable ($V_H$) region of said selected antigen specific antibody and the amino acid sequence of the constant ($C_H$) region of human Ig, wherein the amino acid sequence of the constant ($C_H$) region has been modified so that the hinge region and, as required by the Ig subtype, other regions of the $C_H$ region, such as the $C_H3$ region, does not contain any amino acid residues which participate in the formation of disulphide bonds or covalent or non-covalent inter-heavy chain bonds with other peptides comprising an identical amino acid sequence of the constant ($C_H$) region of the human Ig.

Embodiment 57

A monovalent antibody according to embodiment 56, wherein the human Ig is an IgG1, IgG2, IgG3, IgG4 or IgGA antibody, such as an IgG1, IgG2 or IgG4 antibody.

Embodiment 58

A monovalent antibody comprising a light chain and a heavy chain, wherein
  a) said light chain comprises the amino acid sequence of the variable ($V_L$) region of a selected antigen specific antibody and the amino acid sequence of the constant ($C_L$) region of an Ig, and
  b) said heavy chain comprises the amino acid sequence of the variable ($V_H$) region of said selected antigen specific antibody and the amino acid sequence of the constant ($C_H$) region of human IgG4, wherein the amino acid sequence of the heavy chain has been modified such that none of any amino acid residues present in the region corresponding to the hinge region are capable of participating in the formation of disulphide bonds with other peptides comprising an identical amino acid sequence of the constant ($C_H$) region of human IgG4.

Embodiment 59

A monovalent antibody according to embodiment 54 to 58, wherein the $C_L$ region is the constant region of the kappa light chain of human IgG.

Embodiment 60

A monovalent antibody according to embodiment 59, wherein the $C_L$ region comprises the amino acid sequence of SEQ ID No: 2.

Embodiment 61

A monovalent antibody according to embodiment 54 to 58, wherein the $C_L$ region is the constant region of the lambda light chain of human IgG.

Embodiment 62

A monovalent antibody according to embodiment 61, wherein the $C_L$ region comprises the amino acid sequence of SEQ ID No: 4.

Embodiment 63

A monovalent antibody according to any of embodiments 54 to 62, wherein the light chain and the heavy chain are connected to each other via one or more disulphide bond.

Embodiment 64

A monovalent antibody according to any of embodiments 54 to 63, wherein the light chain and the heavy chain are connected to each other via an amide bond.

Embodiment 65

A monovalent antibody according to any of embodiments 54 to 64, wherein the amino acid sequence of the heavy chain has been modified such that the region corresponding to the hinge region does not comprise any cysteine residues.

Embodiment 66

A monovalent antibody according to any of embodiments 54 to 65, wherein the amino acid sequence of the heavy chain has been modified such that at least one of the amino acid residues of the region corresponding to the hinge region, including any cysteine residues, have been deleted and/or substituted with other amino acid residues.

Embodiment 67

A monovalent antibody according to any of embodiments 54 to 66, wherein the cysteine residues of the hinge region are substituted with amino acid residues that have an uncharged polar side chain, or a non polar side chain.

Embodiment 68

A monovalent antibody according to embodiment 67, wherein the amino acids with uncharged polar side chains are independently selected from glycine, asparagine, glutamine, serine, threonine, tyrosine, tryptophan, and the amino acids with the nonpolar side chain are independently selected from alanine, valine, leucine, isoleucine, proline, phenylalanine, methionine.

Embodiment 69

A monovalent antibody according to embodiment 68, wherein the amino acid sequence of the heavy chain has been modified such that the heavy chain comprises a $C_H$ region, wherein the amino acids corresponding to amino acids 106 and 109 of the sequence of SEQ ID No: 14 have been deleted.

Embodiment 70

A monovalent antibody according to embodiment 66 or embodiment 69, wherein the amino acid sequence of the heavy chain has been modified such that the heavy chain comprises a IgG4 $C_H$ region, wherein at least the amino acid residues corresponding to amino acid residues 106 to 109 of the sequence of SEQ ID No: 14 has been deleted.

Embodiment 71

A monovalent antibody according to any of embodiments 66 to 70, wherein the amino acid sequence of the heavy chain has been modified such that the heavy chain comprises a IgG4 $C_H$ region, wherein at least the amino acid residues corresponding to amino acid residues 99 to 110 of the sequence of SEQ ID No: 14 has been deleted.

Embodiment 72

A monovalent antibody according to any of embodiments 66 to 71, wherein the entire hinge region has been deleted.

Embodiment 73

A monovalent antibody according to any of embodiments 66 to 72, wherein the heavy chain comprises the amino acid sequence of SEQ ID No: 16.

Embodiment 74

A monovalent antibody according to embodiment 66, wherein the amino acid sequence of the heavy chain has been modified such that the heavy chain comprises a IgG4 $C_H$ region, wherein the amino acid residues corresponding to amino acid residues 106 and 109 of the sequence of SEQ ID No: 14 has been substituted with amino acid residues different from cysteine.

Embodiment 75

A monovalent antibody according to embodiment 66, wherein the amino acid sequence of the heavy chain has been modified such that the heavy chain comprises a $C_H$ region, wherein one of the amino acid residues corresponding to amino acid residues 106 and 109 of the sequence of SEQ ID No: 14 has been substituted with an amino acid residue different from cysteine, such as an amino acid residue disclosed in embodiment 67 or 68, and the other of the amino acid residues corresponding to amino acid residues 106 and 109 of the sequence of SEQ ID No: 14 has been deleted.

Embodiment 76

A monovalent antibody according to embodiment 75, wherein the amino acid residue corresponding to amino acid residues 106 has been substituted with an amino acid residue that is different from cysteine, such as an amino acid residue disclosed in embodiment 67 or 68, and wherein the amino acid residue corresponding to amino acid residues 109 has been deleted.

Embodiment 77

A monovalent antibody according to embodiment 75, wherein the amino acid residue corresponding to amino acid residues 106 has been deleted, and the amino acid residue corresponding to amino acid residues 109 has been substituted with an amino acid residue different from cysteine, such as an amino acid residue disclosed in embodiment 67 or 68.

Embodiment 78

A monovalent antibody of any of embodiments 54 to 77, wherein said antibody is obtainable by a method comprising recombinant expression of the antibody in a cell expression system in vitro.

Embodiment 79

A monovalent antibody according to embodiment 78, wherein the method comprises
  i) providing a nucleic acid construct encoding the light chain of said antibody, said construct comprising a nucleotide sequence encoding the $V_L$ region of a selected antigen specific antibody and a nucleotide sequence encoding the $C_L$ region of IgG;
  ii) providing a nucleic acid construct encoding the heavy chain of said antibody, said construct comprising a nucleotide sequence encoding the $V_H$ region of a selected antigen specific antibody and a nucleotide sequence encoding the $C_H$ region of human IgG4, wherein the nucleic acid sequence encoding the $C_H$ region has been modified such that the region corresponding to the hinge region does not comprise any amino acid residues capable of participating in the formation of disulphide bonds;
  iii) providing a cell expression system for the producing said monovalent antibody;
  iv) producing said monovalent antibody comprising a light chain encoded by the nucleic acid construct of (i) and a heavy chain encoded by the nucleic acid construct of (ii) by co-expressing said nucleic acid constructs in cells of the cell expression system of (iii).

Embodiment 80

A monovalent antibody according to embodiment 79, wherein the human Ig is an IgG1, IgG2, IgG3, IgG4 or IgGA antibody, such as an IgG1, IgG2, IgG4 antibody.

Embodiment 81

A monovalent antibody according to embodiment 78, wherein the method comprises
  i) providing a nucleic acid construct encoding the light chain of said antibody, said construct comprising a nucleotide sequence encoding the $V_L$ region of a selected antigen specific antibody and a nucleotide sequence encoding the $C_L$ region of IgG;

ii) providing a nucleic acid construct encoding the heavy chain of said antibody, said construct comprising a nucleotide sequence encoding the $V_H$ region of a selected antigen specific antibody and a nucleotide sequence encoding the $C_H$ region of human IgG4, wherein the nucleic acid sequence encoding the $C_H$ region has been modified such that the region corresponding to the hinge region does not comprise any amino acid residues capable of participating in the formation of disulphide bonds;

iii) providing a cell expression system for producing said monovalent antibody;

iv) producing said monovalent antibody comprising a light chain encoded by the nucleic acid construct of (i) and a heavy chain encoded by the nucleic acid construct of (ii) by co-expressing said nucleic acid constructs in cells of the cell expression system of (iii).

Embodiment 82

A monovalent antibody according to any of embodiments 54 to 81, which monovalent antibody has a plasma concentration above 10 µg/ml for more than 7 days when administered in vivo at a dose of 4 mg per kg.

Embodiment 83

A monovalent antibody according to embodiment 82, wherein the monovalent antibody has a plasma concentration above 10 µg/ml for more than 7 days when administered in vivo in SCID mise at a dose of 4 mg per kg.

Embodiment 84

A monovalent antibody according to any of embodiments 54 to 83, which monovalent antibody has a plasma clearance, which is more than 10 times slower than the plasma clearance of a F(ab')$_2$ fragment.

Embodiment 85

A monovalent antibody according to embodiment 84, wherein the sequence of the F(ab')$_2$ fragment is identical to the sequence of the corresponding region of the monovalent antibody.

Embodiment 86

A monovalent antibody according to embodiment 84, wherein the plasma clearance is measured using SCID mice.

Embodiment 87

A monovalent antibody according to embodiment 86, wherein the $V_H$ region and the $V_L$ region of the F(ab')$_2$ fragment are identical to the $V_H$ region and the $V_L$ region of the monovalent antibody.

Embodiment 88

A monovalent antibody according to any of embodiments 54 to 87, wherein said monovalent antibody has a half-life of at least 5 days when administered in vivo.

Embodiment 89

A monovalent antibody according to any of embodiments 54 to 87, wherein said monovalent antibody has a half-life of at least 5 and up to 21 days when administered in vivo.

Embodiment 90

A monovalent antibody according to any one of embodiments 54 to 87, wherein said monovalent antibody has a half-life of at least 5 and up to 14 days when administered in vivo Embodiment 91

A monovalent antibody according to any one of embodiments 54 to 87, wherein said monovalent antibody has a half-life of at least 14 days.

Embodiment 92

A monovalent antibody according to any one of embodiments 54 to 87, wherein said monovalent antibody has a half-life of at least 21 days.

Embodiment 93

A monovalent antibody according to embodiment 88, wherein said monovalent antibody has a half-life of at least 5 days when administered in vivo in SCID mice.

Embodiment 94

A monovalent antibody according to any of embodiments 54 to 93, wherein said antibody is capable of binding to FcRn.

Embodiment 95

A monovalent antibody according to any of embodiments 54 to 94, which specifically binds a tumor antigen.

Embodiment 96

A monovalent antibody according to any of embodiments 54 to 95, which specifically binds a cell surface receptor that is activated upon receptor dimerization.

Embodiment 97

A monovalent antibody according to any of embodiments 54 to 96, wherein the monovalent antibody when bound to a target molecule inhibits target molecule multimerization and/or aggregation.

Embodiment 98

A monovalent antibody according to any of embodiments 54 to 97, wherein the monovalent antibody binds to a target selected from VEGF, cMet, CD20, CD38, IL-8, CD25, FcalphaRI, FcepsilonRI, acetyl choline receptor, fas, fasL, TRAIL, Hepatitis virus, Hepatitis C virus, Tissue factor, a complex of Tissue factor and Factor VII, EGFr, CD4, and CD28.

Embodiment 99

A monovalent antibody according to any of embodiments 54 to 97, wherein the monovalent antibody specifically binds to a target selected from VEGF, cMet, CD20, CD38, IL-8, CD25, FcalphaRI, FcepsilonRI, acetyl choline receptor, fas, fasL, TRAIL, Hepatitis virus, Hepatitis C virus, Tissue factor, a complex of Tissue factor and Factor VII, EGFr, CD4, and CD28.

Embodiment 100

A monovalent IgG4 anti-cMet antibody according any of embodiments 56 to 97.

Embodiment 101

A monovalent antibody according to any of embodiments 54 to 100, which is in a monovalent form in the presence of polyclonal human IgG.

Embodiment 102

A monovalent antibody according to any of embodiments 54 to 100, which is in a monovalent form when administered to a human being.

Embodiment 103

A monovalent antibody according to any of embodiments 54 to 100, which dissociates into a monovalent form in the presence of polyclonal human IgG.

Embodiment 104

A monovalent antibody according to any of embodiments 54 to 100, which dissociates into in a monovalent form when administered to a human being.

Embodiment 105

A monovalent antibody according to any of embodiments 56 to 104, wherein said antibody is incapable of effector binding.

Embodiment 106

A monovalent antibody according to any one of embodiments 54 to 104, wherein the antibody is made for pharmaceutical use.

Embodiment 107

A method of preparing a monovalent antibody of any of embodiments 54 to 104, the method comprising the steps of:
a) culturing a host cell comprising a nucleic acid encoding said monovalent antibody; and
b) recovering the monovalent antibody from the host cell culture.

Embodiment 108

A method according to embodiment 107, wherein said host cell is prokaryotic.

Embodiment 109

A method according to embodiment 108, wherein the host cell is *E. coli* cells.

Embodiment 110

A method according to embodiment 109, wherein the *E. coli* cells are of a strain deficient in endogenous protease activities.

Embodiment 111

A method according to embodiment 107, wherein said host cell is eukaryotic.

Embodiment 112

A method according to embodiment 111, wherein the host cell is HEK-293F cells.

Embodiment 113

A method according to embodiment 111, wherein the host cell is CHO cells.

Embodiment 114

A method according to embodiment 111, wherein the host cell is a human cell.

Embodiment 115

A method according to any of embodiments 107 to 114, wherein the monovalent antibody is recovered from culture medium.

Embodiment 116

A method according to any of embodiments 107 to 114, wherein the monovalent antibody is recovered from cell lysate.

Embodiment 117

A nucleic acid construct comprising a nucleic acid sequence encoding the $C_H$ region of an IgG4, wherein the nucleic acid sequence encoding the $C_H$ region has been modified such that the region corresponding to the hinge region in said $C_H$ region does not comprise any amino acid residues capable of participating in the formation of disulphide bonds with peptides comprising an amino acid sequence identical to the amino acid sequence of said $C_H$ region, or a sequence complementary thereof.

Embodiment 118

A nucleic acid construct according to embodiment 117, wherein the nucleic acid sequence encoding the $C_H$ region has been modified such that the region corresponding to the hinge region does not comprise any cysteine residues.

Embodiment 119

A nucleic acid construct according to embodiment 117 or embodiment 118, wherein the nucleic acid sequence encoding the $C_H$ region has been modified such that at least one of the amino acid residues of the region corresponding to the hinge region, including any cysteine residues, have been deleted and/or substituted with other amino acid residues.

Embodiment 120

A nucleic acid construct according to embodiment 119, wherein the nucleic acid sequence encoding the $C_H$ region has been modified such that the amino acids corresponding to amino acids 106 and 109 of the sequence of SEQ ID No: 14 have been deleted.

Embodiment 121

A nucleic acid construct according to embodiment 119 or embodiment 120, wherein the nucleic acid sequence encoding the $C_H$ region has been modified such that at least the amino acid residues corresponding to amino acid residues 106 to 109 of the sequence of SEQ ID No: 14 has been deleted.

Embodiment 122

A nucleic acid construct according to any of embodiments 119 to 121, wherein the nucleic acid sequence encoding the $C_H$ region has been modified such that at least the amino acid residues corresponding to amino acid residues 99 to 110 of the sequence of SEQ ID No: 14 has been deleted.

Embodiment 123

A nucleic acid construct according to any of embodiments 119 to 122, wherein the nucleic acid sequence encoding the $C_H$ region has been modified such that the entire hinge region has been deleted.

Embodiment 124

A nucleic acid construct according to any of embodiments 117 to 123, wherein the nucleic acid sequence encoding the $C_H$ region has been modified such that at least one nucleotide of the splice donor site of the nucleic acid sequence encoding the hinge region has been substituted with another nucleotide.

Embodiment 125

A nucleic acid construct according to embodiment 124, wherein the nucleotides corresponding to the nucleotides in position 714 and 722 of the sequence of SEQ ID No: 13 have been substituted with a nucleotide different than the nucleotide present at that position in SEQ ID No: 13.

Embodiment 126

A nucleic acid construct according to embodiment 125, wherein the nucleic acid sequence encoding the $C_H$ region comprises a sequence of SEQ ID No: 13, wherein nucleotides 714 and 722 of the sequence of SEQ ID No: 13 have been substituted with a nucleotide different than the nucleotide present at that position in SEQ ID No: 13.

Embodiment 127

A nucleic acid construct according to embodiment 126, wherein the nucleic acid sequence encoding the $C_H$ region comprises the nucleotide sequence of SEQ ID No: 15.

Embodiment 128

A nucleic acid construct according to embodiment 119, wherein the nucleic acid sequence encoding the $C_H$ region has been modified such that the amino acid residues corresponding to amino acid residues 106 and 109 of the sequence of SEQ ID No: 14 have been substituted with amino acid residues different from cysteine.

Embodiment 129

A nucleic acid construct according to any of embodiments 124 to 128, wherein the substituted nucleotides of the nucleic acid sequence encoding the $C_H$ region are substituted by using site-directed mutagenesis.

Embodiment 130

A nucleic acid construct according to any of embodiments 117 to 129, wherein said construct comprises a nucleic acid sequence encoding the $V_H$ region of an antigen specific antibody, or a sequence complementary thereof.

Embodiment 131

A nucleic acid construct according to embodiment 130, wherein the nucleic acid sequence encoding the $V_H$ region is operably linked to the nucleic acid sequence encoding the $C_H$ region, or a sequence complementary thereof.

Embodiment 132

A nucleic acid construct according to any of embodiments 117 to 131, wherein said construct comprises a nucleotide sequence encoding the heavy chain of a monovalent antibody according to any of embodiments 54 to 106.

Embodiment 133

A nucleic acid construct according to embodiment 132, wherein said construct comprises a nucleic acid sequence encoding the $V_L$ region of a monovalent antibody according to any of embodiments 54 to 106.

Embodiment 134

A nucleic acid construct according to embodiment 133, wherein the nucleic acid construct encoding the light chain of said monovalent antibody comprises a sequence encoding the $C_L$ region of the kappa chain of human IgG.

Embodiment 135

A nucleic acid construct according to embodiment 134, wherein the nucleic acid construct comprises the nucleotide sequence of SEQ ID No: 1

Embodiment 136

A nucleic acid construct according to embodiment 133, wherein the nucleic acid construct encoding the light chain of said monovalent antibody comprises a sequence encoding the $C_L$ region of the lambda chain of human IgG.

Embodiment 137

A nucleic acid construct according to embodiment 136, wherein the nucleic acid construct comprises the nucleotide sequence of SEQ ID No: 3.

Embodiment 138

A nucleic acid construct according to any of embodiments 117 to 137, wherein the nucleic acid construct is a DNA construct.

Embodiment 139

A nucleic acid construct according to any of embodiments 117 to 138, wherein said nucleic acid construct is an expression vector.

Embodiment 140

A nucleic acid construct according to embodiment 139, wherein said expression vector is a prokaryotic expression vector.

Embodiment 141

A nucleic acid construct according to embodiment 139, wherein said expression vector is a eukaryotic expression vector.

Embodiment 142

A nucleic acid construct according to embodiment 141, wherein said expression vector is a mammalian expression vector.

Embodiment 143

A nucleic acid construct according to embodiment 142, wherein said expression vector is suitable for gene therapy in a human.

Embodiment 144

A nucleic acid construct according to embodiment 139, wherein said expression vector is a viral vector suitable for gene therapy in a human.

Embodiment 145

A method of preparing a monovalent antibody according to any of embodiments 54 to 106 comprising culturing a host cell comprising a nucleic acid construct according to any of embodiments 117 to 144, and, if said nucleic acid construct does not encode the light chain of said antibody, also comprising a nucleic acid construct comprising a nucleic acid sequence encoding the light chain of said antibody, so that the polypeptides are expressed, and recovering the monovalent antibody from the cell culture.

Embodiment 146

A method according to embodiment 145, wherein the monovalent antibody is recovered from the cell lysate.

Embodiment 147

A method according to embodiment 145, wherein the monovalent antibody is recovered from the cell culture medium.

Embodiment 148

Use of a nucleic acid construct according to any of embodiments 117 to 144 for the production of a monovalent antibody according to any of embodiments 54 to 106.

Embodiment 149

Use according to embodiment 148 or 170, wherein the production of a monovalent antibody includes the use of a method according to any of embodiments 1 to 53.

Embodiment 150

A host cell comprising a nucleic acid according to any of embodiments 117 to 144.

Embodiment 151

A host cell according to embodiment 150, which host cell is a prokaryotic cell.

Embodiment 152

A host cell according to embodiment 151, which host cell is an *E. coli* cell.

Embodiment 153

A host cell according to embodiment 150, which host cell is a eukaryotic cell.

Embodiment 154

A host cell according to embodiment 153, which host cell is a mammalian cell.

Embodiment 155

A host cell according to embodiment 154, which host cell is a CHO cell.

Embodiment 156

A host cell according to embodiment 154, which host cell is a HEK-293F cell.

Embodiment 157

A host cell according to embodiment 154, which host cell is a human cell.

Embodiment 158

A host cell according to embodiment 154, which host cell is a human cell derived from a patient.

Embodiment 159

A host cell according to embodiment 154, which host cell is a human cell in a patient.

Embodiment 160

A host cell comprising a nucleic acid according to any of embodiments 132 to 144.

Embodiment 161

A host cell according to embodiment 160, which host cell is a prokaryotic cell.

Embodiment 162

A host cell according to embodiment 161, which host cell is an *E. coli* cell.

Embodiment 163

A host cell according to embodiment 162, which host cell is a eukaryotic cell.

Embodiment 164

A host cell according to embodiment 163, which host cell is a mammalian cell.

Embodiment 165

A host cell according to embodiment 164, which host cell is a CHO cell.

Embodiment 166

A host cell according to embodiment 164, which host cell is a HEK-293F cell.

Embodiment 167

A method of preparing a monovalent antibody according to any of embodiments 54 to 106 comprising culturing a host cell according to any of embodiments 160 to 166, which host cell comprises a nucleic acid sequence encoding the light chain of said antibody, so that polypeptides are expressed, and recovering the monovalent antibody from the cell culture.

Embodiment 168

A method according to embodiment 167, wherein the monovalent antibody is recovered from the cell lysate.

Embodiment 169

A method according to embodiment 167, wherein the monovalent antibody is recovered from the cell culture medium.

Embodiment 170

Use of a host cell according to any of embodiments 150 to 159 for the production of a monovalent antibody according to any of embodiments 54 to 106.

Embodiment 171

Use according to embodiment 170, wherein the production of a monovalent antibody includes the use of a method according to any of embodiments 1 to 53.

Embodiment 172

An immunoconjugate comprising a monovalent antibody according to any of embodiments 54 to 106 conjugated to a therapeutic moiety.

Embodiment 173

An immunoconjugate of embodiment 172, wherein the therapeutic moiety is a cytotoxin, a chemotherapeutic drug, an immunosuppressant or a radioisotope.

Embodiment 174

A monovalent antibody according to any of embodiments 54 to 106 for use as a medicament.

Embodiment 175

A monovalent antibody according to embodiment 174 for use as a medicament for treating cancer, a cell proliferative disorder, an (auto)immune disorder, an inflammation disorder and/or an angiogenesis disorder, wherein the antibody specifically binds a given target or target epitope, where the binding of an antibody to said target or target epitope is effective in treating said disease.

Embodiment 176

A monovalent antibody according to embodiment 174 or embodiment 175 for use as a medicament for treating a disease or disorder, which disease or disorder is treatable by administration of an antibody against a certain target, wherein the involvement of immune system-mediated activities is not necessary or is undesirable for achieving the effects of the administration of the antibody, and wherein said antibody specifically binds said antigen.

Embodiment 177

A monovalent antibody according to any of embodiments 174 to 176 for use as a medicament for treating a disease or disorder, which disease or disorder is treatable by blocking or inhibiting a soluble antigen, wherein multimerization of said antigen may form undesirable immune complexes, and wherein said antibody specifically binds said antigen.

Embodiment 178

A monovalent antibody according to any of embodiments 174 to 176 for use as a medicament for treating a disease or disorder, which disease or disorder is treatable by blocking or inhibiting a cell membrane bound receptor, wherein said receptor may be activated by dimerization of said receptor, and wherein said antibody specifically binds said receptor.

Embodiment 179

Use of a monovalent antibody according to any of embodiments 54 to 106 as a medicament.

Embodiment 180

Use according to embodiment 179, wherein the medicament is useful for treating cancer, a cell proliferative disorder, an (auto)immune disorder, an inflammation disorder and/or an angiogenesis disorder, wherein the antibody specifically binds a given target or target epitope, where the binding of an antibody to said target or target epitope is effective in treating said disease.

Embodiment 181

Use according to embodiment 179 or embodiment 180, wherein the medicament is useful for treating a disease or

77 disorder, which disease or disorder is treatable by administration of an antibody against a certain target, wherein the involvement of immune system-mediated activities is not necessary or is undesirable for achieving the effects of the administration of the antibody, and wherein said antibody specifically binds said antigen.

Embodiment 182

Use according to any of embodiments 179 to 181, wherein the medicament is useful for treating a disease or disorder, which disease or disorder is treatable by blocking or inhibiting a soluble antigen, wherein multimerization of said antigen may form undesirable immune complexes, and wherein said antibody specifically binds said antigen.

Embodiment 183

Use according to any of embodiments 179 to 181, wherein the medicament is useful for treating a disease or disorder, which disease or disorder is treatable by blocking or inhibiting a cell membrane bound receptor, wherein said receptor may be activated by dimerization of said receptor, and wherein said antibody specifically binds said receptor.

Embodiment 184

Use of an antibody according to any of embodiments 54 to 106 for the preparation of a pharmaceutical composition for the treatment of cancer, a cell proliferative disorder, an (auto)immune disorder, an inflammation disorder and/or an angiogenesis disorder, wherein the antibody specifically binds a given target or target epitope, where the binding of an antibody to said target or target epitope is effective in treating said disease.

Embodiment 185

Use of an antibody according to any of embodiments 54 to 106 or embodiment 184 for the preparation of a pharmaceutical composition for the treatment of a disease or disorder, which disease or disorder is treatable by administration of an antibody against a certain target, wherein the involvement of immune system-mediated activities is not necessary or is undesirable for achieving the effects of the administration of the antibody, and wherein said antibody specifically binds said antigen.

Embodiment 186

Use of an antibody according to any of embodiments 54 to 106 or embodiment 184 or embodiment 185 for the preparation of a pharmaceutical composition for the treatment of a disease or disorder, which disease or disorder is treatable by blocking or inhibiting a soluble antigen, wherein multimerization of said antigen may form undesirable immune complexes, and wherein said antibody specifically binds said antigen.

Embodiment 187

Use of an antibody according to any of embodiments 54 to 106 or embodiment 184 or embodiment 185 for the preparation of a pharmaceutical composition for the treatment of a disease or disorder, which disease or disorder is treatable by blocking or inhibiting a cell membrane bound receptor, wherein said receptor may be activated by

78 dimerization of said receptor, and wherein said antibody specifically binds said receptor.

Embodiment 188

A method for inhibiting an antigen in a subject suffering from a disease or disorder in which activity of the antigen is undesirable, comprising administering to a subject a monovalent antibody according to any of embodiments 54 to 106, which antibody specifically binds said antigen, a pharmaceutical composition comprising said antibody, immunoconjugate comprising said antibody, or a nucleic acid construct according to any of embodiments 117 to 144, such that the antigen activity in the subject is inhibited.

Embodiment 189

A method of treating a disease or disorder, wherein said method comprises administering to a subject in need of treatment a therapeutically effective amount of a monovalent antibody according to any of embodiments 54 to 106, a pharmaceutical composition comprising said antibody, immunoconjugate comprising said antibody, or a nucleic acid construct according to any of embodiments 117 to 144, whereby the disease or disorder is treated.

Embodiment 190

A method according to embodiment 189, wherein said disease or disorder is cancer, a cell proliferative disorder, an (auto)immune disorder, an inflammation disorder and/or an angiogenesis disorder, and wherein said method comprises administering to a subject in need of treatment a therapeutically effective amount of a monovalent antibody according to any of embodiments 54 to 106, which antibody specifically binds said antigen, a pharmaceutical composition comprising said antibody, immunoconjugate comprising said antibody, or a nucleic acid construct according to any of embodiments 117 to 144, and wherein the antibody specifically binds a given target or target epitope, where the binding of an antibody to said target or target epitope is effective in treating said disease.

Embodiment 191

A method according to embodiment 189 or embodiment 190, wherein said disease or disorder is treatable by administration of an antibody against a certain target, wherein the involvement of immune system-mediated activities is not necessary or is undesirable for achieving the effects of the administration of the antibody, and wherein said method comprises administering to a subject in need of treatment a therapeutically effective amount of a monovalent antibody according to any of embodiments 54 to 106, wherein said antibody specifically binds said receptor, a pharmaceutical composition comprising said antibody, immunoconjugate comprising said antibody, or a nucleic acid construct according to any of embodiments 117 to 144.

Embodiment 192

A method according to any of embodiments 189 to 191, wherein said disease or disorder is treatable by blocking or inhibiting a soluble antigen, wherein multimerization of said antigen may form undesirable immune complexes, and wherein said method comprises administering to a subject in need of treatment a therapeutically effective amount of a monovalent antibody according to any of embodiments 54 to 106, which antibody specifically binds said antigen, a pharmaceutical composition comprising said antibody, immuno-conjugate comprising said antibody, or a nucleic acid construct according to any of embodiments 117 to 144.

Embodiment 193

A method according to any of embodiments 189 to 191, wherein said disease or disorder is treatable by blocking or inhibiting a cell membrane bound receptor, wherein said receptor may be activated by dimerization of said receptor, and wherein said method comprises administering to a subject in need of treatment a therapeutically effective amount of a monovalent antibody according to any of embodiments 54 to 106, wherein said antibody specifically binds said receptor, a pharmaceutical composition comprising said antibody, immuno-conjugate comprising said antibody, or a nucleic acid construct according to any of embodiments 117 to 144.

Embodiment 194

A method of any one of the embodiments 189 to 193, comprising administering one or more further therapeutic agents to the subject.

Embodiment 195

A pharmaceutical composition comprising a monovalent antibody according to any of embodiments 54 to 106, together with one or more pharmaceutically acceptable excipients, diluents or carriers.

Embodiment 196

A transgene animal comprising a nucleic acid construct according to any one of embodiments 117 to 144.

Embodiment 197

Use of a monovalent antibody according to any of embodiments 54 to 106 as a diagnostic agent.

Embodiment 198

A method of identifying a monovalent antibody or a monovalent antibody fragment with a long half life, wherein the monovalent antibody or antibody fragment is tested for protection by FcRn against clearance.

Embodiment 199

A monovalent antibody or a monovalent antibody fragment which is protected from clearance by FcRn.

Embodiment 200

A monovalent antibody or a monovalent antibody fragment according to embodiment 199, wherein said monovalent antibody or monovalent antibody fragment has a half-life of at least 5 days when administered in vivo.

Embodiment 201

A monovalent antibody or a monovalent antibody fragment according to embodiment 199, wherein said monovalent antibody or monovalent antibody fragment has a half-life of at least 5 and up to 21 days when administered in vivo.

Embodiment 202

A monovalent antibody or a monovalent antibody fragment according to embodiment 199, wherein said monovalent antibody or monovalent antibody fragment has a half-life of at least 5 and up to 14 days when administered in vivo.

Embodiment 203

A monovalent antibody or a monovalent antibody fragment according to embodiment 199, wherein said monovalent antibody or monovalent antibody fragment has a half-life of at least 14 days.

Embodiment 204

A monovalent antibody or a monovalent antibody fragment according to embodiment 199, wherein said monovalent antibody or monovalent antibody fragment has a half-life of at least 21 days.

Embodiment 205

A monovalent antibody or a monovalent antibody fragment according to embodiment 199, wherein said monovalent antibody or monovalent antibody fragment has a half-life of at least 5 days when administered in vivo in SCID mice.

Embodiment 206

A monovalent antibody or monovalent antibody fragment according to embodiment 199, wherein said monovalent antibody or monovalent antibody fragment is capable of binding to FcRn.

The present invention is further illustrated by the following examples which should not be construed as further limiting.

EXAMPLES

Example 1

Oligonucleotide Primers and PCR Amplification

Figure 1:
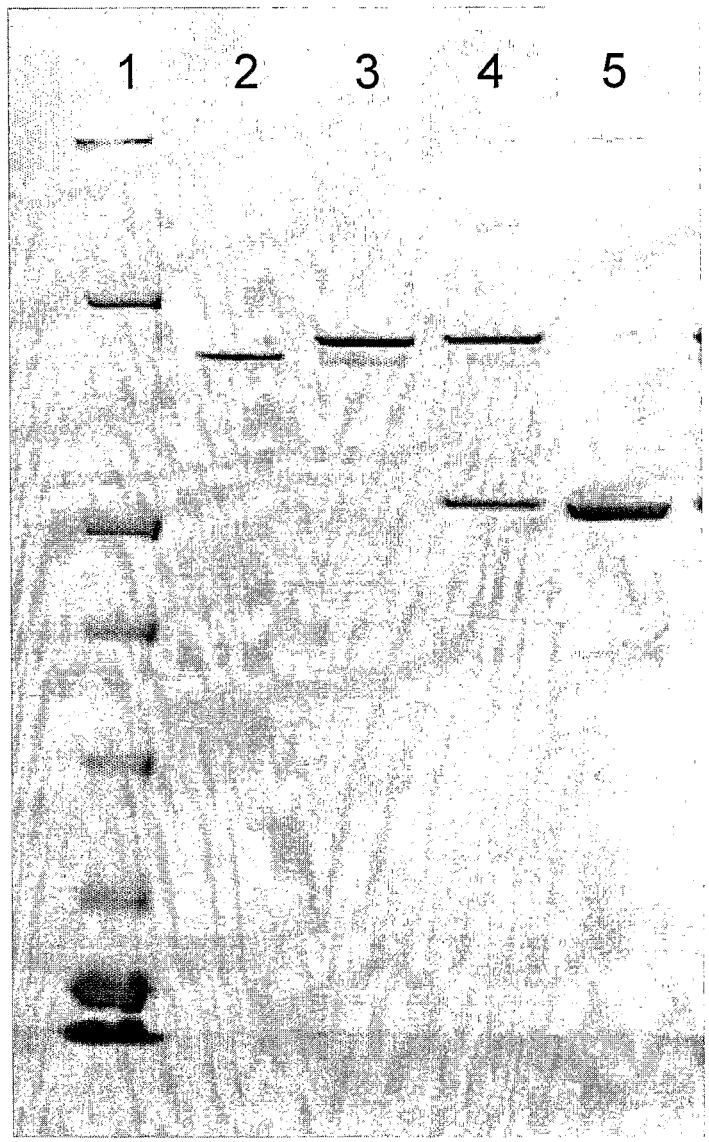
FIG. 1: The CD20-specific antibodies 7D8-IgG1, 7D8-IgG4 and 7D8-HG were evaluated on non-reducing SDS-PAGE.

Oligonucleotide primers were synthesized and quantified by Isogen Bioscience (Maarssen, The Netherlands). Primers were dissolved in $H_2O$ to 100 pmol/µl and stored at −20° C. A summary of all PCR and sequencing primers is tabulated (FIG. 1). For PCR, PfuTurbo® Hotstart DNA polymerase (Stratagene, Amsterdam, The Netherlands) was used according to the manufacturer's instructions. Each reaction mix contained 200 µM mixed dNTPs (Roche Diagnostics, Almere, The Netherlands), 6.7 pmol of both the forward and reverse primer, 100 ng of genomic DNA or 1 ng of plasmid DNA and 1 unit of PfuTurbo® Hotstart DNA polymerase in PCR reaction buffer (supplied with polymerase) in a total volume of 20 µl. PCR reactions were carried out with a TGradient Thermocycler 96 (Whatman Biometra, Goettingen, Germany) using a 32-cycle program: denaturing at 95° C. for 2 min; 30 cycles of 95° C. for 30 sec, a 60-70° C. gradient (or another specific annealing temperature) for 30 sec, and 72° C. for 3 min; final extension at 72° C. for 10 min. If appropriate, the PCR mixtures were stored at 4° C. until further analysis or processing.

Example 2

Agarose Gel Electrophoresis

Agarose gel electrophoresis was performed according to Sambrook (Sambrook J. and Russel, D. V. Molecular Cloning: A Laboratory Manual, 3nd Ed., Cold Spring Harbor, 2000) using gels of 50 ml, in 1× Tris Acetate EDTA buffer. DNA was visualized by the inclusion of ethidium bromide in the gel and observation under UV light. Gel images were recorded by a CCD camera and an image analysis system (GeneGnome; Syngene, via Westburg B. V., Leusden, The Netherlands).

Example 3

Analysis and Purification of PCR Products and Enzymatic Digestion Products

Purification of desired PCR fragments was carried out using a MinElute PCR Purification Kit (Qiagen, via Westburg, Leusden, The Netherlands; product #28006), according to the manufacturer's instructions. Isolated DNA was quantified by UV spectroscopy and the quality was assessed by agarose gel electrophoresis.

Alternatively, PCR or digestion products were separated by agarose gel electrophoresis (for instance when multiple fragments were present) using a 1% Tris Acetate EDTA agarose gel. The desired fragment was excised from the gel and recovered using the QIAEX II Gel Extraction Kit (Qiagen; product #20051), according to the manufacturer's instructions.

Example 4

Quantification of DNA by UV Spectroscopy

Optical density of nucleic acids was determined using a NanoDrop ND-1000 Spectrophotometer (Isogen Life Science, Maarssen, The Netherlands) according to the manufacturer's instructions. The DNA concentration was measured by analysis of the optical density (OD) at 260 nm (one $OD_{260nm}$ unit=50 µg/ml). For all samples, the buffer in which the nucleic acids were dissolved was used as a reference.

Example 5

Restriction Enzyme Digestions

Restriction enzymes and supplements were obtained from New England Biolabs (Beverly, Mass., USA) or Fermetas (Vilnius, Lithuania) and used according to the manufacturer's instructions.

DNA (100 ng) was digested with 5 units of enzyme(s) in the appropriate buffer in a final volume of 10 µl (reaction volumes were scaled up as appropriate). Digestions were incubated at the recommended temperature for a minimum of 60 min. For fragments requiring double digestions with restriction enzymes which involve incompatible buffers or temperature requirements, digestions were performed sequentially. If necessary digestion products were purified by agarose gel electrophoresis and gel extraction.

Example 6

Ligation of DNA Fragments

Ligations of DNA fragments were performed with the Quick Ligation Kit (New England Biolabs) according to the manufacturer's instructions. For each ligation, vector DNA was mixed with approximately three-fold molar excess of insert DNA.

Example 7

Transformation of E. coli

Plasmid DNA (1-5 µl of DNA solution, typically 2 µl of DNA ligation mix) was transformed into One Shot DH5α-T1$^R$ or MACH-1 T1$^R$ competent E. coli cells (Invitrogen, Breda, The Netherlands; product #12297-016) using the heat-shock method, according to the manufacturer's instructions. Next, cells were plated on Luria-Bertani (LB) agar plates containing 50 µg/ml ampicillin. Plates were incubated for 16-18 hours at 37° C. until bacterial colonies became evident.

Example 8

Screening of Bacterial Colonies by PCR

Bacterial colonies were screened for the presence of vectors containing the desired sequences via colony PCR using the HotStarTaq Master Mix Kit (Qiagen; product #203445) and the appropriate forward and reverse primers. Selected colonies were lightly touched with a 20 µl pipette tip and touched briefly in 2 ml LB for small scale culture, and then resuspended in the PCR mix. PCR was performed with a TGradient Thermocycler 96 using a 35-cycle program: denaturation at 95° C. for 15 min; 35 cycles of 94° C. for 30 sec, 55° C. for 30 sec and 72° C. for 2 min; followed by a final extension step of 10 min at 72° C. If appropriate, the PCR mixtures were stored at 4° C. until analysis by agarose gel electrophoresis.

Example 9

Plasmid DNA Isolation from E. coli Culture

Plasmid DNA was isolated from E. coli cultures using the following kits from Qiagen (via Westburg, Leusden, The Netherlands), according to the manufacturer's instructions. For bulk plasmid preparation (50-150 ml culture), either a HiSpeed Plasmid Maxi Kit (product #12663) or a HiSpeed Plasmid Midi Kit (product #12643) was used. For small scale plasmid preparation (±2 ml culture) a Qiaprep Spin Miniprep Kit (product #27106) was used and DNA was eluted in 50 µl elution buffer (supplied with kit).

Example 10

Site-Directed Mutagenesis

Site-directed mutagenesis was performed using the QuickChange II XL Site-Directed Mutagenesis Kit (Stratagene, Amsterdam, The Netherlands) according to the manufacturer's instructions. This method included the introduction of a silent extra XmaI site to screen for successful mutagenesis. Briefly, 5 µl 10× reaction buffer, 1 µl oligonucleotide IgG4S228Pf (P16) (100 pmol/µl), 1 µl oligonucleotide IgG4S228Pr (P17)(100 pmol/µl), 1 µl dNTP mix, 3 µl Quicksolution, 1 µl plasmid pTomG4Tom7D8 (see example 16) (50 ng/µl) and 1 µl PfuUltra HF DNA polymerase were mixed in a total volume of 50 µl and amplified with a TGradient Thermocycler 96 (Whatman Biometra, Goettingen, Germany; product #050-801) using an 18-cycle program: denaturing at 95° C. for 1 min; 18 cycles of 95° C. for 50 sec, 60° C. for 50 sec, and 68° C. for 10 min. PCR mixtures were stored at 4° C. until further processing. Next, PCR mixtures were incubated with 1 µl DpnI for 60 min at 37° C. to digest the pTomG47D8 vector and stored at 4° C. until further processing. The reaction mixture was precipitated with 5 µl sM NaAc and 125 µl Ethanol, incubated for 20 minutes at −20° C. and spundown for 20 minutes at 4° C. at 14000×g. The DNA pellet was washed with 70% ethanol, dried and dissolved in 4 µl water. The total 4 µl reaction volume was transformed in One Shot Top 10 competent *E. coli* cells (Invitrogen, Breda, The Netherlands) according to the manufacturer's instructions (Invitrogen). Next, cells were plated on Luria-Bertani (LB) agar plates containing 50 µg/ml ampicillin. Plates were incubated for 16-18 hours at 37° C. until bacterial colonies became evident.

Example 11

DNA Sequencing

Plasmid DNA samples were sent to AGOWA (Berlin, Germany) for sequence analysis. Sequences were analyzed using Vector NTI advanced software (Informax, Oxford, UK).

Example 12

Transient Expression in HEK-293F Cells

Freestyle™ 293-F (a HEK-293 subclone adapted to suspension growth and chemically defined Freestyle medium, e.g. HEK-293F) cells were obtained from Invitrogen and transfected according to the manufacturer's protocol using 293fectin (Invitrogen).

Example 13

Construction of pConG1fA77: A Vector for the Production of the Heavy Chain of A77-IgG1

The $V_H$ coding region of the mouse anti-FcαRI antibody A77 was amplified from a scFv phage vector, containing the $V_H$ and $V_L$ coding regions of this antibody, by a double overlap extension PCR. This was used to incorporate a mammalian signal peptide, an ideal Kozak sequence and suitable restriction sites for cloning in pConG1f. The first PCR was done using primers A77$V_H$for1 and A77VHrev with the scFv phage vector as template. Part of this first PCR was used in a second PCR using primers A77VHfor2 and A77VHrev. The $V_H$ fragment was gel purified and cloned into pConG1f0.4. For this the pConG1f0.4 vector and the $V_H$ fragment were digested with HindIII and ApaI and purified. The $V_H$ fragment and the pConG1f0.4HindIII-ApaI digested vector were ligated and transformed into competent DH5α-T1$^R$ cells. A clone was selected containing the correct insert size and the sequence was confirmed and was named pConG1fA77.

Example 14

Construction of pConKA77: A Vector for the Production of the Light Chain of A77 Antibodies The $V_L$ coding region of the mouse anti-FcαRI antibody A77 was amplified from a scFv phage vector, containing the $V_H$ and $V_L$ of this antibody, by a double overlap extension PCR. This was used to incorporate a mammalian signal peptide, an ideal Kozak sequence and suitable restriction sites for cloning in pConKappa0.4. The first PCR was done using primers A77VLfor1 and A77VLrev with the scFv phage vector as template. Part of this first PCR was used in a second PCR using primers A77VLfor2 and A77VLrev.

The PCR product and the pConKappa0.4 vector were digested with HindIII and Pfl23II and purified. The $V_L$ fragment and the pConKappa0.4HindIII-Pfl23II digested vector were ligated and transformed into competent DH5a T1$^R$ *E. coli*.

A clone was selected containing the correct insert size and the sequence was confirmed. This plasmid was named pConKA77.

Example 15

Construction of pTomG4A77: A Vector for the Production of the Heavy Chain of A77-IgG4

To construct a vector for expression of A77-IgG4, the VH region of A77 was cloned in pTomG4.

For this, pTomG4 and pConG1fA77 were digested with HindIII and ApaI and the relevant fragments were isolated.

The A77 $V_H$ fragment and the pTomG4HindIII-ApaI digested vector were ligated and transformed into competent DH5α-T1$^R$ cells.

A clone was selected containing the correct insert size. This plasmid was named pTomG4A77.

Example 16

Construction of pTomG4A77HG: A Vector for the Production of the Heavy Chain of A77-HG To make a construct for expression of A77-HG, the VH region of A77 was cloned in pTomG47D8HG, replacing the VH 7D8 region.

For this pTomG47D8HG and pConG1fA77 were digested with HindIII and ApaI and the relevant fragments were isolated.

The A77 $V_H$ fragment and the pTomG47D8HGHindIII-ApaI digested vector fragment were ligated and transformed into competent DH5α-T1$^R$ cells.

A clone was selected containing the correct insert size. This plasmid was named pTomG4A77HG.

Example 17

Construction of pEE6.4A77Fab: A Vector for the Production of the Heavy Chain of A77-Fab To make a construct for expression of A77-Fab, the VH region of A77 was cloned in pEE6.42F8Fab, replacing the VH 2F8 region.

For this pEE6.42F8Fab and pConG1fA77 were digested with HindIII and ApaI and the relevant fragments were isolated.

The A77 $V_H$ fragment and the pEE6.42F8Fab HindIII-ApaI digested vector fragment were ligated and transformed into competent DH5α-T1$^R$ cells.

A clone was selected containing the correct insert. This plasmid was named pEE6.4A77Fab.

Example 18

Cloning of the Variable Regions of a Human Anti-cMet Antibody

Total RNA was prepared from 1×10$^6$ mouse hybridoma cells with the RNeasy kit (Qiagen, Westburg, Leusden, Netherlands) according to the manufacturer's protocol.

5'-RACE-Complementary DNA (cDNA) of RNA was prepared from 60 ng total RNA, using the SMART RACE cDNA Amplification kit (BD Biosciences Clontech, Mountain View, Calif., USA), following the manufacturer's protocol. The VL and VH regions of the cMet antibody were amplified by PCR. For this Pfu-Turbo®) Hotstart DNA polymerase (Stratagene) was used according to the manufacturer's instructions. Each reaction mix contained 5 µl 10×BD Advantage 2 PCR buffer (Clontech), 200 µM mixed dNTPs (Roche Diagnostics), 12 pmol of the reverse primer (RACEG1A1 for the VH region and RACEKA1 for the VL region), 7.2 pmol UPM-Mix (UPM-Mix: 2 µM Short-UPMH3 and 0.4 µM LongUPMH3 oligonucleotide), 1 µl of the 5'RACE cDNA template as described above, and 1 µl 50×BD Advantage 2 polymerase mix (Clontech) in a total volume of 50 µl.

PCR reactions were carried out with a TGradient Thermocycler 96 (Whatman Biometra) using a 35-cycle program: denaturing at 95° C. for 1 min; 35 cycles of 95° C. for 30 sec, 68° C. for 60 sec.

The reaction products were separated by agarose gel electrophoresis on a 1% TAE agarose gel and stained with ethidium bromide. Bands of the correct size were cut from the gels and the DNA was isolated from the agarose using the Qiagen Minelute Reaction Cleanup kit (Qiagen).

Gel isolated PCR fragments were cloned into the pCR4Blunt-TOPO vector (Invitrogen) using the Zero Blunt® TOPO® PCRCloning Kit for Sequencing (Invitrogen), following the manufacturer's protocol. 5 µl of the ligation mixture was transformed into OneShot DH5αT1R competent E. Coli (Invitrogen) and plated on LB/Ampicillin plates.

From six, insert containing, clones, the $V_L$ sequences were determined and from five, insert containing, clones, the $V_H$ sequences were determined.

Example 19

Construction of pConG1fcMet: A Vector for the Production of the Heavy Chain of cMet-IgG1

The $V_H$ coding region of the human anti-cMet antibody was cut from a plasmid containing this region using HindIII and ApaI. The VH fragment was gel purified and cloned into pConG1f0.4. For this pConG1f0.4 vector were digested with HindIII and ApaI and purified. The $V_H$ fragment and the pConG1f0.4HindIII-ApaI digested vector were ligated and transformed into competent DH5α-T1R cells.

A clone was selected containing the correct insert size was isolated and was named pConG1fcMet.

Example 20

Construction of pConKcMet: A Vector for the Production of the Light Chain of cMet Antibodies The $V_L$ coding region of the human anti-cMet antibody was amplified from a plasmid containing this region using the primers shortUPMH3 and RACEVLBsiWI, introducing suitable restriction sites for cloning into pConK0.4.

The PCR product and the pConKappa0.4 vector were digested with HindIII and Pfl23II and purified. The $V_L$ fragment and the pConKappa0.4HindIII-Pfl23II digested vector were ligated and transformed into competent DH5α T1$^R$ E. coli.

A clone was selected containing the correct insert size and the sequence was confirmed. This plasmid was named pConKcMet.

Example 21

Construction of pTomG4cMet: A Vector for the Production of the Heavy Chain of cMet-IgG4

To construct a vector for expression of cMet-IgG4, the VH region of cMet was cloned in pTomG4.

For this, pTomG42F8 and pConG1fcMet were digested with HindIII and ApaI and the relevant fragments were isolated.

The cMet $V_H$ fragment and the pTomG42F8HindIII-ApaI digested vector were ligated and transformed into competent DH5α-T1$^R$ cells.

A clone was selected containing the correct insert size. This plasmid was named pTomG4cMet.

Example 22

Construction of pTomG4cMetHG: A Vector for the Production of the Heavy Chain of cMet-HG To make a construct for expression of cMet-HG, the VH region of cMet was cloned in pTomG42F8HG, replacing the VH 2F8 region.

For this pTomG42F8HG and pConG1fcMet were digested with HindIII and ApaI and the relevant fragments were isolated.

The cMet $V_H$ fragment and the pTomG42F8HGHindIII-ApaI digested vector fragment were ligated and transformed into competent DH5α-T1$^R$ cells.

A clone was selected containing the correct insert size. This plasmid was named pTomG4cMetHG.

Example 23

Construction of pEE6.4cMetFab: A Vector for the Production of the Heavy Chain of cMet-Fab To make a construct for expression of cMet-Fab, the VH region of cMet was cloned in pEE6.42F8Fab, replacing the VH 2F8 region.

For this pEE6.42F8Fab and pConG1fcMet were digested with HindIII and ApaI and the relevant fragments were isolated.

The cMet $V_H$ fragment and the pEE6.42F8Fab HindIII-ApaI digested vector fragment were ligated and transformed into competent DH5α-T1$^R$ cells.

A clone was selected containing the correct insert. This plasmid was named pEE6.4cMetFab.

Example 24

Construction of pConG1f2F8: A Vector for the Production of the Heavy Chain of 2F8-IgG1

The $V_H$ coding region of 2F8 (WO 2002/100348) was amplified by PCR from pIESRα2F8 (Medarex) using the primers 2f8HCexfor and 2f8HCexrev and subcloned in PCRscriptCam(Stratagene). The VH fragment was subsequently cloned in pCONg1f0.4.

For this pConG1f0.4 and the pCRScriptCAMVH2F8 vectors were digested with HindIII and ApaI and the relevant fragments were purified.

The $V_H$ fragment and the pConG1f0.4HindIII-ApaI digested vector were ligated and transformed into competent DH5α-T1$^R$ cells. A clone was selected containing the correct insert size, the sequence was confirmed and the vector was named pConG1f2F8.

Example 25

Construction of pConK2F8: A Vector for the Production of the Light Chain of 2F8 Antibodies pIESRα2F8 was digested with HindIII and BsiWI and the $V_L$ coding region of 2F8 (anti-EGFr) was isolated from gel.

The pConKappa0.4 vector was digested with HindIII and BsiWI and purified. The $V_L$ fragment and the pConKappa0.4HindIII-BsiWI digested vector were ligated and transformed into competent DH5α T1$^R$ E. coli.

A clone was selected containing the correct insert size and the sequence was confirmed. This plasmid was named pConK2F8.

Example 26

Construction of pTomG42F8: A Vector for the Production of the Heavy Chain of 2F8-IgG4

To construct a vector for expression of 2F8-IgG4, the VH region of 2F8 was cloned in pTomG4.

For this, pTomG4 and pConG1f2F8 were digested with HindIII and ApaI and the relevant fragments were isolated.

The 2F8 $V_H$ fragment and the pTomG4HindIII-ApaI digested vector were ligated and transformed into competent DH5α-T1$^R$ cells.

A clone was selected containing the correct insert size. This plasmid was named pTomG42F8.

Example 27

Construction of pTomG42F8HG: A Vector for the Production of the Heavy Chain of 2F8-HG To make a construct for expression of 2F8-HG, the VH region of 2F8 was cloned in pTomG47D8HG, replacing the VH 7D8 region.

For this pTomG47D8HG and pConG1f2F8 were digested with HindIII and ApaI and the relevant fragments were isolated.

The 2F8 $V_H$ fragment and the pTomG47D8HGHindIII-ApaI digested vector fragment were ligated and transformed into competent DH5α-T1$^R$ cells.

A clone was selected containing the correct insert size. This plasmid was named pTomG42F8HG.

Example 28

Construction of pEE6.42F8Fab: A Vector for the Production of the Heavy Chain of 2F8-Fab The Fab coding region was amplified from vector pConG1f2F8 by PCR with primers pConG1seq1 and 2F8fabrev2, introducing a suitable cloning restriction site and a C-terminal his tag coding sequence. The PCR fragment was purified and cloned in PEE6.4.

For this pEE6.4 and the PCR fragment were digested with HindIII and EcoRI and the relevant fragments were isolated.

The 2F8 Fab fragment and the pEE6.4HindIII-EcoRI digested vector fragment were ligated and transformed into competent DH5α-T1$^R$ cells.

A clone was selected containing the correct insert and the sequence was confirmed by DNA sequencing. This plasmid was named pEE6.42F8Fab.

Example 29

Construction of pConG1f7D8: A Vector for Production of the Heavy Chain of 7D8-IgG1

The $V_H$ coding region of CD20 specific HuMab-7D8 (WO 04/035607) was amplified by PCR from a pGemT (Promega, Madison, USA) vector containing this region using the primers 7D8VHexfor (P8) and 2F8HCexrev (P13) (FIG. 14), introducing suitable restriction sites for cloning into pConG1f0.4 (Lonza Biologics, Slough, UK), a mammalian expression vector containing the genomic constant region (allotype f) of human IgG1, and an ideal Kozak sequence (GCCGCCACC, (Kozak M et al., Gene 234(2), 187-208 (1999)). The PCR fragment was cloned in pPCR-Script CAM (Stratagene, Amsterdam, The Netherlands) using a PCR-Script® Cam Cloning Kit (Stratagene), according to the manufacture's instructions. Several clones were sequenced and a clone containing the predicted sequence was chosen for further use.

The $V_H$ fragment was gel purified and cloned into pConG1f0.4. For this the $V_H$ fragment was isolated from the pPCR-Script CAM vector after digestion with HindIII and ApaI and gel purification.

The pConG1f0.4 vector was digested with HindIII and ApaI and the vector fragment was isolated from gel, followed by dephosphorylation with Shrimp Alkaline Phosphatase (New England Biolabs) The $V_H$ fragment and the pConG1f0.4HindIII-ApaI dephosphorylated fragment were ligated and transformed into competent DH5α-T1$^R$ cells (Invitrogen). Eight colonies were checked by colony PCR (using primers pConG1seq1 (P10) and HCseq5 (P11) (FIG. 14) and all colonies were found to contain the correct insert size.

A clone was chosen for further study and named pConG1f7D8.

Example 30

Construction of pConK7D8: A Vector for Production of the Light Chain of 7D8-IgG1, 7D8-IgG4 and 7D8-HG The $V_L$ coding region of CD20 specific HuMab-7D8 (WO 04/035607) was amplified from a plasmid containing this region using the primers 7D8VLexfor (P7) and 7D8VLexrev (P6) (FIG. 14), introducing suitable restriction sites for cloning into pConKappa0.4 (Lonza Biologics), a mammalian expression vector containing the constant kappa light chain region (allotype km3) of human IgG, and an ideal Kozak sequence.

The PCR product and the pConKappa0.4 vector were digested with HindIII and BsiWI. The vector and $V_L$ fragment were purified and the vector was dephosphorylated with Shrimp Alkaline Phosphatase. The $V_L$ fragment and the pConKappa0.4HindIII-BsiWI digested vector were ligated and transformed into competent DH5a T1$^R$ E. coli. Ten colonies were checked by colony PCR (using primers pConKseq1 (P9) and LCseq3 (P5) (FIG. 14) and 9 colonies were found to contain the correct insert size.

From 4 clones plasmid DNA was isolated and the $V_L$ region was sequenced. 3 clones contained the predicted sequence and one clone was chosen for further use and named pConK7D8.

Example 31

Construction of pTomG4: A Vector for the Expression of Variable Heavy Chain Regions of Human IgG with the Constant Region of Human IgG4

Genomic DNA was isolated from a blood sample of a volunteer and used as a template in a PCR with primers IgG4gene2f (P15) and IgG4gene2r (P14) (FIG. 14), amplifying the complete genomic constant region of the heavy chain of IgG4 and introducing suitable restriction sites for cloning into the mammalian expression vector pEE6.4 (Lonza Biologics). The PCR fragment was purified and cloned into pEE6.4. For this the PCR product was digested with HindIII and EcoRI, followed by heat inactivation of the restriction enzymes. The pEE6.4 vector was digested HindIII and EcoRI, followed by heat inactivation of the restriction enzymes and dephosphorylation of the vector fragment with shrimp alkaline phosphatase, followed by heat inactivation of the phosphatase. The IgG4 fragment and the pEE6.4HindIII/EcoRI dephosphorylated vector were ligated and transformed into competent MACH1-T1$^R$ cells (Invitrogen). Three clones were grown in LB and plasmid DNA was isolated from a small culture (1.5 ml). Restriction digestion revealed a pattern consistent with the cloning of the IgG4 fragment in the pEE6.4 vector. Plasmid DNA from two clones was transformed in DH5α-T1$^R$ E. coli and plasmid DNA was isolated and the constructs were checked by sequence analysis of the insert and one clone was found to be identical to a genomic IgG4 clone from the Genbank database, apart from some minor differences in introns. SEQ ID No: 13 shows the sequence of the IgG4 region in pTomG4. These differences are presumably either polymorphisms or sequence faults in the Genbank sequence. The plasmid was named pTomG4.

Example 32

Construction of pTomG47D8: A Vector for the Production of the Heavy Chain of 7D8-IgG4

Plasmid DNA from pConG1f7D8 was digested with HindIII and ApaI and the $V_H$ fragment was gel purified. The pTomG4 vector was digested with HindIII and ApaI and the vector fragment was isolated from gel. The $V_H$ fragment and the pTomG4HindIII-ApaI fragment were ligated and transformed into competent DH5α-T1$^R$ cells. Four colonies were checked by colony PCR (using primers pConKseq1 (P9) and HCseq11 (P12)) and two were found to contain the correct insert size and the presence of the pTomG4 backbone was confirmed by a digestion with MspI on the colony PCR fragment. One of the clones was chosen for further use. This plasmid was named pTomG47D8.

Example 33

Construction of pTomG47D8HG: A Vector for the Expression of the Heavy Chain of 7D8-HG Site directed mutagenesis was used to destroy the splice donor site of the hinge exon of IgG4 in the pTomG47D8 plasmid. A site-directed mutagenesis reaction was done according to the QuickChange XL site-directed mutagenesis method using primers IgG4S228Pf (P16) and IgG4S228Pr (P17). 24 colonies were screened by colony PCR and XmaI digestion (an extra XmaI site was introduced during mutagenesis) and all colonies appeared to contain the correct nucleotide changes. Two positive colonies were grown overnight, plasmid DNA was isolated and sequenced to confirm that the correct mutation was introduced. Both did contain the correct sequence and one was chosen for further propagation and named pTomG47D8HG. To exclude the introduction of additional mutations during the mutagenesis process, the whole IgG4 coding region of pTomG47D8HG was resequenced and no additional mutations were found. The final vector was named pTomG47D8HG.

Example 34

Cloning of the Variable Regions of the Mouse Anti-Betv1 Antibody

Total RNA was prepared from 0.3×10$^5$ mouse hybridoma cells (Clone 2H8 from reference (Akkerdaas J H et al., Allergy 50(3), 215-20 (1995)) with the RNeasy kit (Qiagen, Westburg, Leusden, Netherlands) according to the manufacturer's protocol.

5'-RACE-Complementary DNA (cDNA) of RNA was prepared from 112 ng total RNA, using the SMART RACE cDNA Amplification kit (BD Biosciences Clontech, Mountain View, Calif., USA), following the manufacturer's protocol.

The $V_L$ and $V_H$ regions of the Betv1 antibody were amplified by PCR. For this PfuTurbo® Hotstart DNA polymerase (Stratagene) was used according to the manufacturer's instructions. Each reaction mix contained 200 µM mixed dNTPs (Roche Diagnostics), 12 pmol of the reverse primer (RACEG1 mm1 (P19) for the $V_H$ region and RACEKmm1 (P18) for the $V_L$ region), 7.2 pmol UPM-Mix (UPM-Mix: 2 µM ShortUPMH3 (P20) and 0.4 µM LongUPMH3 (P21) oligonucleotide (FIG. 14)), 0.6 µl of the 5'RACE cDNA template as described above, and 1.5 unit of PfuTurbo® Hotstart DNA polymerase in PCR reaction buffer (supplied with polymerase) in a total volume of 30 µl.

PCR reactions were carried out with a TGradient Thermocycler 96 (Whatman Biometra) using a 35-cycle program: denaturing at 95° C. for 2 min; 35 cycles of 95° C. for 30 sec, a 55° C. for 30 sec, and 72° C. for 1.5 min; final extension at 72° C. for 10 min.

The reaction products were separated by agarose gel electrophoresis on a 1% TAE agarose gel and stained with ethidium bromide. Bands of the correct size were cut from the gels and the DNA was isolated from the agarose using the QiaexII gel extraction kit (Qiagen).

Gel isolated PCR fragments were A tailed by a 10 min 72° C. incubation with 200 µM dATP and 2.5 units Amplitaq (Perkin Elmer) and purified using minielute columns (Qiagen). A-tailed PCR fragments were cloned into the pGEMTeasy vector (Promega) using the pGEMT easy vector system II kit (Promega), following the manufacturer's protocol. 2 µl of the ligation mixture was transformed into OneShot DH5αT1R competent E. Coli (Invitrogen) and plated on LB/Amp/IPTG/XgaI plates.

Four insert containing, white colonies each for the $V_H$ and $V_L$ sequences were picked and the inserts were sequenced. The deduced amino acid sequences of the $V_H$ and $V_L$ of Betv1 are shown as SEQ ID No: 8 and SEQ ID No:12, respectively.

Example 35

Construction of pConG1fBetV1: A Vector for the Production of the Heavy Chain of Betv1-IgG1

The $V_H$ coding region of mouse anti-BetV1 antibody was amplified by PCR from a plasmid containing this region (example 18) using the primers VHexbetv1for (P4) and VHexbetv1rev (P3), introducing suitable restriction sites for cloning into pConG1f0.4 and an ideal Kozak sequence.

The $V_H$ fragment was gel purified and cloned into pConG1f0.4. For this the PCR product and the pConKappa0.4 vector were digested with HindIII and ApaI and purified.

The $V_H$ fragment and the pConG1f0.4HindIII-ApaI digested vector were ligated and transformed into competent DH5α-T1$^R$ cells.

A clone was selected containing the correct insert size and the correct sequence was confirmed. This plasmid was named pConG1fBetv1.

Example 36

Construction of pConKBetv1: A Vector for the Production of the Light Chain of Betv1

The $V_L$ coding region mouse anti-BetV1 antibody was amplified from a plasmid containing this region (example 18) using the primers VLexbetv1for (P2) and VLexbetv1 rev (P1), introducing suitable restriction sites for cloning into pConK0.4 and an ideal Kozak sequence.

The PCR product and the pConKappa0.4 vector were digested with HindIII and BsiWI and purified. The $V_L$ fragment and the pConKappa0.4HindIII-BsiWI digested vector were ligated and transformed into competent DH5α T1$^R$ E. coli.

A clone was selected containing the correct insert size and the sequence was confirmed. This plasmid was named pConKBetv1.

Example 37

Construction of pTomG4Betv1: A Vector for the Production of the Heavy Chain of Betv1-IgG4

To construct a vector for expression of Betv1-IgG4, the $V_H$ region of BetV1 was Cloned in pTomG4.

For this, pTomG4 and pConG1fBetv1 were digested with HindIII and ApaI and the relevant fragments were isolated.

The Betv1 $V_H$ fragment and the pTomG4HindIII-ApaI digested vector were ligated and transformed into competent DH5α-T1$^R$ cells.

A clone was selected containing the correct insert size and the sequence was confirmed. This plasmid was named pTomG4Betv1.

Example 38

Construction of pTomG4Betv1 HG: A Vector for the Production of the Heavy Chain of Betv1-HG To make a construct for expression of Betv1-HG, the $V_H$ region of Betv1 was cloned in pTomG47D8HG, replacing the $V_H$ 7D8 region.

For this pTomG47D8HG and pConG1fBetv1 were digested with HindIII and ApaI and the relevant fragments were isolated.

The Betv1 $V_H$ fragment and the pTomG47D8HGHindIII-ApaI digested vector fragment were ligated and transformed into competent DH5α-$T1^R$ cells.

A clone was selected containing the correct insert size and the sequence was confirmed. This plasmid was named pTomG4Betv1 HG.

Example 39

Production of 7D8-IgG1, 7D8-IgG4, 7D8-HG, Betv1-IgG1, Betv1-IgG4, Betv1-HG, 2F8-IgG1, 2F8-IgG4, 2F8-HG, 2F8-Fab, A77-IgG1, A77-IgG4, A77-HG, A77-Fab, cMet-IgG1, cMet-IgG4, cMet-HG, and cMet-Fab by Transient Expression in Hek-293F Cells Antibodies were produced of all constructs by cotransfecting the relevant heavy and light chain vectors in HEK-293F cells using 293fectin according to the manufacturer's instructions. For 7D8-IgG1, pConG1f7D8 and pConK7D8 were coexpressed. For 7D8-IgG4, pTomG47D8 and pConK7D8 were coexpressed. For 7D8-HG, pTomG47D8HG and pConK7D8 were coexpressed. For Betv1-IgG1, pConG1Betv1 and pConKBetv1 were coexpressed. For Betv1-IgG4, pTomG4Betv1 and pConKBetv1 were coexpressed. For Betv1-HG, pTomG4Betv1HG and pConKBetv1 were coexpressed.

For 2F8-IgG1, pConG1f2F8 and pConK2F8 were coexpressed. For 2F8-IgG4, pTomG42F8 and pConK2F8 were coexpressed. For 2F8-HG, pTomG42F8HG and pConK2F8 were coexpressed. For 2F8-Fab, pEE6.42F8-Fab and pConK2F8 were coexpressed.

For cMet-IgG1, pConG1fcMet and pConKcMet were coexpressed. For cMet-IgG4, pTomG4cMet and pConKcMet were coexpressed. For cMet-HG, pTomG4cMetHG and pConKcMet were coexpressed. For cMet-Fab, pEE6.4cMet-Fab and pConKcMet were coexpressed.

For A77-IgG1, pConG1fA77 and pConKA77 were coexpressed. For A77-IgG4, pTomG4A77 and pConKA77 were coexpressed. For A77-HG, pTomG4A77HG and pConKA77 were coexpressed. For A77-Fab, pEE6.4A77-Fab and pConKA77 were coexpressed.

Example 40

Purification of IgG, IgG4 and IgG4-Hingeless Antibodies

All IgG1, IgG4 and hingeless antibodies were purified. First the supernatants were filtered over 0.20 μM dead-end filter. Then, the supernant was loaded on a 5 ml Protein A column (rProtein A FF, Amersham Bioscience) and eluted with 0.1 M citric acid-NaOH, pH 3. The eluate was immediately neutralized with 2 M Tris-HCl, pH 9 and dialyzed overnight to 12.6 mM sodium phosphate, 140 mM NaCl, pH 7.4 (B. Braun, Oss, The Netherlands). After dialysis samples were sterile filtered over 0.20 μM dead-end filter.

Antibodies were deglycosylated by overnight incubation at 37° C. with 1 unit PNgase F (Roche)/μg antibody, followed by purification on protein A.

Samples were analysed for concentration of IgG by nephelometry and absorbance at 280 nm.

Example 41

Purification of Recombinant Fab Antibodies by Metal Affinity Chromatography

Talon beads (Clontech) were used for purification of the A77-Fab, 2F8-Fab and cMet-Fab antibodies.

Before use, the beads were equilibrated with 1× equilibration/wash buffer pH 7.0 (50 mM sodium phosphate and 300 mM NaCl) followed by incubation with the culture supernatant containing the Fab antibody. The beads were washed with 1× equilibration/wash buffer to remove a specific bound proteins and the His-tagged protein was eluted with 1× elution buffer (50 mM sodium phosphate, 300 mM NaCl and 150 mM Imidazole) at pH 5.0. Incubation was done batch wise, whereas washing and elution were done in packed columns using centrifugation (2 minutes at 700 g). The eluted protein was desalted on a PD-10 column by exchanging to PBS. The yield of purified protein was determined by measuring the absorbance at 280 nm using the theoretic absorbance coefficient as calculated from the amino acid sequence. Purified proteins were analyzed by SDS-PAGE, the protein migrated as one band at the expected size.

Example 42

Non-Reduced SDS-PAGE Analysis of 7D8-IgG4 and 7D8-HG Antibodies

After purification, the CD20 specific antibodies 7D8-IgG1 (IgG1 anti-CD20) 7D8-IgG4 (IgG4 anti-CD20) and 7D8-HG (hingeless IgG4 anti-CD20) were analysed on non-reducing SDS-PAGE.

The Bis-Tris electrophoresis method used is a modification of the Laemmli method (Laemmli UK, Nature 227, 6801 (1970)), where the samples were run at neutral pH. The SDS-PAGE gels were stained with Coomassie and digitally imaged using the GeneGenius (Synoptics, Cambridge, UK).

As can be seen in FIG. 1, 7D8-IgG1 showed 1 major bind representing the full length tetrameric (2 heavy and two light chains) 7D8 IgG1 molecule. 7D8-IgG4 shows to have besides the major band representing the tetrameric IgG4 molecule a substantial amount of half-molecules (i.e. one heavy band one light chain) as has been described in literature (Schuurman J et. al., Mol Immunol 38, 1 (2001); Angal S et al., Mol Immunol 30, 105 (1993); Colcher D et al., Cancer Res 49, 1738 (1989); King D J et al., Biochem J 281 (Pt 2), 317 (1992); Petersen J G et al., J Biol Chem 249, 5633 (1974)). The hingeless IgG4 molecule 7D8-HG is shown to be only half-molecules.

Example 43

Mass Spectrometry of 7D8-HG

For Mass Spectrometry by Nanospray technique the samples were concentrated and buffer was exchanged to 20 mM sodium phosphate, pH 7.2 using Millipore Microcon YM-30 concentrators. Subsequently, approximately 100 µg IgG was digested for 16 hours at 37° C. with 1 U N-glycosidase F (Roche, cat. no. 1365177) to release the N-linked glycans.

Samples were desalted off-line using a C4 micro-trap cartridge and eluted in 30% propanol/5% acetic acid. Molecular weight analysis was performed using nanospray Electrospray-MS using a Q-TOF (Waters, Almere, the Netherlands). The instrument was calibrated using glu-fibrinopeptide. Masslynx 4.0 software was used to deconvolute the multiply-charged data obtained.

A further aliquot of the sample was reduced using dithiothreitol. The products of reduction were desalted off-line using a C4 microtrap and analyzed as described above. MS analysis of 7D8-HG under reducing conditions showed a light chain mass of 23440 dalton which is consistent with the predicted light chain mass of 23440 dalton. No mass of the heavy chain was detected, probably because of precipitation of the heavy chain.

MS analysis under non-reduced conditions showed a predominant mass of 71520 dalton, which correlates well with the predicted mass (71522 dalton) of a half-molecule (combining one heavy and one light chain) missing the hinge. A tiny amount of a product with a mass of 143041 dalton was observed, probably representing a tetrameric molecule with a hingeless heavy chain.

Example 44

Mass Spectometry Peptide Mapping of 7D8-HG

An aliquot (25 µg) of 7D8-HG was digested with CNBr for 5 hours at room temperature. The CNBr digested sample was freeze-dried and then redissolved in 50 mM ammonium bicarbonate buffer adjusted to pH 8.4 with 10% aq. ammonia and digested with TPCK-treated trypsin for 5 hours at 37° C. The products of digestion were lyophilized and reduction was performed on the digested lyophilized sample using a 20 times molar excess of dithiothreitol (DTT) in Tris-acetate buffer at pH 8.5. The products of the reaction were analyzed by on-line LC/ES-MS using a C18 column. Elution was carried out using aqueous formic acid and an acetonitrile gradient. Detection of masses occurred with a LCT Premier Electrospray mass spectrometer, calibrated over the range of m/z 250 to 3000.

A tryptic peptide with a mass of 2026.2 Da corresponding to the theoretic mass of the hingeless specific peptide 220 VAPEFLGGPSVFLFPPKPK 238 was detected (FIG. 2). The identity of this peptide was confirmed by nanospray MS and MS/MS (FIGS. 3 and 4).

This result shows that the 7D8-HG antibody does not contain a hinge region.

Example 45

Molecular Mass Distribution from Sedimentation Velocity by Analytical Ultracentrifuge (AUC) Experiments of 7D8-HG A 1 mg/ml sample of 7D8-HG in PBS was send to Nanolytics (Dalgow, Germany) for AUC analysis. A dominant population of 7D8-HG sediments with a velocity of 6.7 S (95%) was identified. A distinct aggregate was found at 11.5 S (2%). The rest of the material was found in higher aggregates.

The sedimentation coefficient of the major fraction indicates that 7D8-HG in PBS predominantly occurs as a dimer with a frictional ratio of 1.4.

Apparently 7D8-HG forms a dimer by low affinity non-covalent interactions, presumably in the CH3 region (Saphire, Stanfield et al. 2002). This dimerization process can be inhibited by using HG molecules in the presence of an excess of irrelevant antibodies (see example 54)

Saphire, E. O., R. L. Stanfield, et al. (2002). "Contrasting IgG structures reveal extreme asymmetry and flexibility." *J Mol Biol* 319(1): 9-18.

Example 46

Functional Analysis of 7D8-IgG1, 7D8-IgG4 and 7D8-HG Antibodies

Binding to the CD20 antigen of these CD20 specific antibodies was examined by flow cytometry. NSO/CD20 transfected cells (50,000 cells/50 µl) were washed in FACS buffer (FB: PBS, 0.05% BSA, 0.02% NaN$_3$) and incubated in V-bottom 96-well plates with the test antibodies (50 µl at 4° C. for 30 min). After washing, goat F(ab)$_2$ anti-human-IgG-kappa labeled with PE (Southern Biotechnology, cat No: 2062-09, www.southernbiotech.com) was added to the cells. Cells were washed in FB and cells were collected in FACS tubes in a total volume of 150 µl. Samples were measured and analyzed by use of FACScalibur™ (Becton Dickinson, San Diego, Calif., USA).

As can be seen in FIG. 5, all three antibodies were antigen specific and showed good binding to CD20.

In order to determine binding of C1q (the first component of the classical complement cascade) to 7D1-IgG1, 7D8-IgG4 and 7D8-HG an ELISA was performed. In short, microtiter ELISA plates (Greiner, Germany) were coated overnight at RT with the test antibodies serially diluted from 10 µg/ml to 0.06 µg/ml in PBS. Plates were emptied and wells were blocked with 200 µl ELISA-diluent per well (0.1 M NaPO$_4$, 0.1 M NaCl, 0.1% gelatin and 0.05% Tween-20), at RT for 30 minutes. Subsequently, plates were emptied and wells were incubated with 2 µg/ml human C1q (Quidel, lot #900848) in C1q buffer (PBS supplemented with 0.1% w/v gelatine and 0.05% v/v Tween-20, 100 µl/well, 37° C., 1 hour). Plates were washed three times with PBST and wells were incubated with rabbit anti-human C1q (DAK0, A0136), diluted in C1q buffer (100 µl/well, RT, 1 h). After washing the plates (3×) with PBST, wells were incubated with HRP-conjugated swine anti-rabbit IgG-Fc (DAKO, P0300, lot #069) diluted in ELISA diluent (1:2500, 100 μl/well, RT, 1 hour). Thereafter, plates were washed thrice and assays were developed with freshly prepared 1 mg/ml ABTS solution (ABTS: 2,2'-azino-bis[3-ethylbenzthiazoline-6-sulfonic acid]); 2 tablets of 5 mg in 10 ml ABTS buffer, Boehringer Mannheim, Ingelheim, Germany) at RT in the dark for 30 minutes. Absorbance was measured at 405 nm in an ELISA plate reader (Biotek Instruments Inc., Winooski, USA).

As can be seen in FIG. 6, C1q did not bind to both 7D8-IgG4 and 7D8-HG. As a control C1q binding to 7D8-IgG1 was evaluated which showed concentration dependent binding of C1q.

To further investigate the complement properties of the CD20-specific antibodies, the complement-dependent cellular toxicity was examined. After harvesting, Daudi cells (ATCC, www.ATCC.org) were washed trice in PBS and resuspended at 2×10$^6$ cells/ml in RPMI 1640, supplemented with 1% (w/v) bovine serum albumin (BSA; Roche, Basel, Switzerland). Then, cells were put in a 96-well round-bottom plate at 1.0×10$^6$ cells/well in a volume of 50 μl. The same volume of antibody (highest concentration 10 μg/ml, diluted in RPMI 1640 and 1% BSA) was added to the wells and incubated for 15 minutes at room temperature (RT). Then 25 μl normal human serum (NHS) was added and the cells were incubated at 37° C. for 45 minutes. Heat-inactivated serum (serum ΔT) is NHS which has been incubated for 10 minutes on 56° C. After incubation for 45 minutes, cells were resuspended transferred to FACS tubes (Greiner). Then, 10 μl propidium iodide (PI; Sigma-Aldrich Chemie B.V.) was added (10 μg/ml solution) to this suspension. Lysis was detected by flow cytometry (FACScalibur™, Becton Dickinson, San Diego, Calif., USA) by measurement of the number of dead cells (PI-positive cells).

As can be seen in FIG. 7A, 7D8-IgG1 showed good lysis of Daudi cells whereas both 7D8-IgG4 and 7D8-HG showed a decreased lysis of Daudi cells.

To evaluate the role of serum, heat-inactivated serum (serum ΔT) was added to cells incubated with 10 μg antistof. FIG. 7B showed that the induction of lysis was dependent on complement-active serum, addition of heat-inactivated serum resulted in no lysis.

Example 47

Non-Reduced SDS-PAGE Analysis of Betv1-HG Antibody

After purification, the Betv1-HG (hingeless IgG4 anti-Bet v1) was analysed on non-reducing SDS-PAGE. The used Bis-Tris electrophoresis method is a modification of the Laemmli method the samples were run at neutral pH. The SDS-PAGE gels were stained with Coomassie and digitally imaged using the GeneGenius (Synoptics, Cambridge, UK).

As can be seen in FIG. 8, Betv1-HG showed 1 major bind representing a half-molecule (i.e. one heavy and one light chain).

Example 48

Gelfiltration of Betv1-HG Antibody

Betv1-HG was subjected to gelfiltration to investigate whether this mutant would elute as half-molecule or intact dimer. Samples (100 μl) were applied to a Superdex 200 HR 10/30 column (Amersham Biosciences, Uppsala, Sweden), which was connected to a HPLC system (ÅKTA explorer) from Amersham Biosciences, Uppsala, Sweden. The column was first equilibrated in PBS. Fractions of 250 μl were collected, in which Bet v 1 specific IgG was measured using the antigen binding assay. The samples were also followed by measuring the absorption at 214 nm.

To test the antigen binding of the Bet v 1 specific antibodies, a sample of diluted antibody was incubated overnight at room temperature with 0.75 mg Protein-G sepharose (Amersham Biosciences, Uppsala, Sweden) in 750 μl PBS/AT (PBS supplemented with 0.3% BSA, 0.1% Tween-20, 0.05% NaN$_3$) together with 50 μl diluted $^{125}$I-labelled Bet v 1 or $^{125}$I-labelled Fel d 1. Bet v 1 was iodinated by the chloramine-T method with carrier free $^{125}$I (Amersham Biosciences, Uppsala, Sweden) as described in Aalberse et al. (Serological aspects of IgG4 antibodies. 1983. 130:722-726). After washing the Sepharose suspension with PBS-T (PBS supplemented with 0.1% Tween-20), the bound radioactivity was measured. The results were expressed as the amount of radioactivity relative to the amount added.

The Bet v 1 binding activity of the hingeless Betv1-HG eluted in one peak, which was more retained than the elution peak of purified Betv1-IgG4 (IgG4 anti Bet v 1) containing an intact hinge (FIG. 9). Calibration of this column using globular proteins showed that the Betv1-HG eluted in fractions corresponding to proteins with a molecular size of ~70 kD (data not shown). These data support our observations that hingeless IgG4 exists as half-molecules and, in contrast to reported hingeless IgG1 and IgG4 molecules (Silverton E W et al., Proc Natl Acad Sci USA 74, 5140 (1977); Rajan S S et al., Mol Immunol 20, 787 (1983); Horgan C et al., J Immunol 150, 5400 (1993)), does not associate via non-covalent interactions into tetrameric molecules.

Example 49

Functional Characterization of Betv1-IgG4 and Betv1-HG Antibodies

Previously was shown that, in contrast to serum-derived antigen specific IgG4, in vitro produced monoclonal IgG4 antibodies are able to crosslink antigen like IgG1 antibodies and are therefore bivalent antibodies (Schuurman J et al., Immunology 97, 693 (1999); Aalberse R C et al., Immunology 105, 9 (2002)). The ability to crosslink antigen of Betv1-IgG1, Betv1-IgG4 and Betv1-HG was determined by a Radio Immuno Assay using Sepharose bound Bet v 1 and $^{125}$I labelled antigen. Herefore, Birch pollen Sepharose was prepared. Briefly, Birch pollen extract (Allergon, Ängelholm, Sweden) was coupled to CNBr-activated Sepharose 4B (Amersham Biosciences, Uppsala, Sweden) according to the instructions of the manufacturer. Subsequently, the Sepharose was resuspended in PBS supplemented with 0.3% BSA, 0.1% Tween-20, 0.05% NaN$_3$.

To examine the ability of the antibody to crosslink Sepharose bound antigen to $^{125}$I labelled antigen, 50 μl of diluted antibody was incubated overnight at room temperature with 750 μl Sepharose in PBS/AT. Next, the Sepharose suspension was washed with PBS-T, after which the suspension was incubated overnight at room temperature with 50 μl diluted $^{125}$I labelled Bet v1 in a total volume of 750 μl PBS/AT. Finally, the Sepharose was washed with PBS-T and bound radioactivity was measured. The results were expressed as the amount of radioactivity bound relative to the amount of radiolabel added.

As can be seen in FIG. 10, all three antibodies were antigen specific and showed good binding to radiolabelled Betv1.

In FIG. 11 is shown that Betv1-IgG1 and Betv1-IgG4 are able to crosslink Sepharose-bound Bet v 1 to radiolabelled Bet v 1. The IgG1 and IgG4 antibody behave as bivalent antibodies. The Betv1-HG antibody was not able to crosslink the Betv1 antigen and therefore demonstrated monovalent binding.

Example 50

Pharmacokinetic Evaluation of an IgG4 Hingeless Mutant Antibody, Compared to Normal IgG1, IgG4 and IgG1 Fragments.

Twenty-five SCID mice (C.B-17/IcrCrl-scid-BR, Charles-River) with body weights between 24 and 27 g were used for the experiment. The mice were housed in a barrier unit of the Central Laboratory Animal Facility (Utrecht, The Netherlands) and kept in filter-top cages with water and food provided ad libitum. All experiments were approved by the Utrecht University animal ethics committee.

Monoclonal antibodies were administered intravenously via the tail vein. 50 µl blood samples were collected from the saphenal vein at 1 hour, 4 hours, 24 hours, 3 days, 7 days, 14 days, 21 days and 28 days after administration. Blood was collected into heparin containing vials and centrifuged for 5 minutes at 10,000 g. Plasma was stored at −20° C. for determination of mAb concentrations.

In this experiment the clearance of the hingeless IgG4 variant (7D8-HG, lot 570-003-EP) was compared with that of normal human IgG4 (7D8-IgG4, lot 570-002-EP), a IgG1 variant (7D8-IgG1, lot 793-001-EP), F(ab')$_2$ (7D8-G1-F(ab')2, lot 815-004-XX) and Fab fragments (7D8-G1-Fab, 815-003-X) of the latter mAb. Each antibody was administered to 5 mice, at a dose of 0.1 mg in 200 µl per mouse.

Human IgG concentrations were determined using a sandwich ELISA. Mouse mAb anti-human IgG-kappa clone MH19-1 (#M1272, CLB Sanquin, The Netherlands), coated to 96-well Microlon ELISA plates (Greiner, Germany) at a concentration of 100 ng/well was used as capturing antibody. After blocking plates with PBS supplemented with 2% chicken serum, samples were added, serially diluted in ELISA buffer (PBS supplemented with 0.05% Tween 20 and 2% chicken serum), and incubated on a plate shaker for 1 h at room temperature (RT). Plates were subsequently incubated with peroxidase-labeled F(ab')$_2$ fragments of goat anti-human IgG immunoglobulin (#109-035-097, Jackson, West Grace, Pa.) and developed with 2,2'-azino-bis(3-ethylbenzthiazoline-6-sulfonic acid) (ABTS; Roche, Mannheim, Germany). Absorbance was measured in a microplate reader (Biotek, Winooski, Vt.) at 405 nm.

SCID mice were chosen because they have low plasma IgG concentrations and therefore relatively slow clearance of IgG. This provides a PK model that is very sensitive for detecting accelerated clearance due to diminished binding of the Fcγ-part to the neonatal Fc receptor (FcRn).

Pharmacokinetic analysis was done by determining the area under the curve (AUC) from the concentration—time curves, with tail correction. The plasma clearance rate was calculated as Dose/AUC (ml/day). Statistical testing was performed using GraphPad PRISM vs. 4 (Graphpad Software).

FIG. 12 shows a semilogarithmic plot of the concentrations in time. The initial plasma concentrations were in the same order for all intact mAbs 85-105 ug/ml, including the hingeless variant. These initial concentrations correspond to a central distribution volume of about 1 ml, which is consistent with distribution into the plasma compartment of the mice. For the F(ab')2 and Fab fragments lower initial concentrations were observed, 75 and 4 ug/ml, respectively. For the Fab fragments this is likely due to rapid extravascular distribution within the first hour after administration.

FIG. 13 shows the clearance rates calculated for the individual mice. The clearance rate of the hingeless variant was 3 to 4 times higher than that of normal IgG1 and IgG4. However, it was more than 10 times slower than that of F(ab')2 fragments and more than 200 times slower than the clearance of Fab fragments.

Example 51

Pharmacokinetic Evaluation of an IgG4 Hingeless Mutant Antibody Compared to Normal IgG4 and IgG1 F(ab)$_2$ Fragments in Immune-Competent Mice Twelve 8-week old Balb/c mice (Balb/CAnNCrl, Charles-River) were used for the experiment. The mice were housed in a barrier unit of the Central Laboratory Animal Facility (Utrecht, The Netherlands) and kept under sterile conditions in filter-top cages with water and food provided ad libitum. All experiments were approved by the Utrecht University animal ethics committee.

Monoclonal antibodies were administered intravenously via the tail vein. 50 µl blood samples were collected from the saphenal vein at 1 hour, 4 hours, 24 hours, 3 days, 7 days, and 10 days after administration. Blood was collected into heparin containing vials and centrifuged for 5 minutes at 10,000 g. Plasma was stored at −20° C. for determination of mAb concentrations.

In this experiment the plasma clearance rate of the hingeless IgG4 variant (7D8-HG, lot 570-003-EP) was compared with that of normal human IgG4 (7D8-IgG4, lot 570-002-EP), a F(ab')$_2$ fragments from 7D8 IgG1 (7D8-G1-F(ab')$_2$, lot 815-004-XX). Each antibody was administered to 4 mice, at a dose of 0.1 mg in 200 µl per mouse, corresponding to a dose of 4 mg per kg of body weight.

Human IgG plasma concentrations were determined using a sandwich ELISA. Mouse mAb anti-human IgG-kappa clone MH19-1 (#M1272, CLB Sanquin, The Netherlands), coated to 96-well Microlon ELISA plates (Greiner, Germany) at a concentration of 100 ng/well was used as capturing antibody. After blocking plates with PBS supplemented with 2% chicken serum, samples were added, serially diluted in ELISA buffer (PBS supplemented with 0.05% Tween 20 and 2% chicken serum), and incubated on a plate shaker for 1 h at room temperature (RT). After washing, the plates were subsequently incubated with peroxidase-labeled F(ab')$_2$ fragments of goat anti-human IgG immunoglobulin (#109-035-097, Jackson, West Grace, Pa.) and developed with 2,2'-azino-bis(3-ethylbenzthiazoline-6-sulfonic acid) (ABTS; Roche, Mannheim, Germany). Absorbance was measured in a microplate reader (Biotek, Winooski, Vt.) at 405 nm.

Balb/c mice were chosen because they have normal IgG production and therefore faster clearance of IgG than SCID mice. This provides a mouse model in which the administered antibodies have to compete with endogenous mouse IgG for binding to the neonatal Fc receptor (FcRn).

FIG. 15 shows a semilogarithmic plot of the concentrations in time. The initial plasma concentrations were all in the order of 100 µg/ml, which is consistent with an initial distribution into the plasma compartment of the mice. The clearance of the hingeless IgG4 variant was only slightly faster than that of normal IgG4. Importantly, the clearance of the hingeless variant was much slower than that of F(ab')$_2$ fragments, which have a comparable molecular size.

This experiment indicates that the Fc-part has a favorable effect on the plasma residence time in mice having a normal immune system and provides an indication of a functional interaction with the neonatal Fc receptor (FcRn) also in the presence of endogenous IgG.

Example 52

Pharmacokinetic Evaluation of an IgG4 Hingeless Mutant Antibody in Human IgG-Supplemented SCID Mice Sixteen SCID mice (C.B-17/IcrCrl-scid-BR, Charles-River) with body weights between 18 and 22 g were used for the experiment. The mice were housed in a barrier unit of the Central Laboratory Animal Facility (Utrecht, The Netherlands) and kept under sterile conditions in filter-top cages with water and food provided ad libitum. All experiments were approved by the Utrecht University animal ethics committee.

Immunodeficient SCID mice were chosen for studying the pharmacokinetics of the hingeless IgG4 variant, because these mice do not develop antibody responses to human proteins which may affect clearance studies with durations of more than one week. These IgG-deficient mice were supplemented with a high dose of intravenous immunoglobulin (human multidonor polyclonal IgG) to study the clearance of hingeless IgG4 mutant in the presence of human IgG at physiologically relevant concentrations. This provides a mouse model which better represents the conditions in humans, because 1) association of hingeless IgG4 into a bivalent form is prevented by the presence of IVIG, and 2) hingeless IgG4 has to compete with other IgG for binding to the neonatal Fc receptor (FcRn)[1]. Binding to FcRn protects IgG from intracellular degradation after endocytosis and is responsible for its long plasma half-life.

[1] Bazin R, et al. Use of hu-IgG-SCID mice to evaluate the in vivo stability of human monoclonal IgG antibodies. *J Immunol Methods.* 1994; 172: 209-17.

In this model the plasma clearance was studied of variants from the human CD20 specific human mAb clone 7D8. The clearance rate of the hingeless IgG4 variant (7D8-HG, lot 992-001-EP) was compared with that of normal human IgG4 (7D8-IgG4, lot 992-002-EP), of F(ab')$_2$ fragments from 7D8 IgG1 (7D8-F(ab')$_2$, lot 892-020-XX). In addition, a preparation of the hingeless variant tested that was enzymatically deglycosylated (TH3001-7D8-HG deglyc, lot 991-004-EP). Each antibody was administered to 4 mice via the tail vein, at a dose of 0.1 mg in 200 µl, corresponding to a dose of about 5 mg per kg of body weight. The monoclonal antibodies were administered in a 1:1 mixture with Intravenous Immunoglobulin (60 mg/ml, Sanquin, The Netherlands, JFK108ST, charge #04H04H443A). The total injected volume was 400 µl/mouse, giving an IVIG dose of 12.5 mg per mouse.

Fifty µl blood samples were collected from the saphenal vein at 15 minutes, 5 hours, 24 hours, 2 days, 3 days, 7 days, and 10 days after administration. Blood was collected into heparin containing vials and centrifuged for 10 minutes at 14,000 g. Plasma was stored at −20° C. for determination of mAb concentrations. Plasma concentrations of the 7D8 variants were determined using a sandwich ELISA. A mouse mAb anti-7D8-idiotype antibody (clone 2F2 SAB 1.1 (LD2), lot 0347-028-EP) was used as capturing antibody. After blocking plates with PBS supplemented with 0.05% Tween and 2% chicken serum, samples were added, serially diluted in ELISA buffer (PBS supplemented with 0.05% Tween 20 and 2% chicken serum), and incubated on a plate shaker for 2 h at room temperature (RT). The infused antibodies were used as reference. After washing, the plates were subsequently incubated with peroxidase-labeled goat anti-human F(ab')$_2$ specific (109-035-097, Jackson Immunoresearch, West Grace, Pa.) and developed with 2,2'-azino-bis(3-ethylbenzthiazoline-6-sulfonic acid) (ABTS; Roche, Mannheim, Germany). Absorbance was measured in a microplate reader (Biotek, Winooski, Vt.) at 405 nm. Total human IgG plasma concentrations were determined using a similar ELISA. Mouse mAb anti-human IgG-kappa clone MH16 (#M1268, CLB Sanquin, The Netherlands) was used as capturing antibody. Peroxidase-labeled goat anti-human IgG immunoglobulin (#109-035-098, Jackson, West Grace, Pa.) was used for detection.

Pharmacokinetic analysis was done by determining the area under the curve (AUC) from the concentration—time curves, with tail correction. The plasma clearance rate was calculated as Dose/AUC (ml/day). Statistical testing was performed using GraphPad PRISM vs. 4 (Graphpad Software).

FIG. 20 shows in the upper panel semi-logarithmic plots of the concentrations of the mAb 7D8 variants in time and in the lower panel the total human IgG concentrations. The initial total human IgG concentrations were on average 2.3 mg/ml and declined to 0.47 mg/ml after 10 days. The initial plasma concentrations of 7D8 IgG4 and IgG4 HG variants were in the range of 94 to 180 µg/ml, which is consistent with an initial distribution into the plasma compartment of the mice. For the F(ab')2 fragments the initial concentrations were somewhat lower, on average 62 µg/ml. The upper panel makes clear that the clearance of the hingeless variant, including the deglycosylated preparation, is somewhat faster than that of intact IgG4, but much slower than that of F(ab')2 fragments. The table below shows the clearance rates calculated from the concentration-time curves. The clearance rate of the hingeless variant was 2 to 3 times higher than that of normal IgG4. However, it was almost 10 times slower than that of F(ab')$_2$ fragments. Importantly, deglycosylation had no significant effect on the rate of clearance of the hingeless IgG4 variant.

| PLASMA CLEARANCE RATE (D/AUC) in ml/day per kg | IgG1 F(ab')2 | IgG4 | IgG4 HG | IgG4 HG deglyc |
| --- | --- | --- | --- | --- |
| Mean | 380 | 14 | 39 | 29 |
| Lower 95% CI of mean | 346 | 12 | 25 | 19 |
| Upper 95% CI of mean | 415 | 17 | 53 | 38 |
| Number of values | 4 | 4 | 4 | 4 |

Thus, also in the presence of human IgG in physiologically relevant concentrations the clearance of the hingeless variant is much slower than that of F(ab')2 fragments, which have a comparable molecular size. This experiment demonstrates that, also in the presence of competing human IgG at physiologically relevant concentrations, the hingeless IgG4 variant is capable of functional interaction with the neonatal Fc receptor (FcRn). Furthermore, this experiment indicates that the glycosylation of the hingeless IgG4 variant does not affect plasma clearance and that non-glycosylated hingeless IgG4 has a similar half-life in vivo as the fully glycosylated from.

Example 53

Pharmacokinetic Evaluation of an IgG4 Hingeless Mutant Antibody Compared to Normal IgG4 and IgG1 F(ab)$_2$ Fragments in FcRn −/− Mice This experiment was performed to investigate whether the IgG4 hingeless mutant is capable of interacting with the neonatal Fc receptor (FcRn), which is responsible for the long plasma half-life of IgG by protecting IgG from intracellular degradation after endocytosis. B2M knockout mice were used in this experiment because they do not express FcRn.

Twelve female C57Bl/6 B2M knockout mice (Taconic model B2MN12-M, referred to as FcRn −/− mice), and twelve female C57Bl/6 wild type control mice (Taconic, model nr. B6, referred to as WT mice) were used for the experiment. The mice were housed in a barrier unit of the Central Laboratory Animal Facility (Utrecht, The Netherlands) and kept in filter-top cages with water and food provided ad libitum. All experiments were approved by the Utrecht University animal ethics committee.

The plasma clearance was studied of variants from the human CD20 specific human mAb clone 7D8. The clearance rate of the hingeless IgG4 variant (7D8-HG, lot 992-001-EP) was compared with that of normal human IgG4 (7D8-IgG4, lot 992-002-EP), F(ab')$_2$ fragments from 7D8-IgG1 (7D8-G1-F(ab')$_2$, lot 892-020-XX).

Monoclonal antibodies were administered intravenously via the tail vein. Each antibody was administered to 4 mice at a dose of 0.1 mg in 200 μl per mouse, corresponding to a dose of 5 mg per kg of body weight. Fifty μl blood samples were collected from the saphenal vein at 10 minutes, 5 hours, 24 hours, 2 days, 3 days, 7 days, and 10 days after administration. Blood was collected into heparin containing vials and centrifuged for 10 minutes at 14,000 g. Plasma was stored at −20° C. for determination of mAb concentrations. Human IgG plasma concentrations were determined using a sandwich ELISA in which mouse mAb anti-human IgG-kappa clone MH19-1 (#M1272, CLB Sanquin, The Netherlands), coated to 96-well Microlon ELISA plates (Greiner, Germany) at 100 ng/well was used as capturing antibody. After blocking plates with ELISA buffer (PBS supplemented with 0.05% Tween and 2% chicken serum), samples were added, serially diluted in ELISA buffer. Serial dilutions of the corresponding infused antibody preparations were used as reference. After incubation and washing, the plates were incubated with peroxidase-labeled AffiniPure Goat Anti-Human IgG, F(ab')$_2$ Fragment Specific (#109-035-097, Jackson Immunoresearch, West Grace, Pa.) and developed with 2,2'-azino-bis(3-ethylbenzthiazoline-6-sulfonic acid) (ABTS; Roche, Mannheim, Germany). Absorbance was measured in a microplate reader (Biotek, Winooski, Vt.) at 405 nm. Pharmacokinetic analysis was done by determining the area under the curve (AUC) from the concentration—time curves, with tail correction. The plasma clearance rate was calculated as Dose/AUC (ml/day). Statistical analysis was performed using GraphPad PRISM vs. 4 (Graphpad Software).

FIG. 21 shows a semi-logarithmic plot of the concentrations in time. The initial plasma concentrations were all in the order of 100 μg/ml, which is consistent with an initial distribution in the plasma compartment of the mice. The table below shows the plasma clearance rates calculated from the concentration-time curves of individual mice.

For F(ab')$_2$ fragments no significant differences were observed between wild type (WT) and knockout (FcRn −/−) mice. In contrast, for IgG4 and the hingeless IgG4 variant the clearance rates were 3 to 5 times slower in the WT mice compared to that in FcRn −/− mice. This experiment shows that the presence of FcRn has a favorable effect on the plasma residence time of hingeless IgG4. Therefore, it provides evidence that hingeless IgG4 is capable having a functional interaction with FcRn in vivo, which explains its favorable plasma half-life.

Example 54

Functional Analysis of 2F8-HG Anti-EGFr mAb

MAb 2F8 is a human IgG1 monoclonal antibody (mAb) against human Epidermal Growth Factor receptor (EGFr) which is capable to inhibit EGFr signalling by blocking binding of ligands. From this mAb an IgG4 variant, 2F8-IgG4, was made and also a hingeless variant, 2F8-HG.

In the present example, we compared the potency of 2F8-HG with that of 2F8-IgG1 and 2F8-Fab fragments to inhibit ligand-induced EGFr phosphorylation in cells in vitro. This was done both with and without addition of Intravenous Immunoglobulin (IVIG), a polyclonal human IgG preparation, containing all IgG subclasses.

Inhibition of EGFr phosphorylation was measured in a two-step assay using the epidermoid cell line, A431 (ATCC, American Type Culture Collection, Manassas, USA). The cells were cultured overnight in 96-wells plates in serum-free medium containing 0.5% human albumin (human albumin 20%, Sanquin, the Netherlands). Next, mAb were added in serial dilution, with or without IVIG (Immunoglobuline I.V., Sanquin) at a fixed final concentration of either 100 or 1000 μg/ml. After 60 minutes incubation at 37° C., 50 ng/ml recombinant human EGF (Bio-source) was added to induce activation of non-blocked EGFr. Following an additional 30 minutes incubation, cells were solubilized with lysis buffer (Cell Signaling Technology, Beverly, Mass.), and the lysates were transferred to ELISA plates coated with 1 μg/ml of mouse anti-EGF-R antibodies (mAb EGFR1, BD Pharmingen, San Diego, Calif.). After 2 hours incubation at RT, the plates were washed and binding of phosphorylated EGF-R was detected using a europium-labelled mouse mAb, specific for phosphorylated tyrosines (mAb Eu-N1 P-Tyr-100, PerkinElmer). Finally, DEL-FIA enhancement solution was added, and time-resolved fluorescence was measured by exciting at 315 nm and measuring emission at 615 nm on an EnVision plate reader (PerkinElmer). Sigmoidal dose-response curves were calculated using non-linear regression (GraphPad Prism 4).

As can be seen in the upper panel of FIG. 14, 2F8-HG was equally effective as 2F8-IgG1 in inhibiting phosphorylation when culture medium was used without addition IVIG. Both mAb were more potent than 2F8-Fab fragments, which bind monovalently to EGFr. The middle and lower panels of FIG. 14 show that addition of IVIG had negligible effect on 2F8-IgG4 and 2F8-Fab. However, it markedly right-shifted

| PLASMA CLEARANCE RATE ml/day per kg | F(ab')2 WT | F(ab')2 FcRn−/− | IgG4 WT | IgG4 FcRn−/− | IgG4 HG WT | IgG4 HG FcRn−/− |
|---|---|---|---|---|---|---|
| Mean | 183 | 159 | 12 | 45 | 15 | 83 |
| Std. Deviation | 19 | 19 | 10 | 3 | 4 | 29 |
| Number of values | 4 | 4 | 4 | 4 | 4 | 4 |
| Significance difference: | 0.1265 | | 0.0009 | | 0.0033 | |
| Pvalue (t-test) | ns | | * | |  | | the dose-response curve of 2F8-HG, indicating a change in binding characteristics, which is consistent with the idea that under certain conditions 2F8-HG may behave as a bivalent antibody, but dissociates into a monovalent form in the presence of polyclonal human IgG.

Example 55

Proof of Principle: IgG4 Hingeless Against CD89 (CD89-HG) Inhibits IgE-Mediated Asthma in a Mouse Model Pasquier et al. (Pasquier, B et al., Immunity 22, 31 (2005)) showed that FcαRI (CD89 (Monteiro R C et al., Annu Rev Immunol 21, 177 (2003)) has both an anti- and proinflammatory role. Aggregation of FcαRI leads to cell activation by recruitment of Syk and aborting SHP-1 binding. A monomeric interaction with FcαRI inhibits the activating response: SHP-1 is being recruited and impairment of Syk, LAT and ERK phosphorylation occurs.

Fab fragments of an anti-CD89 antibody (clone A77) could inhibit IgG-mediated phagocytosis using human monocytes. Furthermore, IgE-mediated responses in vitro using FcαRI transfected RBL-2H3 cells and in vivo in an IgE-mediated asthma model were inhibited by Fab fragments of this anti-CD89 antibody. In this animal model, FcαRI-transgenic mice (Launay P et al., J Exp Med 191, 1999 (2000)) were sensitized with TNP-OVA. Mice challenged intranasally with IgE-TNP-OVA immune complexes in the presence of A77 Fab-fragments showed reduced bronchial reactivity to methacholine whereas and irrelevant Fab-fragment could reduce the bronchial hyperreactivity.

Proof on principle in vitro of an antigen specific, non-crosslinking, monovalent, non-activating antibody is obtained in the following experiment. Adherent PBMC are incubated with 10 μg/ml A77-HG (IgG4 hingeless) preincubated 24 h with or without irrelevant IgG4 (Genmab BV) or incubated with irrelevant HG antibody for 30 min at 37° C., washed, and incubated at 37° C. for 30 min with Texas-red-conjugated $E.$ $coli$ (50 bacteria/cell) (Molecular Probes, Eugene, Oreg.) opsonized or not with polyclonal rabbit anti-$E.$ $coli$ IgG antibodies according to the manufacturer's instructions. Slides are mounted and examined with a confocal laser microscope. The PBMC receiving opsonized $E.$ $coli$ and A77-HG (pre-incubated with irrelevant IgG4) show reduced phagocytosis of $E.$ $coli$ when compared to PMBC receiving opsonized $E.$ $coli$ and control-HG antibody.

FcαRI-transgenic mice are sensitized with TNP-OVA as described (Pasquier B et al., Immunity 22, 31 (2005)); or alternatively with OVA as described by Deurloo et al. (Deurloo D T et al., Clin Exp Allergy 33, 1297 (2003)). Human FcαRI transgenic mice and littermate controls are immunized twice on day 0 and day 7 intraperitonally with TNP-OVA or OVA (Sigma) in aluminium hydroxide. Mice are challenged intranasally for a few consecutive days with either TNP-OVA complexed with 20 μg anti-DNP-IgE (Zuberi, R I et al., J Immunol 164, 2667 (2000)) or OVA aerosol (Deurloo D T et al., Clin Exp Allergy 33, 1297 (2003)) in the presence of A77-HG (IgG$_4$ hingeless) or an irrelevant hingeless antibody (control-HG).

The mice receive 50 μg A77-HG or control-HG intraperitoneally twice, once during the challenge period and once with the last intranasal challenge. Twelve hours after the final intranasal challenge, the mice are placed in a whole-body plethysmograph chamber (BUXCO Electronics, Sharon Conn., USA), and 300 mM methacholine delivered. Airway resistance is measured after exposure to methacholine. Immunohistological evaluation is performed on lung sections after euthanizing the mice.

The mice receiving A77-HG show a reduced hyper reactivity when compared to the mice receiving the control-HG antibody.

This indicates that a hingeless IgG$_4$ molecule is non-crosslinking, monovalent and non-activating and therefore useful for therapeutic purposes where such inert antibody may be favourable such as in the inhibition of inflammatory reactions through FcαRI.

Example 56

Proof of Concept Study with Hingeless IgG4 cMet (cMet-HG)

The receptor tyrosine kinase c-Met is prominently expressed on a wide variety of epithelial cells. During embryogenesis, cMet and Hepatocyte Growth factor/Scatter factor (HGF/SF) are involved in tissue-specific differentiation, leading to a proper organization of epithelial cells, muscle endothelium, and the nervous and hematopoietic systems. Abnormal cMet signalling has been implicated in tumorogenesis, particularly in the development of invasive and metastatic tumors. As a consequence of enhanced cMet activity, tumor cells may increase their growth rate and become resistant to apoptosis, resulting in a growth and/or survival advantage. Furthermore, cMet activation may lead to cytoskeletal reorganization and integrin activation, as well as to activation of proteolytic systems involved in extracellular matrix degradation, resulting in an increased invasive and metastatic capacity. Inhibition of HGF/SF-cMet signaling, therefore, represents an important therapeutic avenue for the treatment of malignant tumors.

Kong-Beltran et al., in Cancer Cell (2004 volume 6, pages 75-84) raised an antibody (5D5) to the extracellular domain of cMet and inhibited HGF binding. The Fab fragment of anti-Met 5D5 was shown to inhibit HGF-driven cMet phosphorylation, cell motility, migration and tumor growth. They speculate that anti-cMet-5D5-Fab block receptor dimerization by steric hindering.

MAb C6 is a human IgG1 monoclonal antibody (mAb) against human cMet which is capable of binding with high affinity to H441 cells, activate cMet phosphorylation, induce scattering of DU-145 and block HGF binding to cMet in ELISA. From this mAb a Fab fragment (cMet-Fab), an IgG4 variant (cMet-IgG4), and also a hingeless variant was made (cMet-HG).

In a proof-of-concept study with hingeless IgG4 against cMet (cMet-HG) this monovalent antibody inhibited HGF binding, receptor dimerization/activation, cell scattering, and downstream signalling. This experiment was performed both with and without addition of Intravenous Immunoglobulin (IVIG), a polyclonal human IgG preparation, containing all IgG subclasses and with and without rHGF.

DU-145 Scatter Assay

DU-145 (humane prostate carcinoma cell line, ATCC HTB-81) cells were cultured in DMEM+ (containing 500 ml MEM Dulbecco (DMEM-Medium, glucose 4.5 g/ml with NaHCO$_3$, without glutamine, Sigma, D-6546), 50 ml Cosmic Calf Serum (Hyclone SH30087.03), 5 ml of 200 mM/L L-glutamine (Bio Whittatker, BE17-605F), 5 ml sodium pyruvate (Bio Whittaker BE13-115E), 5 ml penicillin/streptamicin (Bio Whittaker, DE17-603E)) and were growing adherent clustered cells. Upon addition of rhHGF (Sigma, H-1404), migration of the cells was induced, which leads to singularized cells. This process was called scattering. Induction or inhibition of scattering was observed by microscopy.

Day 1: cMet, cMet-HG, cMet-Fab, cMet-IgG4 (30/3.0/0.3/0.03 μg/ml), were incubated over night with and without addition of IVIG, 6 mg/ml. DU145 cells were seeded (adherent cells out of T75-culture flask) cell culture supernatant was removed and cells were washed 1 time with 10 ml PBS 2 ml Trypsine/EDTA was added (37° C.) and cells were incubated at 37° C. for 1-2 min. The cells were removed from the surface of the culture flask by tapping and the Trypsine/EDTA reaction was stopped with stored culture supernatant. The cells were counted and a suspension was prepared of $1*10^4$ cells/ml in fresh culture medium and 50 μl/well was plated into 96-well plate (Sterile flat bottom Costar, 3596)(final density 1000 cells/well). Cells were cultured for 15-24 h at 37° C. and 5% $CO_2$ in an incubator.

Day 2: Medium was replaced by fresh medium, 40 μl/well. 40 ul of the preincubated antibody was added to the cells and cells were incubated at 37° C. in an incubator for 60 min, after which 40 μl/well medium or 60 ng/ml rh-HGF was added. (Final concentrations were: 10/1.0/0.1/0.01 μg/ml Ab, 2 mg/ml IVIG, 20 ng/ml HGF). Cells were incubated for at least 24 h.

Day 3 and 4: Scattering was observed double-blinded by microscope after 24 h or after 48 h. Morphological characteristics of scattering: cells detach from the surface, show spindle shaped forms (migrate), and most were single cells not in clusters. Ranking of rh-HGF induced scatter inhibition by antibodies:

3 cells were maximal scattering
2 small inhibition of scattering
1 inhibition of scattering
0 no scattering In this experiment C6-HG pre-incubated with IVIG significantly blocked the HGF induced scattering.

Phosphorylation of the cMet Receptor

A549 cells were cultured in Ham's F12 medium and cMet was not phosphorylated under normal culture conditions. Upon activation by HGF, the cMet receptor becomes phosphorylated. By applying cMet blocking cMet-Fab or cMet-HG with pre-incubation of IVIG the HGF mediated phosphorylation of the receptor was inhibited.

Day 1: cMet-IgG1, cMet-HG (12.5 μg/ml), were incubated over night with and without addition of IVIG, 2.5 mg/ml. A549 cells ($1*10^6$/well) were cultured in a 6 well plate.

Day 2: The culture medium, (containing 500 ml Ham's F12 (Bio Whittaker BE12-615F 50 ml Cosmic Calf Serum (Hyclone SH30087.03), 5 ml of 200 mM/L L-glutamine (Bio Whittatker, BE17-605F), 5 ml penicillin/streptamicin (Bio Whittaker, DE17-603E)) was removed and 800 μl of the preincubated antibody was added to the cells and cells were incubated herewith at 37° C. in an incubator for 15 min, after which 200 μl/well medium or 80 ng/ml rh-HGF was added. (Final concentrations were 10 μg/ml Ab, 2 mg/ml IVIG, 16 ng/ml HGF). After incubation for another 15 min, the incubation medium was removed and the cells were washed twice with ice cold PBS, and 250 μl RIPA lysis buffer (containing 50 mM Tris, pH 7.5, 0.5% Na deoxycholate and 0.1% Nonidet P40, 150 mM NaCl, 0.1% SDS, 2 mM vanadate and Complete (Protease inhibitor, Roche 1836170) was added, and the plate was gently rotated for 10 min. at 4° C. The lysates were transferred into pre-cooled tubes (Eppendorf) and centrifuged at highest speed for 30 min. at 4° C. DNA was removed and the lysate was flash frozen in $N_2$ after a fraction was used to measure BCA protein content analysis (Pierce). Lysates were stored at −80° C. until analysis by Western-blot. 10 μg reduced samples were undergoing electrophoresis on 4-20% Tris-HCl Criterion Precast gel (Biorad 345-0033) and Western blotting on a nitrocellulose membrane (Biorad 162-0114) according standard procedures. The membrane was blocked with blocking solution (containing 5% BSA (Roche, 10735086) in TBST (Tris-HL 20 mM pH 7.5, NaCl 150 mM, 0.1% Tween 20) for 1.5 hours at room temperature on a roller bank. The membrane was incubated over night at 4° C. with 1:1000 dilution of anti-phospho-Met(pYpYpY 1230 1234 1235)-rabbit IgG, (Abcam, ab5662). After washing 6 times with TBST, the secondary antibodies, goat-anti-rabbit-HRP, Cell Signalling, 7074 (1:2000) in blocking reagent were incubated for 60 min. at room temperature on a roller bank. The membrane was washed 6 times with TBST. Finally the bands were developed with Luminol Echancer stop solution (Pierce 1856145) and analyzed on a Lumiimager. cMet-HG pre-incubated with IVIG inhibits the HGF mediated phosphorylation of the receptor.

FIG. 22

DU-145 cells were cultured and incubated with a serial dilution of (A) cMet-Fab, cMet-Fab and IVIG, cMet-Fab and HGF, cMet-Fab and IVIG and HGF (B) cMet-HG, cMet-HG and IVIG, cMet-HG and HGF, cMet-HG and IVIG and HGF. Scattering was observed double-blinded (scored by 14 people) by microscope after 48 h and the averaged score SEM is plotted.

cMet-Fab with or without IVIG (A) and cMet-HG pre-incubated with IVIG (B) significantly blocked the HGF induced scattering dose-dependently.

FIG. 23

DU-145 cells were cultured and incubated with 10 μg/ml of (A) cMet-Fab, cMet-Fab and IVIG, cMet-Fab and HGF, cMet-Fab and IVIG and HGF (B) cMet-HG, cMet-HG and IVIG, cMet-HG and HGF, cMet-HG and IVIG and HGF. Scattering was observed double-blinded (scored by 14 people) by microscope after 48 h. cMet-Fab with or without IVIG and cMet-HG pre-incubated with IVIG significantly inhibited the HGF induced scattering. For statistical analysis a two-tailed Wilcoxon signed ranked test was done with a hypothetical median value of 3 (maximal scattering).

FIG. 24

Extracts prepared from A549 cells incubated with cMet-HG (lane 1), cMet-HG and IVIG (lane 2), cMet-HG and HGF (lane 3), cMet-HG, IVIG and HGF (lane 4), cMet-IgG1 (lane 5), cMet-IgG1 and IVIG (lane 6) were resolved by SDS-PAGE on a 4-20% Tris-HCl Criterion Precast gel and Western blotting on a nitrocellulose membrane. The membrane was incubated over night at 4° C. with anti-phospho-Met(pYpYpY 1230 1234 1235)-rabbit IgG, (Abcam, ab5662). After washing with TBST, the secondary antibodies, goat-anti-rabbit-HRP, Cell Signalling, 7074 in blocking reagent were incubated for 60 min. at room temperature on a roller bank. The membrane was washed 6 times with TBST. Finally the bands were developed with Luminol Echancer stop solution and analyzed on a Lumi-imager. The Western blot shows a 169 Kd band indicating phospho-Met(pYpYpY 1230 1234 1235).

Example 57

In Vitro Evaluation of an IgG4 Hingeless Mutant Antibody Targeting the Epidermal Growth Factor Receptor (EGFr): Binding Avidity and Induction of Antibody Dependent Cell-Mediated Cytotoxicity (ADCC)

In this experiment an IgG4 hingeless mutant antibody targeting the Epidermal Growth Factor Receptor (EGFr), mAb 2F8-HG was compared to an IgG4 version, an IgG1 version and Fab fragments, referred to as 2F8-IgG4, 2F8-IgG1 and 2F8-Fab, respectively. The in vitro evaluation comprised the avidity of binding to EGFr in an ELISA and the induction of ADCC.

ELISA. Binding affinities were determined using an ELISA in which purified EGF-R (Sigma, St Louis, Mo.) was coated to 96-well Microlon ELISA plates (Greiner, Germany), 50 ng/well. Plates were blocked with PBS supplemented with 0.05% Tween 20 and 2% chicken serum. Subsequently, samples, serially diluted in a buffer containing 100 µg/ml polyclonal human IgG (Intravenous Immunoglobulin, IVIG, Sanquin Netherlands) were added and incubated for 1 h at room temperature (RT). Plates were subsequently incubated with peroxidase-conjugated rabbit-anti-human kappa light chain (DAKO, Glostrup, Denmark) as detecting antibody and developed with 2,2'-azino-bis(3-ethylbenzthiazoline-6-sulfonic acid) (ABTS; Roche, Mannheim, Germany). Absorbance was measured in a microplate reader (Biotek, Winooski, Vt.) at 405 nm.

FIG. 16 shows that the binding curves of the 2F8-HG and 2F8-Fab are super-imposable and clearly right-shifted with respect to the binding curves of IgG1 and IgG4. This difference in avidity for the EGFr coat is consistent with the idea that, in the presence of IVIG, 2F8-HG binds monovalently, just like Fab fragments.

Antibody Dependent Cell-Mediated Cytotoxicity (ADCC).

The capacity to induce effector cell-dependent lysis of tumor cells was evaluated in Chromium-51 ($^{51}$Cr) release assay. Target A431 cells ($2-5\times10^6$ cells) were labeled with 100 µCi Na$_2$$^{51}$CrO$_4$ (Amersham Biosciences, Uppsala, Sweden) under shaking conditions at 37° C. for 1 h. Cells were washed thrice with PBS and were re-suspended in culture medium $1\times10^5$ cells/ml. Labeled cells were dispensed in 96 wells plates ($5\times10^3$, in 50 µl/well) and pre-incubated (RT, 30 minutes) with 50 µl of 10-fold serial dilutions of mAb in culture medium, ranging from 20 µg/ml to 0.02 ng/ml (final concentrations). Culture medium was added instead of antibody to determine the spontaneous $^{51}$Cr release, tritonX100 (1% final concentration) was added to determine the maximal $^{51}$Cr release. Thereafter, PBMC were added to the wells ($5\times10^5$/well) and cells were incubated at 37° C. overnight. The next day, supernatants were collected for measurement of the $^{51}$Cr release by determination of the counts per minute (cpm) in a gamma counter. Percentage of cellular cytotoxicity was calculated using the following formula:

% specific lysis=(experimental release (cpm)−spontaneous release (cpm))/(maximal release (cpm)−spontaneous release (cpm))×100 where maximal $^{51}$Cr release determined by adding triton X-100 to target cells, and spontaneous release was measured in the absence of sensitizing antibodies and effector cells.

FIG. 17 shows that 2F8-HG induces no ADCC, like 2F8-IgG4, whereas 2F8-IgG1 is very potent in this respect.

Example 58

AlgoNomics' Epibase® platform was applied to IgG4 constant hingeless monovalent antibody. In short, the platform analyzes the HLA binding specificities of all possible 10-mer peptides derived from a target sequence (Desmet et al. 1992, 1997, 2002, 2005). Profiling is done at the allotype level for 20 DRB1, 7 DRB3/4/5, 14 DQ and 7 DP, i.e. 48 HLA class II receptors in total.

Epibase® calculates a quantitative estimate of the free energy of binding ΔGbind of a peptide for each of the 48 HLA class II receptors. These data are then further processed as follows: Peptides are classified as strong (S), medium (M), weak and non (N) binders.

No strong and only 1 medium binding epitope was encountered within the constant region of IgG4 hingeless monovalent antibody. This single neo-epitope created a medium DRB1*0407 binder. DRB1*0407 is a minor allotype, present in less than 2% of the Caucasian population. In addition, a single epitope of medium strength is insignificant in the total epitope count of even the least immunogenic antibody.

In conclusion the hingeless monovalent IgG4 antibody is predicted to be very unlikely to be immunogenic.

Example 59

Background of Studies and Materials Used in Examples 59 and 60 Presented for Unibody-CD4

In vitro and in vivo experiments were performed to address the ability of a human monoclonal antibody against CD4 (HuMax-CD4) to inhibit HIV-1 infection. The antibody is directed against domain 1 of CD4 and overlaps with the HIV-1 gp120 binding site on CD4.

The present example (59) shows that Fab fragments of anti-CD4 antibodies inhibits the infection of CD4-CCR5 cells or CD4-CXCR4 cells by different primary isolates and T-cell line adapted HIV viruses. The IC50 values of inhibition are in the range of the EC50 values of HuMax-CD4 binding to sCD4 and cell bound CD4 (data not shown), implicating inhibition of HIV-1 envelope binding to CD4 as a mechanism of inhibition. In general Fab fragments of HuMax-CD4 inhibit with a 10 times lesser efficiency than the whole antibody which is as expected from the difference in avidity between the Fab and the whole antibody.

Example 60 shows that in mice treated with HuMax-CD4 a lesser decline in CD4/CD8 ratio compared is observed than in IgG control treatment groups, indicating that HuMax-CD4 protects against depletion of CD4 positive cells by HIV-1. Furthermore, HuMax-CD4 treatment leads to a decrease in the amount of HIV-1 RNA copies in the blood in time, whereas the IgG control treatment does not induce this decrease. The in vitro data indicate that anti-CD4 antibodies can protect against HIV-1-induced CD4 depletion, and decrease the magnitude of HIV infection and viral load.

Norris et al have published on the treatment of HIV-1 infected individuals with a whole anti-CD4 (domain 2) antibody of the IgG4 subclass.

Efficacy results demonstrated significant antiviral activity at primary endpoint (Week 24).

Durable response suggested by Week-48 results in patients receiving TNX-355.

TNX-355 10 mg/kg+OBR demonstrated a 0.96 log 10 reduction in HIV-RNA from baseline at Week 48 versus 0.14 log 10 decrease for placebo+OBR (p<0.001).

TNX-355 15 mg/kg+OBR demonstrated a 0.71 log 10 reduction in HIV-RNA from baseline at Week 48 versus 0.14 log 10 for placebo+OBR (p=0.009).

Treatment with TNX-355+OBR was associated with statistically significant and clinically-meaningful increases in CD4+ cells at Week 48 in both the 10 mg/kg arm (+48 cells, p=0.031) and the 15 mg/kg (+51 cells, p=0.016) arms versus the placebo increase (+1 cell).

LITERATURE

Zwick M. B., Wang M., Poignard P., Stiegler G., Katinger H., Burton D. R., and Parren P. W. H. I. 2001. Neutralization synergy of human immunodeficiency virus type 1 primary isolates by cocktails of broadly neutralizing antibodies. *J Vir* 75:12198.

Poignard P., Sabbe R., Picchio G. R., Wang M., Gulizia R. J., Katinger H., Parren P. W. H. I., Mosier D. E., and Burton D. R. 1999. Neutralizing antibodies have limited effects on the control of established HIV-1 infection in vivo. *Immunity* 10:431.

Norris D., Moralis J., Gathe J., Godafsky E., Garcias F., Hardwick R., and Lewis S. 2006. Phase 2 efficacy and safety of the novel viral-entry inhibitor, TNX-355, in combination with optimized background regimen (OBR). *XVI International AIDS Conference*, Toronto, Canada.

In Vitro HIV-1 Neutralization by HuMax-CD4 Whole Antibody and Fab Fragments of the HuMax-CD4 Antibody The method is described in detail in Zwick et al 2001. In summary, the degree of virus neutralization by antibody was measured by luciferase activity. Viruses competent for a single round of replication were produced by cotransfections of the appropriate virus constructs in a modified pSVIIIenv vector (for instance primary isolates: JR-CSF, JR-FL, SF162, ADA, YU2, 89.6, US143 and T cell line adapted virus: IIIB) and pNL4-3.lec.R-E-. Viruses were pre-incubated with various amounts of antibody (before addition determined to yield about 100,000 counts) to U87.CD4.CCR5 cells (primary isolates) or CD4-CXCR4 cells (for IIIB), and culturing for 3 days. The wells were washed, incubated with luciferase cell culture lysis reagent, and lysates were transferred to opaque assay plate to measure luciferase activity on a luminometer using luciferase assay reagent. For neutralization HuMax-CD4 and Fab fragments of HuMax-CD4 were tested.

According to the method described, the virus constructs YU2, IIIB, ADA, 89.6, US143, JR-FL, JR-CSF, and SF 162 were used in the in vitro neutralization assay using the luciferase assay expression system. HIV-1 IIIB is a T-cell line adapted virus, all the other viruses are primary isolates of HIV-1. The HuMax-CD4 antibody and Fab fragments of HuMax-CD4 were added in a 1:2 dilution response starting at the concentrations indicated in FIG. 25. In FIG. 27, the curves fitted by a 4 parameter logistic analysis are given for the HuMax-CD4 and the Fab fragments of HuMax-CD4 and in FIG. 25 the IC50 calculated from these fits are indicated. The data show that the HuMax-CD4 antibody inhibited the infection of all the viruses tested, and in general did this with a 10 times better efficiency than the Fab fragments (exceptions are YU2 and JR-CSF). The EC50 for binding of HuMax-CD4 to sCD4 has been determined to be about 0.3-1 nM. The IC50 values of inhibition are in the range of these EC50 values, indicating that receptor occupation by HuMax-CD4 relates to degree of infection inhibition.

Our experiments provide proof-of-principle for an effective inhibition of HIV-1 infection of both CXCR4 and CCR5HIV-1 co-receptor expressing cells by monovalent binding of an anti-CD4 antibody (i.e. Fab fragment). This provides evidence that a similar inhibition could be accomplished by a HG anti-CD4 antibody.

Example 60

Protection of CD4+ T Cell Depletion in In Vivo Hu-PBMC-SCID Mouse Model of HIV Infection The experimental procedure is described in detail in Poignard et al 1999. In summary, CB-17 SCID mice were reconstituted with about $25 \times 10^6$ normal human PBMC (peripheral blood mononuclear cells). About two weeks later the animals were infected with HIV-1 (HIV-1$_{JR-CSF}$). Three days later the animals are treated with 1 mg/ml HuMax-CD4, or a human IgG isotype control antibody, or no treatment delivered intraperitoneally. Blood samples were taken at 1 hr, 6 hrs, day 1, 2, 3, 6, 9, 13, and 15 after injection, and two weeks later the animals were euthanized and FACS analysis performed to determined the % of human cells (using H2 Kd-PE and human CD3-APC) and the CD4/CD8 ratio (using CD4-PE and CD8-APC double staining). Furthermore, plasma viral load was measured by measuring HIV-1 RNA levels by the quantitative Roche RT PCR assay. In addition, with a direct sCD4 binding ELISA (coat of sCD4 on the plate, and detection by anti-Fc polyclonal antibody) the concentrations of HuMax-CD4 in plasma were determined.

In FIG. 28 the plasma levels of the animals are given. It is concluded that HuMax-CD4 injection leads to high HuMax-CD4 plasma concentrations that were still above 100 μg/ml at day 15. The non treated mice gave no measurable values above background.

In FIG. 26 the cell numbers harvested from the mice at the end of the experiment are given. The data indicate that HIV-1 infection led to an extensive decrease in CD4 positive T cells as indicated by the drop in CD4/CD8 ratio. This shows that CD4 positive T cells are rapidly depleted from the blood by HIV-1 in contrast to the constant levels in non-infected mice. The mice treated ip with HuMax-CD4 had a much smaller decline in CD4/CD8 ratio, which shows that HuMax-CD4 provides protection of against depletion of CD4 positive cells by HIV-1. In FIG. 29 the HIV-1 RNA copies per ml blood are given in time, and these data indicate that the HuMax-CD4 treatment led to a decrease in the amount of HIV-1 RNA copies in the blood in time, whereas the isotype control antibody did not lead to a decrease.

Our experiment provides proof of principle for the protection against CD4 cell depletion in HIV-1 infection in vivo. The protection against depletion is observed even though the whole anti-CD4 antibody has CD4 depleting properties it self. This indicates that stronger protection against HIV-1-induced T cell depletion can be obtained by treatment with a monovalent non-depleting anti-CD4 antibody such as an anti-CD4 HG antibody. Proof of principle for HIV-1 neutralization by anti-CD4 HG and protection against CD4 depletion can be obtained in a similar experimental set-up. This provides evidence that HuMax-CD4 HG showing a long in vivo half life, could inhibit HIV-1 infection and HIV-1 viral load and protect from depletion of CD4 positive cells.

SUMMARY OF THE RESULTS

The data presented in the examples shows that expression of a hingeless IgG4 antibody by destroying the splice donor site of the hinge exon results in hingeless IgG4 half-molecules (one heavy and one light chain combined). The presence of IgG4 hingeless half-molecules is confirmed by SDS-PAGE under non-reducing conditions, mass spectrometry, size exclusion chromatography and radio immuno assay the absence of cross-linking abilities. The hingeless antibodies retain the same antigen binding specificity as natural format IgG1 and IgG4 antibody molecules. This is shown for two hingeless antibodies with different specificity, 7D8-HG (specific for the B-cell antigen CD20) and Betv1-HG (specific for the Birch pollen antigen Bet v 1). C1q binding of 7D8-HG is absent and only minor complement-dependent cellular toxicity (ADCC) is observed (comparable to the natural format 7D8-IgG4 antibody). Monovalency of the hingeless half-molecule is shown in the crosslinking experiment using Betv1-HG. Whereas both IgG1 and $IgG_4$ show crosslinking of Sepharose bound Bet v 1 to radiolabelled Bet v 1, the hingeless molecule Betv1-HG is unable to crosslink.

Half-life of 7D8-HG is evaluated in vivo in a mouse pharmacokinetic (PK) experiment and compared with 7D8-IgG4. Although 7D8-HG has a 2 to 3 times faster clearance than normal IgG4 in this model, the 6 day half-life is counted favorable to the half-life of less than one day reported for IgG F(ab')2 fragments. We conclude that the favorable PK-profile will make IgG4-hingeless antibodies valuable for therapeutic applications when a non-crosslinking, monovalent and non-complement-activating antibody is needed.

SEQUENCE LISTING

SEQ ID No: 1: The nucleic acid sequence of $C_L$ Kappa at human IgG

```
  1  CGTACGGTGG CTGCACCATC TGTCTTCATC TTCCCGCCAT CTGATGAGCA
 51  GTTGAAATCT GGAACTGCCT CTGTTGTGTG CCTGCTGAAT AACTTCTATC
101  CCAGAGAGGC CAAAGTACAG TGGAAGGTGG ATAACGCCCT CCAATCGGGT
151  AACTCCCAGG AGAGTGTCAC AGAGCAGGAC AGCAAGGACA GCACCTACAG
201  CCTCAGCAGC ACCCTGACGC TGAGCAAAGC AGACTACGAG AAACACAAAG
251  TCTACGCCTG CGAAGTCACC CATCAGGGCC TGAGCTCGCC CGTCACAAAG
301  AGCTTCAACA GGGGAGAGTG T
```

SEQ ID No: 2: The amino acid sequence of $C_L$ kappa of human IgG

```
  1  RTVAAPSVFI FPPSDEQLKS GTASVVCLLN NFYPREAKVQ WKVDNALQSG
 51  NSQESVTEQD SKDSTYSLSS TLTLSKADYE KHKVYACEVT HQGLSSPVTK
101  SFNRGEC
```

SEQ ID No: 3: The nucleic acid sequence of $C_L$ lambda of human IgG

```
  1  ACCGTCCTAG GTCAGCCCAA GGCTGCCCCC TCGGTCACTC TGTTCCCGCC
 51  CTCCTCTGAG GAGCTTCAAG CCAACAAGGC CACACTGGTG TGTCTCATAA
101  GTGACTTCTA CCCGGGAGCC GTGACAGTGG CCTGGAAGGC AGATAGCAGC
151  CCCGTCAAGG CGGGAGTGGA GACCACCACA CCCTCCAAAC AAAGCAACAA
201  CAAGTACGCG GCCAGCAGCT ACCTGAGCCT GACGCCTGAG CAGTGGAAGT
251  CCCACAGAAG CTACAGCTGC CAGGTCACGC ATGAAGGGAG CACCGTGGAG
301  AAGACAGTGG CCCCTACAGA ATGTTCA
```

SEQ ID No: 4: The amino acid sequence of $C_L$ lambda of human IgG

```
  1  TVLGQPKAAP SVTLFPPSSE ELQANKATLV CLISDFYPGA VTVAWKADSS
 51  PVKAGVETTT PSKQSNNKYA ASSYLSLTPE QWKSHRSYSC QVTHEGSTVE
101  KTVAPTECS
```

SEQ ID No: 5: The nucleic acid sequence for the $V_H$ of HuMab-7D8

```
  1  GAAGTGCAGC TGGTGGAGTC TGGGGGAGGC TTGGTACAGC CTGACAGGTC
 51  CCTGAGACTC TCCTGTGCAG CCTCTGGATT CACCTTTCAT GATTATGCCA
101  TGCACTGGGT CCGGCAAGCT CCAGGGAAGG GCCTGGAGTG GGTCTCAACT
151  ATTAGTTGGA ATAGTGGTAC CATAGGCTAT GCGGACTCTG TGAAGGGCCG
201  ATTCACCATC TCCAGAGACA ACGCCAAGAA CTCCCTGTAT CTGCAAATGA
251  ACAGTCTGAG AGCTGAGGAC ACGGCCTTGT ATTACTGTGC AAAAGATATA
301  CAGTACGGCA ACTACTACTA CGGTATGGAC GTCTGGGGCC AAGGGACCAC
351  GGTCACCGTC TCCTCA
```

-continued

SEQ ID No: 6: The amino acid sequence for the $V_H$ of HuMab-7D8
```
  1  EVQLVESGGG LVQPDRSLRL SCAASGFTFH DYAMHWVRQA PGKGLEWVST

51  ISWNSGTIGY ADSVKGRFTI SRDNAKNSLY LQMNSLRAED TALYYCAKDI

101  QYGNYYYGMD VWGQGTTVTV SS
```

SEQ ID No: 7: The nucleic acid sequence for the $V_H$ of mouse anti-Betv-1
```
  1  GAGGTTCAGC TGCAGCAGTC TGGGGCAGAG CTTGTGAAAC CAGGGGCCTC

51  AGTCAAGTTG TCCTGCACAG CTTCTGGCTT CAACATTAAA GACACCTATA

101  TCCACTGGGT GAAGCAGAGG CCTGAACAGG GCCTGGAGTG GGTTGGAAGG

151  ATTGATCCTG CGACTGGCAA TACTAGATAT GACCCGAAGT TCCAGGGCAA

201  GGCCACTATA ACAGCTGACA CATCCTCCAA CACAGCCTAC CTGCAACTCA

251  GCAGCCTGAC ATCTGAGGAC ACTGCCGTCT ATTACTGTGC TAGTTTTAGG

301  CCGGGGTATG CTCTGGACTA CTGGGGTCAA GGAACCTCAG TCACCGTCTC

351  CTCA
```

SEQ ID No: 8: The amino acid sequence for the $V_H$ of mouse anti-Betv-1
```
  1  EVQLQQSGAE LVKPGASVKL SCTASGFNIK DTYIHWVKQR PEQGLEWVGR

51  IDPATGNTRY DPKFQGKATI TADTSSNTAY LQLSSLTSED TAVYYCASFR

101  PGYALDYWGQ GTSVTVSS
```

SEQ ID No: 9: The nucleic acid sequence for the $V_L$ of HuMab-7D8
```
  1  GAAATTGTGT TGACACAGTC TCCAGCCACC CTGTCTTTGT CTCCAGGGGA

51  AAGAGCCACC CTCTCCTGCA GGGCCAGTCA GAGTGTTAGC AGCTACTTAG

101  CCTGGTACCA ACAGAAACCT GGCCAGGCTC CCAGGCTCCT CATCTATGAT

151  GCATCCAACA GGGCCACTGG CATCCCAGCC AGGTTCAGTG GCAGTGGGTC

201  TGGGACAGAC TTCACTCTCA CCATCAGCAG CCTAGAGCCT GAAGATTTTG

251  CAGTTTATTA CTGTCAGCAG CGTAGCAACT GGCCGATCAC CTTCGGCCAA

301  GGGACACGAC TGGAGATTAA A
```

SEQ ID No: 10: The amino acid sequence for the $V_L$ of HuMab-7D8
```
  1  EIVLTQSPAT LSLSPGERAT LSCRASQSVS SYLAWYQQKP GQAPRLLIYD

51  ASNRATGIPA RFSGSGSGTD FTLTISSLEP EDFAVYYCQQ RSNWPITFGQ

101  GTRLEIK
```

SEQ ID No: 11: The nucleic acid sequence for the $V_L$ of mouse anti-Betv-1
```
  1  GACATTGTGA TGACCCAGTC TCACAAATTC ATGTCCACAT CAGTTGGAGA

51  CAGGGTCAGC TTCACCTGCA AGGCCAGTCA GGATGTGTTT ACTGCTGTAG

101  CCTGGTATCA ACAAAAACCA GCGCAATCTC CTAAACTACT GATTTACTGG

151  GCATCCACCC GGCGCACTGG AGTCCCTGAT CGCTTCACAG GCAGTGGATC

201  TGGGACAGAT TATACTCTCA CCATCAGCAG TGTGCAGGCT GAAGACCTGG

251  CACTTTATTA CTGTCAGCAA CATTTTAGCA CTCCTCCGAC GTTCGGTGGA

301  GGCACCAAGC TGGAAATCAA A
```

SEQ ID No: 12: The amino acid sequence for the $V_L$ of mouse anti-Betv-1
```
  1  DIVMTQSHKF MSTSVGDRVS FTCKASQDVF TAVAWYQQKP GQSPKLLIYW

51  ASTRRTGVPD RFTGSGSGTD YTLTISSVQA EDLALYYCQQ HFSTPPTFGG

101  GTKLEIK
```

-continued

SEQ ID No: 13: The nucleic acid sequence of the wildtype C$_H$ region of human IgG4
```
   1    GCTAGCACCA AGGGCCCATC CGTCTTCCCC CTGGCGCCCT GCTCCAGGAG
  51    CACCTCCGAG AGCACAGCCG CCCTGGGCTG CCTGGTCAAG GACTACTTCC
 101    CCGAACCGGT GACGGTGTCG TGGAACTCAG GCGCCCTGAC CAGCGGCGTG
 151    CACACCTTCC CGGCTGTCCT ACAGTCCTCA GGACTCTACT CCCTCAGCAG
 201    CGTGGTGACC GTGCCCTCCA GCAGCTTGGG CACGAAGACC TACACCTGCA
 251    ACGTAGATCA CAAGCCCAGC AACACCAAGG TGGACAAGAG AGTTGGTGAG
 301    AGGCCAGCAC AGGGAGGGAG GGTGTCTGCT GGAAGCCAGG CTCAGCCCTC
 351    CTGCCTGGAC GCACCCCGGC TGTGCAGCCC CAGCCCAGGG CAGCAAGGCA
 401    TGCCCCATCT GTCTCCTCAC CCGGAGGCCT CTGACCACCC CACTCATGCT
 451    CAGGGAGAGG GTCTTCTGGA TTTTTCCACC AGGCTCCGGG CAGCCACAGG
 501    CTGGATGCCC CTACCCCAGG CCCTGCGCAT ACAGGGGCAG GTGCTGCGCT
 551    CAGACCTGCC AAGAGCCATA TCCGGGAGGA CCCTGCCCCT GACCTAAGCC
 601    CACCCCAAAG GCCAAACTCT CCACTCCCTC AGCTCAGACA CCTTCTCTCC
 651    TCCCAGATCT GAGTAACTCC CAATCTTCTC TCTGCAGAGT CCAAATATGG
 701    TCCCCCATGC CCATCATGCC CAGGTAAGCC AACCCAGGCC TCGCCCTCCA
 751    GCTCAAGGCG GGACAGGTGC CCTAGAGTAG CCTGCATCCA GGGACAGGCC
 801    CCAGCCGGGT GCTGACGCAT CCACCTCCAT CTCTTCCTCA GCACCTGAGT
 851    TCCTGGGGGG ACCATCAGTC TTCCTGTTCC CCCCAAAACC CAAGGACACT
 901    CTCATGATCT CCCGGACCCC TGAGGTCACG TGCGTGGTGG TGGACGTGAG
 951    CCAGGAAGAC CCCGAGGTCC AGTTCAACTG GTACGTGGAT GGCGTGGAGG
1001    TGCATAATGC CAACACAAAG CCGCGGGAGG AGCAGTTCAA CAGCACGTAC
1051    CGTGTGGTCA GCGTCCTCAC CGTCCTGCAC CAGGACTGGC TGAACGGCAA
1101    GGAGTACAAG TGCAAGGTCT CCAACAAAGG CCTCCCGTCC TCCATCGAGA
1151    AAACCATCTC CAAAGCCAAA GGTGGGACCC ACGGGGTGCG AGGGCCACAT
1201    GGACAGAGGT CAGCTCGGCC CACCCTCTGC CCTGGGAGTG ACCGCTGTGC
1251    CAACCTCTGT CCCTACAGGG CAGCCCCGAG AGCCACAGGT GTACACCCTG
1301    CCCCCATCCC AGGAGGAGAT GACCAAGAAC CAGGTCAGCC TGACCTGCCT
1351    GGTCAAAGGC TTCTACCCCA GCGACATCGC CGTGGAGTGG GAGAGCAATG
1401    GGCAGCCGGA GAACAACTAC AAGACCACGC CTCCCGTGCT GGACTCCGAC
1451    GGCTCCTTCT TCCTCTACAG CAGGCTAACC GTGGACAAGA GCAGGTGGCA
1501    GGAGGGGAAT GTCTTCTCAT GCTCCGTGAT GCATGAGGCT CTGCACAACC
1551    ACTACACACA GAAGAGCCTC TCCCTGTCTC TGGGTAAA
```

SEQ ID No: 14: The amino acid sequence of the wildtype C$_H$ region of human IgG4
```
   1    ASTKGPSVFP LAPCSRSTSE STAALGCLVK DYFPEPVTVS WNSGALTSGV
  51    HTFPAVLQSS GLYSLSSVVT VPSSSLGTKT YTCNVDHKPS NTKVDKRVES
 101    KYGPPCPSCP APEFLGGPSV FLFPPKPKDT LMISRTPEVT CVVVDVSQED
 151    PEVQFNWYVD GVEVHNAKTK PREEQFNSTY RVVSVLTVLH QDWLNGKEYK
```

```
201  CKVSNKGLPS SIEKTISKAK GQPREPQVYT LPPSQEEMTK NQVSLTCLVK

251  GFYPSDIAVE WESNGQPENN YKTTPPVLDS DGSFFLYSRL TVDKSRWQEG

301  NVFSCSVMHE ALHNHYTQKS LSLSLGK
```

SEQ ID No: 15: The nucleic acid sequence encoding the $C_H$ region of human IgG4 (SEQ ID No: 13) mutated in positions 714 and 722

```
   1  GCTAGCACCA AGGGCCCATC CGTCTTCCCC CTGGCGCCCT GCTCCAGGAG

51  CACCTCCGAG AGCACAGCCG CCCTGGGCTG CCTGGTCAAG GACTACTTCC

101  CCGAACCGGT GACGGTGTCG TGGAACTCAG GCGCCCTGAC CAGCGGCGTG

151  CACACCTTCC CGGCTGTCCT ACAGTCCTCA GGACTCTACT CCCTCAGCAG

201  CGTGGTGACC GTGCCCTCCA GCAGCTTGGG CACGAAGACC TACACCTGCA

251  ACGTAGATCA CAAGCCCAGC AACACCAAGG TGGACAAGAG AGTTGGTGAG

301  AGGCCAGCAC AGGGAGGGAG GGTGTCTGCT GGAAGCCAGG CTCAGCCCTC

351  CTGCCTGGAC GCACCCCGGC TGTGCAGCCC CAGCCCAGGG CAGCAAGGCA

401  TGCCCCATCT GTCTCCTCAC CCGGAGGCCT CTGACCACCC CACTCATGCT

451  CAGGGAGAGG GTCTTCTGGA TTTTTCCACC AGGCTCCGGG CAGCCACAGG

501  CTGGATGCCC CTACCCCAGG CCCTGCGCAT ACAGGGGCAG GTGCTGCGCT

551  CAGACCTGCC AAGAGCCATA TCCGGAGGA CCCTGCCCCT GACCTAAGCC

601  CACCCCAAAG GCCAAACTCT CCACTCCCTC AGCTCAGACA CCTTCTCTCC

651  TCCCAGATCT GAGTAACTCC CAATCTTCTC TCTGCAGAGT CCAAATATGG

701  TCCCCCATGC CCACCATGCC CGGGTAAGCC AACCCAGGCC TCGCCCTCCA

751  GCTCAAGGCG GGACAGGTGC CCTAGAGTAG CCTGCATCCA GGGACAGGCC

801  CCAGCCGGGT GCTGACGCAT CCACCTCCAT CTCTTCCTCA GCACCTGAGT

851  TCCTGGGGGG ACCATCAGTC TTCCTGTTCC CCCCAAAACC CAAGGACACT

901  CTCATGATCT CCCGGACCCC TGAGGTCACG TGCGTGGTGG TGGACGTGAG

951  CCAGGAAGAC CCCGAGGTCC AGTTCAACTG GTACGTGGAT GGCGTGGAGG

1001  TGCATAATGC CAAGACAAAG CCGCGGGAGG AGCAGTTCAA CAGCACGTAC

1051  CGTGTGGTCA GCGTCCTCAC CGTCCTGCAC CAGGACTGGC TGAACGGCAA

1101  GGAGTACAAG TGCAAGGTCT CCAACAAAGG CCTCCCGTCC TCCATCGAGA

1151  AAACCATCTC CAAAGCCAAA GGTGGGACCC ACGGGGTGCG AGGGCCACAT

1201  GGACAGAGGT CAGCTCGGCC CACCCTCTGC CCTGGGAGTG ACCGCTGTGC

1251  CAACCTCTGT CCCTACAGGG CAGCCCCGAG AGCCACAGGT GTACACCCTG

1301  CCCCCATCCC AGGAGGAGAT GACCAAGAAC CAGGTCAGCC TGACCTGCCT

1351  GGTCAAAGGC TTCTACCCCA GCGACATCGC CGTGGAGTGG GAGAGCAATG

1401  GGCAGCCGGA GAACAACTAC AAGACCACGC CTCCCGTGCT GGACTCCGAC

1451  GGCTCCTTCT TCCTCTACAG CAGGCTAACC GTGGACAAGA GCAGGTGGCA

1501  GGAGGGGAAT GTCTTCTCAT GCTCCGTGAT GCATGAGGCT CTGCACAACC

1551  ACTACACACA GAAGAGCCTC TCCCTGTCTC TGGGTAAA
```

SEQ ID No: 16: The amino acid sequence of the hingeless $C_H$ region of a human IgG4.

```
   1  ASTKGPSVFP LAPCSRSTSE STAATLGCLVK DYFPEPVTVS WNSGALTSGV

51  HTFPAVLQSS GLYSLSSVVT VPSSSLGTKT YTCNVDHKPS NTKVDKRVAP

101  EFLGGPSVFL FPPKPKDTLM ISRTPEVTCV VVDVSQEDPE VQFNWYVDGV
```

```
151  EVHNAKTKPR EEQFNSTYRV VSVLTVLHQD WLNGKEYKCK VSNKGLPSSI

201  EKTISKAKGQ PREPQVYTLP PSQEEMTKNQ VSLTCLVKGF YPSDIAVEWE

251  SNGQPENNYK TTPPVLDSDG SFFLYSRLTV DKSRWQEGNV FSCSVMHEAL

301  HNHYTQKSLS LSLGK
```

SEQ ID NO: 17: The amino acid sequence of the lambda chain constant human (accession number S25751)
```
  1  qpkaapsvtl fppsseelqa nkatlvclis dfypgavtva wkadsspvka 51  gvetttpskq snnkyaassy lsltpeqwks hrsyscqvth egstvektva 101  pteCs
```

SEQ ID NO: 18: The amino acid sequence of the kappa chain constant human (accession number P01834)
```
  1  tvaapsvfif ppsdeqlksg tasvvcllnn fypreakvqw kvdnalqsgn 51  sqesvteqds kdstyslsst ltlskadyek hkvyacevth qglsspvtks 101  fnrgeC
```

SEQ ID NO: 19: The amino acid sequence of IgG1 constant region (accession number P01857)
```
  1  astkgpsvfp lapSskstsg gtaalgclvk dyfpepvtvs wnsgaltsgv 51  htfpavlqss glyslssvvt vpssslgtqt yidnvnhkps ntkvdkkvep 101  kscdkthtcp pcpapellgg psvflfppkp kdtlmisrtp evtcvvvdvs 151  hedpevkfnw yvdgvevhna ktkpreeqyn styrvvsvlt vlhqdwlngk 201  eykckvsnka lpapiektis kakgqprepq vytlppsRDe mtknqvsltc 251  lvkgfypsdi avewesngqp ennykttppv ldsdgsffly sKltvdksrw 301  qQgnvfscsv mhealhnhyt qkslslsPgk
```

SEQ ID NO: 20: The amino acid sequence of the IgG2 constant region (accession number P01859)
```
  1  astkgpsvfp lapcsrstse staalgclvk dyfpepvtvs wnsgaltsgv 51  htfpavlqss glyslssvvt vpssnfgtqt ytdnvdhkps ntkvdktver 101  kccvecppcp appvagpsvf lfppkpkdtl misrtpevtc vvvdvshedp 151  evqfnwyvdg vevhnaktkp reeqfnstfr vvsvltvvhq dwlngkeykc 201  kvsnkglpap iektisktkg qprepqvytl ppsReemtkn qvsltclvkg 251  fypsdiavew esngqpenny kttppMldsd gsfflysKlt vdksrwqQgn 301  vfscsvmhea lhnhytqksl slsPgk
```

SEQ ID NO: 21: The amino acid sequence of the IgG3 constant region (accession number A23511)
```
  1  astkgpsvfp lapcsrstsg gtaalgclvk dyfpepvtvs wnsgaltsgv 51  htfpavlqss glyslssvvt vpssslgtqt ytcnvnhkps ntkvdkrvel 101  ktplgdttht cprcpepksc dtpppcprcp epkscdtppp cprcpepksc 151  dtpppcprcp apellggpsv flfppkpkdt lmisrtpevt cvvvdvshed 201  pevqfkwyvd gvevhnaktk preeqynstf rvvsvltvlh qdwlngkeyk 251  ckvsnkalpa piektisktk gqprepqvyt lppsReemtk nqvsltclvk 301  gfypsdiave wesSgqpenn yNttppMlds dgsfflysKl tvdksrwqQg 351  nlfscsvmhe alhnRFtqks lslsPgk
```

The invention claimed is:

1. An isolated monovalent antibody comprising a light chain and a heavy chain, wherein
    a) said light chain comprises the amino acid sequence of the light chain variable (VL) region of a selected antigen specific antibody and the amino acid sequence of the light chain constant (CL) region of an immunoglobulin, and
    b) said heavy chain comprises the amino acid sequence of the heavy chain variable (VH) region of said selected antigen specific antibody and the amino acid sequence of SEQ ID NO: 16.

2. An isolated monovalent antibody according to claim 1, wherein the CL region is the constant region of the kappa light chain of a human IgG.

3. An isolated monovalent antibody according to claim 2, wherein the CL region comprises the amino acid sequence of SEQ ID NO: 2.

4. An isolated monovalent antibody according to claim 1, wherein the CL region is the constant region of the lambda light chain of a human IgG.

5. An isolated monovalent antibody according to claim 4, wherein the CL region comprises the amino acid sequence of SEQ ID NO: 4.

6. An isolated monovalent antibody according to claim 1, wherein the light chain and the heavy chain are connected to each other via one or more disulphide bonds or via an amide bond.

7. An isolated monovalent antibody comprising a light chain and a heavy chain, wherein
    a) said light chain comprises the amino acid sequence of the light chain variable (VL) region of a selected antigen specific antibody and the amino acid sequence of the light chain constant (CL) region of an immunoglobulin, and
    b) said heavy chain comprises the amino acid sequence of the heavy chain variable (VH) region of said selected antigen specific antibody and the amino acid sequence of SEQ ID NO: 22.

8. An isolated monovalent antibody comprising a heavy chain and a light chain, wherein
    a) said light chain comprises the amino acid sequence of the light chain variable (VL) region of a selected antigen specific antibody and the amino acid sequence of the light chain constant (CL) region of an immunoglobulin, and
    b) said heavy chain comprises the amino acid sequence of the heavy chain variable (VH) region of said selected antigen specific antibody and the amino acid sequence of the heavy chain constant (CH) region of human IgG1, wherein the CH region comprises the amino acid sequence set forth in SEQ ID NO: 19, wherein Lys (K) in position 292 of SEQ ID NO: 19 has been replaced by Arg (R); and wherein the hinge region of the heavy chain lacks cysteine residues.

9. An isolated monovalent antibody according to claim 8, wherein the CL region is a kappa light chain CL region comprising the amino acid sequence set forth in SEQ ID NO: 18, wherein the terminal cysteine residue in position 106 of SEQ ID NO: 18 has been replaced with a different amino acid residue or has been deleted.

10. An isolated monovalent antibody according to claim 8, wherein the CL region is a lambda light chain CL region having the amino acid sequence set forth in SEQ ID NO: 17, wherein the cysteine residue in position 104 of SEQ ID NO: 17 has been replaced with a different amino acid residue or has been deleted.

11. An isolated monovalent antibody comprising a heavy chain and a light chain, wherein
   a) said light chain comprises the amino acid sequence of the light chain variable (VL) region of a selected antigen specific antibody and the amino acid sequence of the light chain constant (CL) region of an immunoglobulin, and
   b) said heavy chain comprises the amino acid sequence of the heavy chain variable (VH) region of said selected antigen specific antibody and the amino acid sequence of the heavy chain constant (CH) region of human IgG1, wherein the CH region comprises the amino acid sequence set forth in SEQ ID NO: 19, wherein Lys (K) in position 292 of SEQ ID NO: 19 has been replaced by Arg (R), and Ser (S) in position 14 of SEQ ID NO: 19 has been replaced by Cys (C); and wherein the hinge region of the heavy chain lacks cysteine residues.

12. An isolated monovalent antibody comprising a heavy chain and a light chain, wherein
   a) said light chain comprises the amino acid sequence of the light chain variable (VL) region of a selected antigen specific antibody and the amino acid sequence of the light chain constant (CL) region of an immunoglobulin, and
   b) said heavy chain comprises the amino acid sequence of the heavy chain variable (VH) region of said selected antigen specific antibody and the amino acid sequence of the heavy chain constant (CH) region of IgG2, wherein the CH region comprises the amino acid sequence set forth in SEQ ID NO: 20, wherein the following amino acid substitutions have been made: Arg (R) in position 234 of SEQ ID NO: 20 has been replaced by Gln (Q), Met (M) in position 276 of SEQ ID NO: 20 has been replaced by Val (V), Lys (K) in position 288 of SEQ ID NO: 20 has been replaced by Arg (R), Gln (Q) in position 298 of SEQ ID NO: 20 has been replaced by Glu (E), and Pro (P) in position 324 of SEQ ID NO: 20 has been replaced by Leu (L); and wherein the hinge region lacks cysteine residues.

13. An isolated monovalent antibody comprising a heavy chain and a light chain, wherein
   a) said light chain comprises the amino acid sequence of the light chain variable (VL) region of a selected antigen specific antibody and the amino acid sequence of the light chain constant (CL) region of an immunoglobulin, and
   b) said heavy chain comprises the amino acid sequence of the heavy chain variable (VH) region of said selected antigen specific antibody and the amino acid sequence of the heavy chain constant (CH) region of IgG3, wherein the CH region comprises the amino acid sequence set forth in SEQ ID NO: 21, wherein one or more following amino acid substitutions have been made: Arg (R) in position 285 of SEQ ID NO: 21 has been replaced by Gln (Q), Ser (S) in position 314 of SEQ ID NO: 21 has been replaced by Asn (N), Asn (N) in position 322 of SEQ ID NO: 21 has been replaced by Lys (K), Met (M) in position 327 of SEQ ID NO: 21 has been replaced by Val (V), Lys (K) in position 339 of SEQ ID NO: 21 has been replaced by Arg (R), Gln (Q) in position 349 of SEQ ID NO: 21 has been replaced by Glu (E), Ile (I) in position 352 of SEQ ID NO: 21 has been replaced by Val (V), Arg (R) in position 365 of SEQ ID NO: 21 has been replaced by His (H), Phe (F) in position 366 of SEQ ID NO: 21 has been replaced by Tyr (Y), and Pro (P) in position 375 of SEQ ID NO: 21 has been replaced by Leu (L); and wherein the hinge region of the heavy chain lacks cysteine residues.

14. An isolated monovalent antibody according to claim 13, wherein Lys (K) in position 339 of SEQ ID NO: 21 has been replaced by Arg (R).

15. An isolated monovalent antibody according to claim 1, wherein the monovalent antibody produced is a human antibody.

16. An immunoconjugate comprising an isolated monovalent antibody according to claim 1 conjugated to a therapeutic moiety.

17. A pharmaceutical composition comprising an isolated monovalent antibody according to claim 1 and one or more pharmaceutically acceptable excipients, diluents or carriers.

* * * * *

UNITED STATES PATENT AND TRADEMARK OFFICE
CERTIFICATE OF CORRECTION

PATENT NO. : 10,155,816 B2
APPLICATION NO. : 12/095023
DATED : December 18, 2018
INVENTOR(S) : Paul Parren et al.

It is certified that error appears in the above-identified patent and that said Letters Patent is hereby corrected as shown below:

In the Claims

At Column 148, Claim number 13, Line number 22, delete "more following amino acid substitutions have been" and replace with -- more of the following amino acid substitutions have been --.

Signed and Sealed this
Thirtieth Day of April, 2019

Andrei Iancu
*Director of the United States Patent and Trademark Office*

UNITED STATES PATENT AND TRADEMARK OFFICE
CERTIFICATE OF CORRECTION

| | | |
|---|---|---|
| PATENT NO. | : 10,155,816 B2 | Page 1 of 1 |
| APPLICATION NO. | : 12/095023 | |
| DATED | : December 18, 2018 | |
| INVENTOR(S) | : Parren et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 908 days.

Signed and Sealed this
Twenty-sixth Day of May, 2020

Andrei Iancu
*Director of the United States Patent and Trademark Office*

SEQUENCE LISTING

<160> NUMBER OF SEQ ID NOS: 23

<210> SEQ ID NO 1
<211> LENGTH: 321
<212> TYPE: DNA
<213> ORGANISM: Homo sapiens

<400> SEQUENCE: 1

| | | | | | |
|---|---|---|---|---|---|
| cgtacggtgg | ctgcaccatc | tgtcttcatc | ttcccgccat | ctgatgagca | gttgaaatct | 60 |
| ggaactgcct | ctgttgtgtg | cctgctgaat | aacttctatc | ccagagaggc | caaagtacag | 120 |
| tggaaggtgg | ataacgccct | ccaatcgggt | aactcccagg | agagtgtcac | agagcaggac | 180 |
| agcaaggaca | gcacctacag | cctcagcagc | accctgacgc | tgagcaaagc | agactacgag | 240 |
| aaacacaaag | tctacgcctg | cgaagtcacc | catcagggcc | tgagctcgcc | cgtcacaaag | 300 |
| agcttcaaca | ggggagagtg | t | | | | 321 |

<210> SEQ ID NO 2
<211> LENGTH: 107
<212> TYPE: PRT
<213> ORGANISM: Homo sapiens

<400> SEQUENCE: 2

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 3
<211> LENGTH: 327
<212> TYPE: DNA
<213> ORGANISM: Homo sapiens

<400> SEQUENCE: 3

| | | | | | |
|---|---|---|---|---|---|
| accgtcctag | gtcagcccaa | ggctgccccc | tcggtcactc | tgttcccgcc | ctcctctgag | 60 |
| gagcttcaag | ccaacaaggc | cacactggtg | tgtctcataa | gtgacttcta | cccgggagcc | 120 |
| gtgacagtgg | cctggaaggc | agatagcagc | cccgtcaagg | cgggagtgga | gaccaccaca | 180 |
| ccctccaaac | aaagcaacaa | caagtacgcg | gccagcagct | acctgagcct | gacgcctgag | 240 |
| cagtggaagt | cccacagaag | ctacagctgc | caggtcacgc | atgaagggag | caccgtggag | 300 |
| aagacagtgg | cccctacaga | atgttca | | | | 327 |

<210> SEQ ID NO 4
<211> LENGTH: 109
<212> TYPE: PRT
<213> ORGANISM: Homo sapiens

<400> SEQUENCE: 4

```
Thr Val Leu Gly Gln Pro Lys Ala Ala Pro Ser Val Thr Leu Phe Pro
1               5                   10                  15

Pro Ser Ser Glu Glu Leu Gln Ala Asn Lys Ala Thr Leu Val Cys Leu
            20                  25                  30

Ile Ser Asp Phe Tyr Pro Gly Ala Val Thr Val Ala Trp Lys Ala Asp
                35                  40                  45

Ser Ser Pro Val Lys Ala Gly Val Glu Thr Thr Thr Pro Ser Lys Gln
    50                  55                  60

Ser Asn Asn Lys Tyr Ala Ala Ser Ser Tyr Leu Ser Leu Thr Pro Glu
65                  70                  75                  80

Gln Trp Lys Ser His Arg Ser Tyr Ser Cys Gln Val Thr His Glu Gly
                85                  90                  95

Ser Thr Val Glu Lys Thr Val Ala Pro Thr Glu Cys Ser
                100                 105
```

<210> SEQ ID NO 5
<211> LENGTH: 366
<212> TYPE: DNA
<213> ORGANISM: Homo sapiens

<400> SEQUENCE: 5

```
gaagtgcagc tggtggagtc tgggggaggc ttggtacagc ctgacaggtc cctgagactc      60
tcctgtgcag cctctggatt cacctttcat gattatgcca tgcactgggt ccggcaagct     120
ccagggaagg gcctggagtg ggtctcaact attagttgga atagtggtac cataggctat     180
gcggactctg tgaagggccg attcaccatc tccagagaca acgccaagaa ctccctgtat     240
ctgcaaatga acagtctgag agctgaggac acggccttgt attactgtgc aaaagatata     300
cagtacggca actactacta cggtatggac gtctggggcc aagggaccac ggtcaccgtc     360
tcctca                                                                366
```

<210> SEQ ID NO 6
<211> LENGTH: 122
<212> TYPE: PRT
<213> ORGANISM: Homo sapiens

<400> SEQUENCE: 6

```
Glu Val Gln Leu Val Glu Ser Gly Gly Gly Leu Val Gln Pro Asp Arg
1               5                   10                  15

Ser Leu Arg Leu Ser Cys Ala Ala Ser Gly Phe Thr Phe His Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Thr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
                100                 105                 110

Gly Gln Gly Thr Thr Val Thr Val Ser Ser
            115                 120
```

<210> SEQ ID NO 7
<211> LENGTH: 354
<212> TYPE: DNA

<213> ORGANISM: Mus

<400> SEQUENCE: 7

```
gaggttcagc tgcagcagtc tggggcagag cttgtgaaac caggggcctc agtcaagttg    60
tcctgcacag cttctggctt caacattaaa gacacctata tccactgggt gaagcagagg   120
cctgaacagg gcctggagtg ggttggaagg attgatcctg cgactggcaa tactagatat   180
gacccgaagt tccagggcaa ggccactata acagctgaca catcctccaa cacagcctac   240
ctgcaactca gcagcctgac atctgaggac actgccgtct attactgtgc tagttttagg   300
ccggggtatg ctctggacta ctggggtcaa ggaacctcag tcaccgtctc ctca          354
```

<210> SEQ ID NO 8
<211> LENGTH: 118
<212> TYPE: PRT
<213> ORGANISM: mus

<400> SEQUENCE: 8

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Val
        35                  40                  45

Gly Arg Ile Asp Pro Ala Thr Gly Asn Thr Arg Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Ser Phe Arg Pro Gly Tyr Ala Leu Asp Tyr Trp Gly Gln Gly Thr
            100                 105                 110

Ser Val Thr Val Ser Ser
        115

<210> SEQ ID NO 9
<211> LENGTH: 321
<212> TYPE: DNA
<213> ORGANISM: Homo sapiens

<400> SEQUENCE: 9

```
gaaattgtgt tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggccgatcac cttcggccaa   300
gggacacgac tggagattaa a                                             321
```

<210> SEQ ID NO 10
<211> LENGTH: 107
<212> TYPE: PRT
<213> ORGANISM: Homo sapiens

<400> SEQUENCE: 10

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105

<210> SEQ ID NO 11
<211> LENGTH: 321
<212> TYPE: DNA
<213> ORGANISM: mus

<400> SEQUENCE: 11
gacattgtga tgacccagtc tcacaaattc atgtccacat cagttggaga cagggtcagc      60
ttcacctgca aggccagtca ggatgtgttt actgctgtag cctggtatca acaaaaacca     120
gggcaatctc ctaaactact gatttactgg gcatccaccc ggcgcactgg agtccctgat     180
cgcttcacag gcagtggatc tgggacagat tatactctca ccatcagcag tgtgcaggct     240
gaagacctgg cactttatta ctgtcagcaa cattttagca ctcctccgac gttcggtgga     300
ggcaccaagc tggaaatcaa a                                              321

<210> SEQ ID NO 12
<211> LENGTH: 107
<212> TYPE: PRT
<213> ORGANISM: mus

<400> SEQUENCE: 12

Asp Ile Val Met Thr Gln Ser His Lys Phe Met Ser Thr Ser Val Gly
1               5                   10                  15

Asp Arg Val Ser Phe Thr Cys Lys Ala Ser Gln Asp Val Phe Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg Arg Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Phe Ser Thr Pro Pro
                85                  90                  95

Thr Phe Gly Gly Gly Thr Lys Leu Glu Ile Lys
            100                 105

<210> SEQ ID NO 13
<211> LENGTH: 1588
<212> TYPE: DNA
<213> ORGANISM: Homo sapiens

<400> SEQUENCE: 13
gctagcacca agggcccatc cgtcttcccc ctggcgccct gctccaggag cacctccgag      60
agcacagccg ccctgggctg cctggtcaag gactacttcc ccgaaccggt gacggtgtcg     120

```
tggaactcag gcgccctgac cagcggcgtg cacaccttcc cggctgtcct acagtcctca      180
ggactctact ccctcagcag cgtggtgacc gtgccctcca gcagcttggg cacgaagacc      240
tacacctgca acgtagatca caagcccagc aacaccaagg tggacaagag agttggtgag      300
aggccagcac agggagggag ggtgtctgct ggaagccagg ctcagccctc ctgcctggac      360
gcacccggc tgtgcagccc cagccagggg cagcaaggca tgccccatct gtctcctcac       420
ccggaggcct ctgaccaccc cactcatgct caggagagag tcttctgga ttttccacc        480
aggctccggg cagccacagg ctggatgccc ctaccccagg ccctgcgcat acaggggcag      540
gtgctgcgct cagacctgcc aagagccata tccgggagga ccctgcccct gacctaagcc      600
cacccaaag gccaaactct ccactccctc agctcagaca ccttctctcc tcccagatct       660
gagtaactcc caatcttctc tctgcagagt ccaaatatgg tccccatgc ccatcatgcc       720
caggtaagcc aacccaggcc tcgccctcca gctcaaggcg ggacaggtgc cctagagtag      780
cctgcatcca gggacaggcc ccagccgggt gctgacgcat ccactccat ctcttcctca       840
gcacctgagt tcctggggg accatcagtc ttcctgttcc ccccaaaacc caaggacact       900
ctcatgatct cccggacccc tgaggtcacg tgcgtggtgg tggacgtgag ccaggaagac      960
cccgaggtcc agttcaactg gtacgtggat ggcgtggagg tgcataatgc caagacaaag     1020
ccgcgggagg agcagttcaa cagcacgtac cgtgtggtca gcgtcctcac cgtcctgcac     1080
caggactggc tgaacggcaa ggagtacaag tgcaaggtct ccaacaaagg cctcccgtcc     1140
tccatcgaga aaccatctc caaagccaaa ggtgggaccc acggggtgcg agggccacat      1200
ggacagaggt cagctcggcc caccctctgc cctgggagtg accgctgtgc caacctctgt     1260
ccctacaggg cagccccgag agccacaggt gtacaccctg ccccatccc aggaggagat      1320
gaccaagaac caggtcagcc tgacctgcct ggtcaaaggc ttctacccca gcgacatcgc     1380
cgtggagtgg gagagcaatg ggcagccgga gaacaactac aagaccacgc ctcccgtgct     1440
ggactccgac ggctccttct tcctctacag caggctaacc gtggacaaga gcaggtggca     1500
ggagggaat gtcttctcat gctccgtgat gcatgaggct ctgcacaacc actacacaca      1560
gaagagcctc tccctgtctc tgggtaaa                                        1588
```

<210> SEQ ID NO 14
<211> LENGTH: 327
<212> TYPE: PRT
<213> ORGANISM: Homo sapiens

<400> SEQUENCE: 14

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110
```

```
Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 15
<211> LENGTH: 1588
<212> TYPE: DNA
<213> ORGANISM: Homo sapiens

<400> SEQUENCE: 15
gctagcacca agggcccatc cgtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttggtgag     300
aggccagcac agggagggag ggtgtctgct ggaagccagg ctcagccctc ctgcctggac     360
gcaccccggc tgtgcagccc cagcccaggg cagcaaggca tgccccatct gtctcctcac     420
ccggaggcct ctgaccaccc cactcatgct caggagaggg tcttctggat ttttccacc     480 aggctccggg cagccacagg ctggatgccc taccccaggc cctgcgcat acaggggcag     540 gtgctgcgct cagacctgcc aagagccata tccggagga ccctgcccct gacctaagcc     600 cacccccaaag gccaaactct ccactccctc agctcagaca ccttctctcc tcccagatct     660
gagtaactcc caatcttctc tctgcagagt ccaaatatgg tccccatgc ccaccatgcc     720 cgggtaagcc aacccaggcc tcgccctcca gctcaaggcg gacaggtgc cctagagtag     780 cctgcatcca gggacaggcc ccagccgggt gctgacgcat ccacctccat ctcttcctca     840
gcacctgagt tcctgggggg accatcagtc ttcctgttcc ccccaaaaacc caaggacact     900
```

```
ctcatgatct cccggacccc tgaggtcacg tgcgtggtgg tggacgtgag ccaggaagac    960
cccgaggtcc agttcaactg gtacgtggat ggcgtggagg tgcataatgc caagacaaag   1020
ccgcgggagg agcagttcaa cagcacgtac cgtgtggtca gcgtcctcac cgtcctgcac   1080
caggactggc tgaacggcaa ggagtacaag tgcaaggtct ccaacaaagg cctcccgtcc   1140
tccatcgaga aaaccatctc caaagccaaa ggtgggaccc acggggtgcg agggccacat   1200
ggacagaggt cagctcggcc caccctctgc cctgggagtg accgctgtgc caacctctgt   1260
ccctacaggg cagccccgag agccacaggt gtacaccctg cccccatccc aggaggagat   1320
gaccaagaac caggtcagcc tgacctgcct ggtcaaaggc ttctacccca gcgacatcgc   1380
cgtggagtgg gagagcaatg ggcagccgga gaacaactac aagaccacgc ctcccgtgct   1440
ggactccgac ggctccttct tcctctacag caggctaacc gtggacaaga gcaggtggca   1500 ggagggaat gtcttctcat gctccgtgat gcatgaggct ctgcacaacc actacacaca    1560
gaagagcctc tccctgtctc tgggtaaa                                      1588
```

<210> SEQ ID NO 16
<211> LENGTH: 315
<212> TYPE: PRT
<213> ORGANISM: Homo sapiens

<400> SEQUENCE: 16

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Ala Pro Glu Phe Leu Gly Gly Pro Ser Val Phe Leu Phe Pro
            100                 105                 110

Pro Lys Pro Lys Asp Thr Leu Met Ile Ser Arg Thr Pro Glu Val Thr
        115                 120                 125

Cys Val Val Val Asp Val Ser Gln Glu Asp Pro Glu Val Gln Phe Asn
    130                 135                 140

Trp Tyr Val Asp Gly Val Glu Val His Asn Ala Lys Thr Lys Pro Arg
145                 150                 155                 160

Glu Glu Gln Phe Asn Ser Thr Tyr Arg Val Val Ser Val Leu Thr Val
                165                 170                 175

Leu His Gln Asp Trp Leu Asn Gly Lys Glu Tyr Lys Cys Lys Val Ser
            180                 185                 190

Asn Lys Gly Leu Pro Ser Ser Ile Glu Lys Thr Ile Ser Lys Ala Lys
        195                 200                 205

Gly Gln Pro Arg Glu Pro Gln Val Tyr Thr Leu Pro Pro Ser Gln Glu
    210                 215                 220

Glu Met Thr Lys Asn Gln Val Ser Leu Thr Cys Leu Val Lys Gly Phe
225                 230                 235                 240

Tyr Pro Ser Asp Ile Ala Val Glu Trp Glu Ser Asn Gly Gln Pro Glu
```

```
                    245                 250                 255
Asn Asn Tyr Lys Thr Thr Pro Pro Val Leu Asp Ser Asp Gly Ser Phe
            260                 265                 270

Phe Leu Tyr Ser Arg Leu Thr Val Asp Lys Ser Arg Trp Gln Glu Gly
        275                 280                 285

Asn Val Phe Ser Cys Ser Val Met His Glu Ala Leu His Asn His Tyr
    290                 295                 300

Thr Gln Lys Ser Leu Ser Leu Ser Leu Gly Lys
305                 310                 315

<210> SEQ ID NO 17
<211> LENGTH: 105
<212> TYPE: PRT
<213> ORGANISM: Homo sapiens

<400> SEQUENCE: 17

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 18
<211> LENGTH: 106
<212> TYPE: PRT
<213> ORGANISM: Homo sapiens

<400> SEQUENCE: 18

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 19
<211> LENGTH: 330
<212> TYPE: PRT
<213> ORGANISM: Homo sapiens

<400> SEQUENCE: 19
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 20
<211> LENGTH: 326
<212> TYPE: PRT
<213> ORGANISM: Homo sapiens

<400> SEQUENCE: 20

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
```

35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 21
<211> LENGTH: 377
<212> TYPE: PRT
<213> ORGANISM: Homo sapiens

<400> SEQUENCE: 21

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

```
Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
                180                 185                 190

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
        210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
                260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
                340                 345                 350

Phe Ser Cys Ser Val Met His Glu Ala Leu His Asn Arg Phe Thr Gln
            355                 360                 365

Lys Ser Leu Ser Leu Ser Pro Gly Lys
    370                 375

<210> SEQ ID NO 22
<211> LENGTH: 323
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: corresponds to SEQ ID NO: 14 with amino acids
      106-109 deleted

<400> SEQUENCE: 22

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45
```

```
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                     85                  90                  95

Arg Val Glu Ser Lys Tyr Gly Pro Pro Ala Pro Glu Phe Leu Gly
            100                 105                 110

Gly Pro Ser Val Phe Leu Phe Pro Pro Lys Pro Lys Asp Thr Leu Met
                115                 120                 125

Ile Ser Arg Thr Pro Glu Val Thr Cys Val Val Val Asp Val Ser Gln
        130                 135                 140

Glu Asp Pro Glu Val Gln Phe Asn Trp Tyr Val Asp Gly Val Glu Val
145                 150                 155                 160

His Asn Ala Lys Thr Lys Pro Arg Glu Glu Gln Phe Asn Ser Thr Tyr
                    165                 170                 175

Arg Val Val Ser Val Leu Thr Val Leu His Gln Asp Trp Leu Asn Gly
                180                 185                 190

Lys Glu Tyr Lys Cys Lys Val Ser Asn Lys Gly Leu Pro Ser Ser Ile
            195                 200                 205

Glu Lys Thr Ile Ser Lys Ala Lys Gly Gln Pro Arg Glu Pro Gln Val
210                 215                 220

Tyr Thr Leu Pro Pro Ser Gln Glu Glu Met Thr Lys Asn Gln Val Ser
225                 230                 235                 240

Leu Thr Cys Leu Val Lys Gly Phe Tyr Pro Ser Asp Ile Ala Val Glu
                    245                 250                 255

Trp Glu Ser Asn Gly Gln Pro Glu Asn Asn Tyr Lys Thr Thr Pro Pro
                260                 265                 270

Val Leu Asp Ser Asp Gly Ser Phe Phe Leu Tyr Ser Arg Leu Thr Val
            275                 280                 285

Asp Lys Ser Arg Trp Gln Glu Gly Asn Val Phe Ser Cys Ser Val Met
290                 295                 300

His Glu Ala Leu His Asn His Tyr Thr Gln Lys Ser Leu Ser Leu Ser
305                 310                 315                 320

Leu Gly Lys

<210> SEQ ID NO 23
<211> LENGTH: 315
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: corresponds to SEQ ID NO: 14 with amino acids
      99 to 110 deleted

<400> SEQUENCE: 23

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
 50                  55                  60
```

```
Leu Ser Ser Val Val Thr Val Pro Ser Ser Leu Gly Thr Lys Thr
65              70              75              80

Tyr Thr Cys Asn Val Asp His Lys Pro Ser Asn Thr Lys Val Asp Lys
            85              90              95

Arg Val Ala Pro Glu Phe Leu Gly Gly Pro Ser Val Phe Leu Phe Pro
            100             105             110

Pro Lys Pro Lys Asp Thr Leu Met Ile Ser Arg Thr Pro Glu Val Thr
            115             120             125

Cys Val Val Val Asp Val Ser Gln Glu Asp Pro Glu Val Gln Phe Asn
130             135             140

Trp Tyr Val Asp Gly Val Glu Val His Asn Ala Lys Thr Lys Pro Arg
145             150             155             160

Glu Glu Gln Phe Asn Ser Thr Tyr Arg Val Val Ser Val Leu Thr Val
            165             170             175

Leu His Gln Asp Trp Leu Asn Gly Lys Glu Tyr Lys Cys Lys Val Ser
            180             185             190

Asn Lys Gly Leu Pro Ser Ser Ile Glu Lys Thr Ile Ser Lys Ala Lys
            195             200             205

Gly Gln Pro Arg Glu Pro Gln Val Tyr Thr Leu Pro Pro Ser Gln Glu
    210             215             220

Glu Met Thr Lys Asn Gln Val Ser Leu Thr Cys Leu Val Lys Gly Phe
225             230             235             240

Tyr Pro Ser Asp Ile Ala Val Glu Trp Glu Ser Asn Gly Gln Pro Glu
            245             250             255

Asn Asn Tyr Lys Thr Thr Pro Pro Val Leu Asp Ser Asp Gly Ser Phe
            260             265             270

Phe Leu Tyr Ser Arg Leu Thr Val Asp Lys Ser Arg Trp Gln Glu Gly
            275             280             285

Asn Val Phe Ser Cys Ser Val Met His Glu Ala Leu His Asn His Tyr
            290             295             300

Thr Gln Lys Ser Leu Ser Leu Ser Leu Gly Lys
305             310             315
```